United States Patent
Watson et al.

(10) Patent No.: US 6,328,978 B1
(45) Date of Patent: *Dec. 11, 2001

(54) METHODS FOR THE TREATMENT OF IMMUNOLOGICALLY-MEDIATED SKIN DISORDERS

(75) Inventors: James D. Watson; Paul L. J. Tan; Ross Prestidge, all of Auckland (NZ)

(73) Assignee: Genesis Research & Development Corp. Ltd., Parnell (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 09/324,542

(22) Filed: Jun. 2, 1999

Related U.S. Application Data

(63) Continuation-in-part of application No. 08/997,080, filed on Dec. 23, 1997, now Pat. No. 5,968,524.

(51) Int. Cl.[7] .......................... A61K 45/00; A61K 39/04; A61K 39/02; A61K 39/38; A61K 38/00

(52) U.S. Cl. .................... 424/282.1; 424/278.1; 424/248.1; 424/234.1; 424/190.1; 424/184.1; 514/2; 514/863; 514/886; 514/885; 530/350; 530/825

(58) Field of Search .............................. 424/248.1, 234.1, 424/184.1, 93.1, 93.4, 278.1, 282.1, 190.1; 514/863, 2, 886, 885; 530/350, 825

(56) References Cited

U.S. PATENT DOCUMENTS

| | | |
|---|---|---|
| 3,956,481 | 5/1976 | Jolles et al. . |
| 4,036,953 | 7/1977 | Adam et al. . |
| 4,716,038 | 12/1987 | Stanford et al. . |
| 4,724,144 | 2/1988 | Rook et al. . |
| 5,599,545 | 2/1997 | Stanford et al. . |
| 5,833,996 * | 11/1998 | Stanford et al. .................. 424/248.1 |
| 5,968,524 * | 10/1999 | Watson et al. ..................... 424/248.1 |
| 5,985,287 * | 11/1999 | Tan et al. .......................... 424/248.1 |
| 6,001,361 * | 12/1999 | Tan et al. .......................... 424/190.1 |

FOREIGN PATENT DOCUMENTS

| | | | |
|---|---|---|---|
| 0556248B1 * | 8/1993 | (EP) . | |
| 9007935 | 7/1990 | (WO) | ............................ A61K/39/02 |
| 9101751 | 2/1991 | (WO) | ............................ A61K/39/04 |
| 9102542 | 3/1991 | (WO) | ............................ A61K/39/04 |
| 9208484 | 5/1992 | (WO) | ............................ A61K/39/04 |
| 9208488 | 5/1992 | (WO) | ............................ A61K/39/39 |
| 9316727 | 9/1993 | (WO) | ............................ A61K/39/04 |
| 9406466 | 3/1994 | (WO) | ............................ A61K/39/04 |
| 9526742 | 10/1995 | (WO) | ............................ A61K/35/74 |

OTHER PUBLICATIONS

Ramu et al. Indian J. Med. Gazette 124: 381–382 1990.*
Evan Medical Marketletter, Apr. 22, p. 21, 1991.*
Lehrer, A. et al. Immunotherapy with Mycobacterium vaccae in the treatment of psoriasis, FEMS Immunology and Medical Microbiology 21:71–77, 1998.
R.G. White et al., "Correlation of Adjuvant Activity and Chemical Structure of Wax D Fractions of Mycobacteria," Immunology 7, pp. 158–171. 1964.
R.G. White, "Characterization of Microbacterial Components of Adjuvant Mixtures," Symposium Series Immunobiol. Standard 6, pp. 49–58, 1967.
R.G. White et al., The Influence of Components of M. Tuberculosis and other Mycobacteria upon Antibody Production to Ovalbumin, Immunology I, pp. 54–66, 1958.

* cited by examiner

*Primary Examiner*—S. Devi
(74) *Attorney, Agent, or Firm*—Janet Sleath; Ann W. Speckman

(57) ABSTRACT

Methods for the treatment of skin disorders, including psoriasis, atopic dermatitis, allergic contact dermatitis, alopecia areata and skin cancers are provided, such methods comprising administering a composition having antigenic and/or adjuvant properties. Compositions which may be usefully employed in the inventive methods include inactivated *M. vaccae* cells, delipidated and deglycolipidated *M. vaccae* cells, *M. vaccae* culture filtrate and compounds present in or derived therefrom, together with combinations of such compositions.

9 Claims, 8 Drawing Sheets

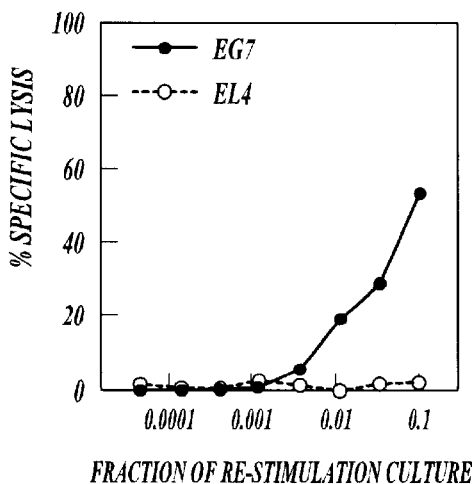
*Fig.3A(i)*
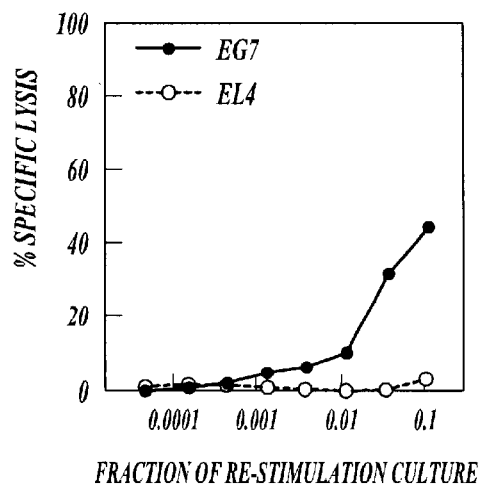
*Fig.3A(ii)*
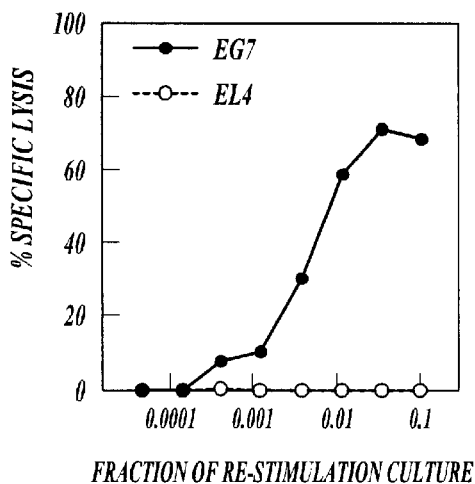
*Fig.3A(iii)*
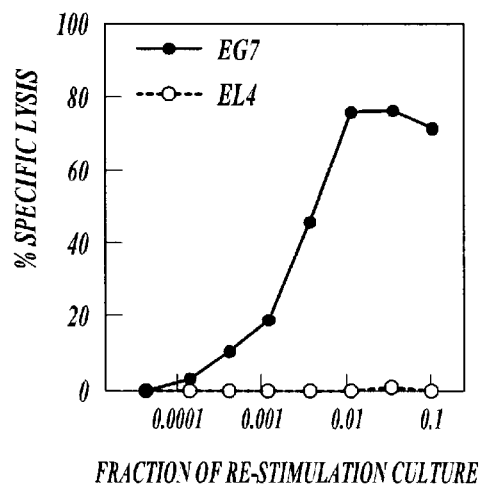
*Fig.3A(iv)*

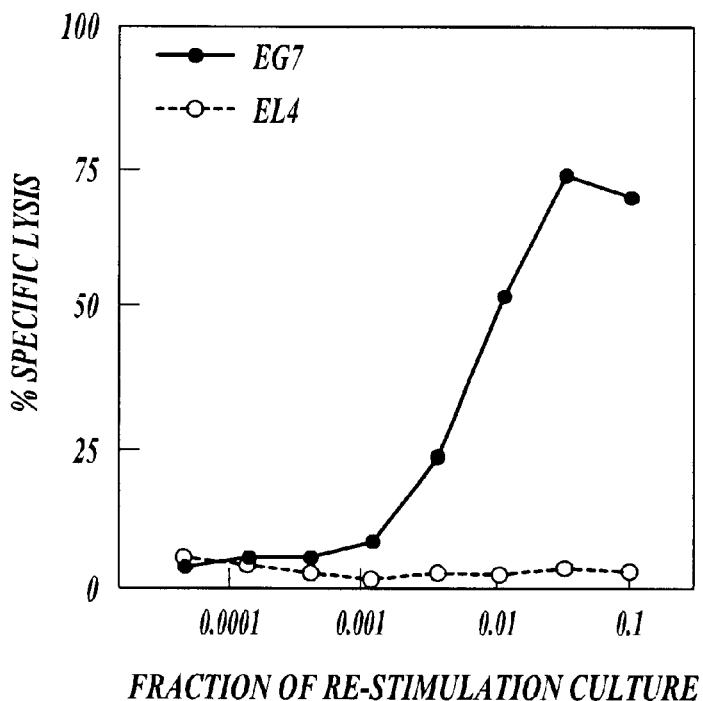
*Fig.3B(i)*
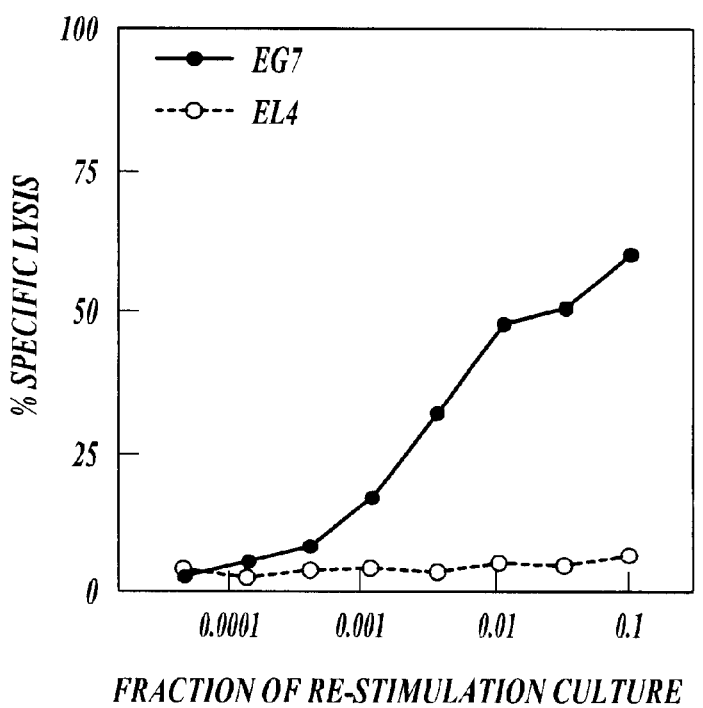
*Fig.3B(ii)*

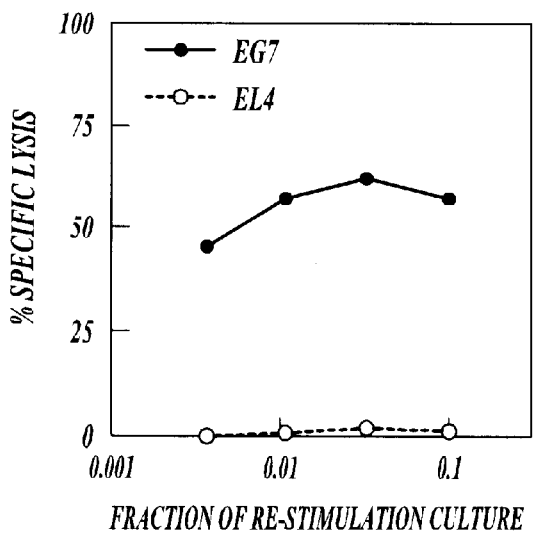
Fig.3C(i)
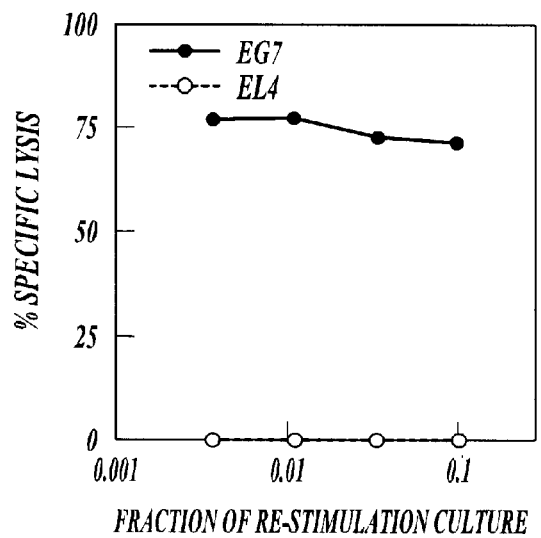
Fig.3C(ii)
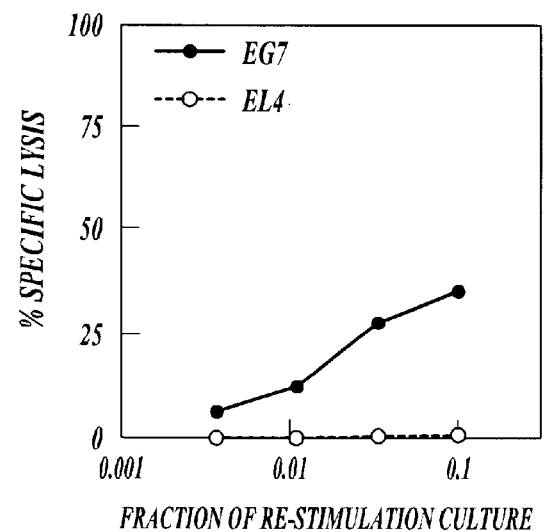
Fig.3C(iii)

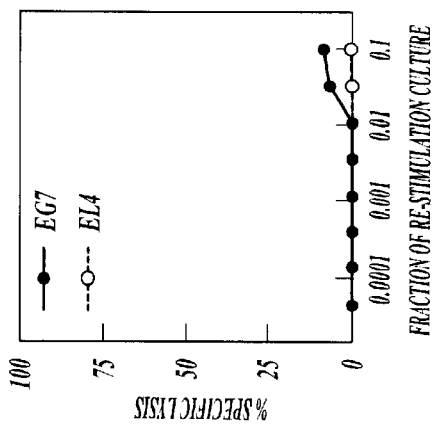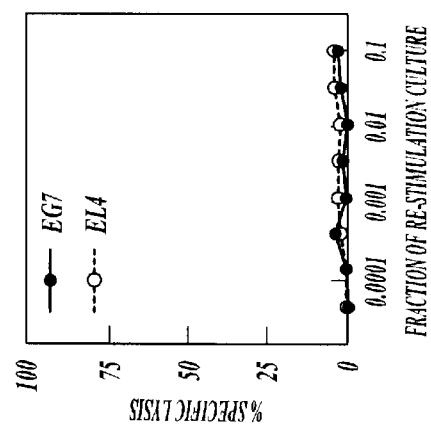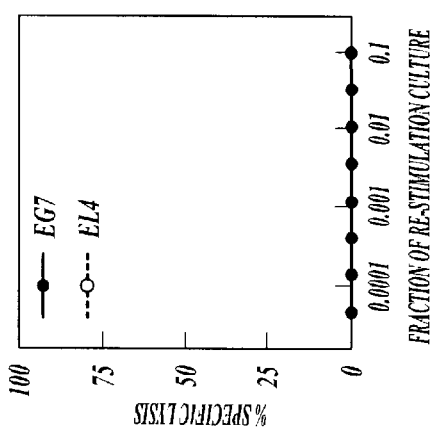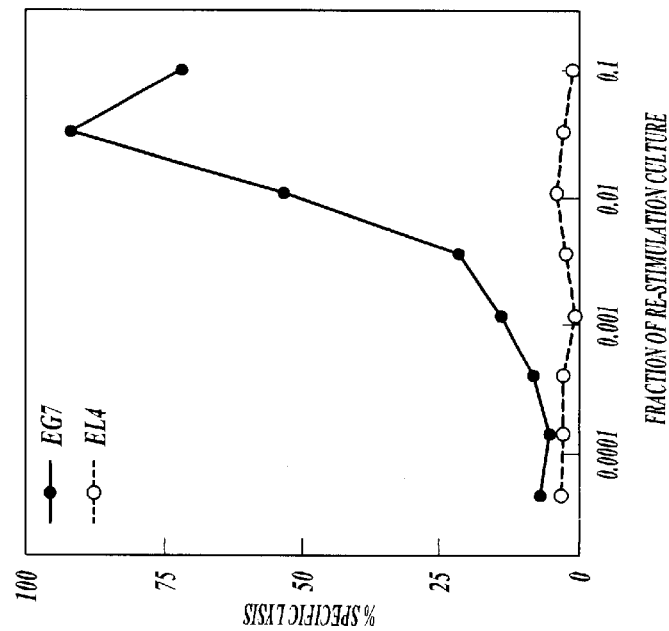

SEQUENCE LISTING

<160> NUMBER OF SEQ ID NOS: 194

<210> SEQ ID NO 1
<211> LENGTH: 25
<212> TYPE: PRT
<213> ORGANISM: Mycobacterium vaccae
<220> FEATURE:
<221> NAME/KEY: UNSURE
<222> LOCATION: (7)...(7)

<400> SEQUENCE: 1

Ala Pro Val Gly Pro Gly Xaa Ala Ala Tyr Val Gln Gln Val Pro Asp
1               5                   10                  15

Gly Pro Gly Ser Val Gln Gly Met Ala
            20                  25

<210> SEQ ID NO 2
<211> LENGTH: 10
<212> TYPE: PRT
<213> ORGANISM: Mycobacterium vaccae
<220> FEATURE:
<221> NAME/KEY: UNSURE
<222> LOCATION: (2)...(2)

<400> SEQUENCE: 2

Met Xaa Asp Gln Leu Lys Val Asn Asp Asp
1               5                   10

<210> SEQ ID NO 3
<211> LENGTH: 11
<212> TYPE: PRT
<213> ORGANISM: Mycobacterium vaccae
<220> FEATURE:
<221> NAME/KEY: UNSURE
<222> LOCATION: (2)...(2)

<400> SEQUENCE: 3

Met Xaa Pro Val Pro Val Ala Thr Ala Ala Tyr
1               5                   10

<210> SEQ ID NO 4
<211> LENGTH: 21
<212> TYPE: PRT
<213> ORGANISM: Mycobacterium vaccae

<400> SEQUENCE: 4

Thr Pro Ala Pro Ala Pro Pro Pro Tyr Val Asp His Val Glu Gln Ala
1               5                   10                  15

Lys Phe Gly Asp Leu
            20

<210> SEQ ID NO 5
<211> LENGTH: 29
<212> TYPE: PRT
<213> ORGANISM: Mycobacterium vaccae
<220> FEATURE:
<221> NAME/KEY: UNSURE
<222> LOCATION: (25)...(25)

<400> SEQUENCE: 5

Met Gln Ala Phe Asn Ala Asp Ala Tyr Ala Phe Ala Lys Arg Glu Lys
1               5                   10                  15
Val Ser Leu Ala Pro Gly Val Pro Xaa Val Phe Glu Thr
            20                  25

<210> SEQ ID NO 6
<211> LENGTH: 21
<212> TYPE: PRT
<213> ORGANISM: Mycobacterium vaccae
<220> FEATURE:
<221> NAME/KEY: UNSURE
<222> LOCATION: (6)...(6)

<400> SEQUENCE: 6

Met Ala Asp Pro Asn Xaa Ala Ile Leu Gln Val Ser Lys Thr Thr Arg
1               5                   10                  15

Gly Gly Gln Ala Ala
            20

<210> SEQ ID NO 7
<211> LENGTH: 11
<212> TYPE: PRT
<213> ORGANISM: Mycobacterium vaccae

<400> SEQUENCE: 7

Met Pro Ile Leu Gln Val Ser Gln Thr Gly Arg
1               5                   10

<210> SEQ ID NO 8

```
<211> LENGTH: 14
<212> TYPE: PRT
<213> ORGANISM: Mycobacterium vaccae
<220> FEATURE:
<221> NAME/KEY: UNSURE
<222> LOCATION: (2)...(2)
<221> NAME/KEY: UNSURE
<222> LOCATION: (6)...(6)

<400> SEQUENCE: 8

Met Xaa Asp Pro Ile Xaa Leu Gln Leu Gln Val Ser Ser Thr
1               5                   10

<210> SEQ ID NO 9
<211> LENGTH: 16
<212> TYPE: PRT
<213> ORGANISM: Mycobacterium vaccae

<400> SEQUENCE: 9

Lys Ala Thr Tyr Val Gln Gly Gly Leu Gly Arg Ile Glu Ala Arg Val
1               5                   10                  15

<210> SEQ ID NO 10
<211> LENGTH: 9
<212> TYPE: PRT
<213> ORGANISM: Mycobacterium vaccae
<220> FEATURE:
<221> NAME/KEY: UNSURE
<222> LOCATION: (2)...(2)

<400> SEQUENCE: 10

Lys Xaa Gly Leu Ala Asp Leu Ala Pro
1               5

<210> SEQ ID NO 11
<211> LENGTH: 14
<212> TYPE: PRT
<213> ORGANISM: Mycobacterium vaccae
<220> FEATURE:
<221> NAME/KEY: UNSURE
<222> LOCATION: (12)...(12)
<223> OTHER INFORMATION: Residue can be either Glu or Ile
<220> FEATURE:
<221> NAME/KEY: UNSURE
<222> LOCATION: (2)...(2)

<400> SEQUENCE: 11

Lys Xaa Tyr Ala Leu Ala Leu Met Ser Ala Val Xaa Ala Ala
1               5                   10

<210> SEQ ID NO 12
<211> LENGTH: 11
<212> TYPE: PRT
<213> ORGANISM: Mycobacterium vaccae
<220> FEATURE:
<221> NAME/KEY: UNSURE
<222> LOCATION: (10)...(10)

<400> SEQUENCE: 12

Lys Asn Pro Gln Val Ser Asp Glu Leu Xaa Thr
1               5                   10

<210> SEQ ID NO 13
<211> LENGTH: 21
<212> TYPE: PRT
<213> ORGANISM: Mycobacterium vaccae
<220> FEATURE:
<221> NAME/KEY: UNSURE
<222> LOCATION: (9)...(9)
```

<400> SEQUENCE: 13

Ala Pro Ala Pro Ala Ala Pro Ala Xaa Gly Asp Pro Ala Ala Val Val
1               5                   10                  15

Ala Ala Met Ser Thr
            20

<210> SEQ ID NO 14
<211> LENGTH: 15
<212> TYPE: PRT
<213> ORGANISM: Mycobacterium vaccae
<220> FEATURE:
<221> NAME/KEY: UNSURE
<222> LOCATION: (5)...(5)

<400> SEQUENCE: 14

Glu Ala Glu Val Xaa Tyr Leu Gly Gln Pro Gly Glu Leu Val Asn
1               5                   10                  15

<210> SEQ ID NO 15
<211> LENGTH: 15
<212> TYPE: PRT
<213> ORGANISM: Mycobacterium vaccae
<220> FEATURE:
<221> NAME/KEY: UNSURE
<222> LOCATION: (2)...(2)
<223> OTHER INFORMATION: Residue can be either Gly or Ala
<220> FEATURE:
<221> NAME/KEY: UNSURE
<222> LOCATION: (15)...(15)
<223> OTHER INFORMATION: Residue can be either Pro or Ala
<220> FEATURE:
<221> NAME/KEY: UNSURE
<222> LOCATION: (7)...(7)

<400> SEQUENCE: 15

Ala Xaa Val Val Pro Pro Xaa Gly Pro Pro Ala Pro Gly Ala Xaa
1               5                   10                  15

<210> SEQ ID NO 16
<211> LENGTH: 15
<212> TYPE: PRT
<213> ORGANISM: Mycobacterium vaccae

<400> SEQUENCE: 16

Ala Pro Ala Pro Asp Leu Gln Gly Pro Leu Val Ser Thr Leu Ser
1               5                   10                  15

<210> SEQ ID NO 17
<211> LENGTH: 25
<212> TYPE: PRT
<213> ORGANISM: Mycobacterium vaccae

<400> SEQUENCE: 17

Ala Thr Pro Asp Trp Ser Gly Arg Tyr Thr Val Val Thr Phe Ala Ser
1               5                   10                  15

Asp Lys Leu Gly Thr Ser Val Ala Ala
            20                  25

<210> SEQ ID NO 18
<211> LENGTH: 25
<212> TYPE: PRT
<213> ORGANISM: Mycobacterium vaccae
<220> FEATURE:
<221> NAME/KEY: UNSURE
<222> LOCATION: (15)...(15)
<223> OTHER INFORMATION: Residue can be either Ala or Arg

```
<220> FEATURE:
<221> NAME/KEY: UNSURE
<222> LOCATION: (23)...(23)
<223> OTHER INFORMATION: Residue can be either Val or Leu
<220> FEATURE:
<221> NAME/KEY: UNSURE
<222> LOCATION: (16)...(16)

<400> SEQUENCE: 18

Ala Pro Pro Tyr Asp Asp Arg Gly Tyr Val Asp Ser Thr Ala Xaa Xaa
 1               5                  10                  15

Ala Ser Pro Pro Thr Leu Xaa Val Val
            20                  25

<210> SEQ ID NO 19
<211> LENGTH: 8
<212> TYPE: PRT
<213> ORGANISM: Mycobacterium vaccae

<400> SEQUENCE: 19

Glu Pro Glu Gly Val Ala Pro Pro
 1               5

<210> SEQ ID NO 20
<211> LENGTH: 25
<212> TYPE: PRT
<213> ORGANISM: Mycobacterium vaccae
<220> FEATURE:
<221> NAME/KEY: UNSURE
<222> LOCATION: (21)...(22)

<400> SEQUENCE: 20

Glu Pro Ala Gly Ile Pro Ala Gly Phe Pro Asp Val Ser Ala Tyr Ala
 1               5                  10                  15

Ala Val Asp Pro Xaa Xaa Tyr Val Val
            20                  25

<210> SEQ ID NO 21
<211> LENGTH: 15
<212> TYPE: PRT
<213> ORGANISM: Mycobacterium vaccae
<220> FEATURE:
<221> NAME/KEY: UNSURE
<222> LOCATION: (7)...(7)

<400> SEQUENCE: 21

Ala Pro Val Gly Pro Gly Xaa Ala Ala Tyr Val Gln Gln Val Pro
 1               5                  10                  15

<210> SEQ ID NO 22
<211> LENGTH: 15
<212> TYPE: PRT
<213> ORGANISM: Mycobacterium vaccae

<400> SEQUENCE: 22

Phe Ser Arg Pro Gly Leu Pro Val Glu Tyr Leu Met Val Pro Ser
 1               5                  10                  15

<210> SEQ ID NO 23
<211> LENGTH: 19
<212> TYPE: PRT
<213> ORGANISM: Mycobacterium vaccae

<400> SEQUENCE: 23

Phe Ser Arg Pro Gly Leu Pro Val Glu Tyr Leu Met Val Pro Ser Pro
 1               5                  10                  15
```

Ser Met Gly

<210> SEQ ID NO 24
<211> LENGTH: 15
<212> TYPE: PRT
<213> ORGANISM: Mycobacterium vaccae

<400> SEQUENCE: 24

Phe Ser Arg Pro Gly Leu Pro Val Glu Tyr Leu Asp Val Phe Ser
1               5                   10                  15

<210> SEQ ID NO 25
<211> LENGTH: 14
<212> TYPE: PRT
<213> ORGANISM: Mycobacterium vaccae
<220> FEATURE:
<221> NAME/KEY: UNSURE
<222> LOCATION: (1)...(2)

<400> SEQUENCE: 25

Xaa Xaa Thr Gly Leu His Arg Leu Arg Met Met Val Pro Asn
1               5                   10

<210> SEQ ID NO 26
<211> LENGTH: 20
<212> TYPE: PRT
<213> ORGANISM: Mycobacterium vaccae
<220> FEATURE:
<221> NAME/KEY: UNSURE
<222> LOCATION: (16)...(16)
<223> OTHER INFORMATION: Residue can be either Ser or Val
<220> FEATURE:
<221> NAME/KEY: UNSURE
<222> LOCATION: (17)...(17)
<223> OTHER INFORMATION: Residue can be either Gln or Val

<400> SEQUENCE: 26

Val Pro Ala Asp Pro Val Gly Ala Ala Ala Gln Ala Glu Pro Ala Xaa
1               5                   10                  15

Xaa Arg Ile Asp
            20

<210> SEQ ID NO 27
<211> LENGTH: 14
<212> TYPE: PRT
<213> ORGANISM: Mycobacterium vaccae
<220> FEATURE:
<221> NAME/KEY: UNSURE
<222> LOCATION: (4)...(4)
<223> OTHER INFORMATION: Residue can be either Tyr or Pro
<220> FEATURE:
<221> NAME/KEY: UNSURE
<222> LOCATION: (8)...(8)
<223> OTHER INFORMATION: Residue can be either Val or Gly
<220> FEATURE:
<221> NAME/KEY: UNSURE
<222> LOCATION: (9)...(9)
<223> OTHER INFORMATION: Residue can be either Ile or Tyr
<220> FEATURE:
<221> NAME/KEY: UNSURE
<222> LOCATION: (3)...(3)

<400> SEQUENCE: 27

Asp Pro Xaa Xaa Asp Ile Glu Xaa Xaa Phe Ala Arg Gly Thr
1               5                   10

<210> SEQ ID NO 28
<211> LENGTH: 15

-continued

```
<212> TYPE: PRT
<213> ORGANISM: Mycobacterium vaccae

<400> SEQUENCE: 28

Ala Pro Ser Leu Ser Val Ser Asp Tyr Ala Arg Asp Ala Gly Phe
 1               5                  10                  15

<210> SEQ ID NO 29
<211> LENGTH: 16
<212> TYPE: PRT
<213> ORGANISM: Mycobacterium vaccae
<220> FEATURE:
<221> NAME/KEY: UNSURE
<222> LOCATION: (2)...(2)
<223> OTHER INFORMATION: Residue can be either Leu or Pro
<220> FEATURE:
<221> NAME/KEY: UNSURE
<222> LOCATION: (1)...(1)
<221> NAME/KEY: UNSURE
<222> LOCATION: (5)...(5)
<221> NAME/KEY: UNSURE
<222> LOCATION: (7)...(7)
<221> NAME/KEY: UNSURE
<222> LOCATION: (10)...(10)

<400> SEQUENCE: 29

Xaa Xaa Leu Ala Xaa Ala Xaa Leu Gly Xaa Thr Val Asp Ala Asp Gln
 1               5                  10                  15

<210> SEQ ID NO 30
<211> LENGTH: 330
<212> TYPE: PRT
<213> ORGANISM: Mycobacterium leprae

<400> SEQUENCE: 30

Met Lys Phe Val Asp Arg Phe Arg Gly Ala Val Ala Gly Met Leu Arg
 1               5                  10                  15

Arg Leu Val Val Glu Ala Met Gly Val Ala Leu Leu Ser Ala Leu Ile
                20                  25                  30

Gly Val Val Gly Ser Ala Pro Ala Glu Ala Phe Ser Arg Pro Gly Leu
            35                  40                  45

Pro Val Glu Tyr Leu Gln Val Pro Ser Pro Ser Met Gly Arg Asp Ile
        50                  55                  60

Lys Val Gln Phe Gln Asn Gly Gly Ala Asn Ser Pro Ala Leu Tyr Leu
 65                  70                  75                  80

Leu Asp Gly Leu Arg Ala Gln Asp Asp Phe Ser Gly Trp Asp Ile Asn
                85                  90                  95

Thr Thr Ala Phe Glu Trp Tyr Tyr Gln Ser Gly Ile Ser Val Val Met
            100                 105                 110

Pro Val Gly Gly Gln Ser Ser Phe Tyr Ser Asp Trp Tyr Ser Pro Ala
        115                 120                 125

Cys Gly Lys Ala Gly Cys Gln Thr Tyr Lys Trp Glu Thr Phe Leu Thr
130                 135                 140

Ser Glu Leu Pro Glu Tyr Leu Gln Ser Asn Lys Gln Ile Lys Pro Thr
145                 150                 155                 160

Gly Ser Ala Ala Val Gly Leu Ser Met Ala Gly Leu Ser Ala Leu Thr
                165                 170                 175

Leu Ala Ile Tyr His Pro Asp Gln Phe Ile Tyr Val Gly Ser Met Ser
            180                 185                 190

Gly Leu Leu Asp Pro Ser Asn Ala Met Gly Pro Ser Leu Ile Gly Leu
        195                 200                 205
```

-continued

Ala Met Gly Asp Ala Gly Gly Tyr Lys Ala Ala Asp Met Trp Gly Pro
210 215 220

Ser Thr Asp Pro Ala Trp Lys Arg Asn Asp Pro Thr Val Asn Val Gly
225 230 235 240

Thr Leu Ile Ala Asn Asn Thr Arg Ile Trp Met Tyr Cys Gly Asn Gly
245 250 255

Lys Pro Thr Glu Leu Gly Gly Asn Asn Leu Pro Ala Lys Leu Leu Glu
260 265 270

Gly Leu Val Arg Thr Ser Asn Ile Lys Phe Gln Asp Gly Tyr Asn Ala
275 280 285

Gly Gly Gly His Asn Ala Val Phe Asn Phe Pro Asp Ser Gly Thr His
290 295 300

Ser Trp Glu Tyr Trp Gly Glu Gln Leu Asn Asp Met Lys Pro Asp Leu
305 310 315 320

Gln Gln Tyr Leu Gly Ala Thr Pro Gly Ala
325 330

<210> SEQ ID NO 31
<211> LENGTH: 327
<212> TYPE: PRT
<213> ORGANISM: Mycobacterium leprae

<400> SEQUENCE: 31

Met Ile Asp Val Ser Gly Lys Ile Arg Ala Trp Gly Arg Trp Leu Leu
1 5 10 15

Val Gly Ala Ala Ala Thr Leu Pro Ser Leu Ile Ser Leu Ala Gly Gly
20 25 30

Ala Ala Thr Ala Ser Ala Phe Ser Arg Pro Gly Leu Pro Val Glu Tyr
35 40 45

Leu Gln Val Pro Ser Glu Ala Met Gly Arg Thr Ile Lys Val Gln Phe
50 55 60

Gln Asn Gly Gly Asn Gly Ser Pro Ala Val Tyr Leu Leu Asp Gly Leu
65 70 75 80

Arg Ala Gln Asp Asp Tyr Asn Gly Trp Asp Ile Asn Thr Ser Ala Phe
85 90 95

Glu Trp Tyr Tyr Gln Ser Gly Leu Ser Val Val Met Pro Val Gly Gly
100 105 110

Gln Ser Ser Phe Tyr Ser Asp Trp Tyr Ser Pro Ala Cys Gly Lys Ala
115 120 125

Gly Cys Thr Thr Tyr Lys Trp Glu Thr Phe Leu Thr Ser Glu Leu Pro
130 135 140

Lys Trp Leu Ser Ala Asn Arg Ser Val Lys Ser Thr Gly Ser Ala Val
145 150 155 160

Val Gly Leu Ser Met Ala Gly Ser Ser Ala Leu Ile Leu Ala Ala Tyr
165 170 175

His Pro Asp Gln Phe Ile Tyr Ala Gly Ser Leu Ser Ala Leu Met Asp
180 185 190

Ser Ser Gln Gly Ile Glu Pro Gln Leu Ile Gly Leu Ala Met Gly Asp
195 200 205

Ala Gly Gly Tyr Lys Ala Ala Asp Met Trp Gly Pro Pro Asn Asp Pro
210 215 220

Ala Trp Gln Arg Asn Asp Pro Ile Leu Gln Ala Gly Lys Leu Val Ala
225 230 235 240

Asn Asn Thr His Leu Trp Val Tyr Cys Gly Asn Gly Thr Pro Ser Glu
245 250 255

-continued

Leu Gly Gly Thr Asn Val Pro Ala Glu Phe Leu Glu Asn Phe Val His
            260                 265                 270

Gly Ser Asn Leu Lys Phe Gln Asp Ala Tyr Asn Gly Ala Gly Gly His
        275                 280                 285

Asn Ala Val Phe Asn Leu Asn Ala Asp Gly Thr His Ser Trp Glu Tyr
        290                 295                 300

Trp Gly Ala Gln Leu Asn Ala Met Lys Pro Asp Leu Gln Asn Thr Leu
305                 310                 315                 320

Met Ala Val Pro Arg Ser Gly
                325

<210> SEQ ID NO 32
<211> LENGTH: 338
<212> TYPE: PRT
<213> ORGANISM: Mycobacterium tuberculosis

<400> SEQUENCE: 32

Met Gln Leu Val Asp Arg Val Arg Gly Ala Val Thr Gly Met Ser Arg
1               5                   10                  15

Arg Leu Val Val Gly Ala Val Gly Ala Ala Leu Val Ser Gly Leu Val
            20                  25                  30

Gly Ala Val Gly Gly Thr Ala Thr Ala Gly Ala Phe Ser Arg Pro Gly
        35                  40                  45

Leu Pro Val Glu Tyr Leu Gln Val Pro Ser Pro Ser Met Gly Arg Asp
    50                  55                  60

Ile Lys Val Gln Phe Gln Ser Gly Gly Ala Asn Ser Pro Ala Leu Tyr
65                  70                  75                  80

Leu Leu Asp Gly Leu Arg Ala Gln Asp Asp Phe Ser Gly Trp Asp Ile
                85                  90                  95

Asn Thr Pro Ala Phe Glu Trp Tyr Asp Gln Ser Gly Leu Ser Val Val
            100                 105                 110

Met Pro Val Gly Gly Gln Ser Ser Phe Tyr Ser Asp Trp Tyr Gln Pro
        115                 120                 125

Ala Cys Gly Lys Ala Gly Cys Gln Thr Tyr Lys Trp Glu Thr Phe Leu
    130                 135                 140

Thr Ser Glu Leu Pro Gly Trp Leu Gln Ala Asn Arg His Val Lys Pro
145                 150                 155                 160

Thr Gly Ser Ala Val Val Gly Leu Ser Met Ala Ala Ser Ser Ala Leu
                165                 170                 175

Thr Leu Ala Ile Tyr His Pro Gln Gln Phe Val Tyr Ala Gly Ala Met
            180                 185                 190

Ser Gly Leu Leu Asp Pro Ser Gln Ala Met Gly Pro Thr Leu Ile Gly
        195                 200                 205

Leu Ala Met Gly Asp Ala Gly Gly Tyr Lys Ala Ser Asp Met Trp Gly
    210                 215                 220

Pro Lys Glu Asp Pro Ala Trp Gln Arg Asn Asp Pro Leu Leu Asn Val
225                 230                 235                 240

Gly Lys Leu Ile Ala Asn Asn Thr Arg Val Trp Val Tyr Cys Gly Asn
                245                 250                 255

Gly Lys Pro Ser Asp Leu Gly Gly Asn Asn Leu Pro Ala Lys Phe Leu
            260                 265                 270

Glu Gly Phe Val Arg Thr Ser Asn Ile Lys Phe Gln Asp Ala Tyr Asn
        275                 280                 285

Ala Gly Gly Gly His Asn Gly Val Phe Asp Phe Pro Asp Ser Gly Thr

```
                    290                 295                 300
His Ser Trp Glu Tyr Trp Gly Ala Gln Leu Asn Ala Met Lys Pro Asp
305                 310                 315                 320

Leu Gln Arg Ala Leu Gly Ala Thr Pro Asn Thr Gly Pro Ala Pro Gln
                325                 330                 335

Gly Ala

<210> SEQ ID NO 33
<211> LENGTH: 325
<212> TYPE: PRT
<213> ORGANISM: Mycobacterium tuberculosis

<400> SEQUENCE: 33

Met Thr Asp Val Ser Arg Lys Ile Arg Ala Trp Gly Arg Arg Leu Met
  1               5                  10                  15

Ile Gly Thr Ala Ala Val Val Leu Pro Gly Leu Val Gly Leu Ala
             20                  25                  30

Gly Gly Ala Ala Thr Ala Gly Ala Phe Ser Arg Pro Gly Leu Pro Val
             35                  40                  45

Glu Tyr Leu Gln Val Pro Ser Pro Ser Met Gly Arg Asp Ile Lys Val
 50                  55                  60

Gln Phe Gln Ser Gly Gly Asn Asn Ser Pro Ala Val Tyr Leu Leu Asp
 65                  70                  75                  80

Gly Leu Arg Ala Gln Asp Asp Tyr Asn Gly Trp Asp Ile Asn Thr Pro
                 85                  90                  95

Ala Phe Glu Trp Tyr Tyr Gln Ser Gly Leu Ser Ile Val Met Pro Val
                100                 105                 110

Gly Gly Gln Ser Ser Phe Tyr Ser Asp Trp Tyr Ser Pro Ala Cys Gly
            115                 120                 125

Lys Ala Gly Cys Gln Thr Tyr Lys Trp Glu Thr Phe Leu Thr Ser Glu
130                 135                 140

Leu Pro Gln Trp Leu Ser Ala Asn Arg Ala Val Lys Pro Thr Gly Ser
145                 150                 155                 160

Ala Ala Ile Gly Leu Ser Met Ala Gly Ser Ser Ala Met Ile Leu Ala
                165                 170                 175

Ala Tyr His Pro Gln Gln Phe Ile Tyr Ala Gly Ser Leu Ser Ala Leu
                180                 185                 190

Leu Asp Pro Ser Gln Gly Met Gly Pro Ser Leu Ile Gly Leu Ala Met
            195                 200                 205

Gly Asp Ala Gly Gly Tyr Lys Ala Ala Asp Met Trp Gly Pro Ser Ser
210                 215                 220

Asp Pro Ala Trp Glu Arg Asn Asp Pro Thr Gln Gln Ile Pro Lys Leu
225                 230                 235                 240

Val Ala Asn Asn Thr Arg Leu Trp Val Tyr Cys Gly Asn Gly Thr Pro
                245                 250                 255

Asn Glu Leu Gly Gly Ala Asn Ile Pro Ala Glu Phe Leu Glu Asn Phe
            260                 265                 270

Val Arg Ser Ser Asn Leu Lys Phe Gln Asp Ala Tyr Asn Ala Ala Gly
        275                 280                 285

Gly His Asn Ala Val Phe Asn Phe Pro Pro Asn Gly Thr His Ser Trp
    290                 295                 300

Glu Tyr Trp Gly Ala Gln Leu Asn Ala Met Lys Gly Asp Leu Gln Ser
305                 310                 315                 320

Ser Leu Gly Ala Gly
```

```
<210> SEQ ID NO 34
<211> LENGTH: 338
<212> TYPE: PRT
<213> ORGANISM: Mycobacterium bovis

<400> SEQUENCE: 34
```

Met

-continued

<213> ORGANISM: Mycobacterium bovis

<400> SEQUENCE: 35

Met Thr Asp Val Ser Arg Lys Ile Arg Ala Trp Gly Arg Arg Leu Met
1 5 10 15

Ile Gly Thr Ala Ala Ala Val Val Leu Pro Gly Leu Val Gly Leu Ala
20 25 30

Gly Gly Ala Ala Thr Ala Gly Ala Phe Ser Arg Pro Gly Leu Pro Val
35 40 45

Glu Tyr Leu Gln Val Pro Ser Pro Ser Met Gly Arg Asp Ile Lys Val
50 55 60

Gln Phe Gln Ser Gly Gly Asn Asn Ser Pro Ala Val Tyr Leu Leu Asp
65 70 75 80

Gly Leu Arg Ala Gln Asp Asp Tyr Asn Gly Trp Asp Ile Asn Thr Pro
85 90 95

Ala Phe Glu Trp Tyr Tyr Gln Ser Gly Leu Ser Ile Val Met Pro Val
100 105 110

Gly Gly Gln Ser Ser Phe Tyr Ser Asp Trp Tyr Ser Pro Ala Cys Gly
115 120 125

Lys Ala Gly Cys Gln Thr Tyr Lys Trp Glu Thr Leu Leu Thr Ser Glu
130 135 140

Leu Pro Gln Trp Leu Ser Ala Asn Arg Ala Val Lys Pro Thr Gly Ser
145 150 155 160

Ala Ala Ile Gly Leu Ser Met Ala Gly Ser Ser Ala Met Ile Leu Ala
165 170 175

Ala Tyr His Pro Gln Gln Phe Ile Tyr Ala Gly Ser Leu Ser Ala Leu
180 185 190

Leu Asp Pro Ser Gln Gly Met Gly Leu Ile Gly Leu Ala Met Gly Asp
195 200 205

Ala Gly Gly Tyr Lys Ala Ala Asp Met Trp Gly Pro Ser Ser Asp Pro
210 215 220

Ala Trp Glu Arg Asn Asp Pro Thr Gln Gln Ile Pro Lys Leu Val Ala
225 230 235 240

Asn Asn Thr Arg Leu Trp Val Tyr Cys Gly Asn Gly Thr Pro Asn Glu
245 250 255

Leu Gly Gly Ala Asn Ile Pro Ala Glu Phe Leu Glu Asn Phe Val Arg
260 265 270

Ser Ser Asn Leu Lys Phe Gln Asp Ala Tyr Lys Pro Ala Gly Gly His
275 280 285

Asn Ala Val Phe Asn Phe Pro Pro Asn Gly Thr His Ser Trp Glu Tyr
290 295 300

Trp Gly Ala Gln Leu Asn Ala Met Lys Gly Asp Leu Gln Ser Ser Leu
305 310 315 320

Gly Ala Gly

<210> SEQ ID NO 36
<211> LENGTH: 333
<212> TYPE: PRT
<213> ORGANISM: Mycobacterium leprae

<400> SEQUENCE: 36

Met Lys Phe Leu Gln Gln Met Arg Lys Leu Phe Gly Leu Ala Ala Lys
1 5 10 15

Phe Pro Ala Arg Leu Thr Ile Ala Val Ile Gly Thr Ala Leu Leu Ala
20 25 30

```
Gly Leu Val Gly Val Gly Asp Thr Ala Ile Ala Val Ala Phe Ser
         35                  40                  45
Lys Pro Gly Leu Pro Val Glu Tyr Leu Gln Val Pro Ser Pro Ser Met
 50                  55                  60
Gly His Asp Ile Lys Ile Gln Phe Gln Gly Gly Gln His Ala Val
 65                  70                  75                  80
Tyr Leu Leu Asp Gly Leu Arg Ala Gln Glu Asp Tyr Asn Gly Trp Asp
                 85                  90                  95
Ile Asn Thr Pro Ala Phe Glu Glu Tyr Tyr His Ser Gly Leu Ser Val
                100                 105                 110
Ile Met Pro Val Gly Gln Ser Ser Phe Tyr Ser Asn Trp Tyr Gln
         115                 120                 125
Pro Ser Gln Gly Asn Gly Gln His Tyr Thr Tyr Lys Trp Glu Thr Phe
 130                 135                 140
Leu Thr Gln Glu Met Pro Ser Trp Leu Gln Ala Asn Lys Asn Val Leu
145                 150                 155                 160
Pro Thr Gly Asn Ala Ala Val Gly Leu Ser Met Ser Gly Ser Ser Ala
                165                 170                 175
Leu Ile Leu Ala Ser Tyr Tyr Pro Gln Gln Phe Pro Tyr Ala Ala Ser
                180                 185                 190
Leu Ser Gly Phe Leu Asn Pro Ser Glu Gly Trp Trp Pro Thr Met Ile
         195                 200                 205
Gly Leu Ala Met Asn Asp Ser Gly Gly Tyr Asn Ala Asn Ser Met Trp
         210                 215                 220
Gly Pro Ser Thr Asp Pro Ala Trp Lys Arg Asn Asp Pro Met Val Gln
225                 230                 235                 240
Ile Pro Arg Leu Val Ala Asn Asn Thr Arg Ile Trp Val Tyr Cys Gly
                245                 250                 255
Asn Gly Ala Pro Asn Glu Leu Gly Gly Asp Asn Ile Pro Ala Lys Phe
                260                 265                 270
Leu Glu Ser Leu Thr Leu Ser Thr Asn Glu Ile Phe Gln Asn Thr Tyr
         275                 280                 285
Ala Ala Ser Gly Gly Arg Asn Gly Val Phe Asn Phe Pro Pro Asn Gly
 290                 295                 300
Thr His Ser Trp Pro Tyr Trp Asn Gln Gln Leu Val Ala Met Lys Pro
305                 310                 315                 320
Asp Ile Gln Gln Ile Leu Asn Gly Ser Asn Asn Ala
                325                 330

<210> SEQ ID NO 37
<211> LENGTH: 340
<212> TYPE: PRT
<213> ORGANISM: Mycobacterium tuberculosis

<400> SEQUENCE: 37

Met Thr Phe Phe Glu Gln Val Arg Arg Leu Arg Ser Ala Ala Thr Thr
 1               5                  10                  15
Leu Pro Arg Arg Val Ala Ile Ala Ala Met Gly Ala Val Leu Val Tyr
                 20                  25                  30
Gly Leu Val Gly Thr Phe Gly Pro Ala Thr Ala Gly Ala Phe Ser
         35                  40                  45
Arg Pro Gly Leu Pro Val Glu Tyr Leu Gln Val Pro Ser Ala Ser Met
 50                  55                  60
Gly Arg Asp Ile Lys Val Gln Phe Gln Gly Gly Gly Pro His Ala Val
```

-continued

```
                65                  70                  75                  80
Tyr Leu Leu Asp Gly Leu Arg Ala Gln Asp Asp Tyr Asn Gly Trp Asp
                    85                  90                  95

Ile Asn Thr Pro Ala Phe Glu Glu Tyr Tyr Gln Ser Gly Leu Ser Val
                100                 105                 110

Ile Met Pro Val Gly Gly Gln Ser Ser Phe Tyr Thr Asp Trp Tyr Gln
                115                 120                 125

Pro Ser Gln Ser Asn Gly Gln Asn Tyr Thr Tyr Lys Trp Glu Thr Phe
            130                 135                 140

Leu Thr Arg Glu Met Pro Ala Trp Leu Gln Ala Asn Lys Gly Val Ser
145                 150                 155                 160

Pro Thr Gly Asn Ala Ala Val Gly Leu Ser Met Ser Gly Gly Ser Ala
                165                 170                 175

Leu Ile Leu Ala Ala Tyr Tyr Pro Gln Gln Phe Pro Tyr Ala Ala Ser
                180                 185                 190

Leu Ser Gly Phe Leu Asn Pro Ser Glu Gly Trp Trp Pro Thr Leu Ile
                195                 200                 205

Gly Leu Ala Met Asn Asp Ser Gly Gly Tyr Asn Ala Asn Ser Met Trp
            210                 215                 220

Gly Pro Ser Ser Asp Pro Ala Trp Lys Arg Asn Asp Pro Met Val Gln
225                 230                 235                 240

Ile Pro Arg Leu Val Ala Asn Asn Thr Arg Ile Trp Val Tyr Cys Gly
                245                 250                 255

Asn Gly Thr Pro Ser Asp Leu Gly Gly Asp Asn Ile Pro Ala Lys Phe
                260                 265                 270

Leu Glu Gly Leu Thr Leu Arg Thr Asn Gln Thr Phe Arg Asp Thr Tyr
            275                 280                 285

Ala Ala Asp Gly Gly Arg Asn Gly Val Phe Asn Phe Pro Pro Asn Gly
290                 295                 300

Thr His Ser Trp Pro Tyr Trp Asn Glu Gln Leu Val Ala Met Lys Ala
305                 310                 315                 320

Asp Ile Gln His Val Leu Asn Gly Ala Thr Pro Pro Ala Pro Ala
                325                 330                 335

Ala Pro Ala Ala
            340
```

<210> SEQ ID NO 38
<211> LENGTH: 20
<212> TYPE: DNA
<213> ORGANISM: Artificial Sequence
<220> FEATURE:
<223> OTHER INFORMATION: Probe made in a lab

<400> SEQUENCE: 38
agcggctggg acatcaacac                                                  20

<210> SEQ ID NO 39
<211> LENGTH: 20
<212> TYPE: DNA
<213> ORGANISM: Artificial Sequence
<220> FEATURE:
<223> OTHER INFORMATION: Probe made in a lab

<400> SEQUENCE: 39
cagacgcggg tgttgttggc                                                  20

<210> SEQ ID NO 40

<211> LENGTH: 1211
<212> TYPE: DNA
<213> ORGANISM: Mycobacterium vaccae

<400> SEQUENCE: 40

```
ggtaccggaa gctggaggat tgacggtatg agacttcttg acaggattcg tgggccttgg      60
gcacgccgtt tcggcgtcgt ggctgtcgcg acagcgatga tgcctgcttt ggtgggcctg     120
gctggagggt cggcgaccgc cggagcattc tcccggccag gtctgccggt ggagtacctg     180
atggtgcctt cgccgtcgat ggggcgcgac atcaagatcc agttccagag cggtggcgag     240
aactcgccgg ctctctacct gctcgacggc ctgcgtgcgc aggaggactt caacggctgg     300
gacatcaaca ctcaggcttt cgagtggttc tcgacagcg gcatctccgt ggtgatgccg     360
gtcggtggcc agtccagctt ctacaccgac tggtacgccc ccgcccgtaa caagggcccg     420
accgtgacct acaagtggga gaccttcctg acccaggagc tcccgggctg gctgcaggcc     480
aaccgcgcgg tcaagccgac cggcagcggc cctgtcggtc tgtcgatggc gggttcggcc     540
gcgctgaacc tggcgacctg gcaccccgag cagttcatct acgcgggctc gatgtccggc     600
ttcctgaacc cctccgaggg ctggtggccg ttcctgatca acatctcgat gggtgacgcc     660
ggcggcttca aggccgacga catgtggggc aagaccgagg ggatcccaac agcggttgga     720
cagcgcaacg atccgatgct gaacatcccg accctggtcg ccaacaacac ccgtatctgg     780
gtctactgcg gtaacggcca gcccaccgag ctcggcggcg gcgacctgcc cgccacgttc     840
ctcgaaggtc tgaccatccg caccaacgag accttccgcg acaactacat cgccgcgggt     900
ggccacaacg gtgtgttcaa cttcccggcc aacggcacgc acaactgggc gtactgggt      960 cgcgagctgc aggcgatgaa gcctgacctg caggcgcacc ttctctgacg gttgcacgaa    1020
acgaagcccc cggccgattg cggccgaggg tttcgtcgtc cggggctact gtggccgaca    1080
taaccgaaat caacgcgatg gtggctcatc aggaacgccg aggggtcat tgcgctacga    1140 cacgaggtgg gcgagcaatc cttcctgccc gacggagagg tcaacatcca cgtcgagtac    1200
tccagcgtga a                                                         1211
```

<210> SEQ ID NO 41
<211> LENGTH: 485
<212> TYPE: DNA
<213> ORGANISM: Mycobacterium vaccae

<400> SEQUENCE: 41

```
agcggctggg acatcaacac cgccgccttc gagtggtacg tcgactcggg tctcgcggtg      60
atcatgcccg tcggcgggca gtccagcttc tacagcgact ggtacagccc ggcctgcggt     120
aaggccggct gccagaccta caagtgggag acgttcctga cccaggagct gccggcctac     180
ctcgccgcca acaagggggt cgaccccgaac cgcaacgcgg ccgtcggtct gtccatggcc     240
ggttcggcgg cgctgacgct ggcgatctac cacccgcagc agttccagta cgccgggtcg     300
ctgtcgggct acctgaaccc gtccgagggg tggtggccga tgctgatcaa catctcgatg     360
ggtgacgcgg gcggctacaa ggccaacgac atgtggggtc accgaaggga cccgagcagc     420
gcctggaagc gcaacgaccc gatggtcaac atcggcaagc tggtggccaa caacaccccc     480
ctctc                                                                  485
```

<210> SEQ ID NO 42
<211> LENGTH: 1052
<212> TYPE: DNA
<213> ORGANISM: Mycobacterium vaccae -continued

<400> SEQUENCE: 42

```
gttgatgaga aagtgggtt gtttgccgtt atgaagttca cagagaagtg gcggggctcc      60
gcaaaggcgg cgatgcaccg ggtgggcgtt gccgatatgg ccgccgttgc gctgcccgga    120
ctgatcggct tcgccggggg ttcggcaacg gccggggcat tctcccggcc cggtcttcct    180
gtcgagtacc tcgacgtgtt ctcgccgtcg atgggccgcg acatccgggt ccagttccag    240
ggtggcggta tcatgcggt ctacctgctc gacggtctgc gtgcccagga cgactacaac     300
ggctgggaca tcaacacccc tgcgttcgag tggttctacg agtccggctt gtcgacgatc    360
atgccggtcg cggacagtc cagcttctac agcgactggt accagccgtc tcggggcaac    420
gggcagaact acacctacaa gtgggagacg ttcctgaccc aggagctgcc gacgtggctg    480
gaggccaacc gcggagtgtc gcgcaccggc aacgcgttcg tcggcctgtc gatggcgggc   540
agcgcggcgc tgacctacgc gatccatcac ccgcagcagt tcatctacgc ctcgtcgctg    600
tcaggcttcc tgaacccgtc cgagggctgg tggccgatgc tgatcgggct ggcgatgaac   660
gacgcaggcg gcttcaacgc cgagagcatg tgggcccgt cctcggaccc ggcgtggaag    720
cgcaacgacc cgatggtcaa catcaaccag ctggtggcca acaacacccg gatctggatc   780
tactgcggca ccggcacccc gtcggagctg acaccgggaa ccccgggcca gaacctgatg   840
gccgcgcagt tcctcgaagg attcacgttg cggaccaaca tcgccttccg tgacaactac    900
atcgcagccg gcggcaccaa cggtgtcttc aacttcccgg cctcgggcac ccacagctgg    960
gggtactggg ggcagcagct gcagcagatg aagcccgaca tccagcgggt tctgggagct  1020
caggccaccg cctagccacc cacccacac cc                                  1052
```

<210> SEQ ID NO 43
<211> LENGTH: 326
<212> TYPE: PRT
<213> ORGANISM: Mycobacterium vaccae

<400> SEQUENCE: 43

```
Met Arg Leu Leu Asp Arg Ile Arg Gly Pro Trp Ala Arg Arg Phe Gly
 1               5                  10                  15

Val Val Ala Val Ala Thr Ala Met Met Pro Ala Leu Val Gly Leu Ala
                20                  25                  30

Gly Gly Ser Ala Thr Ala Gly Ala Phe Ser Arg Pro Gly Leu Pro Val
            35                  40                  45

Glu Tyr Leu Met Val Pro Ser Pro Ser Met Gly Arg Asp Ile Lys Ile
        50                  55                  60

Gln Phe Gln Ser Gly Gly Glu Asn Ser Pro Ala Leu Tyr Leu Leu Asp
 65                  70                  75                  80

Gly Leu Arg Ala Gln Glu Asp Phe Asn Gly Trp Asp Ile Asn Thr Gln
                85                  90                  95

Ala Phe Glu Trp Phe Leu Asp Ser Gly Ile Ser Val Val Met Pro Val
            100                 105                 110

Gly Gly Gln Ser Ser Phe Tyr Thr Asp Trp Tyr Ala Pro Ala Arg Asn
        115                 120                 125

Lys Gly Pro Thr Val Thr Tyr Lys Trp Glu Thr Phe Leu Thr Gln Glu
    130                 135                 140

Leu Pro Gly Trp Leu Gln Ala Asn Arg Ala Val Lys Pro Thr Gly Ser
145                 150                 155                 160

Gly Pro Val Gly Leu Ser Met Ala Gly Ser Ala Ala Leu Asn Leu Ala
                165                 170                 175
```

```
Thr Trp His Pro Glu Gln Phe Ile Tyr Ala Gly Ser Met Ser Gly Phe
            180                 185                 190

Leu Asn Pro Ser Glu Gly Trp Trp Pro Phe Leu Ile Asn Ile Ser Met
        195                 200                 205

Gly Asp Ala Gly Gly Phe Lys Ala Asp Asp Met Trp Gly Lys Thr Glu
    210                 215                 220

Gly Ile Pro Thr Ala Val Gly Gln Arg Asn Asp Pro Met Leu Asn Ile
225                 230                 235                 240

Pro Thr Leu Val Ala Asn Asn Thr Arg Ile Trp Val Tyr Cys Gly Asn
            245                 250                 255

Gly Gln Pro Thr Glu Leu Gly Gly Asp Leu Pro Ala Thr Phe Leu
        260                 265                 270

Glu Gly Leu Thr Ile Arg Thr Asn Glu Thr Phe Arg Asp Asn Tyr Ile
        275                 280                 285

Ala Ala Gly Gly His Asn Gly Val Phe Asn Phe Pro Ala Asn Gly Thr
        290                 295                 300

His Asn Trp Ala Tyr Trp Gly Arg Glu Leu Gln Ala Met Lys Pro Asp
305                 310                 315                 320

Leu Gln Ala His Leu Leu
            325

<210> SEQ ID NO 44
<211> LENGTH: 161
<212> TYPE: PRT
<213> ORGANISM: Mycobacterium vaccae

<400> SEQUENCE: 44

Ser Gly Trp Asp Ile Asn Thr Ala Ala Phe Glu Trp Tyr Val Asp Ser
1               5                   10                  15

Gly Leu Ala Val Ile Met Pro Val Gly Gly Gln Ser Ser Phe Tyr Ser
            20                  25                  30

Asp Trp Tyr Ser Pro Ala Cys Gly Lys Ala Gly Cys Gln Thr Tyr Lys
        35                  40                  45

Trp Glu Thr Phe Leu Thr Gln Glu Leu Pro Ala Tyr Leu Ala Ala Asn
    50                  55                  60

Lys Gly Val Asp Pro Asn Arg Asn Ala Val Gly Leu Ser Met Ala
65                  70                  75                  80

Gly Ser Ala Ala Leu Thr Leu Ala Ile Tyr His Pro Gln Gln Phe Gln
            85                  90                  95

Tyr Ala Gly Ser Leu Ser Gly Tyr Leu Asn Pro Ser Glu Gly Trp Trp
        100                 105                 110

Pro Met Leu Ile Asn Ile Ser Met Gly Asp Ala Gly Gly Tyr Lys Ala
    115                 120                 125

Asn Asp Met Trp Gly Pro Pro Lys Asp Pro Ser Ser Ala Trp Lys Arg
130                 135                 140

Asn Asp Pro Met Val Asn Ile Gly Lys Leu Val Ala Asn Asn Thr Pro
145                 150                 155                 160

Leu

<210> SEQ ID NO 45
<211> LENGTH: 334
<212> TYPE: PRT
<213> ORGANISM: Mycobacterium vaccae

<400> SEQUENCE: 45
```

```
Met Lys Phe Thr Glu Lys Trp Arg Gly Ser Ala Lys Ala Ala Met His
 1               5                  10                  15

Arg Val Gly Val Ala Asp Met Ala Ala Val Ala Leu Pro Gly Leu Ile
            20                  25                  30

Gly Phe Ala Gly Gly Ser Ala Thr Ala Gly Ala Phe Ser Arg Pro Gly
        35                  40                  45

Leu Pro Val Glu Tyr Leu Asp Val Phe Ser Pro Ser Met Gly Arg Asp
    50                  55                  60

Ile Arg Val Gln Phe Gln Gly Gly Thr His Ala Val Tyr Leu Leu
65                  70                  75                  80

Asp Gly Leu Arg Ala Gln Asp Asp Tyr Asn Gly Trp Asp Ile Asn Thr
                85                  90                  95

Pro Ala Phe Glu Trp Phe Tyr Glu Ser Gly Leu Ser Thr Ile Met Pro
                100                 105                 110

Val Gly Gly Gln Ser Ser Phe Tyr Ser Asp Trp Tyr Gln Pro Ser Arg
            115                 120                 125

Gly Asn Gly Gln Asn Tyr Thr Tyr Lys Trp Glu Thr Phe Leu Thr Gln
        130                 135                 140

Glu Leu Pro Thr Trp Leu Glu Ala Asn Arg Gly Val Ser Arg Thr Gly
145                 150                 155                 160

Asn Ala Phe Val Gly Leu Ser Met Ala Gly Ser Ala Ala Leu Thr Tyr
                165                 170                 175

Ala Ile His His Pro Gln Gln Phe Ile Tyr Ala Ser Ser Leu Ser Gly
            180                 185                 190

Phe Leu Asn Pro Ser Glu Gly Trp Trp Pro Met Leu Ile Gly Leu Ala
        195                 200                 205

Met Asn Asp Ala Gly Gly Phe Asn Ala Glu Ser Met Trp Gly Pro Ser
    210                 215                 220

Ser Asp Pro Ala Trp Lys Arg Asn Asp Pro Met Val Asn Ile Asn Gln
225                 230                 235                 240

Leu Val Ala Asn Asn Thr Arg Ile Trp Ile Tyr Cys Gly Thr Gly Thr
                245                 250                 255

Pro Ser Glu Leu Asp Thr Gly Thr Pro Gly Gln Asn Leu Met Ala Ala
            260                 265                 270

Gln Phe Leu Glu Gly Phe Thr Leu Arg Thr Asn Ile Ala Phe Arg Asp
        275                 280                 285

Asn Tyr Ile Ala Ala Gly Gly Thr Asn Gly Val Phe Asn Phe Pro Ala
    290                 295                 300

Ser Gly Thr His Ser Trp Gly Tyr Trp Gly Gln Gln Leu Gln Gln Met
305                 310                 315                 320

Lys Pro Asp Ile Gln Arg Val Leu Gly Ala Gln Ala Thr Ala
                325                 330
```

<210> SEQ ID NO 46
<211> LENGTH: 795
<212> TYPE: DNA
<213> ORGANISM: Mycobacterium vaccae

<400> SEQUENCE: 46

```
ctgccgcggg tttgccatct cttgggtcct gggtcgggag gccatgttct gggtaacgat    60
ccggtaccgt ccggcgatgt gaccaacatg cgaacagcga caacgaagct aggagcggcg   120
ctcggcgcag cagcattggt ggccgccacg gggatggtca gcgcggcgac ggcgaacgcc   180
caggaagggc accaggtccg ttacacgctc acctcggccg gcgcttacga gttcgacctg   240
```

-continued

```
ttctatctga cgacgcagcc gccgagcatg caggcgttca acgccgacgc gtatgcgttc    300
gccaagcggg agaaggtcag cctcgccccg gtgtgccgt gggtcttcga aaccacgatg     360
gccgacccga actgggcgat ccttcaggtc agcagcacca cccgcggtgg gcaggccgcc    420
ccgaacgcgc actgcgacat cgccgtcgat ggccaggagg tgctcagcca gcacgacgac   480
ccctacaacg tgcggtgcca gctcggtcag tggtgagtca cctcgccgag agtccggcca   540
gcgccggcgg cagcggctcg cggtgcagca ccccgaggcg ctgggtcgcg cgggtcagcg   600
cgacgtaaag atcgctggcc ccgcgcggcc cctcggcgag gatctgctcc gggtagacca   660
ccagcacggc gtctaactcc agaccttgg tctgcgtggg tgccaccgcg cccgggacac    720
cgggcgggcc gatcaccacg ctggtgccct cccggtccgc ctccgcacgc acgaaatcgt   780
cgatggcacc ggcga                                                    795
```

<210> SEQ ID NO 47
<211> LENGTH: 142
<212> TYPE: PRT
<213> ORGANISM: Mycobacterium vaccae
<400> SEQUENCE: 47

```
Met Arg Thr Ala Thr Thr Lys Leu Gly Ala Ala Leu Gly Ala Ala Ala
 1               5                  10                  15

Leu Val Ala Ala Thr Gly Met Val Ser Ala Ala Thr Ala Asn Ala Gln
            20                  25                  30

Glu Gly His Gln Val Arg Tyr Thr Leu Thr Ser Ala Gly Ala Tyr Glu
        35                  40                  45

Phe Asp Leu Phe Tyr Leu Thr Thr Gln Pro Pro Ser Met Gln Ala Phe
    50                  55                  60

Asn Ala Asp Ala Tyr Ala Phe Ala Lys Arg Glu Lys Val Ser Leu Ala
65                  70                  75                  80

Pro Gly Val Pro Trp Val Phe Glu Thr Thr Met Ala Asp Pro Asn Trp
                85                  90                  95

Ala Ile Leu Gln Val Ser Ser Thr Thr Arg Gly Gly Gln Ala Ala Pro
            100                 105                 110

Asn Ala His Cys Asp Ile Ala Val Asp Gly Gln Glu Val Leu Ser Gln
        115                 120                 125

His Asp Asp Pro Tyr Asn Val Arg Cys Gln Leu Gly Gln Trp
    130                 135                 140
```

<210> SEQ ID NO 48
<211> LENGTH: 300
<212> TYPE: DNA
<213> ORGANISM: Mycobacterium vaccae
<400> SEQUENCE: 48

```
gccagtgcgc caacggtttt catcgatgcc gcacacaacc ccggtgggcc ctgcgcttgc     60
cgaaggctgc gcgacgagtt cgacttccgg tatctcgtcg gcgtcgtctc ggtgatgggg   120
gacaaggacg tggacgggat ccgccaggac ccgggcgtgc ggacgggcg cggtctcgca    180 ctgttcgtct cgggcgacaa ccttcgaaag ggtgcggcgc tcaacacgat ccagatcgcc   240
gagctgctgg ccgcccagtt gtaagtgttc gccgaaatt gcattccacg ccgataatcg    300
```

<210> SEQ ID NO 49
<211> LENGTH: 563
<212> TYPE: DNA
<213> ORGANISM: Mycobacterium vaccae

<400> SEQUENCE: 49

```
ggatcctcgg ccggctcaag agtccgcgcc gaggtggatg tgacgctgga cggctacgag      60
ttcagtcggg cctgcgaggc gctgtaccac ttcgcctggg acgagttctg cgactggtat     120
gtcgagcttg ccaaagtgca actgggtgaa ggtttctcgc acaccacggc cgtgttggcc     180
accgtgctcg atgtgctgct caagcttctg cacccggtca tgccgttcgt caccgaggtg     240
ctgtggaagg ccctgaccgg cgggccggc gcgagcgaac gtctgggaaa tgtggagtca      300
ctggtcgtcg cggactggcc cacgcccacc ggatacgcgc tggatcaggc tgccgcacaa     360
cggatcgccg acacccagaa gttgatcacc gaggtgcgcc ggttccgcag cgatcagggt     420
ctggccgacc gccagcgggt gcctgcccgg ttgtccggca tcgacaccgc gggtctggac     480
gcccatgtcc cggcggtgcg cgcgctggcc tggcttgacc gagggtgatg agggcttcac     540
cgcgtccgaa tcggtcgagg tgc                                             563
```

<210> SEQ ID NO 50
<211> LENGTH: 434
<212> TYPE: DNA
<213> ORGANISM: Mycobacterium vaccae

<400> SEQUENCE: 50

```
gggccgggcc cgaggatgag caagttcgaa gtcgtcaccg gatggcgtt cgcggctttc       60
gccgacgcgc ccatcgacgt cgccgtcgtc gaggtcgggc tcggtggtcg ctgggacgcg     120
acgaacgtgg tgaacgcacc ggtcgcgtc atcaccccga tcgggtgga ccacaccgac       180
tacctcggtg acacgatcgc cgagatcgcc ggggagaagg ccggaaatca tcacccgcca     240
gccgacgacc tggtgccgac cgacaccgtc gccgtgctgg cgcggcaggt tcccgaggcc     300
atggaggtgc tgctggccca ggcggtgcgc tcggatgcgg ctgtagcgcg cgaggattcg     360
gagtgcgcg tgctgggccg tcaggtcgcc atcggcggca gctgctccgg ttgcaggggc      420
tcggtggcgt ctac                                                       434
```

<210> SEQ ID NO 51
<211> LENGTH: 438
<212> TYPE: DNA
<213> ORGANISM: Mycobacterium vaccae

<400> SEQUENCE: 51

```
ggatcccact cccgcgccgg cggcggccag ctggtacggc cattccagcg tgctgatcga     60
ggtcgacggc taccgcgtgc tggccgaccc ggtgtggagc aacagatgtt cgccctcacg    120
ggcggtcgga ccgcagcgca tgcacgacgt cccggtgccg ctggaggcgc ttcccgccgt    180
ggacgcggtg gtgatcgcca acgaccacta cgaccacctc gacatcgaca ccatcgtcgc    240
gttggcgcac acccagcggg ccccgttcgt ggtgccgttg ggcatcggcg cacacctgcg    300
caagtggggc gtccccgagg cgcggatcgt cgagttggac tggcacgaag cccaccgcat    360
cgacgacctg acgctggtct gcacccccgc ccggcacttc tccggccggt tgttctcccg    420
cgactcgacg ctgtgggc                                                  438
```

<210> SEQ ID NO 52
<211> LENGTH: 87
<212> TYPE: PRT
<213> ORGANISM: Mycobacterium vaccae

<400> SEQUENCE: 52

```
Ala Ser Ala Pro Thr Val Phe Ile Asp Ala Ala His Asn Pro Gly Gly
```

```
              1               5                  10                 15
    Pro Cys Ala Cys Arg Arg Leu Arg Asp Glu Phe Asp Phe Arg Tyr Leu
                        20                  25                  30
    Val Gly Val Val Ser Val Met Gly Asp Lys Asp Val Asp Gly Ile Arg
                    35                  40                  45
    Gln Asp Pro Gly Val Pro Asp Gly Arg Gly Leu Ala Leu Phe Val Ser
                50                  55                  60
    Gly Asp Asn Leu Arg Lys Gly Ala Ala Leu Asn Thr Ile Gln Ile Ala
    65                  70                  75                  80
    Glu Leu Leu Ala Ala Gln Leu
                        85
```

```
<210> SEQ ID NO 53
<211> LENGTH: 175
<212> TYPE: PRT
<213> ORGANISM: Mycobacterium vaccae

<400> SEQUENCE: 53

Gly Ser Ser Ala Gly Ser Arg Val Arg Ala Glu Val Asp Val Thr Leu
    1               5                  10                 15
    Asp Gly Tyr Glu Phe Ser Arg Ala Cys Glu Ala Leu Tyr His Phe Ala
                    20                  25                  30
    Trp Asp Glu Phe Cys Asp Trp Tyr Val Glu Leu Ala Lys Val Gln Leu
                    35                  40                  45
    Gly Glu Gly Phe Ser His Thr Thr Ala Val Leu Ala Thr Val Leu Asp
                50                  55                  60
    Val Leu Leu Lys Leu Leu His Pro Val Met Pro Phe Val Thr Glu Val
    65                  70                  75                  80
    Leu Trp Lys Ala Leu Thr Gly Arg Ala Gly Ala Ser Glu Arg Leu Gly
                        85                  90                  95
    Asn Val Glu Ser Leu Val Val Ala Asp Trp Pro Thr Pro Thr Gly Tyr
                    100                 105                 110
    Ala Leu Asp Gln Ala Ala Ala Gln Arg Ile Ala Asp Thr Gln Lys Leu
                    115                 120                 125
    Ile Thr Glu Val Arg Arg Phe Arg Ser Asp Gln Gly Leu Ala Asp Arg
                130                 135                 140
    Gln Arg Val Pro Ala Arg Leu Ser Gly Ile Asp Thr Ala Gly Leu Asp
    145                 150                 155                 160
    Ala His Val Pro Ala Val Arg Ala Leu Ala Trp Leu Asp Arg Gly
                        165                 170                 175
```

```
<210> SEQ ID NO 54
<211> LENGTH: 144
<212> TYPE: PRT
<213> ORGANISM: Mycobacterium vaccae

<400> SEQUENCE: 54

Gly Pro Gly Pro Arg Asn Ser Lys Phe Glu Val Val Thr Gly Met Ala
    1               5                  10                 15
    Phe Ala Ala Phe Ala Asp Ala Pro Ile Asp Val Ala Val Val Glu Val
                        20                  25                  30
    Gly Leu Gly Gly Arg Trp Asp Ala Thr Asn Val Val Asn Ala Pro Val
                    35                  40                  45
    Ala Val Ile Thr Pro Ile Gly Val Asp His Thr Asp Tyr Leu Gly Asp
                50                  55                  60
    Thr Ile Ala Glu Ile Ala Gly Glu Lys Ala Gly Asn His His Pro Pro
```

```
                     65                  70                  75                  80
Ala Asp Asp Leu Val Pro Thr Asp Thr Val Ala Val Leu Ala Arg Gln
                         85                  90                  95

Val Pro Glu Ala Asn Glu Val Leu Leu Ala Gln Ala Val Arg Ser Asp
                100                 105                 110

Ala Ala Val Ala Arg Glu Asp Ser Glu Cys Ala Val Leu Gly Arg Gln
            115                 120                 125

Val Ala Ile Gly Gly Ser Cys Ser Gly Cys Arg Gly Ser Val Ala Ser
        130                 135                 140
```

<210> SEQ ID NO 55
<211> LENGTH: 145
<212> TYPE: PRT
<213> ORGANISM: Mycobacterium vaccae

<400> SEQUENCE: 55

```
Asp Pro Thr Pro Ala Pro Ala Ala Ala Ser Trp Tyr Gly His Ser Ser
1               5                   10                  15

Val Leu Ile Glu Val Asp Gly Tyr Arg Val Leu Ala Asp Pro Val Trp
            20                  25                  30

Ser Asn Arg Cys Ser Pro Ser Arg Ala Val Gly Pro Gln Arg Met His
        35                  40                  45

Asp Val Pro Val Pro Leu Glu Ala Leu Pro Ala Val Asp Ala Val Val
    50                  55                  60

Ile Ser Asn Asp His Tyr Asp His Leu Asp Ile Asp Thr Ile Val Ala
65                  70                  75                  80

Leu Ala His Thr Gln Arg Ala Pro Phe Val Val Pro Leu Gly Ile Gly
                85                  90                  95

Ala His Leu Arg Lys Trp Gly Val Pro Glu Ala Arg Ile Val Glu Leu
            100                 105                 110

Asp Trp His Glu Ala His Arg Ile Asp Asp Leu Thr Leu Val Cys Thr
        115                 120                 125

Pro Ala Arg His Phe Ser Gly Arg Leu Phe Ser Arg Asp Ser Thr Leu
    130                 135                 140

Trp
145
```

<210> SEQ ID NO 56
<211> LENGTH: 10
<212> TYPE: PRT
<213> ORGANISM: Mycobacterium vaccae
<220> FEATURE:
<221> NAME/KEY: UNSURE
<222> LOCATION: (1)...(1)
<223> OTHER INFORMATION: Residue can be either Gly, Ile, Leu or Val
<220> FEATURE:
<221> NAME/KEY: UNSURE
<222> LOCATION: (2)...(2)
<223> OTHER INFORMATION: Residue can be either Ile, Leu, Gly, or Ala
<220> FEATURE:
<221> NAME/KEY: UNSURE
<222> LOCATION: (5)...(5)
<221> NAME/KEY: UNSURE
<222> LOCATION: (9)...(9)

<400> SEQUENCE: 56

```
Xaa Xaa Ala Pro Xaa Gly Asp Ala Xaa Arg
1               5                   10
```

<210> SEQ ID NO 57
<211> LENGTH: 8

```
<212> TYPE: PRT
<213> ORGANISM: Mycobacterium vaccae
<220> FEATURE:
<221> NAME/KEY: UNSURE
<222> LOCATION: (7)...(7)
<223> OTHER INFORMATION: Residue can be either Ile or Leu

<400> SEQUENCE: 57

Pro Glu Ala Glu Ala Asn Xaa Arg
 1               5

<210> SEQ ID NO 58
<211> LENGTH: 11
<212> TYPE: PRT
<213> ORGANISM: Mycobacterium vaccae
<220> FEATURE:
<221> NAME/KEY: UNSURE
<222> LOCATION: (4)...(4)
<223> OTHER INFORMATION: Residue can be either Gln or Gly
<220> FEATURE:
<221> NAME/KEY: UNSURE
<222> LOCATION: (5)...(5)
<223> OTHER INFORMATION: Residue can be either Gly or Gln

<400> SEQUENCE: 58

Thr Ala Asn Xaa Xaa Glu Tyr Tyr Asp Asn Arg
 1               5                  10

<210> SEQ ID NO 59
<211> LENGTH: 34
<212> TYPE: PRT
<213> ORGANISM: Mycobacterium vaccae

<400> SEQUENCE: 59

Asn Ser Pro Arg Ala Glu Ala Glu Ala Asn Leu Arg Gly Tyr Phe Thr
 1               5                  10                  15

Ala Asn Pro Ala Glu Tyr Tyr Asp Leu Arg Gly Ile Leu Ala Pro Ile
            20                  25                  30

Gly Asp

<210> SEQ ID NO 60
<211> LENGTH: 20
<212> TYPE: DNA
<213> ORGANISM: Artificial Sequence
<220> FEATURE:
<223> OTHER INFORMATION: Made in a lab

<400> SEQUENCE: 60
ccggtgggcc cgggctgcgc                                              20

<210> SEQ ID NO 61
<211> LENGTH: 20
<212> TYPE: DNA
<213> ORGANISM: Artificial Sequence
<220> FEATURE:
<223> OTHER INFORMATION: Made in a lab

<400> SEQUENCE: 61
tggccggcca ccacgtggta                                              20

<210> SEQ ID NO 62
<211> LENGTH: 313
<212> TYPE: DNA
<213> ORGANISM: Mycobacterium vaccae

<400> SEQUENCE: 62
```

```
gccggtgggc cgggctgcg cggaatacgc ggcagccaat cccactgggc cggcctcggt      60
gcagggaatg tcgcaggacc cggtcgcggt ggcggcctcg aacaatccgg agttgacaac     120
gctgtacggc tgcactgtcg ggccagctca atccgcaagt aaacctggtg gacaccctca    180
acagcggtca gtacacggtg ttcgcaccga ccaacgcggc atttagcaag ctgccggcat    240
ccacgatcga cgagctcaag accaattcgt cactgctgac cagcatcctg acctaccacg    300
tggtggccgg cca                                                       313
```

<210> SEQ ID NO 63
<211> LENGTH: 18
<212> TYPE: PRT
<213> ORGANISM: Mycobacterium vaccae
<220> FEATURE:
<221> NAME/KEY: UNSURE
<222> LOCATION: (7)...(17)

<400> SEQUENCE: 63

Glu Pro Ala Gly Pro Leu Pro Xaa Tyr Asn Glu Arg Leu His Thr Leu
 1               5                  10                  15

Xaa Gln

<210> SEQ ID NO 64
<211> LENGTH: 25
<212> TYPE: PRT
<213> ORGANISM: Mycobacterium vaccae
<220> FEATURE:
<221> NAME/KEY: UNSURE
<222> LOCATION: (21)...(21)

<400> SEQUENCE: 64

Gly Leu Asp Asn Glu Leu Ser Leu Val Asp Gly Gln Gly Arg Thr Leu
 1               5                  10                  15

Thr Val Gln Gln Xaa Asp Thr Phe Leu
            20                  25

<210> SEQ ID NO 65
<211> LENGTH: 26
<212> TYPE: PRT
<213> ORGANISM: Mycobacterium vaccae
<220> FEATURE:
<221> NAME/KEY: UNSURE
<222> LOCATION: (3)...(3)
<221> NAME/KEY: UNSURE
<222> LOCATION: (21)...(22)
<221> NAME/KEY: UNSURE
<222> LOCATION: (24)...(24)

<400> SEQUENCE: 65

Asp Pro Xaa Pro Asp Ile Glu Val Glu Phe Ala Arg Gly Thr Gly Ala
 1               5                  10                  15

Glu Pro Gly Leu Xaa Xaa Val Xaa Asp Ala
            20                  25

<210> SEQ ID NO 66
<211> LENGTH: 32
<212> TYPE: DNA
<213> ORGANISM: Artificial Sequence
<220> FEATURE:
<223> OTHER INFORMATION: Made in a lab
<400> SEQUENCE: 66

```
accgccctcg agttctcccg gccaggtctg cc                                   32
```

-continued

```
<210> SEQ ID NO 67
<211> LENGTH: 32
<212> TYPE: DNA
<213> ORGANISM: Artificial Sequence
<220> FEATURE:
<223> OTHER INFORMATION: Made in a lab

<400> SEQUENCE: 67
aagcacgagc tcagtctctt ccacgcggac gt                                    32

<210> SEQ ID NO 68
<211> LENGTH: 30
<212> TYPE: DNA
<213> ORGANISM: Artificial Sequence
<220> FEATURE:
<223> OTHER INFORMATION: Made in a lab

<400> SEQUENCE: 68
catggatcca ttctcccggc ccggtcttcc                                       30

<210> SEQ ID NO 69
<211> LENGTH: 26
<212> TYPE: DNA
<213> ORGANISM: Artificial Sequence
<220> FEATURE:
<223> OTHER INFORMATION: Made in a lab

<400> SEQUENCE: 69
tttgaattct aggcggtggc ctgagc                                           26

<210> SEQ ID NO 70
<211> LENGTH: 161
<212> TYPE: PRT
<213> ORGANISM: Mycobacterium vaccae

<400> SEQUENCE: 70

Ser Gly Trp Asp Ile Asn Thr Ala Ala Phe Glu Trp Tyr Val Asp Ser
 1               5                  10                  15

Gly Leu Ala Val Ile Met Pro Val Gly Gly Gln Ser Ser Phe Tyr Ser
                20                  25                  30

Asp Trp Tyr Ser Pro Ala Cys Gly Lys Ala Gly Cys Gln Thr Tyr Lys
            35                  40                  45

Trp Glu Thr Phe Leu Thr Gln Glu Leu Pro Ala Tyr Leu Ala Ala Asn
        50                  55                  60

Lys Gly Val Asp Pro Asn Arg Asn Ala Val Gly Leu Ser Met Ala
65                  70                  75                  80

Gly Ser Ala Ala Leu Thr Leu Ala Ile Tyr His Pro Gln Gln Phe Gln
                85                  90                  95

Tyr Ala Gly Ser Leu Ser Gly Tyr Leu Asn Pro Ser Glu Gly Trp Trp
            100                 105                 110

Pro Met Leu Ile Asn Ile Ser Met Gly Asp Ala Gly Tyr Lys Ala
        115                 120                 125

Asn Asp Met Trp Gly Arg Thr Glu Asp Pro Ser Ser Ala Trp Lys Arg
    130                 135                 140

Asn Asp Pro Met Val Asn Ile Gly Lys Leu Val Ala Asn Asn Thr Pro
145                 150                 155                 160

Leu

<210> SEQ ID NO 71
<211> LENGTH: 33
<212> TYPE: DNA
```

```
<213> ORGANISM: Artificial Sequence
<220> FEATURE:
<223> OTHER INFORMATION: Made in a lab

<400> SEQUENCE: 71
gagagactcg agaacgccca ggaagggcac cag                                    33

<210> SEQ ID NO 72
<211> LENGTH: 32
<212> TYPE: DNA
<213> ORGANISM: Artificial Sequence
<220> FEATURE:
<223> OTHER INFORMATION: Made in a lab

<400> SEQUENCE: 72
gagagactcg agtgactcac cactgaccga gc                                     32

<210> SEQ ID NO 73
<211> LENGTH: 20
<212> TYPE: DNA
<213> ORGANISM: Artificial Sequence
<220> FEATURE:
<223> OTHER INFORMATION: Made in a lab
<220> FEATURE:
<221> NAME/KEY: unsure
<222> LOCATION: (3)...(3)
<221> NAME/KEY: unsure
<222> LOCATION: (6)...(6)
<221> NAME/KEY: unsure
<222> LOCATION: (9)...(9)
<221> NAME/KEY: unsure
<222> LOCATION: (15)...(15)

<400> SEQUENCE: 73
ggngcngcnc argcngarcc                                                   20

<210> SEQ ID NO 74
<211> LENGTH: 825
<212> TYPE: DNA
<213> ORGANISM: Mycobacterium vaccae

<400> SEQUENCE: 74
ttggatccca ctcccgcgcc ggcggcggcc agctggtacg gccattccag cgtgctgatc       60
gaggtcgacg gctaccgcgt gctggccgac ccggtgtgga gcaacagatg ttcgccctca      120
cgggcggtcg gaccgcagcg catgcacgac gtcccggtgc cgctggaggc gcttcccgcc      180
gtggacgcgg tggtgatcag ccacgaccac tacgaccacc tcgacatcga caccatcgtc      240
gcgttggcgc acacccagcg ggccccgttc gtggtgccgt tgggcatcgg cgcacacctg      300
cgcaagtggg gcgtccccga ggcgcggatc gtcgagttgg actggcacga agcccaccgc      360
atagacgacc tgacgctggt ctgcaccccc gcccggcact tctccggacg gttgttctcc      420
cgcgactcga cgctgtgggc gtcgtgggtg gtcaccggct cgtcgcacaa ggcgttcttc      480
ggtggcgaca ccggatacac gaagagcttc gccgagatcg cgacgagta cggtccgttc       540
gatctgaccc tgctgccgat cggggcctac catcccgcgt tcgccgacat ccacatgaac      600
cccgaggagg cggtgcgcgc ccatctggac ctgaccgagg tggacaacag cctgatggtg      660
cccatccact gggcgacatt ccgcctcgcc ccgcatccgt ggtccgagcc cgccgaacgc      720
ctgctgaccg ctgccgacgc cgagcgggta cgcctgaccg tgccgattcc cggtcagcgg      780
gtggacccgg agtcgacgtt cgacccgtgg tggcggttct gaacc                     825

<210> SEQ ID NO 75
```

<211> LENGTH: 273
<212> TYPE: PRT
<213> ORGANISM: Mycobacterium vaccae

<400> SEQUENCE: 75

```
Leu Asp Pro Thr Pro Ala Pro Ala Ala Ser Trp Tyr Gly His Ser
 1               5                  10                  15

Ser Val Leu Ile Glu Val Asp Gly Tyr Arg Val Leu Ala Asp Pro Val
            20                  25                  30

Trp Ser Asn Arg Cys Ser Pro Ser Arg Ala Val Gly Pro Gln Arg Met
        35                  40                  45

His Asp Val Pro Val Pro Leu Glu Ala Leu Pro Ala Val Asp Ala Val
    50                  55                  60

Val Ile Ser His Asp His Tyr Asp His Leu Asp Ile Asp Thr Ile Val
65                  70                  75                  80

Ala Leu Ala His Thr Gln Arg Ala Pro Phe Val Val Pro Leu Gly Ile
                85                  90                  95

Gly Ala His Leu Arg Lys Trp Gly Val Pro Glu Ala Arg Ile Val Glu
            100                 105                 110

Leu Asp Trp His Glu Ala His Arg Ile Asp Asp Leu Thr Leu Val Cys
        115                 120                 125

Thr Pro Ala Arg His Phe Ser Gly Arg Leu Phe Ser Arg Asp Ser Thr
    130                 135                 140

Leu Trp Ala Ser Trp Val Val Thr Gly Ser Ser His Lys Ala Phe Phe
145                 150                 155                 160

Gly Gly Asp Thr Gly Tyr Thr Lys Ser Phe Ala Glu Ile Gly Asp Glu
                165                 170                 175

Tyr Gly Pro Phe Asp Leu Thr Leu Leu Pro Ile Gly Ala Tyr His Pro
            180                 185                 190

Ala Phe Ala Asp Ile His Met Asn Pro Glu Glu Ala Val Arg Ala His
        195                 200                 205

Leu Asp Leu Thr Glu Val Asp Asn Ser Leu Met Val Pro Ile His Trp
    210                 215                 220

Ala Thr Phe Arg Leu Ala Pro His Pro Trp Ser Glu Pro Ala Glu Arg
225                 230                 235                 240

Leu Leu Thr Ala Ala Asp Ala Glu Arg Val Arg Leu Thr Val Pro Ile
                245                 250                 255

Pro Gly Gln Arg Val Asp Pro Glu Ser Thr Phe Asp Pro Trp Trp Arg
            260                 265                 270

Phe
```

<210> SEQ ID NO 76
<211> LENGTH: 10
<212> TYPE: PRT
<213> ORGANISM: Mycobacterium vaccae

<400> SEQUENCE: 76

```
Ala Lys Thr Ile Ala Tyr Asp Glu Glu Ala
 1               5                  10
```

<210> SEQ ID NO 77
<211> LENGTH: 337
<212> TYPE: DNA
<213> ORGANISM: Mycobacterium vaccae

<400> SEQUENCE: 77
gatccctaca tcctgctggt cagctccaag gtgtcgaccg tcaaggatct gctcccgctg    60

```
ctggagaagg tcatccaggc cggcaagccg ctgctgatca tcgccgagga cgtcgagggc      120
gaggccctgt ccacgctggt ggtcaacaag atccgcggca ccttcaagtc cgtcgccgtc      180
aaggctccgg gcttcggtga ccgccgcaag gcgatgctgc aggacatggc catcctcacc      240
ggtggtcagg tcgtcagcga aagagtcggg ctgtccctgg agaccgccga cgtctcgctg      300
ctgggccagg cccgcaaggt cgtcgtcacc aaggaca                              337
```

<210> SEQ ID NO 78
<211> LENGTH: 112
<212> TYPE: PRT
<213> ORGANISM: Mycobacterium vaccae

<400> SEQUENCE: 78

```
Asp Pro Tyr Ile Leu Val Ser Ser Lys Val Ser Thr Val Lys Asp
 1               5                  10                  15

Leu Leu Pro Leu Leu Glu Lys Val Ile Gln Ala Gly Lys Pro Leu Leu
                20                  25                  30

Ile Ile Ala Glu Asp Val Glu Gly Glu Ala Leu Ser Thr Leu Val Val
                35                  40                  45

Asn Lys Ile Arg Gly Thr Phe Lys Ser Val Ala Val Lys Ala Pro Gly
        50                  55                  60

Phe Gly Asp Arg Arg Lys Ala Met Leu Gln Asp Met Ala Ile Leu Thr
65                  70                  75                  80

Gly Gly Gln Val Val Ser Glu Arg Val Gly Leu Ser Leu Glu Thr Ala
                85                  90                  95

Asp Val Ser Leu Leu Gly Gln Ala Arg Lys Val Val Thr Lys Asp
                100                 105                 110
```

<210> SEQ ID NO 79
<211> LENGTH: 360
<212> TYPE: DNA
<213> ORGANISM: Mycobacterium vaccae

<400> SEQUENCE: 79

```
ccgtacgaga agatcggcgc tgagctggtc aaagaggtcg ccaagaagac cgacgacgtc      60
gcgggcgacg gcaccaccac cgccaccgtg ctcgctcagg ctctggttcg cgaaggcctg     120
cgcaacgtcg cagccggcgc caacccgctc ggcctcaagc gtggcatcga aaggctgtc      180 gaggctgtca cccagtcgct gctgaagtcg gccaaggagg tcgagaccaa ggagcagatt     240
tctgccaccg cggcgatctc cgccggcgac acccagatcg gcgagctcat cgccgaggcc     300
atggacaagg tcggcaacga gggtgtcatc accgtcgagg agtcgaacac cttcggcctg     360
```

<210> SEQ ID NO 80
<211> LENGTH: 120
<212> TYPE: PRT
<213> ORGANISM: Mycobacterium vaccae

<400> SEQUENCE: 80

```
Pro Tyr Glu Lys Ile Gly Ala Glu Leu Val Lys Glu Val Ala Lys Lys
 1               5                  10                  15

Thr Asp Asp Val Ala Gly Asp Gly Thr Thr Thr Ala Thr Val Leu Ala
                20                  25                  30

Gln Ala Leu Val Arg Glu Gly Leu Arg Asn Val Ala Ala Gly Ala Asn
            35                      40                  45

Pro Leu Gly Leu Lys Arg Gly Ile Glu Lys Ala Val Glu Ala Val Thr
    50                  55                  60
```

Gln Ser Leu Leu Lys Ser Ala Lys Glu Val Glu Thr Lys Glu Gln Ile
65                  70                  75                  80

Ser Ala Thr Ala Ala Ile Ser Ala Gly Asp Thr Gln Ile Gly Glu Leu
                85                  90                  95

Ile Ala Glu Ala Met Asp Lys Val Gly Asn Glu Gly Val Ile Thr Val
            100                 105                 110

Glu Glu Ser Asn Thr Phe Gly Leu
        115                 120

<210> SEQ ID NO 81
<211> LENGTH: 43
<212> TYPE: DNA
<213> ORGANISM: Artificial Sequence
<220> FEATURE:
<223> OTHER INFORMATION: Made in a lab

<400> SEQUENCE: 81
actgacgctg aggagcgaaa gcgtggggag cgaacaggat tag         43

<210> SEQ ID NO 82
<211> LENGTH: 43
<212> TYPE: DNA
<213> ORGANISM: Artificial Sequence
<220> FEATURE:
<223> OTHER INFORMATION: Made in a lab

<400> SEQUENCE: 82
cgacaaggaa cttcgctacc ttaggaccgt catagttacg ggc         43

<210> SEQ ID NO 83
<211> LENGTH: 20
<212> TYPE: DNA
<213> ORGANISM: Artificial Sequence
<220> FEATURE:
<223> OTHER INFORMATION: Made in a lab

<400> SEQUENCE: 83
aaaaaaaaaa aaaaaaaaaa                                   20

<210> SEQ ID NO 84
<211> LENGTH: 31
<212> TYPE: DNA
<213> ORGANISM: Artificial Sequence
<220> FEATURE:
<223> OTHER INFORMATION: Made in a lab

<400> SEQUENCE: 84
ggaaggaagc ggccgctttt tttttttttt t                      31

<210> SEQ ID NO 85
<211> LENGTH: 31
<212> TYPE: DNA
<213> ORGANISM: Artificial Sequence
<220> FEATURE:
<223> OTHER INFORMATION: Made in a lab

<400> SEQUENCE: 85
gagagagagc ccgggcatgc tsctsctsct s                      31

<210> SEQ ID NO 86
<211> LENGTH: 238
<212> TYPE: DNA
<213> ORGANISM: Mycobacterium vaccae

```
<400> SEQUENCE: 86
ctcgatgaac cgctcggagc gctcgacctg aagctgcgcc acgtcatgca gttcgagctc      60
aagcgcatcc agcgggaggt cgggatcacg ttcatctacg tgacccacga ccaggaagag     120
gcgctcacga tgagtgaccg catcgcggtg atgaacgccg gcaacgtcga acagatcggc     180
agcccgaccg agatctacga ccgtcccgcg acggtgttcg tcgccagctt catcgaat       238

<210> SEQ ID NO 87
<211> LENGTH: 79
<212> TYPE: PRT
<213> ORGANISM: Mycobacterium vaccae

<400> SEQUENCE: 87

Leu Asp Glu Pro Leu Gly Ala Leu Asp Leu Lys Leu Arg His Val Met
 1               5                  10                  15

Gln Phe Glu Leu Lys Arg Ile Gln Arg Glu Val Gly Ile Thr Phe Ile
                20                  25                  30

Tyr Val Thr His Asp Gln Glu Glu Ala Leu Thr Met Ser Asp Arg Ile
            35                  40                  45

Ala Val Met Asn Ala Gly Asn Val Glu Gln Ile Gly Ser Pro Thr Glu
        50                  55                  60

Ile Tyr Asp Arg Pro Ala Thr Val Phe Val Ala Ser Phe Ile Glu
65                  70                  75

<210> SEQ ID NO 88
<211> LENGTH: 1518
<212> TYPE: DNA
<213> ORGANISM: Mycobacterium vaccae

<400> SEQUENCE: 88
cactcgccat gggtgttaca ataccccacc agttcctcga agtaaacgaa cagaaccgtg      60
acatccagct gagaaaatat tcacagcgac gaagcccggc cgatgcctga tggggtccgg     120
catcagtaca gcgcgctttc ctgcgcggat tctattgtcg agtccggggt gtgacgaagg     180
aatccattgt cgaaatgtaa attcgttgcg gaatcacttg cataggtccg tcagatccgc     240
gaaggtttac cccacagcca cgacggctgt ccccgaggag gacctgccct gaccggcaca     300
cacatcaccg ctgcagaacc tgcagaacag acggcggatt ccgcggcacc gcccaagggc     360
gcgccggtga tcgagatcga ccatgtcacg aagcgcttcg cgactacct ggccgtcgcg      420 gacgcagact tctccatcgc gcccggggag ttcttctcca tgctcggccc gtccgggtgt     480
gggaagacga ccacgttgcg catgatcgcg ggattcgaga ccccgactga aggggcgatc     540
cgcctcgaag gcgccgacgt gtcgaggacc ccacccaaca agcgcaacgt caacacggtg     600
ttccagcact acgcgctgtt cccgcacatg acggtctggg acaacgtcgc gtacggcccg     660
cgcagcaaga aactcggcaa aggcgaggtc cgcaagcgcg tcgacgagct gctggagatc     720
gtccggctga ccgaatttgc cgagcgcagg cccgcccagc tgtccggcgg gcagcagcag     780
cgggtggcgt tggcccgggc actggtgaac taccccagcg cgctgctgct cgatgaaccg     840
ctcggagcgc tcgacctgaa gctgcgccac gtcatgcagt tcgagctcaa gcgcatccag     900 cggggaggtcg ggatcacgtt catctacgtg acccacgacc aggaagaggc gctcacgatg     960
agtgaccgca tcgcggtgat gaacgccggc aacgtcgaac agatcggcag cccgaccgag    1020
atctacgacc gtcccgcgac ggtgttcgtc gccagcttca tcgacaggc caacctctgg    1080 gcgggccggt gcaccggccg ctccaaccgc gattacgtcg agatcgacgt tctcggctcg    1140
```

-continued

```
acgctgaagg cacgcccggg cgagaccacg atcgagcccg gcgggcacgc caccctgatg   1200
gtgcgtccgg aacgcatccg ggtcaccccg ggctcccagg acgcgccgac cggtgacgtc   1260
gcctgcgtgc gtgccaccgt caccgacctg accttccaag gtccggtggt gcggctctcg   1320
ctggccgctc cggacgactc gaccgtgatc gcccacgtcg ccccgagca ggatctgccg    1380 ctgctgcgcc ccggcgacga cgtgtacgtc agctgggcac cggaagcctc cctggtgctt   1440
cccggcgacg acatccccac caccgaggac ctcgaagaga tgctcgacga ctcctgagtc   1500
acgcttcccg attgccga                                                 1518
```

<210> SEQ ID NO 89
<211> LENGTH: 376
<212> TYPE: PRT
<213> ORGANISM: Mycobacterium vaccae

<400> SEQUENCE: 89

```
Val Ile Glu Ile Asp His Val Thr Lys Arg Phe Gly Asp Tyr Leu Ala
 1               5                  10                  15

Val Ala Asp Ala Asp Phe Ser Ile Ala Pro Gly Glu Phe Phe Ser Met
            20                  25                  30

Leu Gly Pro Ser Gly Cys Gly Lys Thr Thr Thr Leu Arg Met Ile Ala
        35                  40                  45

Gly Phe Glu Thr Pro Thr Glu Gly Ala Ile Arg Leu Glu Gly Ala Asp
    50                  55                  60

Val Ser Arg Thr Pro Pro Asn Lys Arg Asn Val Asn Thr Val Phe Gln
65                  70                  75                  80

His Tyr Ala Leu Phe Pro His Met Thr Val Trp Asp Asn Val Ala Tyr
                85                  90                  95

Gly Pro Arg Ser Lys Lys Leu Gly Lys Gly Glu Val Arg Lys Arg Val
            100                 105                 110

Asp Glu Leu Leu Glu Ile Val Arg Leu Thr Glu Phe Ala Glu Arg Arg
        115                 120                 125

Pro Ala Gln Leu Ser Gly Gly Gln Gln Gln Arg Val Ala Leu Ala Arg
    130                 135                 140

Ala Leu Val Asn Tyr Pro Ser Ala Leu Leu Asp Glu Pro Leu Gly
145                 150                 155                 160

Ala Leu Asp Leu Lys Leu Arg His Val Met Gln Phe Glu Leu Lys Arg
                165                 170                 175

Ile Gln Arg Glu Val Gly Ile Thr Phe Ile Tyr Val Thr His Asp Gln
            180                 185                 190

Glu Glu Ala Leu Thr Met Ser Asp Arg Ile Ala Val Met Asn Ala Gly
        195                 200                 205

Asn Val Glu Gln Ile Gly Ser Pro Thr Glu Ile Tyr Asp Arg Pro Ala
    210                 215                 220

Thr Val Phe Val Ala Ser Phe Ile Gly Gln Ala Asn Leu Trp Ala Gly
225                 230                 235                 240

Arg Cys Thr Gly Arg Ser Asn Arg Asp Tyr Val Glu Ile Asp Val Leu
                245                 250                 255

Gly Ser Thr Leu Lys Ala Arg Pro Gly Glu Thr Thr Ile Glu Pro Gly
            260                 265                 270

Gly His Ala Thr Leu Met Val Arg Pro Glu Arg Ile Arg Val Thr Pro
        275                 280                 285

Gly Ser Gln Asp Ala Pro Thr Gly Asp Val Ala Cys Val Arg Ala Thr
    290                 295                 300
```

-continued

```
Val Thr Asp Leu Thr Phe Gln Gly Pro Val Val Arg Leu Ser Leu Ala
305                 310                 315                 320

Ala Pro Asp Asp Ser Thr Val Ile Ala His Val Gly Pro Glu Gln Asp
                325                 330                 335

Leu Pro Leu Leu Arg Pro Gly Asp Asp Val Tyr Val Ser Trp Ala Pro
            340                 345                 350

Glu Ala Ser Leu Val Leu Pro Gly Asp Asp Ile Pro Thr Thr Glu Asp
        355                 360                 365

Leu Glu Glu Met Leu Asp Asp Ser
    370                 375

<210> SEQ ID NO 90
<211> LENGTH: 33
<212> TYPE: DNA
<213> ORGANISM: Artificial Sequence
<220> FEATURE:
<223> OTHER INFORMATION: Made in a lab

<400> SEQUENCE: 90
gagagactcg aggtgatcga gatcgaccat gtc                                  33

<210> SEQ ID NO 91
<211> LENGTH: 31
<212> TYPE: DNA
<213> ORGANISM: Artificial Sequence
<220> FEATURE:
<223> OTHER INFORMATION: Made in a lab

<400> SEQUENCE: 91
agagactcga gcaatcggga agcgtgactc a                                    31

<210> SEQ ID NO 92
<211> LENGTH: 323
<212> TYPE: DNA
<213> ORGANISM: Mycobacterium vaccae

<400> SEQUENCE: 92
gtcgactaca aagaagactt caacgacaac gagcagtggt tcgccaaggt caaggagccg      60
ttgtcgcgca agcaggacat aggcgccgac ctggtgatcc ccaccgagtt catggccgcg     120
cgcgtcaagg gcctgggatg gctcaatgag atcagcgaag ccggcgtgcc caatcgcaag     180
aatctgcgtc aggacctgtt ggactcgagc atcgacgagg gccgcaagtt caccgcgccg     240
tacatgaccg gcatggtcgg tctcgcctac aacaaggcag ccaccggacg cgatatccgc     300
accatcgacg acctctggga tcc                                             323

<210> SEQ ID NO 93
<211> LENGTH: 1341
<212> TYPE: DNA
<213> ORGANISM: Mycobacterium vaccae

<400> SEQUENCE: 93
ccccaccccc ttccctggag ccgacgaaag gcacccgcac atgtcccgtg acatcgatcc      60
ccacctgctg gcccgaatga ccgcacgccg caccttgcgt cgccgcttca tcggcggtgg     120
cgccgcggcc gccgcgggcc tgaccctcgg ttcgtcgttc ctggcggcgt gcgggtccga     180
cagtgggacc tcgagcacca cgtcacagga cagcggcccc gccagcggcg ccctgcgcgt     240
ctccaactgg ccgctctata tggccgacgg tttcatcgca gcgttccaga ccgcctcggg     300
catcacggtc gactacaaag aagacttcaa cgacaacgag cagtggttcg ccaaggtcaa     360
```

-continued

```
ggagccgttg tcgcgcaagc aggacatagg cgccgacctg gtgatcccca ccgagttcat     420
ggccgcgcgc gtcaagggcc tgggatggct caatgagatc agcgaagccg gcgtgcccaa     480
tcgcaagaat ctgcgtcagg acctgttgga ctcgagcatc gacgagggcc gcaagttcac     540
cgcgccgtac atgaccggca tggtcggtct cgcctacaac aaggcagcca ccggacgcga     600
tatccgcacc atcgacgacc tctgggatcc gcgttcaag ggccgcgtca gtctgttctc      660
cgacgtccag gacggcctcg gcatgatcat gctctcgcag ggcaactcgc ggagaatcc      720 gaccaccgag tccattcagc aggcggtcga tctggtccgc aacagaacg acaggggtc       780 agatccgtcg cttcaccggc aacgactacg ccgacgacct ggccgcagaa acatcgccat     840
cgcgcaggcg tactccggtg acgtcgtgca gctgcaggcg acaaccccg atctgcagtt      900 catcgttccc gaatccggcg gcgactggtt cgtcgacacg atggtgatcc cgtacaccac     960
gcagaaccag aaggccgccg aggcgtggat cgactacatc tacgaccgag ccaactacgc    1020
caagctggtc gcgttcaccc agttcgtgcc cgcactctcg gacatgaccg acgaactcgc    1080
caaggtcgat cctgcatcgg cggagaaccc gctgatcaac ccgtcggccg aggtgcaggc    1140
gaacctgaag tcgtgggcgg cactgaccga cgagcagacg caggagttca acactgcgta    1200
cgccgccgtc accggcggct gacgcggtgg tagtgccgat cgaggggca taaatggccc     1260 tgcggacgcg aggagcataa atggccggtg tcgccaccag cagccgtcag cggacaaggt    1320
cgctccgtat ctgatggtcc t                                              1341
```

<210> SEQ ID NO 94
<211> LENGTH: 393
<212> TYPE: PRT
<213> ORGANISM: Mycobacterium vaccae

<400> SEQUENCE: 94

```
Met Ser Arg Asp Ile Asp Pro His Leu Leu Ala Arg Met Thr Ala Arg
 1               5                  10                  15

Arg Thr Leu Arg Arg Arg Phe Ile Gly Gly Gly Ala Ala Ala Ala Ala
            20                  25                  30

Gly Leu Thr Leu Gly Ser Ser Phe Leu Ala Ala Cys Gly Ser Asp Ser
        35                  40                  45

Gly Thr Ser Ser Thr Thr Ser Gln Asp Ser Gly Pro Ala Ser Gly Ala
    50                  55                  60

Leu Arg Val Ser Asn Trp Pro Leu Tyr Met Ala Asp Gly Phe Ile Ala
65                  70                  75                  80

Ala Phe Gln Thr Ala Ser Gly Ile Thr Val Asp Tyr Lys Glu Asp Phe
                85                  90                  95

Asn Asp Asn Glu Gln Trp Phe Ala Lys Val Lys Glu Pro Leu Ser Arg
            100                 105                 110

Lys Gln Asp Ile Gly Ala Asp Leu Val Ile Pro Thr Glu Phe Met Ala
        115                 120                 125

Ala Arg Val Lys Gly Leu Gly Trp Leu Asn Glu Ile Ser Glu Ala Gly
    130                 135                 140

Val Pro Asn Arg Lys Asn Leu Arg Gln Asp Leu Leu Asp Ser Ser Ile
145                 150                 155                 160

Asp Glu Gly Arg Lys Phe Thr Ala Pro Tyr Met Thr Gly Met Val Gly
                165                 170                 175

Leu Ala Tyr Asn Lys Ala Ala Thr Gly Arg Asp Ile Arg Thr Ile Asp
            180                 185                 190

Asp Leu Trp Asp Pro Ala Phe Lys Gly Arg Val Ser Leu Phe Ser Asp
```

-continued

```
                195                 200                     205
Val Gln Asp Gly Leu Gly Met Ile Met Leu Ser Gln Gly Asn Ser Pro
    210                 215                 220
Glu Asn Pro Thr Thr Glu Ser Ile Gln Gln Ala Val Asp Leu Val Arg
225                 230                 235                 240
Glu Gln Asn Asp Arg Gly Ser Asp Pro Ser Leu His Arg Gln Arg Leu
                245                 250                 255
Arg Arg Arg Pro Gly Arg Arg Asn Ile Ala Ile Ala Gln Ala Tyr Ser
                260                 265                 270
Gly Asp Val Val Gln Leu Gln Ala Asp Asn Pro Asp Leu Gln Phe Ile
                275                 280                 285
Val Pro Glu Ser Gly Gly Asp Trp Phe Val Asp Thr Met Val Ile Pro
                290                 295                 300
Tyr Thr Thr Gln Asn Gln Lys Ala Ala Glu Ala Trp Ile Asp Tyr Ile
305                 310                 315                 320
Tyr Asp Arg Ala Asn Tyr Ala Lys Leu Val Ala Phe Thr Gln Phe Val
                325                 330                 335
Pro Ala Leu Ser Asp Met Thr Asp Glu Leu Ala Lys Val Asp Pro Ala
                340                 345                 350
Ser Ala Glu Asn Pro Leu Ile Asn Pro Ser Ala Glu Val Gln Ala Asn
                355                 360                 365
Leu Lys Ser Trp Ala Ala Leu Thr Asp Glu Gln Thr Gln Glu Phe Asn
                370                 375                 380
Thr Ala Tyr Ala Ala Val Thr Gly Gly
385                 390
```

<210> SEQ ID NO 95
<211> LENGTH: 22
<212> TYPE: DNA
<213> ORGANISM: Mycobacterium vaccae

<400> SEQUENCE: 95
atgtcccgtg acatcgatcc cc                                              22

<210> SEQ ID NO 96
<211> LENGTH: 21
<212> TYPE: DNA
<213> ORGANISM: Mycobacterium vaccae

<400> SEQUENCE: 96
atcggcacta ccaccgcgtc a                                               21

<210> SEQ ID NO 97
<211> LENGTH: 861
<212> TYPE: DNA
<213> ORGANISM: Mycobacterium vaccae

<400> SEQUENCE: 97
gccggcgctc gcatatctcg cgatcttctt ccgtggtgcc gttcttctcg ctggcacgca      60
cctcgttgtc ggagaccggc ggctcggtgt tcatgccgac gctgacgttc gcctgggact     120
tcggcaacta cgtcgacgcg ttcacgatgt accacgagca gatcttccgc tcgttcggct     180
acgcgttcgt cgccacggtg ctgtgcctgt tgctggcgtt cccgctggcc tacgtcatcg     240
cgttcaaggc cggccggttc aagaacctga tcctggggct ggtgatcctg ccgttcttcg     300
tcacgttcct gatccgcacc attgcgtgga agacgatcct ggccgacgaa ggctgggtgg     360
tcaccgcgct gggcgccatc gggctgctgc tgacgagggc cggctgctg tccaccagct     420

-continued

```
gggcggtcat cggcggtctg acctacaact ggatcatctt catgatcctg ccgctgtacg    480
tcagcctgga gaagatcgac ccgcgtctgc tggaggcctc ccaggacctc tactcgtcgg    540
cgccgcgcag cttcggcaag gtgatcctgc cgatggcgat gcccggggtg ctggccggga    600
gcatgctggt gttcatcccg gccgtcggcg acttcatcaa cgccgactat ctcggcagta    660
cccagaccac catgatcggc aacgtgatcc agaagcagtt cctggtcgtc aaggactatc    720
cggcggcggc cgcgctgagt ctggggctga tgttgctgat cctgatcggc gtgctcctct    780
acacacgggc gctgggttcg gaggatctgg tatgaccacc caggcaggcg ccgcactggc    840
caccgccgcc cagcaggatc c                                             861
```

<210> SEQ ID NO 98
<211> LENGTH: 259
<212> TYPE: PRT
<213> ORGANISM: Mycobacterium vaccae

<400> SEQUENCE: 98

```
Val Val Pro Phe Phe Ser Leu Ala Arg Thr Ser Leu Ser Glu Thr Gly
  1               5                  10                  15

Gly Ser Val Phe Met Pro Thr Leu Thr Phe Ala Trp Asp Phe Gly Asn
             20                  25                  30

Tyr Val Asp Ala Phe Thr Met Tyr His Glu Gln Ile Phe Arg Ser Phe
         35                  40                  45

Gly Tyr Ala Phe Val Ala Thr Val Leu Cys Leu Leu Leu Ala Phe Pro
     50                  55                  60

Leu Ala Tyr Val Ile Ala Phe Lys Ala Gly Arg Phe Lys Asn Leu Ile
 65                  70                  75                  80

Leu Gly Leu Val Ile Leu Pro Phe Phe Val Thr Phe Leu Ile Arg Thr
                 85                  90                  95

Ile Ala Trp Thr Ile Leu Ala Asp Glu Gly Trp Val Val Thr Ala Leu
            100                 105                 110

Gly Ala Ile Gly Leu Leu Pro Asp Glu Gly Arg Leu Leu Ser Thr Ser
        115                 120                 125

Trp Ala Val Ile Gly Gly Leu Thr Tyr Asn Trp Ile Ile Phe Met Ile
    130                 135                 140

Leu Pro Leu Tyr Val Ser Leu Glu Lys Ile Asp Pro Arg Leu Leu Glu
145                 150                 155                 160

Ala Ser Gln Asp Leu Tyr Ser Ser Ala Pro Arg Ser Phe Gly Lys Val
                165                 170                 175

Ile Leu Pro Met Ala Met Pro Gly Val Leu Ala Gly Ser Met Leu Val
            180                 185                 190

Phe Ile Pro Ala Val Gly Asp Phe Ile Asn Ala Asp Tyr Leu Gly Ser
        195                 200                 205

Thr Gln Thr Thr Met Ile Gly Asn Val Ile Gln Lys Gln Phe Leu Val
    210                 215                 220

Val Lys Asp Tyr Pro Ala Ala Ala Leu Ser Leu Gly Leu Met Leu
225                 230                 235                 240

Leu Ile Leu Ile Gly Val Leu Leu Tyr Thr Arg Ala Leu Gly Ser Glu
                245                 250                 255

Asp Leu Val
```

<210> SEQ ID NO 99
<211> LENGTH: 277
<212> TYPE: DNA

-continued

<213> ORGANISM: Mycobacterium vaccae

<400> SEQUENCE: 99

```
gtaatctttg ctggagcccg tacgccggta ggcaaactca tgggttcgct caaggacttc 60
aagggcagcg atctcggtgc cgtggcgatc aagggcgccc tggagaaagc cttccccggc 120
gtcgacgacc ctgctcgtct cgtcgagtac gtgatcatgg gccaagtgct ctccgccggc 180
gccggccaga tgcccgcccg ccaggccgcc gtcgccgccg gcatcccgtg ggacgtcgcc 240
tcgctgacga tcaacaagat gtgcctgtcg ggcatcg 277
```

<210> SEQ ID NO 100
<211> LENGTH: 92
<212> TYPE: PRT
<213> ORGANISM: Mycobacterium vaccae

<400> SEQUENCE: 100

```
Val Ile Phe Ala Gly Ala Arg Thr Pro Val Gly Lys Leu Met Gly Ser
1 5 10 15

Leu Lys Asp Phe Lys Gly Ser Asp Leu Gly Ala Val Ala Ile Lys Gly
20 25 30

Ala Leu Glu Lys Ala Phe Pro Gly Val Asp Asp Pro Ala Arg Leu Val
35 40 45

Glu Tyr Val Ile Met Gly Gln Val Leu Ser Ala Gly Ala Gly Gln Met
50 55 60

Pro Ala Arg Gln Ala Ala Val Ala Ala Gly Ile Pro Trp Asp Val Ala
65 70 75 80

Ser Leu Thr Ile Asn Lys Met Cys Leu Ser Gly Ile
85 90

<210> SEQ ID NO 101
<211> LENGTH: 12
<212> TYPE: PRT
<213> ORGANISM: Mycobacterium vaccae
<220> FEATURE:
<221> NAME/KEY: UNSURE
<222> LOCATION: (1)...(1)
<223> OTHER INFORMATION: Residue can be either Glu or Pro
<220> FEATURE:
<221> NAME/KEY: UNSURE
<222> LOCATION: (2)...(2)
<223> OTHER INFORMATION: Residue can be either Pro or Glu
<220> FEATURE:
<221> NAME/KEY: UNSURE
<222> LOCATION: (7)...(7)
<221> NAME/KEY: UNSURE
<222> LOCATION: (12)...(12)

<400> SEQUENCE: 101

Xaa Xaa Ala Asp Arg Gly Xaa Ser Lys Tyr Arg Xaa
1 5 10

<210> SEQ ID NO 102
<211> LENGTH: 24
<212> TYPE: PRT
<213> ORGANISM: Mycobacterium vaccae
<220> FEATURE:
<221> NAME/KEY: UNSURE
<222> LOCATION: (1)...(1)

<400> SEQUENCE: 102
```

-continued

```
Xaa Ile Asp Glu Ser Leu Phe Asp Ala Glu Glu Lys Met Glu Lys Ala
 1               5                  10                  15

Val Ser Val Ala Arg Asp Ser Ala
                  20

<210> SEQ ID NO 103
<211> LENGTH: 23
<212> TYPE: PRT
<213> ORGANISM: Mycobacterium vaccae
<220> FEATURE:
<221> NAME/KEY: UNSURE
<222> LOCATION: (1)...(2)
<221> NAME/KEY: UNSURE
<222> LOCATION: (15)...(15)
<221> NAME/KEY: UNSURE
<222> LOCATION: (17)...(17)

<400> SEQUENCE: 103

Xaa Xaa Ile Ala Pro Ala Thr Ser Gly Thr Leu Ser Glu Phe Xaa Ala
 1               5                  10                  15

Xaa Lys Gly Val Thr Met Glu
            20

<210> SEQ ID NO 104
<211> LENGTH: 15
<212> TYPE: PRT
<213> ORGANISM: Mycobacterium vaccae

<400> SEQUENCE: 104

Pro Asn Val Pro Asp Ala Phe Ala Val Leu Ala Asp Arg Val Gly
 1               5                  10                  15

<210> SEQ ID NO 105
<211> LENGTH: 9
<212> TYPE: PRT
<213> ORGANISM: Mycobacterium vaccae
<220> FEATURE:
<221> NAME/KEY: UNSURE
<222> LOCATION: (1)...(1)

<400> SEQUENCE: 105

Xaa Ile Arg Val Gly Val Asn Gly Phe
 1               5

<210> SEQ ID NO 106
<211> LENGTH: 485
<212> TYPE: DNA
<213> ORGANISM: Mycobacterium vaccae

<400> SEQUENCE: 106
agcggctggg acatcaacac cgccgccttc gagtggtacg tcgactcggg tctcgcggtg      60
atcatgcccg tcggcgggca gtccagcttc tacagcgact ggtacagccc ggcctgcggt     120
aaggccggct gccagaccta caagtgggag acgttcctga cccaggagct gccggcctac     180
ctcgccgcca acaagggggt cgacccgaac cgcaacgcgg ccgtcggtct gtccatggcc     240
ggttcggcgg cgctgacgct ggcgatctac cacccgcagc agttccagta cgccgggtcg     300
ctgtcgggct acctgaaccc gtccgagggg tggtggccga tgctgatcaa catctcgatg     360
ggtgacgcgg gcggctacaa ggccaacgac atgtggggtc gcaccgagga cccgagcagc     420
gcctggaagc gcaacgaccc gatggtcaac atcggcaagc tggtcgccaa caacaccccc     480
ctctc                                                                 485
```

<210> SEQ ID NO 107
<211> LENGTH: 501
<212> TYPE: DNA
<213> ORGANISM: Mycobacterium vaccae
<220> FEATURE:
<221> NAME/KEY: unsure
<222> LOCATION: (441)...(441)
<221> NAME/KEY: unsure
<222> LOCATION: (450)...(450)

<400> SEQUENCE: 107

```
atgccggtgc gacgtgcgcg cagtgcgctt gcgtccgtga ccttcgtcgc ggccgcgtgc      60
gtgggcgctg agggcaccgc actggcggcg acgccggact ggagcgggcg ctacacggtg     120
gtgacgttcg cctccgacaa actcggcacg agtgtggccg cccgccagcc agaacccgac     180
ttcagcggtc agtacacctt cagcacgtcc tgtgtgggca cctgcgtggc caccgcgtcc     240
gacggcccgg cgccgtcgaa cccgacgatt ccgcagcccg cgcgctacac ctgggacggc     300
aggcagtggg tgttcaacta caactggcag tgggagtgct tccgcggcgc cgacgtcccg     360
cgcgagtacg ccgccgcgcg ttcgctggtg ttctacgccc cgaccgccga cgggtcgatg     420
ttcggcacct ggcgcaccga natcctggan ggcctctgca agggcaccgt gatcatgccg     480
gtcgcggcct atccggcgta g                                               501
```

<210> SEQ ID NO 108
<211> LENGTH: 180
<212> TYPE: DNA
<213> ORGANISM: Mycobacterium vaccae

<400> SEQUENCE: 108

```
atgaaccagc cgcggcccga ggccgaggcg aacctgcggg gctacttcac cgccaacccg      60
gcggagtact acgacctgcg gggcatcctc gccccgatcg gtgacgcgca gcgcaactgc     120
aacatcaccg tgctgccggt agagctgcag acggcctacg acacgttcat ggccggctga     180
```

<210> SEQ ID NO 109
<211> LENGTH: 166
<212> TYPE: PRT
<213> ORGANISM: Mycobacterium vaccae

<400> SEQUENCE: 109

```
Met Pro Val Arg Arg Ala Arg Ser Ala Leu Ala Ser Val Thr Phe Val
  1               5                  10                  15

Ala Ala Ala Cys Val Gly Ala Glu Gly Thr Ala Leu Ala Ala Thr Pro
                 20                  25                  30

Asp Trp Ser Gly Arg Tyr Thr Val Val Thr Phe Ala Ser Asp Lys Leu
             35                  40                  45

Gly Thr Ser Val Ala Ala Arg Gln Pro Glu Pro Asp Phe Ser Gly Gln
         50                  55                  60

Tyr Thr Phe Ser Thr Ser Cys Val Gly Thr Cys Val Ala Thr Ala Ser
 65                  70                  75                  80

Asp Gly Pro Ala Pro Ser Asn Pro Thr Ile Pro Gln Pro Ala Arg Tyr
                 85                  90                  95

Thr Trp Asp Gly Arg Gln Trp Val Phe Asn Tyr Asn Trp Gln Trp Glu
            100                 105                 110

Cys Phe Arg Gly Ala Asp Val Pro Arg Glu Tyr Ala Ala Ala Arg Ser
        115                 120                 125

Leu Val Phe Tyr Ala Pro Thr Ala Asp Gly Ser Met Phe Gly Thr Trp
    130                 135                 140
```

```
Arg Thr Asp Ile Leu Asp Gly Leu Cys Lys Gly Thr Val Ile Met Pro
145                 150                 155                 160

Val Ala Ala Tyr Pro Ala
                165
```

<210> SEQ ID NO 110
<211> LENGTH: 74
<212> TYPE: PRT
<213> ORGANISM: Mycobacterium vaccae

<400> SEQUENCE: 110

```
Pro Arg Asp Thr His Pro Gly Ala Asn Gln Ala Val Thr Ala Ala Met
1               5                   10                  15

Asn Gln Pro Arg Pro Glu Ala Glu Ala Asn Leu Arg Gly Tyr Phe Thr
                20                  25                  30

Ala Asn Pro Ala Glu Tyr Tyr Asp Leu Arg Gly Ile Leu Ala Pro Ile
            35                  40                  45

Gly Asp Ala Gln Arg Asn Cys Asn Ile Thr Val Leu Pro Val Glu Leu
        50                  55                  60

Gln Thr Ala Tyr Asp Thr Phe Met Ala Gly
65                  70
```

<210> SEQ ID NO 111
<211> LENGTH: 503
<212> TYPE: DNA
<213> ORGANISM: Mycobacterium vaccae
<220> FEATURE:
<221> NAME/KEY: unsure
<222> LOCATION: (358)...(358)

<400> SEQUENCE: 111

```
atgcaggtgc ggcgtgttct gggcagtgtc ggtgcagcag tcgcggtttc ggccgcgtta      60
tggcagacgg gggtttcgat accgaccgcc tcagcggatc cgtgtccgga catcgaggtg     120
atcttcgcgc gcgggaccgg tcggaaccgg gcctcgggt gggtcggtga tgcgttcgtc      180
aacgcgctgc ggcccaaggt cggtgagcag tcggtgggca cctacgcggt gaactacccg     240
gcaggattcg gacttcgaca aatcggcgcc catgggcgcg gccgacgcat cggggcgggt     300
gcagtggatg gccgacaact gcccggacac caagcttgtc ctgggcggca tgtcgcangg     360
cgccggcgtc atcgacctga tcaccgtcga tccgcgaccg ctgggccggt tcaccccac     420
cccgatgccg ccccgcgtcg ccgaccacgt ggccgccgtt gtggtcttcg gaaatccgtt     480
gcgcgacatc cgtggtggcg gtc                                            503
```

<210> SEQ ID NO 112
<211> LENGTH: 167
<212> TYPE: PRT
<213> ORGANISM: Mycobacterium vaccae
<220> FEATURE:
<221> NAME/KEY: UNSURE
<222> LOCATION: (119)...(119)

<400> SEQUENCE: 112

```
Met Gln Val Arg Arg Val Leu Gly Ser Val Gly Ala Ala Val Ala Val
1               5                   10                  15

Ser Ala Ala Leu Trp Gln Thr Gly Val Ser Ile Pro Thr Ala Ser Ala
                20                  25                  30

Asp Pro Cys Pro Asp Ile Glu Val Ile Phe Ala Arg Gly Thr Gly Ala
            35                  40                  45
```

| Glu | Pro | Gly | Leu | Gly | Trp | Val | Gly | Asp | Ala | Phe | Val | Asn | Ala | Leu | Arg |
| | 50 | | | | | 55 | | | | 60 | | | | | |

| Pro | Lys | Val | Gly | Glu | Gln | Ser | Val | Gly | Thr | Tyr | Ala | Val | Asn | Tyr | Pro |
| 65 | | | | | 70 | | | | | 75 | | | | | 80 |

| Ala | Gly | Phe | Asp | Phe | Asp | Lys | Ser | Ala | Pro | Met | Gly | Ala | Ala | Asp | Ala |
| | | | | 85 | | | | | 90 | | | | | 95 | |

| Ser | Gly | Arg | Val | Gln | Trp | Met | Ala | Asp | Asn | Cys | Pro | Thr | Lys | Leu |
| | | | 100 | | | | | 105 | | | | 110 | | |

| Val | Leu | Gly | Gly | Met | Ser | Xaa | Gly | Ala | Gly | Val | Ile | Asp | Leu | Ile | Thr |
| | | | 115 | | | | 120 | | | | | 125 | | | |

| Val | Asp | Pro | Arg | Pro | Leu | Gly | Arg | Phe | Thr | Pro | Thr | Pro | Met | Pro | Pro |
| | | 130 | | | | 135 | | | | | 140 | | | | |

| Arg | Val | Ala | Asp | His | Val | Ala | Ala | Val | Val | Val | Phe | Gly | Asn | Pro | Leu |
| 145 | | | | | 150 | | | | | 155 | | | | | 160 |

| Arg | Asp | Ile | Arg | Gly | Gly | Gly |
| | | | | 165 | | |

<210> SEQ ID NO 113
<211> LENGTH: 1569
<212> TYPE: DNA
<213> ORGANISM: Mycobacterium vaccae

<400> SEQUENCE: 113

| atggccaaga | caattgcgta | tgacgaagag | gcccgccgtg | gcctcgagcg | gggcctcaac | 60 |
| gccctcgcag | acgccgtaaa | ggtgacgttg | gcccgaaggt | gtcgcaacgt | cgtgctggag | 120 |
| aagaagtggg | gcgcccccac | gatcaccaac | gatggtgtgt | ccatcgccaa | ggagatcgag | 180 |
| ctggaggacc | cgtacgagaa | gatcggcgct | gagctggtca | agaggtcgc | caagaagacc | 240 |
| gacgacgtcg | cgggcgacgg | caccaccacc | gccaccgtgc | tcgctcaggc | tctggttcgc | 300 |
| gaaggcctgc | gcaacgtcgc | agccggcgcc | aacccgctcg | gcctcaagcg | tggcatcgag | 360 |
| aaggctgtcg | aggctgtcac | ccagtcgctg | ctgaagtcgg | ccaaggaggt | cgagaccaag | 420 |
| gagcagattt | ctgccaccgc | ggcgatttcc | gccggcgaca | cccagatcgg | cgagctcatc | 480 |
| gccgaggcca | tggacaaggt | cggcaacgag | ggtgtcatca | ccgtcgagga | gtcgaacacc | 540 |
| ttcggcctgc | agctcgagct | caccgagggt | atgcgcttcg | acaagggcta | catctcgggt | 600 |
| tacttcgtga | ccgacgccga | gcgccaggaa | gccgtcctgg | aggatcccta | catcctgctg | 660 |
| gtcagctcca | aggtgtcgac | cgtcaaggat | ctgctcccgc | tgctggagaa | ggtcatccag | 720 |
| gccggcaagc | cgctgctgat | catcgccgag | gacgtcgagg | gcgaggccct | gtccacgctg | 780 |
| gtggtcaaca | agatccgcgg | caccttcaag | tccgtcgccg | tcaaggctcc | gggcttcggt | 840 |
| gaccgccgca | aggcgatgct | gcaggacatg | gccatcctca | ccggtggtca | ggtcgtcagc | 900 |
| gaaagagtcg | ggctgtccct | ggagaccgcc | gacgtctcgc | tgctgggcca | ggcccgcaag | 960 |
| gtcgtcgtca | ccaaggacga | gaccaccatc | gtcgagggct | cgggcgattc | cgatgccatc | 1020 |
| gccgccgggg | tggctcagat | ccgcgccgag | atcgagaaca | gcgactccga | ctacgaccgc | 1080 |
| gagaagctgc | aggagcgcct | ggccaagctg | gccggcggtg | ttgcggtgat | caaggccgga | 1140 |
| gctgccaccg | aggtggagct | caaggagcgc | aagcaccgca | tcgaggacgc | cgtccgcaac | 1200 |
| gcgaaggctg | ccgtcgaaga | gggcatcgtc | gccggtggcg | gcgtggctct | gctgcagtcg | 1260 |
| gctcctgcgc | tggacgacct | cggcctgacg | ggcgacgagg | ccaccggtgc | caacatcgtc | 1320 |
| cgcgtggcgc | tgtcggctcc | gctcaagcag | atcgccttca | acggcggcct | ggagcccggc | 1380 |
| gtcgttgccg | agaaggtgtc | caacctgccc | gcgggtcacg | gcctcaacgc | cgcgaccggt | 1440 |

-continued

```
gagtacgagg acctgctcaa ggccggcgtc gccgacccgg tgaaggtcac ccgctcggcg      1500
ctgcagaacg cggcgtccat cgcggctctg ttcctcacca ccgaggccgt cgtcgccgac      1560
aagccggag                                                              1569
```

<210> SEQ ID NO 114
<211> LENGTH: 523
<212> TYPE: PRT
<213> ORGANISM: Mycobacterium vaccae

<400> SEQUENCE: 114

```
Met Ala Lys Thr Ile Ala Tyr Asp Glu Glu Ala Arg Arg Gly Leu Glu
 1               5                   10                  15

Arg Gly Leu Asn Ala Leu Ala Asp Ala Val Lys Val Thr Leu Gly Pro
                20                  25                  30

Lys Gly Arg Asn Val Val Leu Glu Lys Lys Trp Gly Ala Pro Thr Ile
            35                  40                  45

Thr Asn Asp Gly Val Ser Ile Ala Lys Glu Ile Glu Leu Glu Asp Pro
        50                  55                  60

Tyr Glu Lys Ile Gly Ala Glu Leu Val Lys Glu Val Ala Lys Lys Thr
 65                  70                  75                  80

Asp Asp Val Ala Gly Asp Gly Thr Thr Thr Ala Thr Val Leu Ala Gln
                85                  90                  95

Ala Leu Val Arg Glu Gly Leu Arg Asn Val Ala Gly Ala Asn Pro
                100                 105                 110

Leu Gly Leu Lys Arg Gly Ile Glu Lys Ala Val Glu Ala Val Thr Gln
            115                 120                 125

Ser Leu Leu Lys Ser Ala Lys Glu Val Glu Thr Lys Glu Gln Ile Ser
        130                 135                 140

Ala Thr Ala Ala Ile Ser Ala Gly Asp Thr Gln Ile Gly Glu Leu Ile
145                 150                 155                 160

Ala Glu Ala Met Asp Lys Val Gly Asn Glu Gly Val Ile Thr Val Glu
                165                 170                 175

Glu Ser Asn Thr Phe Gly Leu Gln Leu Glu Leu Thr Glu Gly Met Arg
            180                 185                 190

Phe Asp Lys Gly Tyr Ile Ser Gly Tyr Phe Val Thr Asp Ala Glu Arg
        195                 200                 205

Gln Glu Ala Val Leu Glu Asp Pro Tyr Ile Leu Leu Val Ser Ser Lys
    210                 215                 220

Val Ser Thr Val Lys Asp Leu Leu Pro Leu Leu Glu Lys Val Ile Gln
225                 230                 235                 240

Ala Gly Lys Pro Leu Leu Ile Ile Ala Glu Asp Val Glu Gly Glu Ala
                245                 250                 255

Leu Ser Thr Leu Val Val Asn Lys Ile Arg Gly Thr Phe Lys Ser Val
            260                 265                 270

Ala Val Lys Ala Pro Gly Phe Gly Asp Arg Arg Lys Ala Met Leu Gln
        275                 280                 285

Asp Met Ala Ile Leu Thr Gly Gly Gln Val Val Ser Glu Arg Val Gly
    290                 295                 300

Leu Ser Leu Glu Thr Ala Asp Val Ser Leu Leu Gly Gln Ala Arg Lys
305                 310                 315                 320

Val Val Val Thr Lys Asp Glu Thr Thr Ile Val Glu Gly Ser Gly Asp
                325                 330                 335

Ser Asp Ala Ile Ala Gly Arg Val Ala Gln Ile Arg Ala Glu Ile Glu
```

```
                    340             345             350
Asn Ser Asp Ser Asp Tyr Asp Arg Glu Lys Leu Gln Glu Arg Leu Ala
            355             360             365
Lys Leu Ala Gly Gly Val Ala Val Ile Lys Ala Gly Ala Thr Glu
    370             375             380
Val Glu Leu Lys Glu Arg Lys His Arg Ile Glu Asp Ala Val Arg Asn
385             390             395             400
Ala Lys Ala Ala Val Glu Gly Ile Val Ala Gly Gly Val Ala
            405             410             415
Leu Leu Gln Ser Ala Pro Ala Leu Asp Asp Leu Gly Leu Thr Gly Asp
            420             425             430
Glu Ala Thr Gly Ala Asn Ile Val Arg Val Ala Leu Ser Ala Pro Leu
            435             440             445
Lys Gln Ile Ala Phe Asn Gly Gly Leu Glu Pro Gly Val Val Ala Glu
            450             455             460
Lys Val Ser Asn Leu Pro Ala Gly His Gly Leu Asn Ala Ala Thr Gly
465             470             475             480
Glu Tyr Glu Asp Leu Leu Lys Ala Gly Val Ala Asp Pro Val Lys Val
            485             490             495
Thr Arg Ser Ala Leu Gln Asn Ala Ala Ser Ile Ala Ala Leu Phe Leu
            500             505             510
Thr Thr Glu Ala Val Val Ala Asp Lys Pro Glu
            515             520
```

<210> SEQ ID NO 115
<211> LENGTH: 647
<212> TYPE: DNA
<213> ORGANISM: Mycobacterium vaccae

<400> SEQUENCE: 115

```
atggccaaga caattgcgta tgacgaagag gcccgccgtg gcctcgagcg gggcctcaac      60
gccctcgcag acgccgtaaa ggtgacgttg ggcccgaagg tcgcaacgt cgtgctggag      120
aagaagtggg gcgcccccac gatcaccaac gatggtgtgt ccatcgccaa ggagatcgag      180
ctggaggacc cgtacgagaa gatcggcgct gagctggtca agaggtcgc caagaagacc      240
gacgacgtcg cgggcgacgg caccaccacc gccaccgtgc tcgctcaggc tctggttcgc      300
gaaggcctgc gcaacgtcgc agccggcgcc aacccgctcg gcctcaagcg tggcatcgag      360
aaggctgtcg aggctgtcac ccagtcgctg ctgaagtcgg ccaaggaggt cgagaccaag      420
gagcagattt ctgccaccgc ggcgatttcc gccggcgaca cccagatcgg cgagctcatc      480
gccgaggcca tggacaaggt cggcaacgag ggtgtcatca ccgtcgagga gtcgaacacc      540
ttcggcctgc agctcgagct caccgagggt atgcgcttcg acaagggcta catctcgggt      600
tacttcgtga ccgacgccga gcgccaggaa gccgtcctgg aggatcc      647
```

<210> SEQ ID NO 116
<211> LENGTH: 927
<212> TYPE: DNA
<213> ORGANISM: Mycobacterium vaccae

<400> SEQUENCE: 116

```
gatccctaca tcctgctggt cagctccaag gtgtcgaccg tcaaggatct gctcccgctg      60
ctggagaagg tcatccaggc cggcaagccg ctgctgatca tcgccgagga cgtcgagggc      120
gaggccctgt ccacgctggt ggtcaacaag atccgcggca ccttcaagtc cgtcgccgtc      180
```

-continued

```
aaggctccgg gcttcggtga ccgccgcaag gcgatgctgc aggacatggc catcctcacc     240
ggtggtcagg tcgtcagcga aagagtcggg ctgtccctgg agaccgccga cgtctcgctg     300
ctgggccagg cccgcaaggt cgtcgtcacc aaggacgaga ccaccatcgt cgagggctcg     360
ggcgattccg atgccatcgc cggccgggtg gctcagatcc gcgccgagat cgagaacagc     420
gactccgact acgaccgcga gaagctgcag gagcgcctgg ccaagctggc cggcggtgtt     480
gcggtgatca aggccggagc tgccaccgag gtggagctca aggagcgcaa gcaccgcatc     540
gaggacgccg tccgcaacgc gaaggctgcc gtcgaagagg gcatcgtcgc cggtggcggc     600
gtggctctgc tgcagtcggc tcctgcgctg gacgacctcg gcctgacggg cgacgaggcc     660
accggtgcca acatcgtccg cgtggcgctg tcggctccgc tcaagcagat cgccttcaac     720
ggcggcctgg agcccggcgt cgttgccgag aaggtgtcca acctgcccgc gggtcacggc     780
ctcaacgccg cgaccggtga gtacgaggac ctgctcaagg ccggcgtcgc cgacccggtg     840
aaggtcaccc gctcggcgct gcagaacgcg gcgtccatcg cggctctgtt cctcaccacc     900
gaggccgtcg tcgccgacaa gccggag                                         927
```

<210> SEQ ID NO 117
<211> LENGTH: 215
<212> TYPE: PRT
<213> ORGANISM: Mycobacterium vaccae

<400> SEQUENCE: 117

```
Met Ala Lys Thr Ile Ala Tyr Asp Glu Glu Ala Arg Arg Gly Leu Glu
 1               5                  10                  15

Arg Gly Leu Asn Ala Leu Ala Asp Ala Val Lys Val Thr Leu Gly Pro
                20                  25                  30

Lys Gly Arg Asn Val Val Leu Glu Lys Lys Trp Gly Ala Pro Thr Ile
            35                  40                  45

Thr Asn Asp Gly Val Ser Ile Ala Lys Glu Ile Glu Leu Glu Asp Pro
        50                  55                  60

Tyr Glu Lys Ile Gly Ala Glu Leu Val Lys Glu Val Ala Lys Lys Thr
65                  70                  75                  80

Asp Asp Val Ala Gly Asp Gly Thr Thr Thr Ala Thr Val Leu Ala Gln
                85                  90                  95

Ala Leu Val Arg Glu Gly Leu Arg Asn Val Ala Ala Gly Ala Asn Pro
            100                 105                 110

Leu Gly Leu Lys Arg Gly Ile Glu Lys Ala Val Glu Ala Val Thr Gln
        115                 120                 125

Ser Leu Leu Lys Ser Ala Lys Glu Val Glu Thr Lys Glu Gln Ile Ser
    130                 135                 140

Ala Thr Ala Ala Ile Ser Ala Gly Asp Thr Gln Ile Gly Glu Leu Ile
145                 150                 155                 160

Ala Glu Ala Met Asp Lys Val Gly Asn Glu Gly Val Ile Thr Val Glu
                165                 170                 175

Glu Ser Asn Thr Phe Gly Leu Gln Leu Glu Leu Thr Glu Gly Met Arg
            180                 185                 190

Phe Asp Lys Gly Tyr Ile Ser Gly Tyr Phe Val Thr Asp Ala Glu Arg
        195                 200                 205

Gln Glu Ala Val Leu Glu Asp
    210                 215
```

<210> SEQ ID NO 118
<211> LENGTH: 309

-continued

<212> TYPE: PRT
<213> ORGANISM: Mycobacterium vaccae

<400> SEQUENCE: 118

```
Asp Pro Tyr Ile Leu Leu Val Ser Ser Lys Val Ser Thr Val Lys Asp
 1               5                  10                  15

Leu Leu Pro Leu Leu Glu Lys Val Ile Gln Ala Gly Lys Pro Leu Leu
            20                  25                  30

Ile Ile Ala Glu Asp Val Glu Gly Glu Ala Leu Ser Thr Leu Val Val
        35                  40                  45

Asn Lys Ile Arg Gly Thr Phe Lys Ser Val Ala Val Lys Ala Pro Gly
    50                  55                  60

Phe Gly Asp Arg Arg Lys Ala Met Leu Gln Asp Met Ala Ile Leu Thr
65                  70                  75                  80

Gly Gly Gln Val Val Ser Glu Arg Val Gly Leu Ser Leu Glu Thr Ala
                85                  90                  95

Asp Val Ser Leu Leu Gly Gln Ala Arg Lys Val Val Val Thr Lys Asp
            100                 105                 110

Glu Thr Thr Ile Val Glu Gly Ser Gly Asp Ser Asp Ala Ile Ala Gly
        115                 120                 125

Arg Val Ala Gln Ile Arg Ala Glu Ile Glu Asn Ser Asp Ser Asp Tyr
    130                 135                 140

Asp Arg Glu Lys Leu Gln Glu Arg Leu Ala Lys Leu Ala Gly Gly Val
145                 150                 155                 160

Ala Val Ile Lys Ala Gly Ala Ala Thr Glu Val Glu Leu Lys Glu Arg
                165                 170                 175

Lys His Arg Ile Glu Asp Ala Val Arg Asn Ala Lys Ala Ala Val Glu
            180                 185                 190

Glu Gly Ile Val Ala Gly Gly Gly Val Ala Leu Leu Gln Ser Ala Pro
        195                 200                 205

Ala Leu Asp Asp Leu Gly Leu Thr Gly Asp Glu Ala Thr Gly Ala Asn
    210                 215                 220

Ile Val Arg Val Ala Leu Ser Ala Pro Leu Lys Gln Ile Ala Phe Asn
225                 230                 235                 240

Gly Gly Leu Glu Pro Gly Val Val Ala Glu Lys Val Ser Asn Leu Pro
                245                 250                 255

Ala Gly His Gly Leu Asn Ala Ala Thr Gly Glu Tyr Glu Asp Leu Leu
            260                 265                 270

Lys Ala Gly Val Ala Asp Pro Val Lys Val Thr Arg Ser Ala Leu Gln
        275                 280                 285

Asn Ala Ala Ser Ile Ala Ala Leu Phe Leu Thr Thr Glu Ala Val Val
    290                 295                 300

Ala Asp Lys Pro Glu
305
```

<210> SEQ ID NO 119
<211> LENGTH: 162
<212> TYPE: DNA
<213> ORGANISM: Mycobacterium vaccae

<400> SEQUENCE: 119

```
ctcgtacagg cgacggagat ctccgacgac gccacgtcgg tacggttggt cgccaccctg     60
ttcggcgtcg tgttgttgac gttggtgctg tccgggctca acgccaccct catccagggc    120
gcaccagaag acagctggcg caggcggatt ccgtcgatct tc                      162
```

<210> SEQ ID NO 120
<211> LENGTH: 1366
<212> TYPE: DNA
<213> ORGANISM: Mycobacterium vaccae
<220> FEATURE:
<221> NAME/KEY: unsure
<222> LOCATION: (955)...(955)
<221> NAME/KEY: unsure
<222> LOCATION: (973)...(973)

<400> SEQUENCE: 120

| | | | | | |
|---|---|---|---|---|---|
| gatgagcagc | gtgctgaact | cgacctggtt | ggcctgggcc | gtcgcggtcg | cggtcgggtt | 60 |
| cccggtgctg | ctggtcgtgc | tgaccgaggt | gcacaacgcg | ttgcgtcggc | gcggcagcgc | 120 |
| gctggcccgc | ccggtgcaac | tcctgcgtac | ctacatcctg | ccgctgggcg | cgttgctgct | 180 |
| cctgctggta | caggcgatgg | agatctccga | cgacgccacg | tcggtacggt | tggtcgccac | 240 |
| cctgttcggc | gtcgtgttgt | tgacgttggt | gctgtccggg | ctcaacgcca | ccctcatcca | 300 |
| gggcgcacca | gaagacagct | ggcgcaggcg | gattccgtcg | atcttcctcg | acgtcgcgcg | 360 |
| cttcgcgctc | atcgcggtcg | gtatcaccgt | gatcatggcc | tatgtctggg | gcgcgaacgt | 420 |
| gggggggcctg | ttcaccgcac | tgggcgtcac | ttccatcgtt | cttggcctgg | ctctgcagaa | 480 |
| ttcggtcggt | cagatcatct | cggtctgct | gctgctgttc | gagcaaccgt | tccggctcgg | 540 |
| cgactggatc | accgtcccca | ccgcggcggg | ccggccgtcc | gcccacggcc | gcgtggtgga | 600 |
| agtcaactgg | cgtgcaacac | atatcgacac | cggcggcaac | ctgctggtaa | tgcccaacgc | 660 |
| cgaactcgcc | ggcgcgtcgt | tcaccaatta | cagccggccc | gtgggagagc | accggctgac | 720 |
| cgtcgtcacc | accttcaacg | ccgcggacac | ccccgatgat | gtctgcgaga | tgctgtcgtc | 780 |
| ggtcgcggcg | tcgctgcccg | aactgcgcac | cgacggacag | atcgccacgc | tctatctcgg | 840 |
| tgcggccgaa | tacgagaagt | cgatcccgtt | gcacacaccc | gcggtggacg | actcggtcag | 900 |
| gagcacgtac | ctgcgatggg | tctggtacgc | cgcgcgccgg | caggaacttc | gcctnaacgg | 960 |
| cgtcgccgac | ganttcgaca | cgccggaacg | gatcgcctcg | gccatgcggg | ctgtggcgtc | 1020 |
| cacactgcgc | ttggcagacg | acgaacagca | ggagatcgcc | gacgtggtgc | gtctggtccg | 1080 |
| ttacggcaac | ggggaacgcc | tccagcagcc | gggtcaggta | ccgaccggga | tgaggttcat | 1140 |
| cgtagacggc | agggtgagtc | tgtccgtgat | cgatcaggac | ggcgacgtga | tcccggcgcg | 1200 |
| ggtgctcgag | cgtggcgact | tcctggggca | gaccacgctg | acgcgggaac | cggtactggc | 1260 |
| gaccgcgcac | gcgctggagg | aagtcaccgt | gctggagatg | gcccgtgacg | agatcgagcg | 1320 |
| cctggtgcac | cgaaagccga | tcctgctgca | cgtgatcggg | gccgtg | | 1366 |

<210> SEQ ID NO 121
<211> LENGTH: 455
<212> TYPE: PRT
<213> ORGANISM: Mycobacterium vaccae
<220> FEATURE:
<221> NAME/KEY: UNSURE
<222> LOCATION: (318)...(318)
<221> NAME/KEY: UNSURE
<222> LOCATION: (324)...(324)

<400> SEQUENCE: 121

Met Ser Ser Val Leu Asn Ser Thr Trp Leu Ala Trp Ala Val Ala Val
1               5                   10                  15

Ala Val Gly Phe Pro Val Leu Leu Val Val Leu Thr Glu Val His Asn
                20                  25                  30

Ala Leu Arg Arg Arg Gly Ser Ala Leu Ala Arg Pro Val Gln Leu Leu

```
            35                  40                  45
Arg Thr Tyr Ile Leu Pro Leu Gly Ala Leu Leu Leu Leu Val Gln
        50                  55                  60

Ala Met Glu Ile Ser Asp Asp Ala Thr Ser Val Arg Leu Val Ala Thr
65                  70                  75                  80

Leu Phe Gly Val Leu Leu Thr Leu Val Leu Ser Gly Leu Asn Ala
                85                  90                  95

Thr Leu Ile Gln Gly Ala Pro Glu Asp Ser Trp Arg Arg Ile Pro
            100                 105                 110

Ser Ile Phe Leu Asp Val Ala Arg Phe Ala Leu Ile Ala Val Gly Ile
            115                 120                 125

Thr Val Ile Met Ala Tyr Val Trp Gly Ala Asn Val Gly Gly Leu Phe
        130                 135                 140

Thr Ala Leu Gly Val Thr Ser Ile Val Leu Gly Leu Ala Leu Gln Asn
145                 150                 155                 160

Ser Val Gly Gln Ile Ile Ser Gly Leu Leu Leu Leu Phe Glu Gln Pro
                165                 170                 175

Phe Arg Leu Gly Asp Trp Ile Thr Val Pro Thr Ala Ala Gly Arg Pro
            180                 185                 190

Ser Ala His Gly Arg Val Val Glu Val Asn Trp Arg Ala Thr His Ile
        195                 200                 205

Asp Thr Gly Gly Asn Leu Leu Val Met Pro Asn Ala Glu Leu Ala Gly
    210                 215                 220

Ala Ser Phe Thr Asn Tyr Ser Arg Pro Val Gly Glu His Arg Leu Thr
225                 230                 235                 240

Val Val Thr Thr Phe Asn Ala Ala Asp Thr Pro Asp Val Cys Glu
                245                 250                 255

Met Leu Ser Ser Val Ala Ala Ser Leu Pro Glu Leu Arg Thr Asp Gly
            260                 265                 270

Gln Ile Ala Thr Leu Tyr Leu Gly Ala Ala Glu Tyr Glu Lys Ser Ile
        275                 280                 285

Pro Leu His Thr Pro Ala Val Asp Asp Ser Val Arg Ser Thr Tyr Leu
            290                 295                 300

Arg Trp Val Trp Tyr Ala Ala Arg Arg Gln Glu Leu Arg Xaa Asn Gly
305                 310                 315                 320

Val Ala Asp Xaa Phe Asp Thr Pro Glu Arg Ile Ala Ser Ala Met Arg
                325                 330                 335

Ala Val Ala Ser Thr Leu Arg Leu Ala Asp Asp Glu Gln Gln Glu Ile
            340                 345                 350

Ala Asp Val Val Arg Leu Val Arg Tyr Gly Asn Gly Glu Arg Leu Gln
        355                 360                 365

Gln Pro Gly Gln Val Pro Thr Gly Met Arg Phe Ile Val Asp Gly Arg
    370                 375                 380

Val Ser Leu Ser Val Ile Asp Gln Asp Gly Asp Val Ile Pro Ala Arg
385                 390                 395                 400

Val Leu Glu Arg Gly Asp Phe Leu Gly Gln Thr Thr Leu Thr Arg Glu
                405                 410                 415

Pro Val Leu Ala Thr Ala His Ala Leu Glu Glu Val Thr Val Leu Glu
            420                 425                 430

Met Ala Arg Asp Glu Ile Glu Arg Leu Val His Arg Lys Pro Ile Leu
        435                 440                 445

Leu His Val Ile Gly Ala Val
450                 455
```

-continued

<210> SEQ ID NO 122
<211> LENGTH: 898
<212> TYPE: DNA
<213> ORGANISM: Mycobacterium vaccae

<400> SEQUENCE: 122

```
atgacaattc tgccctggaa tgcgcgaacg tctgaacacc cgacgcgaaa aagacgcggg     60
cgctaccacc tcctgtcgcg gatgagcatc cagtccaagt tgctgctgat gctgcttctg    120
accagcattc tctcggctgc ggtggtcggt ttcatcggct atcagtccgg acggtcctcg    180
ctgcgcgcat cggtgttcga ccgcctcacc gacatccgcg agtcgcagtc gcgcgggttg    240
gagaatcagt tcgcggacct gaagaactcg atggtgattt actcgcgcgg cagcactgcc    300
acggaggcga tcggcgcgtt cagcgacggt ttccgtcagc tcggcgatgc gacgatcaat    360
accgggcagg cggcgtcatt gcgccgttac tacgaccgga cgttcgccaa caccaccctc    420
gacgacagcg gaaaccgcgt cgacgtccgc gcgctcatcc cgaaatccaa cccccagcgc    480
tatctgcagg cgctctatac cccgccgttt cagaactggg agaaggcgat cgcgttcgac    540
gacgcgcgcg acggcagcgc ctggtcggcc gccaatgcca gattcaacga gttcttccgc    600
gagatcgtgc accgcttcaa cttcgaggat ctgatgctgc tcgacctcga gggcaacgtg    660
gtgtactccg cctacaaggg gccggatctc gggacaaaca tcgtcaacgg cccctatcgc    720
aaccgggaac tgtcggaagc ctacgagaag gcggtcgcgt cgaactcgat cgactatgtc    780
ggtgtcaccg acttcgggtg gtacctgcct gccgaggaac cgaccgcctg gttcctgtcc    840
ccggtcgggt tgaaggaccg agtcgacggt gtgatggcgg tccagttccc cggaattc       898
```

<210> SEQ ID NO 123
<211> LENGTH: 1259
<212> TYPE: DNA
<213> ORGANISM: Mycobacterium vaccae

<400> SEQUENCE: 123

```
cgcaattgat gacggcgcgg ggacagtggc gtgacaccgg gatgggagac accggtgaga     60
ccatcctggt cggaccggac aatctgatgc gctcggactc ccggctgttc cgcgagaacc    120
gggagaagtt cctggccgac gtcgtcgagg ggggaacccc gccggaggtc gccgacgaat    180
cggttgaccg ccgcggcacc acgctggtgc agccggtgac cacccgctcc gtcgaggagg    240
cccaacgcgg caacaccggg acgacgatcg aggacgacta tctcggccac gaggcgttac    300
aggcgtactc accggtggac ctgccgggac tgcactgggt gatcgtggcc aagatcgaca    360
ccgacgaggc gttcgccccg gtggcgcagt tcaccaggac cctggtgctg tcgacggtga    420
tcatcatctt cggcgtgtcg ctggcggcca tgctgctggc gcggttgttc gtccgtccga    480
tccggcggtt gcaggccggc gcccagcaga tcagcggcgg tgactaccgc ctcgctctgc    540
cggtgttgtc tcgtgacgaa ttcggcgatc tgacaacagc tttcaacgac atgagtcgca    600
atctgtcgat caaggacgag ctgctcggcg aggagcgcgc cgagaaccaa cggctgatgc    660
tgtccctgat gcccgaaccg gtgatgcagc gctacctcga cggggaggag acgatcgccc    720
aggaccacaa gaacgtcacg gtgatcttcg ccgacatgat gggcctcgac gagttgtcgc    780
gcatgttgac ctccgaggaa ctgatggtgg tggtcaacga cctgacccgc cagttcgacg    840
ccgccgccga gagtctcggg gtcgaccacg tgcggacgct gcacgacggg tacctggcca    900
gctgcgggtt aggcgtgccg cggctggaca acgtccggcg cacggtcaat ttcgcgatcg    960
```

```
aaatggaccg catcatcgac cggcacgccg ccgagtccgg gcacgacctg cggctccgcg    1020
cgggcatcga caccgggtcg gcggccagcg ggctggtggg gcggtccacg ttggcgtacg    1080
acatgtgggg ttcggcggtc gatgtcgcct accaggtgca gcgcggctcc ccccagcccg    1140
gcatctacgt cacctcgcgg gtgcacgagg tcatgcagga aactctcgac ttcgtcgccg    1200
ccggggaggt cgtcggcgag cgcggcgtcg agacggtctg gcggttgcag ggccacccg     1259
```

<210> SEQ ID NO 124
<211> LENGTH: 299
<212> TYPE: PRT
<213> ORGANISM: Mycobacterium vaccae

<400> SEQUENCE: 124

```
Met Thr Ile Leu Pro Trp Asn Ala Arg Thr Ser Glu His Pro Thr Arg
1               5                   10                  15

Lys Arg Arg Gly Arg Tyr His Leu Leu Ser Arg Met Ser Ile Gln Ser
            20                  25                  30

Lys Leu Leu Leu Met Leu Leu Leu Thr Ser Ile Leu Ser Ala Ala Val
        35                  40                  45

Val Gly Phe Ile Gly Tyr Gln Ser Gly Arg Ser Ser Leu Arg Ala Ser
    50                  55                  60

Val Phe Asp Arg Leu Thr Asp Ile Arg Glu Ser Gln Ser Arg Gly Leu
65                  70                  75                  80

Glu Asn Gln Phe Ala Asp Leu Lys Asn Ser Met Val Ile Tyr Ser Arg
                85                  90                  95

Gly Ser Thr Ala Thr Glu Ala Ile Gly Ala Phe Ser Asp Gly Phe Arg
            100                 105                 110

Gln Leu Gly Asp Ala Thr Ile Asn Thr Gly Gln Ala Ala Ser Leu Arg
        115                 120                 125

Arg Tyr Tyr Asp Arg Thr Phe Ala Asn Thr Thr Leu Asp Asp Ser Gly
    130                 135                 140

Asn Arg Val Asp Val Arg Ala Leu Ile Pro Lys Ser Asn Pro Gln Arg
145                 150                 155                 160

Tyr Leu Gln Ala Leu Tyr Thr Pro Pro Phe Gln Asn Trp Glu Lys Ala
                165                 170                 175

Ile Ala Phe Asp Asp Ala Arg Asp Gly Ser Ala Trp Ser Ala Ala Asn
            180                 185                 190

Ala Arg Phe Asn Glu Phe Phe Arg Glu Ile Val His Arg Phe Asn Phe
        195                 200                 205

Glu Asp Leu Met Leu Leu Asp Leu Glu Gly Asn Val Val Tyr Ser Ala
    210                 215                 220

Tyr Lys Gly Pro Asp Leu Gly Thr Asn Ile Val Asn Gly Pro Tyr Arg
225                 230                 235                 240

Asn Arg Glu Leu Ser Glu Ala Tyr Glu Lys Ala Val Ala Ser Asn Ser
                245                 250                 255

Ile Asp Tyr Val Gly Val Thr Asp Phe Gly Trp Tyr Leu Pro Ala Glu
            260                 265                 270

Glu Pro Thr Ala Trp Phe Leu Ser Pro Val Gly Leu Lys Asp Arg Val
        275                 280                 285

Asp Gly Val Met Ala Val Gln Phe Pro Gly Ile
    290                 295
```

<210> SEQ ID NO 125
<211> LENGTH: 419
<212> TYPE: PRT

-continued

<213> ORGANISM: Mycobacterium vaccae

<400> SEQUENCE: 125

```
Gln Leu Met Thr Ala Arg Gly Gln Trp Arg Asp Thr Gly Met Gly Asp
  1               5                  10                  15
Thr Gly Glu Thr Ile Leu Val Gly Pro Asp Asn Leu Met Arg Ser Asp
             20                  25                  30
Ser Arg Leu Phe Arg Glu Asn Arg Glu Lys Phe Leu Ala Asp Val Val
         35                  40                  45
Glu Gly Gly Thr Pro Pro Glu Val Ala Asp Gly Ser Val Asp Arg Arg
     50                  55                  60
Gly Thr Thr Leu Val Gln Pro Val Thr Thr Arg Ser Val Glu Glu Ala
 65                  70                  75                  80
Gln Arg Gly Asn Thr Gly Thr Thr Ile Glu Asp Asp Tyr Leu Gly His
                 85                  90                  95
Glu Ala Leu Gln Ala Tyr Ser Pro Val Asp Leu Pro Gly Leu His Trp
            100                 105                 110
Val Ile Val Ala Lys Ile Asp Thr Asp Glu Ala Phe Ala Pro Val Ala
        115                 120                 125
Gln Phe Thr Arg Thr Leu Val Leu Ser Thr Val Ile Ile Phe Gly
    130                 135                 140
Val Ser Leu Ala Ala Met Leu Leu Ala Arg Leu Phe Val Arg Pro Ile
145                 150                 155                 160
Arg Arg Leu Gln Ala Gly Ala Gln Gln Ile Ser Gly Gly Asp Tyr Arg
                165                 170                 175
Leu Ala Leu Pro Val Leu Ser Arg Asp Glu Phe Gly Asp Leu Thr Thr
            180                 185                 190
Ala Phe Asn Asp Met Ser Arg Asn Leu Ser Ile Lys Asp Glu Leu Leu
        195                 200                 205
Gly Glu Glu Arg Ala Glu Asn Gln Arg Leu Met Leu Ser Leu Met Pro
    210                 215                 220
Glu Pro Val Met Gln Arg Tyr Leu Asp Gly Glu Glu Thr Ile Ala Gln
225                 230                 235                 240
Asp His Lys Asn Val Thr Val Ile Phe Ala Asp Met Met Gly Leu Asp
                245                 250                 255
Glu Leu Ser Arg Met Leu Thr Ser Glu Glu Leu Met Val Val Val Asn
            260                 265                 270
Asp Leu Thr Arg Gln Phe Asp Ala Ala Ala Glu Ser Leu Gly Val Asp
        275                 280                 285
His Val Arg Thr Leu His Asp Gly Tyr Leu Ala Ser Cys Gly Leu Gly
    290                 295                 300
Val Pro Arg Leu Asp Asn Val Arg Arg Thr Val Asn Phe Ala Ile Glu
305                 310                 315                 320
Met Asp Arg Ile Ile Asp Arg His Ala Ala Glu Ser Gly His Asp Leu
                325                 330                 335
Arg Leu Arg Ala Gly Ile Asp Thr Gly Ser Ala Ala Ser Gly Leu Val
            340                 345                 350
Gly Arg Ser Thr Leu Ala Tyr Asp Met Trp Gly Ser Ala Val Asp Val
        355                 360                 365
Ala Tyr Gln Val Gln Arg Gly Ser Pro Gln Pro Gly Ile Tyr Val Thr
    370                 375                 380
Ser Arg Val His Glu Val Met Gln Glu Thr Leu Asp Phe Val Ala Ala
385                 390                 395                 400
```

Gly Glu Val Val Gly Glu Arg Gly Val Glu Thr Val Trp Arg Leu Gln
            405                 410                 415

Gly His Pro

<210> SEQ ID NO 126
<211> LENGTH: 27
<212> TYPE: DNA
<213> ORGANISM: Artificial Sequence
<220> FEATURE:
<223> OTHER INFORMATION: Made in a lab

<400> SEQUENCE: 126
ccggatccga tgagcagcgt gctgaac                               27

<210> SEQ ID NO 127
<211> LENGTH: 26
<212> TYPE: DNA
<213> ORGANISM: Artificial Sequence
<220> FEATURE:
<223> OTHER INFORMATION: Made in a lab

<400> SEQUENCE: 127
gcggatccca cggccccgat cacgtg                                26

<210> SEQ ID NO 128
<211> LENGTH: 33
<212> TYPE: DNA
<213> ORGANISM: Artificial Sequence
<220> FEATURE:
<223> OTHER INFORMATION: Made in a lab

<400> SEQUENCE: 128
ccggatccaa tgacatttct gccctggaat gcg                        33

<210> SEQ ID NO 129
<211> LENGTH: 32
<212> TYPE: DNA
<213> ORGANISM: Artificial Sequence
<220> FEATURE:
<223> OTHER INFORMATION: Made in a lab

<400> SEQUENCE: 129
ccggatccat tcggtggccc tgcaaccgcc ag                         32

<210> SEQ ID NO 130
<211> LENGTH: 27
<212> TYPE: DNA
<213> ORGANISM: Artificial Sequence
<220> FEATURE:
<223> OTHER INFORMATION: Made in a lab

<400> SEQUENCE: 130
ccggatccgg agcaaccgtt ccggctc                               27

<210> SEQ ID NO 131
<211> LENGTH: 27
<212> TYPE: DNA
<213> ORGANISM: Artificial Sequence
<220> FEATURE:
<223> OTHER INFORMATION: Made in a lab

<400> SEQUENCE: 131
ccggatcccg gctatcagtc cggacgg                               27

<210> SEQ ID NO 132

<211> LENGTH: 844
<212> TYPE: DNA
<213> ORGANISM: Mycobacterium vaccae

<400> SEQUENCE: 132

```
gagcaaccgt tccggctcgg cgactggatc accgtcccca ccgcggcggg ccggccgtcc     60
gcccacggcc gcgtggtgga agtcaactgg cgtgcaacac atatcgacac cggcggcaac    120
ctgctggtaa tgcccaacgc cgaactcgcc ggcgcgtcgt tcaccaatta cagccggccc    180
gtgggagagc accggctgac cgtcgtcacc accttcaacg ccgcggacac ccccgatgat    240
gtctgcgaga tgctgtcgtc ggtcgcggcg tcgctgcccg aactgcgcac cgacggacag    300
atcgccacgc tctatctcgg tgcggccgaa tacgagaagt cgatcccgtt gcacacaccc    360
gcggtggacg actcggtcag gagcacgtac ctgcgatggg tctggtacgc cgcgcgccgg    420
caggaacttc gcctaacggc gtcgccgacg attcgacacg ccggaacgga tcgcctcggc    480
catgcgggct gtggcgtcca cactgcgctt ggcagacgac gaacagcagg agatcgccga    540
cgtggtgcgt ctggtccgtt acggcaacgg ggaacgcctc cagcagccgg gtcaggtacc    600
gaccgggatg aggttcatcg tagacggcag ggtgagtctg tccgtgatcg atcaggacgg    660
cgacgtgatc ccggcgcggg tgctcgagcg tggcgacttc ctgggcagaa ccacgctgac    720
gcgggaaccg gtactggcga ccgcgcacgc gctggaggaa gtcaccgtgc tggagatggc    780
ccgtgacgag atcgagcgcc tggtgcaccg aaagccgatc ctgctgcacg tgatcggggc    840
cgtg                                                                 844
```

<210> SEQ ID NO 133
<211> LENGTH: 742
<212> TYPE: DNA
<213> ORGANISM: Mycobacterium vaccae

<400> SEQUENCE: 133

```
ggctatcagt ccggacggtc ctcgctgcgc gcatcggtgt tcgaccgcct caccgacatc     60
cgcgagtcgc agtcgcgcgg gttggagaat cagttcgcgg acctgaagaa ctcgatggtg    120
atttactcgc gcggcagcac tgccacggag gcgatcggcg cgttcagcga cggtttccgt    180
cagctcggcg atgcgacgat caataccggg caggcggcgt cattgcgccg ttactacgac    240
cggacgttcg ccaacaccac cctcgacgac agcggaaacc gcgtcgacgt ccgcgcgctc    300
atcccgaaat ccaaccccca gcgctatctg caggcgctct ataccccgcc gtttcagaac    360
tgggagaagg cgatcgcgtt cgacgacgcg cgcgacggca gcgcctggtc ggccgccaat    420
gccagattca acgagttctt ccgcgagatc gtgcaccgct caacttcga ggatctgatg     480
ctgctcgacc tcgagggcaa cgtggtgtac tccgcctaca aggggccgga tctcgggaca    540
aacatcgtca acgcccccta tcgcaaccgg gaactgtcgg aagcctacga gaaggcggtc    600
gcgtcgaact cgatcgacta tgtcggtgtc accgacttcg ggtggtacct gcctgccgag    660
gaaccgaccg cctggttcct gtccccggtc gggttgaagg accgagtcga cggtgtgatg    720
gcggtccagt tccccggaat tc                                             742
```

<210> SEQ ID NO 134
<211> LENGTH: 282
<212> TYPE: PRT
<213> ORGANISM: Mycobacterium vaccae
<220> FEATURE:
<221> NAME/KEY: UNSURE
<222> LOCATION: (145)...(145)
<221> NAME/KEY: UNSURE

```
<222> LOCATION: (151)...(151)

<400> SEQUENCE: 134
```

| | | | | | | | | | | | | | | |
|---|---|---|---|---|---|---|---|---|---|---|---|---|---|---|
| Glu | Gln | Pro | Phe | Arg | Leu | Gly | Asp | Trp | Ile | Thr | Val | Pro | Thr | Ala | Ala |
| 1 | | | | 5 | | | | | 10 | | | | | 15 | |

Glu Gln Pro Phe Arg Leu Gly Asp Trp Ile Thr Val Pro Thr Ala Ala
1               5                   10                  15

Gly Arg Pro Ser Ala His Gly Arg Val Val Glu Val Asn Trp Arg Ala
                20              25                  30

Thr His Ile Asp Thr Gly Gly Asn Leu Leu Val Met Pro Asn Ala Glu
            35              40              45

Leu Ala Gly Ala Ser Phe Thr Asn Tyr Ser Arg Pro Val Gly Glu His
    50              55                  60

Arg Leu Thr Val Thr Thr Phe Asn Ala Ala Asp Thr Pro Asp Asp
65              70                  75                  80

Val Cys Glu Met Leu Ser Ser Val Ala Ala Ser Leu Pro Glu Leu Arg
                85              90                  95

Thr Asp Gly Gln Ile Ala Thr Leu Tyr Leu Gly Ala Ala Glu Tyr Glu
                100             105                 110

Lys Ser Ile Pro Leu His Thr Pro Ala Val Asp Asp Ser Val Arg Ser
            115             120                 125

Thr Tyr Leu Arg Trp Val Trp Tyr Ala Ala Arg Gln Glu Leu Arg
    130             135                 140

Xaa Asn Gly Val Ala Asp Xaa Phe Asp Thr Pro Glu Arg Ile Ala Ser
145             150                 155                 160

Ala Met Arg Ala Val Ala Ser Thr Leu Arg Leu Ala Asp Asp Glu Gln
                165             170                 175

Gln Glu Ile Ala Asp Val Val Arg Leu Val Arg Tyr Gly Asn Gly Glu
                180             185                 190

Arg Leu Gln Gln Pro Gly Gln Val Pro Thr Gly Met Arg Phe Ile Val
                195             200                 205

Asp Gly Arg Val Ser Leu Ser Val Ile Asp Gln Asp Gly Asp Val Ile
            210             215                 220

Pro Ala Arg Val Leu Glu Arg Gly Asp Phe Leu Gly Gln Thr Thr Leu
225             230                 235                 240

Thr Arg Glu Pro Val Leu Ala Thr Ala His Ala Leu Glu Glu Val Thr
                245                 250                 255

Val Leu Glu Met Ala Arg Asp Glu Ile Glu Arg Leu Val His Arg Lys
                260                 265                 270

Pro Ile Leu Leu His Val Ile Gly Ala Val
            275                 280

```
<210> SEQ ID NO 135
<211> LENGTH: 247
<212> TYPE: PRT
<213> ORGANISM: Mycobacterium vaccae

<400> SEQUENCE: 135
```

Gly Tyr Gln Ser Gly Arg Ser Ser Leu Arg Ala Ser Val Phe Asp Arg
1               5                   10                  15

Leu Thr Asp Ile Arg Glu Ser Gln Ser Arg Gly Leu Glu Asn Gln Phe
                20              25                  30

Ala Asp Leu Lys Asn Ser Met Val Ile Tyr Ser Arg Gly Ser Thr Ala
            35              40                  45

Thr Glu Ala Ile Gly Ala Phe Ser Asp Gly Phe Arg Gln Leu Gly Asp
    50              55                  60

Ala Thr Ile Asn Thr Gly Gln Ala Ala Ser Leu Arg Arg Tyr Tyr Asp

-continued

```
                65                  70                  75                  80
            Arg Thr Phe Ala Asn Thr Thr Leu Asp Asp Ser Gly Asn Arg Val Asp
                            85                  90                  95

Val Arg Ala Leu Ile Pro Lys Ser Asn Pro Gln Arg Tyr Leu Gln Ala
                        100                 105                 110

Leu Tyr Thr Pro Pro Phe Gln Asn Trp Glu Lys Ala Ile Ala Phe Asp
                    115                 120                 125

Asp Ala Arg Asp Gly Ser Ala Trp Ser Ala Ala Asn Ala Arg Phe Asn
                130                 135                 140

Glu Phe Phe Arg Glu Ile Val His Arg Phe Asn Phe Glu Asp Leu Met
            145                 150                 155                 160

Leu Leu Asp Leu Glu Gly Asn Val Val Tyr Ser Ala Tyr Lys Gly Pro
                            165                 170                 175

Asp Leu Gly Thr Asn Ile Val Asn Gly Pro Tyr Arg Asn Arg Glu Leu
                        180                 185                 190

Ser Glu Ala Tyr Glu Lys Ala Val Ala Ser Asn Ser Ile Asp Tyr Val
                    195                 200                 205

Gly Val Thr Asp Phe Gly Trp Tyr Leu Pro Ala Glu Glu Pro Thr Ala
                210                 215                 220

Trp Phe Leu Ser Pro Val Gly Leu Lys Asp Arg Val Asp Gly Val Met
            225                 230                 235                 240

Ala Val Gln Phe Pro Gly Ile
                            245

<210> SEQ ID NO 136
<211> LENGTH: 45
<212> TYPE: DNA
<213> ORGANISM: Mycobacterium vaccae
<220> FEATURE:
<221> NAME/KEY: unsure
<222> LOCATION: (18)...(18)

<400> SEQUENCE: 136
atgagcgaaa tcgcccgncc ctggcgggtt ctggcatgtg gcatc              45

<210> SEQ ID NO 137
<211> LENGTH: 340
<212> TYPE: DNA
<213> ORGANISM: Mycobacterium vaccae
<220> FEATURE:
<221> NAME/KEY: unsure
<222> LOCATION: (273)...(273)
<221> NAME/KEY: unsure
<222> LOCATION: (286)...(286)

<400> SEQUENCE: 137
gccaccggcg gcgccgccgc ggtgcccgcc ggggtgagcg ccccggcggt cgcgccggcc      60
cccgcgatgc ccgcccgccc ggtgtccacg atcgcgccgg cgacctcggg cacgctcagc    120 gagttttctcg ccgccaaggg cgtcacgatg gagccgcagt ccagccgcga cttccgcgcc    180
ctcaacatcg tgctgccgaa gccgcggggc tgggagcaca tcccggaccc gaacgtgccg    240
gacgcgttcg cggtgctggc cgaccgggtc agnggtaaag gtcagnagtc gacaaacgcc    300
cacgtggtgg tcgacaaaca cgtaggcgag ttcgacggca                          340

<210> SEQ ID NO 138
<211> LENGTH: 235
<212> TYPE: DNA
<213> ORGANISM: Mycobacterium vaccae
<220> FEATURE:
```

```
<221> NAME/KEY: unsure
<222> LOCATION: (16)...(16)

<400> SEQUENCE: 138
ggtgaccacc agcgtngaac aggtcgttgc cgaagccgcg gaggccaccg acgcgattgt      60
caacggcttc aaggtcagcg ttccgggtcc gggtccggcc gcaccgccac ctgcacccgg     120 tgccccggt gtcccgcccg ccccggcgc cccggcgctg ccgctggccg tcgcaccacc      180
cccggctccc gctgttcccg ccgtggcgcc cgcgccacag ctgctgggac tgcag         235

<210> SEQ ID NO 139
<211> LENGTH: 15
<212> TYPE: PRT
<213> ORGANISM: Mycobacterium vaccae

<400> SEQUENCE: 139

Met Ser Glu Ile Ala Arg Pro Trp Arg Val Leu Ala Cys Gly Ile
 1               5                  10                  15

<210> SEQ ID NO 140
<211> LENGTH: 113
<212> TYPE: PRT
<213> ORGANISM: Mycobacterium vaccae
<220> FEATURE:
<221> NAME/KEY: UNSURE
<222> LOCATION: (96)...(96)

<400> SEQUENCE: 140

Ala Thr Gly Gly Ala Ala Ala Val Pro Ala Gly Val Ser Ala Pro Ala
 1               5                  10                  15

Val Ala Pro Ala Pro Ala Met Pro Ala Arg Pro Val Ser Thr Ile Ala
                20                  25                  30

Pro Ala Thr Ser Gly Thr Leu Ser Glu Phe Phe Ala Ala Lys Gly Val
            35                  40                  45

Thr Met Glu Pro Gln Ser Ser Arg Asp Phe Arg Ala Leu Asn Ile Val
        50                  55                  60

Leu Pro Lys Pro Arg Gly Trp Glu His Ile Pro Asp Pro Asn Val Pro
 65                  70                  75                  80

Asp Ala Phe Ala Val Leu Ala Asp Arg Val Gly Gly Lys Gly Gln Xaa
                85                  90                  95

Ser Thr Asn Ala His Val Val Asp Lys His Val Gly Glu Phe Asp
            100                 105                 110

Gly

<210> SEQ ID NO 141
<211> LENGTH: 73
<212> TYPE: PRT
<213> ORGANISM: Mycobacterium vaccae

<400> SEQUENCE: 141

Val Thr Thr Ser Val Glu Gln Val Val Ala Ala Asp Ala Thr Glu
 1               5                  10                  15

Ala Ile Val Asn Gly Phe Lys Val Ser Val Pro Gly Pro Gly Pro Ala
                20                  25                  30

Ala Pro Pro Pro Ala Pro Gly Ala Pro Gly Val Pro Ala Pro Gly
            35                  40                  45

Ala Pro Ala Leu Pro Leu Ala Val Ala Pro Pro Ala Pro Ala Val
        50                  55                  60

Pro Ala Val Ala Pro Ala Pro Gln Leu
```

<210> SEQ ID NO 142
<211> LENGTH: 273
<212> TYPE: DNA
<213> ORGANISM: Mycobacterium vaccae

<400> SEQUENCE: 142

| | | | | | |
|---|---|---|---|---|---|
| gcgacctacg | tgcagggggg | tctcggccgc | atcgaggccc | gggtggccga | cagcggatac | 60 |
| agcaacgccg | cggccaaggg | ctacttcccg | ctgagcttca | ccgtcgccgg | catcgaccag | 120 |
| aacggtccga | tcgtgaccgc | caacgtcacc | gcggcggccc | cgacgggcgc | cgtggccacc | 180 |
| cagccgctga | cgttcatcgc | cgggccgagc | ccgaccggat | ggcagctgtc | caagcagtcc | 240 |
| gcactggccc | tgatgtccgc | ggtcatcgcc | gca | | | 273 |

<210> SEQ ID NO 143
<211> LENGTH: 91
<212> TYPE: PRT
<213> ORGANISM: Mycobacterium vaccae

<400> SEQUENCE: 143

Ala Thr Tyr Val Gln Gly Gly Leu Gly Arg Ile Glu Ala Arg Val Ala
1               5                   10                  15

Asp Ser Gly Tyr Ser Asn Ala Ala Lys Gly Tyr Phe Pro Leu Ser
            20                  25                  30

Phe Thr Val Ala Gly Ile Asp Gln Asn Gly Pro Ile Val Thr Ala Asn
        35                  40                  45

Val Thr Ala Ala Ala Pro Thr Gly Ala Val Ala Thr Gln Pro Leu Thr
    50                  55                  60

Phe Ile Ala Gly Pro Ser Pro Thr Gly Trp Gln Leu Ser Lys Gln Ser
65                  70                  75                  80

Ala Leu Ala Leu Met Ser Ala Val Ile Ala Ala
                85                  90

<210> SEQ ID NO 144
<211> LENGTH: 554
<212> TYPE: DNA
<213> ORGANISM: Mycobacterium vaccae

<400> SEQUENCE: 144

| | | | | | |
|---|---|---|---|---|---|
| gatgtcacgc | ccggagaatg | taacgttcga | ccggagaacg | ccgtcggcac | aacgagttac | 60 |
| gtttgagcac | ttcagatctc | ggttaccttg | gatttcaggc | gggggaagca | gtaaccgatc | 120 |
| caagattcga | aggacccaaa | caacatgaaa | ttcactggaa | tgaccgtgcg | cgcaagccgc | 180 |
| gcgccctggc | cggcgtcggg | gcggcatgtc | tgttcggcgg | cgtggccgcg | caaccgtgg | 240 |
| cggcacagat | ggcgggcgcc | cagccggccg | agtgcaacgc | cagctcactc | accggcaccg | 300 |
| tcagctcggt | gaccggtcag | gcgcgtcagt | acctagacac | ccacccgggc | gccaaccagg | 360 |
| ccgtcaccgc | ggcgatgaac | cagccgcggc | ccgaggccga | ggcgaacctg | cggggctact | 420 |
| tcaccgccaa | cccggcggag | tactacgacc | tgcggggcat | cctcgccccg | atcggtgacg | 480 |
| cgcagcgcaa | ctgcaacatc | accgtgctgc | cggtagagct | gcagacggcc | tacgacacgt | 540 |
| tcatggccgg | ctga | | | | | 554 |

<210> SEQ ID NO 145
<211> LENGTH: 136
<212> TYPE: PRT
<213> ORGANISM: Mycobacterium vaccae

<400> SEQUENCE: 145

Met Lys Phe Thr Gly Met Thr Val Arg Ala Ser Arg Arg Ala Leu Ala
1               5                   10                  15

Gly Val Gly Ala Ala Cys Leu Phe Gly Val Ala Ala Thr Val
            20                  25                  30

Ala Ala Gln Met Ala Gly Ala Gln Pro Ala Glu Cys Asn Ala Ser Ser
            35                  40                  45

Leu Thr Gly Thr Val Ser Ser Val Thr Gly Gln Ala Arg Gln Tyr Leu
            50                  55                  60

Asp Thr His Pro Gly Ala Asn Gln Ala Val Thr Ala Ala Met Asn Gln
65                  70                  75                  80

Pro Arg Pro Glu Ala Glu Ala Asn Leu Arg Gly Tyr Phe Thr Ala Asn
                85                  90                  95

Pro Ala Glu Tyr Tyr Asp Leu Arg Gly Ile Leu Ala Pro Ile Gly Asp
                100                 105                 110

Ala Gln Arg Asn Cys Asn Ile Thr Val Leu Pro Val Glu Leu Gln Thr
            115                 120                 125

Ala Tyr Asp Thr Phe Met Ala Gly
130                 135

<210> SEQ ID NO 146
<211> LENGTH: 808
<212> TYPE: DNA
<213> ORGANISM: Mycobacterium vaccae
<220> FEATURE:
<221> NAME/KEY: unsure
<222> LOCATION: (15)...(15)

<400> SEQUENCE: 146
ccaagtgtga cgcgngtgtg acggtagacg ttccgaccaa tccaacgacg ccgcagctgg     60
gaatcacccg tgtgccaatt cagtgcgggc aacggtgtcc gtccacgaag ggattcagga    120
aatgatgaca actcgccgga agtcagccga agtggcggga atcgctgcgg tggccatcct    180
cggtgcggcc gcatgttcga gtgaggacgg tgggagcacg gcctcgtcgg ccagcagcac    240
ggcctcctcc gcgatggagt ccgcgaccga cgagatgacc acgtcgtcgg cggccccttc    300
ggccgaccct gcggccaacc tgatcggctc cggctgcgcg gcctacgccg agcaggtccc    360
cgaaggtccc gggtcggtgg ccgggatggc agccgatccg gtgacggtgg cggcgtcgaa    420
caacccgatg ctgcagacgc tgtcccaggc gctgtccggc agctcaatc cgcaggtcaa     480 tctcgtcgac accctcgacg gcggtgagtt caccgtgttc gcgccgaccg acgacgcgtt    540
cgccaagatc gatccggcca cgctggagac cctcaagacg gactccgaca tgctgaccaa    600
catcctgacc taccacgtcg tgcccggcca ggccgcgccc gatcaggtgg tcggcgagca    660
tgtgacggtg gaggggcgc cggtcacggt gtccgggatg ccgaccagc tcaaggtcaa     720 cgacgcgtcg gtggtgtgcg gtggggtgca gaccgccaac gcgacggtgt atctgatcga    780
caccgtgctg atgccgccgg cagcgtag                                       808

<210> SEQ ID NO 147
<211> LENGTH: 228
<212> TYPE: PRT
<213> ORGANISM: Mycobacterium vaccae

<400> SEQUENCE: 147

Met Met Thr Thr Arg Arg Lys Ser Ala Ala Val Ala Gly Ile Ala Ala
1               5                   10                  15

-continued

```
Val Ala Ile Leu Gly Ala Ala Cys Ser Ser Glu Asp Gly Ser
            20                  25                  30

Thr Ala Ser Ser Ala Ser Ser Thr Ala Ser Ser Ala Met Glu Ser Ala
        35                  40                  45

Thr Asp Glu Met Thr Thr Ser Ser Ala Ala Pro Ser Ala Asp Pro Ala
 50                  55                  60

Ala Asn Leu Ile Gly Ser Gly Cys Ala Ala Tyr Ala Glu Gln Val Pro
 65                  70                  75                  80

Glu Gly Pro Gly Ser Val Ala Gly Met Ala Ala Asp Pro Val Thr Val
                85                  90                  95

Ala Ala Ser Asn Asn Pro Met Leu Gln Thr Leu Ser Gln Ala Leu Ser
            100                 105                 110

Gly Gln Leu Asn Pro Gln Val Asn Leu Val Asp Thr Leu Asp Gly Gly
            115                 120                 125

Glu Phe Thr Val Phe Ala Pro Thr Asp Asp Ala Phe Ala Lys Ile Asp
    130                 135                 140

Pro Ala Thr Leu Glu Thr Leu Lys Thr Asp Ser Asp Met Leu Thr Asn
145                 150                 155                 160

Ile Leu Thr Tyr His Val Val Pro Gly Gln Ala Ala Pro Asp Gln Val
                165                 170                 175

Val Gly Glu His Val Thr Val Glu Gly Ala Pro Val Thr Val Ser Gly
            180                 185                 190

Met Ala Asp Gln Leu Lys Val Asn Asp Ala Ser Val Val Cys Gly Gly
            195                 200                 205

Val Gln Thr Ala Asn Ala Thr Val Tyr Leu Ile Asp Thr Val Leu Met
    210                 215                 220

Pro Pro Ala Ala
225
```

<210> SEQ ID NO 148
<211> LENGTH: 22
<212> TYPE: DNA
<213> ORGANISM: Artificial Sequence
<220> FEATURE:
<223> OTHER INFORMATION: Made in a lab
<220> FEATURE:
<221> NAME/KEY: unsure
<222> LOCATION: (12)...(12)
<221> NAME/KEY: unsure
<222> LOCATION: (17)...(17)

<400> SEQUENCE: 148
gcsccsgtsg gnccggntgy gc                                          22

<210> SEQ ID NO 149
<211> LENGTH: 21
<212> TYPE: DNA
<213> ORGANISM: Artificial Sequence
<220> FEATURE:
<223> OTHER INFORMATION: Made in a lab
<220> FEATURE:
<221> NAME/KEY: unsure
<222> LOCATION: (10)...(10)
<221> NAME/KEY: unsure
<222> LOCATION: (13)...(13)
<221> NAME/KEY: unsure
<222> LOCATION: (16)...(16)
<221> NAME/KEY: unsure
<222> LOCATION: (20)...(20)

<400> SEQUENCE: 149

-continued

```
rtasgcsgcn gtngcnacng g                                              21

<210> SEQ ID NO 150
<211> LENGTH: 102
<212> TYPE: DNA
<213> ORGANISM: Artificial Sequence
<220> FEATURE:
<223> OTHER INFORMATION: Made in a lab

<400> SEQUENCE: 150 gccccgtcg gccccggctg tgcggcctac gtgcaacagg tgccggacgg gccgggatcg      60
gtgcagggca tggcgagctc gcccgtagcg accgccgcgt at                      102

<210> SEQ ID NO 151
<211> LENGTH: 683
<212> TYPE: DNA
<213> ORGANISM: Mycobacterium vaccae

<400> SEQUENCE: 151
gcccgccaac taaaaccgcc gatcatccac tgcaggaagg aatctcacga tcatgaacat     60
cagcatgaaa actcttgccg gagcgggttt cgcgatgacc gccgccgtcg gtctgtcgct    120
gggtaccgca ggcagcgccg cagccgcgcc ggtcggaccg gggtgtgcgg cctacgtgca    180
acaggtgccg gacgggccgg gatcggtgca gggcatggcg agctcgccgg tggccaccgc    240
ggcggccgac aacccgctgc tcaccacgct ctcgcaggcg atctcgggtc agctcaaccc    300
gaacgtcaat ctcgtcgaca cgttcaacgg cggccagttc accgtgttcg cgccgaccaa    360
tgacgccttc gccaagatcg atccggccac gctggagacc ctcaagaccg attccgacct    420
gctgaccaag atcctcacct accacgtcgt gcccggccag gccgcgcccg atcaggtggt    480
cggcgagcat gtgacggtgg aggggcgcc ggtcacggtg tccgggatgg ccgaccagct    540
caaggtcaac gacgcgtcgg tggtgtgcgg tggggtgcag accgccaacg cgacggtgta    600
tctgatcgac accgtgctga tgccgccggc agcgtagccg ggcggcacca cagaagaggg    660 tccccgcac ccggcctccc ccg                                            683

<210> SEQ ID NO 152
<211> LENGTH: 231
<212> TYPE: PRT
<213> ORGANISM: Mycobacterium vaccae

<400> SEQUENCE: 152

Asp Thr Val Leu Met Pro Pro Ala Asn Asn Arg Arg Ser Ser Thr Ala
 1               5                  10                  15

Gly Arg Asn Leu Thr Ile Met Asn Ile Ser Met Lys Thr Leu Ala Gly
            20                  25                  30

Ala Gly Phe Ala Met Thr Ala Ala Val Gly Leu Ser Leu Gly Thr Ala
        35                  40                  45

Gly Ser Ala Ala Ala Pro Val Gly Pro Gly Cys Ala Ala Tyr Val
    50                  55                  60

Gln Gln Val Pro Asp Gly Pro Gly Ser Val Gln Gly Met Ala Ser Ser
65                  70                  75                  80

Pro Val Ala Thr Ala Ala Ala Asp Asn Pro Leu Leu Thr Thr Leu Ser
                85                  90                  95

Gln Ala Ile Ser Gly Gln Leu Asn Pro Asn Val Asn Leu Val Asp Thr
            100                 105                 110

Phe Asn Gly Gly Gln Phe Thr Val Phe Ala Pro Thr Asn Asp Ala Phe
        115                 120                 125
```

```
Ala Lys Ile Asp Pro Ala Thr Leu Glu Thr Leu Lys Thr Asp Ser Asp
    130                 135                 140

Leu Leu Thr Lys Ile Leu Thr Tyr His Val Val Pro Gly Gln Ala Ala
145                 150                 155                 160

Pro Asp Gln Val Val Gly Glu His Val Thr Val Glu Gly Ala Pro Val
                165                 170                 175

Thr Val Ser Gly Met Ala Asp Gln Leu Lys Val Asn Asp Ala Ser Val
            180                 185                 190

Val Cys Gly Gly Val Gln Thr Ala Asn Ala Thr Val Tyr Leu Ile Asp
        195                 200                 205

Thr Val Leu Met Pro Pro Ala Ala Pro Gly Gly Thr Thr Glu Glu Gly
    210                 215                 220

Pro Pro His Pro Ala Ser Pro
225                 230
```

```
<210> SEQ ID NO 153
<211> LENGTH: 1125
<212> TYPE: DNA
<213> ORGANISM: Mycobacterium vaccae
<220> FEATURE:
<221> NAME/KEY: unsure
<222> LOCATION: (358)...(358)

<400> SEQUENCE: 153
```

| | | | | | |
|---|---|---|---|---|---|
| atgcaggtgc | ggcgtgttct | gggcagtgtc | ggtgcagcag | tcgcggtttc | ggccgcgtta | 60 |
| tggcagacgg | gggtttcgat | accgaccgcc | tcagcggatc | cgtgtccgga | catcgaggtg | 120 |
| atcttcgcgc | gcgggaccgg | tgcggaaccc | ggcctcgggt | gggtcggtga | tgcgttcgtc | 180 |
| aacgcgctgc | ggcccaaggt | cggtgagcag | tcggtgggca | cctacgcggt | gaactacccg | 240 |
| gcaggattcg | gacttcgaca | aatcggcgcc | catgggcgcg | gccgacgcat | cggggcgggt | 300 |
| gcagtggatg | gccgacaact | gcccggacac | caagcttgtc | ctgggcggca | tgtcgcangg | 360 |
| cgccggcgtc | atcgacctga | tcaccgtcga | tccgcgaccg | ctgggccggt | tcacccccac | 420 |
| cccgatgccg | ccccgcgtcg | ccgaccacgt | ggccgccgtt | gtggtcttcg | gaaatccgtt | 480 |
| gcgcgacatc | cgtggtggcg | gtccgctgcc | gcagatgagc | ggcacctacg | gccgaagtc | 540 |
| gatcgatctg | tgtgcgctcg | acgatccgtt | ctgctcgccc | ggcttcaacc | tgccggccca | 600 |
| cttcgcctac | gccgacaacg | gcatggtgga | ggaagccgcg | aacttcgccc | gcctggaacc | 660 |
| gggccagagc | gtcgagctgc | cgaggcgcc | ctacctgcac | ctgttcgtcc | cgcggggcga | 720 |
| ggtaacgctg | gaggacgccg | gaccgctgcg | cgaaggcgac | gcagtgcgtt | tcaccgcatc | 780 |
| gggcggccag | cgggtgaccg | ccaccgcgcc | cgcggagatc | ctcgtctggg | agatgcatgc | 840 |
| gggactcggt | gcggcataag | cgaataggag | tcctgctggc | cggcgcagca | ctgctcgccg | 900 |
| gatgcacatc | cgaacctgga | cccgggccgt | cggcggcacc | ggccccgacg | agcacaaccg | 960 |
| agagcgcacc | cggtcccgga | ctcgtcccgg | tgaccgtcgc | ggtcgacgaa | cctctggccg | 1020 |
| acgccgtt | cgaccagccc | cgggaggccc | tggtgccgca | gggttggacg | ctgtcggtgt | 1080 |
| gggcgcggac | cgcccggccg | cggctggccg | cgtgggcccc | ggacg | | 1125 |

```
<210> SEQ ID NO 154
<211> LENGTH: 748
<212> TYPE: PRT
<213> ORGANISM: Mycobacterium vaccae
<220> FEATURE:
<221> NAME/KEY: UNSURE
<222> LOCATION: (119)...(119)
```

-continued

```
<400> SEQUENCE: 154

Met Gln Val Arg Arg Val Leu Gly Ser Val Gly Ala Ala Val Ala Val
 1               5                  10                  15

Ser Ala Ala Leu Trp Gln Thr Gly Val Ser Ile Pro Thr Ala Ser Ala
             20                  25                  30

Asp Pro Cys Pro Asp Ile Glu Val Ile Phe Ala Arg Gly Thr Gly Ala
         35                  40                  45

Glu Pro Gly Leu Gly Trp Val Gly Asp Ala Phe Val Asn Ala Leu Arg
     50                  55                  60

Pro Lys Val Gly Glu Gln Ser Val Gly Thr Tyr Ala Val Asn Tyr Pro
 65                  70                  75                  80

Ala Gly Phe Asp Phe Asp Lys Ser Ala Pro Met Gly Ala Ala Asp Ala
                 85                  90                  95

Ser Gly Arg Val Gln Trp Met Ala Asp Asn Cys Pro Asp Thr Lys Leu
            100                 105                 110

Val Leu Gly Gly Met Ser Xaa Gly Ala Gly Val Ile Asp Leu Ile Thr
        115                 120                 125

Val Asp Pro Arg Pro Leu Gly Arg Phe Thr Pro Thr Pro Met Pro Pro
    130                 135                 140

Arg Val Ala Asp His Val Ala Ala Val Val Phe Gly Asn Pro Leu
145                 150                 155                 160

Arg Asp Ile Arg Gly Gly Pro Arg Leu Glu Pro Arg Gly Leu Asn
                165                 170                 175

Met Glu Thr Ser Glu Arg Gly Leu Tyr Thr His Arg Thr Tyr Arg Gly
                180                 185                 190

Leu Tyr Pro Arg Leu Tyr Ser Ser Glu Arg Ile Leu Glu Ala Ser Pro
            195                 200                 205

Leu Glu Cys Tyr Ser Ala Leu Ala Leu Glu Ala Ser Pro Ala Ser Pro
    210                 215                 220

Pro Arg Pro His Glu Cys Tyr Ser Ser Glu Arg Pro Arg Gly Leu Tyr
225                 230                 235                 240

Pro His Glu Ala Ser Asn Leu Glu Pro Arg Ala Leu Ala His Ile Ser
                245                 250                 255

Pro His Glu Ala Leu Ala Thr Tyr Arg Ala Leu Ala Ala Ser Pro Ala
            260                 265                 270

Ser Asn Gly Leu Tyr Met Glu Thr Val Ala Leu Gly Leu Gly Leu Ala
    275                 280                 285

Leu Ala Ala Leu Ala Ala Ser Asn Pro His Glu Ala Leu Ala Ala Arg
    290                 295                 300

Gly Leu Glu Gly Leu Pro Arg Gly Leu Tyr Gly Leu Asn Ser Glu Arg
305                 310                 315                 320

Val Ala Leu Gly Leu Leu Glu Pro Arg Gly Leu Ala Leu Ala Pro Arg
                325                 330                 335

Thr Tyr Arg Leu Glu His Ile Ser Leu Glu Pro His Glu Val Ala Leu
            340                 345                 350

Pro Arg Ala Arg Gly Gly Leu Tyr Gly Leu Val Ala Leu Thr His Arg
    355                 360                 365

Leu Glu Gly Leu Ala Ser Pro Ala Leu Ala Gly Leu Tyr Pro Arg Leu
    370                 375                 380

Glu Ala Arg Gly Gly Leu Gly Leu Tyr Ala Ser Pro Ala Leu Ala Val
385                 390                 395                 400

Ala Leu Ala Arg Gly Pro His Glu Thr His Arg Ala Leu Ala Ser Glu
```

```
                405                 410                 415
Arg Gly Leu Tyr Gly Leu Tyr Gly Leu Asn Ala Arg Gly Val Ala Leu
            420                 425                 430
Thr His Arg Ala Leu Ala Thr His Arg Ala Leu Ala Pro Arg Ala Leu
            435                 440                 445
Ala Gly Leu Ile Leu Glu Leu Glu Val Ala Leu Thr Arg Pro Gly Leu
            450                 455                 460
Met Glu Thr His Ile Ser Ala Leu Ala Gly Leu Tyr Leu Glu Gly Leu
465                 470                 475                 480
Tyr Ala Leu Ala Ala Leu Ala Leu Ala Ala Ser Asn Ala Arg Gly
                485                 490                 495
Ser Glu Arg Pro Arg Ala Leu Ala Gly Leu Tyr Ala Arg Gly Ala Arg
            500                 505                 510
Gly Ser Glu Arg Thr His Arg Ala Leu Ala Ala Arg Gly Ala Arg Gly
            515                 520                 525
Met Glu Thr His Ile Ser Ile Leu Glu Ala Arg Gly Thr His Arg Thr
            530                 535                 540
Arg Pro Thr His Arg Ala Arg Gly Ala Leu Ala Val Ala Leu Gly Leu
545                 550                 555                 560
Tyr Gly Leu Tyr Thr His Arg Gly Leu Tyr Pro Arg Ala Ser Pro Gly
            565                 570                 575
Leu His Ile Ser Ala Ser Asn Ala Arg Gly Gly Leu Ala Arg Gly Thr
            580                 585                 590
His Arg Ala Arg Gly Ser Glu Arg Ala Arg Gly Thr His Arg Ala Arg
            595                 600                 605
Gly Pro Arg Gly Leu Tyr Ala Ser Pro Ala Arg Gly Ala Arg Gly Gly
            610                 615                 620
Leu Tyr Ala Arg Gly Ala Arg Gly Thr His Arg Ser Glu Arg Gly Leu
625                 630                 635                 640
Tyr Ala Arg Gly Ala Arg Gly Ala Leu Ala Val Ala Leu Ala Arg Gly
            645                 650                 655
Pro Arg Ala Leu Ala Pro Arg Gly Leu Tyr Gly Leu Tyr Pro Arg Gly
            660                 665                 670
Leu Tyr Ala Leu Ala Ala Leu Ala Gly Leu Tyr Leu Glu Ala Ser Pro
            675                 680                 685
Ala Leu Ala Val Ala Leu Gly Leu Tyr Val Ala Leu Gly Leu Tyr Ala
            690                 695                 700
Leu Ala Ala Ser Pro Ala Arg Gly Pro Arg Ala Leu Ala Ala Leu Ala
705                 710                 715                 720
Ala Leu Ala Gly Leu Tyr Ala Arg Gly Val Ala Leu Gly Leu Tyr Pro
            725                 730                 735
Arg Gly Leu Tyr Ala Arg Gly Pro Arg Gly Leu Tyr
            740                 745

<210> SEQ ID NO 155
<211> LENGTH: 666
<212> TYPE: DNA
<213> ORGANISM: Mycobacterium vaccae

<400> SEQUENCE: 155
atgaaggcaa atcattcggg atgctacaaa tccgccggcc cgatatggtc gcatccatcg      60
ccgctttgtt cgcccgcact ggcaccatct catgcaggtc tggacaatga gctgagcctg     120
ggcatccacg gccagggccc ggaacgactg accattcagc agtgggacac cttcctcaac     180
```

-continued

```
ggcgtcttcc cgttggaccg caaccggttg acccgggagt ggttccactc gggcaaggcg    240
acctacgtcg tggccggtga aggtgccgac gagttcgagg gcacgctgga gctgggctac    300
caggtgggct tccgtggtc gctgggcgtg ggcatcaact tcagctacac caccccgaac    360
atcacgtacg acggttacgg cctcaacttc gccgaccgc tgctgggctt cggtgattcc    420
atcgtgaccc cgccgctgtt cccgggtgtc tcgatcacgg cggacctggg caacggcccc    480
ggcatccagg aggtcgcgac cttctccgtg gacgtggccg gccccggtgg ttccgtggtg    540
gtgtccaacg cgcacggcac ggtcaccggt gctgccggtg gtgtgctgct gcgtccgttc    600
gcccgcctga tctcgtcgac cggcgacagc gtcaccacct acggcgcacc ctggaacatg    660
aactga                                                               666
```

```
<210> SEQ ID NO 156
<211> LENGTH: 221
<212> TYPE: PRT
<213> ORGANISM: Mycobacterium vaccae

<400> SEQUENCE: 156
```

```
Met Lys Ala Asn His Ser Gly Cys Tyr Lys Ser Ala Gly Pro Ile Trp
  1               5                  10                  15

Ser His Pro Ser Pro Leu Cys Ser Pro Ala Leu Ala Pro Ser His Ala
                 20                  25                  30

Gly Leu Asp Asn Glu Leu Ser Leu Gly Val His Gly Gln Gly Pro Glu
             35                  40                  45

His Leu Thr Ile Gln Gln Trp Asp Thr Phe Leu Asn Gly Val Phe Pro
 50                  55                  60

Leu Asp Arg Asn Arg Leu Thr Arg Glu Trp Phe His Ser Gly Lys Ala
 65                  70                  75                  80

Thr Tyr Val Val Ala Gly Glu Gly Ala Asp Glu Phe Glu Gly Thr Leu
                 85                  90                  95

Glu Leu Gly Tyr His Val Gly Phe Pro Trp Ser Leu Gly Val Gly Ile
            100                 105                 110

Asn Phe Ser Tyr Thr Thr Pro Asn Ile Thr Tyr Asp Gly Tyr Gly Leu
        115                 120                 125

Asn Phe Ala Asp Pro Leu Leu Gly Phe Gly Asp Ser Ile Val Thr Pro
130                 135                 140

Pro Leu Phe Pro Gly Val Ser Ile Thr Ala Asp Leu Gly Asn Gly Pro
145                 150                 155                 160

Gly Ile Gln Glu Val Ala Thr Phe Ser Val Asp Val Ala Gly Pro Gly
                165                 170                 175

Gly Ser Val Val Val Ser Asn Ala His Gly Thr Val Thr Gly Ala Ala
                180                 185                 190

Gly Gly Val Leu Leu Arg Pro Phe Ala Arg Leu Ile Ser Ser Thr Gly
            195                 200                 205

Asp Ser Val Thr Thr Tyr Gly Ala Pro Trp Asn Met Asn
210                 215                 220
```

```
<210> SEQ ID NO 157
<211> LENGTH: 480
<212> TYPE: DNA
<213> ORGANISM: Mycobacterium vaccae

<400> SEQUENCE: 157
```

```
aacggctggg acatcaacac ccctgcgttc gagtggttct acgagtccgg cttgtcgacg     60
atcatgccgg tcggcggaca gtccagcttc tacagcgact ggtaccagcc gtctcggggc    120
```

```
aacgggcaga actacaccta caagtgggag acgttcctga cccaggagct gccgacgtgg      180
ctggaggcca accgcggagt gtcgcgcacc ggcaacgcgt tcgtcggcct gtcgatggcg      240
ggcagcgcgg cgctgaccta cgcgatccat cacccgcagc agttcatcta cgcctcgtcg      300
ctgtcaggct tcctgaaccc gtccgagggc tggtggccga tgctgatcgg gctggcgatg      360
aacgacgcag gcggcttcaa cgccgagagc atgtggggcc cgtcctcgga cccggcgtgg      420
aagcgcaacg acccgatggt caacatcaac cagctggtgg ccaacaacac ccggatctgg      480
```

<210> SEQ ID NO 158
<211> LENGTH: 161
<212> TYPE: PRT
<213> ORGANISM: Mycobacterium vaccae

<400> SEQUENCE: 158

```
Asn Gly Trp Asp Ile Asn Thr Pro Ala Phe Glu Trp Phe Tyr Glu Ser
 1               5                  10                  15

Gly Leu Ser Thr Ile Met Pro Val Gly Gly Gln Ser Ser Phe Tyr Ser
            20                  25                  30

Asp Trp Tyr Gln Pro Ser Arg Gly Asn Gly Gln Asn Tyr Thr Tyr Lys
        35                  40                  45

Trp Glu Thr Phe Leu Thr Gln Glu Leu Pro Thr Trp Leu Glu Ala Asn
    50                  55                  60

Arg Gly Val Ser Arg Thr Gly Asn Ala Phe Val Gly Leu Ser Met Ala
65                  70                  75                  80

Gly Ser Ala Ala Leu Thr Tyr Ala Ile His His Pro Gln Gln Phe Ile
                85                  90                  95

Tyr Ala Ser Ser Leu Ser Gly Phe Leu Asn Pro Ser Glu Gly Trp Trp
            100                 105                 110

Pro Met Leu Ile Gly Leu Ala Met Asn Asp Ala Gly Gly Phe Asn Ala
        115                 120                 125

Glu Ser Met Trp Gly Pro Ser Ser Asp Pro Ala Trp Lys Arg Asn Asp
    130                 135                 140

Pro Met Val Asn Ile Asn Gln Leu Val Ala Asn Asn Thr Arg Ile Trp
145                 150                 155                 160

Ile
```

<210> SEQ ID NO 159
<211> LENGTH: 1626
<212> TYPE: DNA
<213> ORGANISM: Mycobacterium vaccae

<400> SEQUENCE: 159

```
atggccaaga caattgcgta tgacgaagag gcccgccgtg gcctcgagcg gggcctcaac       60
gccctcgcag acgccgtaaa ggtgacgttg gcccgaaggg tcgcaacgt cgtgctggag      120 aagaagtggg gcgcccccac gatcaccaac gatggtgtgt ccatcgccaa ggagatcgag      180
ctggaggacc gtacgagaa gatcggcgct gagctggtca agaggtcgc caagaagacc      240 gacgacgtcg cgggcgacgg caccaccacc gccaccgtgc tcgctcaggc tctggttcgc      300
gaaggcctgc gcaacgtcgc agccggcgcc aaccgctcg gcctcaagcg tggcatcgag      360
aaggctgtcg aggctgtcac ccagtcgctg ctgaagtcgg ccaaggaggt cgagaccaag      420
gagcagattt ctgccaccgc ggcgatttcc gccggcgaca cccagatcgg cgagctcatc      480
gccgaggcca tggacaaggt cggcaacgag ggtgtcatca ccgtcgagga gtcgaacacc      540
```

-continued

```
ttcggcctgc agctcgagct caccgagggt atgcgcttcg acaagggcta catctcgggt      600
tacttcgtga ccgacgccga gcgccaggaa gccgtcctgg aggatccota catcctgctg      660 gtcagctcca aggtgtcgac cgtcaaggat ctgctcccgc tgctggagaa ggtcatccag      720
gccggcaagc cgctgctgat catcgccgag gacgtcgagg gcgaggccct gtccacgctg      780
gtggtcaaca gatccgcgg caccttcaag tccgtcgccg tcaaggctcc gggcttcggt       840
gaccgccgca aggcgatgct gcaggacatg gccatcctca ccggtggtca ggtcgtcagc      900
gaaagagtcg gctgtccct ggagaccgcc gacgtctcgc tgctgggcca ggcccgcaag       960
gtcgtcgtca ccaaggacga gaccaccatc gtcgagggct cggcgattc cgatgccatc      1020 gccgccgggt ggctcagat ccgcgccgag atcgagaaca gcgactccga ctacgaccgc     1080
gagaagctgc aggagcgcct ggccaagctg gccggcggtg ttgcggtgat caaggccgga    1140
gctgccaccg aggtggagct caaggagcgc aagcaccgca tcgaggacgc cgtccgcaac    1200
gcgaaggctg ccgtcgaaga gggcatcgtc gccggtggcg gcgtggctct gctgcagtcg    1260
gctcctgcgc tggacgacct cggcctgacg ggcgacgagg ccaccggtgc caacatcgtc    1320
cgcgtggcgc tgtcggctcc gctcaagcag atcgccttca acggcggcct ggagcccggc    1380
gtcgttgccg agaaggtgtc caacctgccc gcgggtcacg gcctcaacgc cgcgaccggt    1440
gagtacgagg acctgctcaa ggccggcgtc gccgacccgg tgaaggtcac ccgctcggcg    1500
ctgcagaacg cggcgtccat cgcggctctg ttcctcacca ccgaggccgt cgtcgccgac    1560
aagccggaga aggcgtccgc acccgcgggc gacccgaccg gtggcatggg cggtatggac    1620
ttctaa                                                               1626
```

<210> SEQ ID NO 160
<211> LENGTH: 541
<212> TYPE: PRT
<213> ORGANISM: Mycobacterium vaccae

<400> SEQUENCE: 160

```
Met Ala Lys Thr Ile Ala Tyr Asp Glu Glu Ala Arg Arg Gly Leu Glu
  1               5                  10                  15

Arg Gly Leu Asn Ala Leu Ala Asp Ala Val Lys Val Thr Leu Gly Pro
             20                  25                  30

Lys Gly Arg Asn Val Val Leu Glu Lys Lys Trp Gly Ala Pro Thr Ile
         35                  40                  45

Thr Asn Asp Gly Val Ser Ile Ala Lys Glu Ile Glu Leu Glu Asp Pro
     50                  55                  60

Tyr Glu Lys Ile Gly Ala Glu Leu Val Lys Glu Val Ala Lys Lys Thr
 65                  70                  75                  80

Asp Asp Val Ala Gly Asp Gly Thr Thr Thr Ala Thr Val Leu Ala Gln
                 85                  90                  95

Ala Leu Val Arg Glu Gly Leu Arg Asn Val Ala Ala Gly Ala Asn Pro
            100                 105                 110

Leu Gly Leu Lys Arg Gly Ile Glu Lys Ala Val Glu Ala Val Thr Gln
        115                 120                 125

Ser Leu Leu Lys Ser Ala Lys Glu Val Glu Thr Lys Glu Gln Ile Ser
    130                 135                 140

Ala Thr Ala Ala Ile Ser Ala Gly Asp Thr Gln Ile Gly Glu Leu Ile
145                 150                 155                 160

Ala Glu Ala Met Asp Lys Val Gly Asn Glu Gly Val Ile Thr Val Glu
                165                 170                 175
```

-continued

```
Glu Ser Asn Thr Phe Gly Leu Gln Leu Glu Leu Thr Glu Gly Met Arg
            180                 185                 190

Phe Asp Lys Gly Tyr Ile Ser Gly Tyr Phe Val Thr Asp Ala Glu Arg
            195                 200                 205

Gln Glu Ala Val Leu Glu Asp Pro Tyr Ile Leu Leu Val Ser Ser Lys
            210                 215                 220

Val Ser Thr Val Lys Asp Leu Pro Leu Leu Glu Lys Val Ile Gln
225                 230                 235                 240

Ala Gly Lys Pro Leu Leu Ile Ile Ala Glu Asp Val Glu Gly Glu Ala
            245                 250                 255

Leu Ser Thr Leu Val Val Asn Lys Ile Arg Gly Thr Phe Lys Ser Val
            260                 265                 270

Ala Val Lys Ala Pro Gly Phe Gly Asp Arg Arg Lys Ala Met Leu Gln
            275                 280                 285

Asp Met Ala Ile Leu Thr Gly Gly Gln Val Val Ser Glu Arg Val Gly
            290                 295                 300

Leu Ser Leu Glu Thr Ala Asp Val Ser Leu Leu Gly Gln Ala Arg Lys
305                 310                 315                 320

Val Val Val Thr Lys Asp Glu Thr Thr Ile Val Glu Gly Ser Gly Asp
            325                 330                 335

Ser Asp Ala Ile Ala Gly Arg Val Ala Gln Ile Arg Ala Glu Ile Glu
            340                 345                 350

Asn Ser Asp Ser Asp Tyr Asp Arg Glu Lys Leu Gln Glu Arg Leu Ala
            355                 360                 365

Lys Leu Ala Gly Gly Val Ala Val Ile Lys Ala Gly Ala Ala Thr Glu
            370                 375                 380

Val Glu Leu Lys Glu Arg Lys His Arg Ile Glu Asp Ala Val Arg Asn
385                 390                 395                 400

Ala Lys Ala Ala Val Glu Glu Gly Ile Val Ala Gly Gly Val Ala
            405                 410                 415

Leu Leu Gln Ser Ala Pro Ala Leu Asp Asp Leu Gly Leu Thr Gly Asp
            420                 425                 430

Glu Ala Thr Gly Ala Asn Ile Val Arg Val Ala Leu Ser Ala Pro Leu
            435                 440                 445

Lys Gln Ile Ala Phe Asn Gly Gly Leu Glu Pro Gly Val Val Ala Glu
            450                 455                 460

Lys Val Ser Asn Leu Pro Ala Gly His Gly Leu Asn Ala Ala Thr Gly
465                 470                 475                 480

Glu Tyr Glu Asp Leu Leu Lys Ala Gly Val Ala Asp Pro Val Lys Val
            485                 490                 495

Thr Arg Ser Ala Leu Gln Asn Ala Ala Ser Ile Ala Ala Leu Phe Leu
            500                 505                 510

Thr Thr Glu Ala Val Val Ala Asp Lys Pro Glu Lys Ala Ser Ala Pro
            515                 520                 525

Ala Gly Asp Pro Thr Gly Gly Met Gly Gly Met Asp Phe
            530                 535                 540
```

<210> SEQ ID NO 161
<211> LENGTH: 985
<212> TYPE: DNA
<213> ORGANISM: Mycobacterium vaccae

<400> SEQUENCE: 161
ggatccctac atcctgctgg tcagctccaa ggtgtcgacc gtcaaggatc tgctcccgct    60

-continued

```
gctggagaag gtcatccagg ccggcaagcc gctgctgatc atcgccgagg acgtcgaggg    120
cgaggccctg tccacgctgg tggtcaacaa gatccgcggc accttcaagt ccgtcgccgt    180
caaggctccg ggcttcggtg accgccgcaa ggcgatgctg caggacatgg ccatcctcac    240
cggtggtcag gtcgtcagcg aaagagtcgg gctgtccctg agaccgccg acgtctcgct     300 gctgggccag gcccgcaagg tcgtcgtcac caaggacgag accaccatcg tcgagggctc    360
gggcgattcc gatgccatcg ccggccgggt ggctcagatc cgcgccgaga tcgagaacag    420
cgactccgac tacgaccgcg agaagctgca ggagcgcctg gccaagctgg ccggcggtgt    480
tgcggtgatc aaggccggag ctgccaccga ggtggagctc aaggagcgca agcaccgcat    540
cgaggacgcc gtccgcaacg cgaaggctgc cgtcgaagag ggcatcgtcg ccggtggcgg    600
cgtggctctg ctgcagtcgg ctcctgcgct ggacgacctc ggcctgacgg cgacgaggc    660 caccggtgcc aacatcgtcc gcgtggcgct gtcggctccg ctcaagcaga tcgccttcaa    720
cggcggcctg gagcccggcg tcgttgccga gaaggtgtcc aacctgcccg cgggtcacgg    780
cctcaacgcc gcgaccggtg agtacgagga cctgctcaag gccggcgtcg ccgacccggt    840
gaaggtcacc cgctcggcgc tgcagaacgc ggcgtccatc gcggctctgt tcctcaccac    900
cgaggccgtc gtcgccgaca agccggagaa ggcgtccgca cccgcgggcg acccgaccgg    960
tggcatgggc ggtatggact ctaa                                           985
```

<210> SEQ ID NO 162
<211> LENGTH: 327
<212> TYPE: PRT
<213> ORGANISM: Mycobacterium vaccae

<400> SEQUENCE: 162

```
Asp Pro Tyr Ile Leu Val Ser Ser Lys Val Ser Thr Val Lys Asp
 1               5                  10                  15

Leu Leu Pro Leu Glu Lys Val Ile Gln Ala Gly Lys Pro Leu Leu
             20                  25                  30

Ile Ile Ala Glu Asp Val Glu Gly Glu Ala Leu Ser Thr Leu Val Val
 35                  40                  45

Asn Lys Ile Arg Gly Thr Phe Lys Ser Val Ala Val Lys Ala Pro Gly
 50                  55                  60

Phe Gly Asp Arg Arg Lys Ala Met Leu Gln Asp Met Ala Ile Leu Thr
 65                  70                  75                  80

Gly Gly Gln Val Val Ser Glu Arg Val Gly Leu Ser Leu Glu Thr Ala
             85                  90                  95

Asp Val Ser Leu Leu Gly Gln Ala Arg Lys Val Val Thr Lys Asp
            100                 105                 110

Glu Thr Thr Ile Val Glu Gly Ser Gly Asp Ser Asp Ala Ile Ala Gly
            115                 120                 125

Arg Val Ala Gln Ile Arg Ala Glu Ile Glu Asn Ser Asp Ser Asp Tyr
        130                 135                 140

Asp Arg Glu Lys Leu Gln Glu Arg Leu Ala Lys Leu Ala Gly Gly Val
145                 150                 155                 160

Ala Val Ile Lys Ala Gly Ala Ala Thr Glu Val Glu Leu Lys Glu Arg
                165                 170                 175

Lys His Arg Ile Glu Asp Ala Val Arg Asn Ala Lys Ala Ala Val Glu
            180                 185                 190

Glu Gly Ile Val Ala Gly Gly Val Ala Leu Leu Gln Ser Ala Pro
            195                 200                 205
```

```
Ala Leu Asp Asp Leu Gly Leu Thr Gly Asp Glu Ala Thr Gly Ala Asn
    210                 215                 220
Ile Val Arg Val Ala Leu Ser Ala Pro Leu Lys Gln Ile Ala Phe Asn
225                 230                 235                 240
Gly Gly Leu Glu Pro Gly Val Val Ala Glu Lys Val Ser Asn Leu Pro
                245                 250                 255
Ala Gly His Gly Leu Asn Ala Ala Thr Gly Glu Tyr Glu Asp Leu Leu
            260                 265                 270
Lys Ala Gly Val Ala Asp Pro Val Lys Val Thr Arg Ser Ala Leu Gln
        275                 280                 285
Asn Ala Ala Ser Ile Ala Ala Leu Phe Leu Thr Thr Glu Ala Val Val
    290                 295                 300
Ala Asp Lys Pro Glu Lys Ala Ser Ala Pro Ala Gly Asp Pro Thr Gly
305                 310                 315                 320
Gly Met Gly Gly Met Asp Phe
                325
```

<210> SEQ ID NO 163
<211> LENGTH: 403
<212> TYPE: DNA
<213> ORGANISM: Mycobacterium vaccae

<400> SEQUENCE: 163

| | |
|---|---:|
| ggatccgcgg caccggctgg tgacgaccaa gtacaacccg gcccgcacct ggacggccga | 60 |
| gaactccgtc ggcatcggcg gcgcgtacct gtgcatctac gggatggagg cccccggcgg | 120 |
| ctatcagttc gtcggccgca ccacccaggt gtggagtcgt taccgccaca cggcgccgtt | 180 |
| cgaacccgga agtccctggc tgctgcggtt tttcgaccga atttcgtggt atccggtgtc | 240 |
| ggccgaggag ctgctggaat tgcgagccga catggccgca ggccggggct cggtcgacat | 300 |
| caccgacggc gtgttctccc tcgccagca cgaacggttc ctggccgaca acgccgacga | 360 |
| catcgccgcg ttccgttccc ggcaggcggc cgcgttctcc gcc | 403 |

<210> SEQ ID NO 164
<211> LENGTH: 336
<212> TYPE: DNA
<213> ORGANISM: Mycobacterium vaccae

<400> SEQUENCE: 164

| | |
|---|---:|
| cggaccgcgt gggcggccgc cggcgagttc gaccgcgccg agaaagccgc gtcgaaggcc | 60 |
| accgacgccg ataccgggga cctggtgctc tacgacggtg cgagcgggtc gacgctccgt | 120 |
| tcgcgtcgag cgtgtggaag gtcgacgtcg ccgtcggtga ccgggtggtg gccggacagc | 180 |
| cgttgctggc gctggaggcg atgaagatgg agaccgtgct gcgcgccccg gccgacgggg | 240 |
| tggtcaccca gatcctggtc tccgctgggc atctcgtcga tcccggcacc ccactggtcg | 300 |
| tggtcggcac cggagtgcgc gcatgagcgc cgtcga | 336 |

<210> SEQ ID NO 165
<211> LENGTH: 134
<212> TYPE: PRT
<213> ORGANISM: Mycobacterium vaccae

<400> SEQUENCE: 165

```
Asp Pro Arg His Arg Leu Val Thr Thr Lys Tyr Asn Pro Ala Arg Thr
1               5                   10                  15
Trp Thr Ala Glu Asn Ser Val Gly Ile Gly Gly Ala Tyr Leu Cys Ile
            20                  25                  30
```

-continued

Tyr Gly Met Glu Gly Pro Gly Gly Tyr Gln Phe Val Gly Arg Thr Thr
            35                  40                  45

Gln Val Trp Ser Arg Tyr Arg His Thr Ala Pro Phe Glu Pro Gly Ser
 50                  55                  60

Pro Trp Leu Leu Arg Phe Phe Asp Arg Ile Ser Trp Tyr Pro Val Ser
 65                  70                  75                  80

Ala Glu Glu Leu Leu Glu Leu Arg Ala Asp Met Ala Ala Gly Arg Gly
                 85                  90                  95

Ser Val Asp Ile Thr Asp Gly Val Phe Ser Leu Ala Glu His Glu Arg
                100                 105                 110

Phe Leu Ala Asp Asn Ala Asp Asp Ile Ala Ala Phe Arg Ser Arg Gln
            115                 120                 125

Ala Ala Ala Phe Ser Ala
            130

<210> SEQ ID NO 166
<211> LENGTH: 108
<212> TYPE: PRT
<213> ORGANISM: Mycobacterium vaccae

<400> SEQUENCE: 166

Arg Thr Ala Trp Ala Ala Ala Gly Glu Phe Asp Arg Ala Glu Lys Ala
  1               5                  10                  15

Ala Ser Lys Ala Thr Asp Ala Asp Thr Gly Asp Leu Val Leu Tyr Asp
                 20                  25                  30

Gly Asp Glu Arg Val Asp Ala Pro Phe Ala Ser Ser Val Trp Lys Val
            35                  40                  45

Asp Val Ala Val Gly Asp Arg Val Val Ala Gly Gln Pro Leu Leu Ala
 50                  55                  60

Leu Glu Ala Met Lys Met Glu Thr Val Leu Arg Ala Pro Ala Asp Gly
 65                  70                  75                  80

Val Val Thr Gln Ile Leu Val Ser Ala Gly His Leu Val Asp Pro Gly
                 85                  90                  95

Thr Pro Leu Val Val Val Gly Thr Gly Val Arg Ala
                100                 105

<210> SEQ ID NO 167
<211> LENGTH: 31
<212> TYPE: DNA
<213> ORGANISM: Artificial Sequence
<220> FEATURE:
<223> OTHER INFORMATION: Made in a lab

<400> SEQUENCE: 167
atagaattcg tccgacagtg ggacctcgag c                                31

<210> SEQ ID NO 168
<211> LENGTH: 27
<212> TYPE: DNA
<213> ORGANISM: Artificial Sequence
<220> FEATURE:
<223> OTHER INFORMATION: Made in a lab

<400> SEQUENCE: 168
atagaattcc caccgcgtca gccgccg                                     27

<210> SEQ ID NO 169
<211> LENGTH: 1111
<212> TYPE: DNA

<213> ORGANISM: Mycobacterium vaccae

<400> SEQUENCE: 169

| | | | | |
|---|---|---|---|---|
| gtccgacagt gggacctcga gcaccacgtc acaggacagc ggccccgcca gcggcgccct | 60 |
| gcgcgtctcc aactggccgc tctatatggc cgacggtttc atcgcagcgt tccagaccgc | 120 |
| ctcgggcatc acggtcgact acaaagaaga cttcaacgac aacgagcagt ggttcgccaa | 180 |
| ggtcaaggag ccgttgtcgc gcaagcagga cataggcgcc gacctggtga tccccaccga | 240 |
| gttcatggcc gcgcgcgtca agggcctggg atggctcaat gagatcagcg aagccggcgt | 300 |
| gcccaatcgc aagaatctgc gtcaggacct gttggactcg agcatcgacg agggccgcaa | 360 |
| gttcaccgcg ccgtacatga ccggcatggt cggtctcgcc tacaacaagg cagccaccgg | 420 |
| acgcgatatc cgcaccatcg acgacctctg ggatcccgcg ttcaagggcc gcgtcagtct | 480 |
| gttctccgac gtccaggacg gcctcggcat gatcatgctc tcgcagggca actcgccgga | 540 |
| gaatccgacc accgagtcca ttcagcaggc ggtcgatctg gtccgcgaac agaacgacag | 600 |
| ggggtcagat ccgtcgcttc accggcaacg actacgccga cgacctggcc gcagaaacat | 660 |
| cgccatcgcg caggcgtact ccggtgacgt cgtgcagctg caggcggaca ccccgatct | 720 |
| gcagttcatc gttcccgaat ccggcggcga ctggttcgtc gacacgatgg tgatcccgta | 780 |
| caccacgcag aaccagaagg ccgccgaggc gtggatcgac tacatctacg accgagccaa | 840 |
| ctacgccaag ctggtcgcgt tcacccagtt cgtgcccgca ctctcggaca tgaccgacga | 900 |
| actcgccaag gtcgatcctg catcggcgga gaacccgctg atcaacccgt cggccgaggt | 960 |
| gcaggcgaac ctgaagtcgt gggcggcact gaccgacgag cagacgcagg agttcaacac | 1020 |
| tgcgtacgcc gccgtcaccg gcggctgacg cggtggtagt gccgatgcga ggggcataaa | 1080 |
| tggccctgcg gacgcgagga gcataaatgg c | 1111 |

<210> SEQ ID NO 170
<211> LENGTH: 348
<212> TYPE: PRT
<213> ORGANISM: Mycobacterium vaccae

<400> SEQUENCE: 170

Ser Asp Ser Gly Thr Ser Ser Thr Thr Ser Gln Asp Ser Gly Pro Ala
1               5                   10                  15

Ser Gly Ala Leu Arg Val Ser Asn Trp Pro Leu Tyr Met Ala Asp Gly
            20                  25                  30

Phe Ile Ala Ala Phe Gln Thr Ala Ser Gly Ile Thr Val Asp Tyr Lys
        35                  40                  45

Glu Asp Phe Asn Asp Asn Glu Gln Trp Phe Ala Lys Val Lys Glu Pro
    50                  55                  60

Leu Ser Arg Lys Gln Asp Ile Gly Ala Asp Leu Val Ile Pro Thr Glu
65                  70                  75                  80

Phe Met Ala Ala Arg Val Lys Gly Leu Gly Trp Leu Asn Glu Ile Ser
                85                  90                  95

Glu Ala Gly Val Pro Asn Arg Lys Asn Leu Arg Gln Asp Leu Leu Asp
            100                 105                 110

Ser Ser Ile Asp Glu Gly Arg Lys Phe Thr Ala Pro Tyr Met Thr Gly
        115                 120                 125

Met Val Gly Leu Ala Tyr Asn Lys Ala Ala Thr Gly Arg Asp Ile Arg
    130                 135                 140

Thr Ile Asp Asp Leu Trp Asp Pro Ala Phe Lys Gly Arg Val Ser Leu
145                 150                 155                 160

```
Phe Ser Asp Val Gln Asp Gly Leu Gly Met Ile Met Leu Ser Gln Gly
                165                 170                 175
Asn Ser Pro Glu Asn Pro Thr Thr Glu Ser Ile Gln Gln Ala Val Asp
            180                 185                 190
Leu Val Arg Glu Gln Asn Asp Arg Gly Gln Ile Arg Arg Phe Thr Gly
        195                 200                 205
Asn Asp Tyr Ala Asp Asp Leu Ala Ala Gly Asn Ile Ala Ile Ala Gln
    210                 215                 220
Ala Tyr Ser Gly Asp Val Val Gln Leu Gln Ala Asp Asn Pro Asp Leu
225                 230                 235                 240
Gln Phe Ile Val Pro Glu Ser Gly Gly Asp Trp Phe Val Asp Thr Met
                245                 250                 255
Val Ile Pro Tyr Thr Thr Gln Asn Gln Lys Ala Ala Glu Ala Trp Ile
                260                 265                 270
Asp Tyr Ile Tyr Asp Arg Ala Asn Tyr Ala Lys Leu Val Ala Phe Thr
            275                 280                 285
Gln Phe Val Pro Ala Leu Ser Asp Met Thr Asp Glu Leu Ala Lys Val
        290                 295                 300
Asp Pro Ala Ser Ala Glu Asn Pro Leu Ile Asn Pro Ser Ala Glu Val
305                 310                 315                 320
Gln Ala Asn Leu Lys Ser Trp Ala Ala Leu Thr Asp Glu Gln Thr Gln
                325                 330                 335
Glu Phe Asn Thr Ala Tyr Ala Ala Val Thr Gly Gly
            340                 345

<210> SEQ ID NO 171
<211> LENGTH: 1420
<212> TYPE: DNA
<213> ORGANISM: Mycobacterium vaccae
<220> FEATURE:
<221> NAME/KEY: unsure
<222> LOCATION: (955)...(955)
<221> NAME/KEY: unsure
<222> LOCATION: (973)...(973)

<400> SEQUENCE: 171
gatgagcagc gtgctgaact cgacctggtt ggcctgggcc gtcgcggtcg cggtcgggtt     60
cccggtgctg ctggtcgtgc tgaccgaggt gcacaacgcg ttgcgtcggc gcggcagcgc    120
gctggcccgc ccggtgcaac tcctgcgtac ctacatcctg ccgctgggcg cgttgctgct    180
cctgctggta caggcgatgg agatctccga cgacgccacg tcggtacggt tggtcgccac    240
cctgttcggc gtcgtgttgt tgacgttggt gctgtccggg ctcaacgcca ccctcatcca    300
gggcgcacca gaagacagct ggcgcaggcg gattccgtcg atcttcctcg acgtcgcgcg    360
cttcgcgctg atcgcggtcg gtatcaccgt gatcatggcc tatgtctggg cgcgaacgt    420 gggggggcctg ttcaccgcac tgggcgtcac ttccatcgtt cttggcctgg ctctgcagaa    480
ttcggtcggt cagatcatct cgggtctgct gctgctgttc gagcaaccgt tccggctcgg    540
cgactggatc accgtcccca ccgcggcggg ccggccgtcc gccacggcc gcgtggtgga    600 agtcaactgg cgtgcaacac atatcgacac cggcggcaac ctgctggtaa tgcccaacgc    660
cgaactcgcc ggcgcgtcgt tcaccaatta cagccggccc gtgggagagc accggctgac    720
cgtcgtcacc accttcaacg ccgcggacac ccccgatgat gtctgcgaga tgctgtcgtc    780
ggtcgcggcg tcgctgcccg aactgcgcac cgacggacag atcgccacgc tctatctcgg    840
tgcggccgaa tacgagaagt cgatcccgtt gcacacaccc gcggtggacg actcggtcag    900
```

-continued

```
gagcacgtac ctgcgatggg tctggtacgc cgcgcgccgg caggaacttc gcctnaacgg    960
cgtcgccgac ganttcgaca cgccggaacg gatcgcctcg gccatgcggg ctgtggcgtc   1020
cacactgcgc ttggcagacg acgaacagca ggagatcgcc gacgtggtgc gtctggtccg   1080
ttacggcaac ggggaacgcc tccagcagcc gggtcaggta ccgaccggga tgaggttcat   1140
cgtagacggc agggtgagtc tgtccgtgat cgatcaggac ggcgacgtga tcccggcgcg   1200
ggtgctcgag cgtggcgact tcctgggcga gaccacgctg acgcgggaac cggtactggc   1260
gaccgcgcac gcgctggagg aagtcaccgt gctggagatg gcccgtgacg agatcgagcg   1320
cctggtgcac cgaaagccga tcctgctgca cgtgatcggg gccgtgatcg ccgaccggcg   1380
cgcgcacgaa cttcggttga tggcggactc gcaggactga                         1420
```

<210> SEQ ID NO 172
<211> LENGTH: 471
<212> TYPE: PRT
<213> ORGANISM: Mycobacterium vaccae
<220> FEATURE:
<221> NAME/KEY: UNSURE
<222> LOCATION: (318)...(318)
<221> NAME/KEY: UNSURE
<222> LOCATION: (324)...(324)

<400> SEQUENCE: 172

```
Met Ser Ser Val Leu Asn Ser Thr Trp Leu Ala Trp Ala Val Ala Val
  1               5                  10                  15

Ala Val Gly Phe Pro Val Leu Val Val Leu Thr Glu Val His Asn
                 20                  25                  30

Ala Leu Arg Arg Arg Gly Ser Ala Leu Ala Arg Pro Val Gln Leu Leu
         35                  40                  45

Arg Thr Tyr Ile Leu Pro Leu Gly Ala Leu Leu Leu Leu Val Gln
     50                  55                  60

Ala Met Glu Ile Ser Asp Asp Ala Thr Ser Val Arg Leu Val Ala Thr
 65                  70                  75                  80

Leu Phe Gly Val Val Leu Leu Thr Leu Val Leu Ser Gly Leu Asn Ala
                 85                  90                  95

Thr Leu Ile Gln Gly Ala Pro Glu Asp Ser Trp Arg Arg Arg Ile Pro
            100                 105                 110

Ser Ile Phe Leu Asp Val Ala Arg Phe Ala Leu Ile Ala Val Gly Ile
        115                 120                 125

Thr Val Ile Met Ala Tyr Val Trp Gly Ala Asn Val Gly Gly Leu Phe
    130                 135                 140

Thr Ala Leu Gly Val Thr Ser Ile Val Leu Gly Leu Ala Leu Gln Asn
145                 150                 155                 160

Ser Val Gly Gln Ile Ile Ser Gly Leu Leu Leu Phe Glu Gln Pro
                165                 170                 175

Phe Arg Leu Gly Asp Trp Ile Thr Val Pro Thr Ala Ala Gly Arg Pro
            180                 185                 190

Ser Ala His Gly Arg Val Val Glu Val Asn Trp Arg Ala Thr His Ile
        195                 200                 205

Asp Thr Gly Gly Asn Leu Leu Val Met Pro Asn Ala Glu Leu Ala Gly
    210                 215                 220

Ala Ser Phe Thr Asn Tyr Ser Arg Pro Val Gly Glu His Arg Leu Thr
225                 230                 235                 240

Val Val Thr Thr Phe Asn Ala Ala Asp Thr Pro Asp Asp Val Cys Glu
                245                 250                 255
```

Met Leu Ser Ser Val Ala Ala Ser Leu Pro Glu Leu Arg Thr Asp Gly
            260                 265                 270

Gln Ile Ala Thr Leu Tyr Leu Gly Ala Ala Glu Tyr Glu Lys Ser Ile
            275                 280                 285

Pro Leu His Thr Pro Ala Val Asp Asp Ser Val Arg Ser Thr Tyr Leu
            290                 295                 300

Arg Trp Val Trp Tyr Ala Ala Arg Arg Gln Glu Leu Arg Xaa Asn Gly
305                 310                 315                 320

Val Ala Asp Xaa Phe Asp Thr Pro Glu Arg Ile Ala Ser Ala Met Arg
                325                 330                 335

Ala Val Ala Ser Thr Leu Arg Leu Ala Asp Asp Glu Gln Gln Glu Ile
            340                 345                 350

Ala Asp Val Val Arg Leu Val Arg Tyr Gly Asn Gly Glu Arg Leu Gln
            355                 360                 365

Gln Pro Gly Gln Val Pro Thr Gly Met Arg Phe Ile Val Asp Gly Arg
            370                 375                 380

Val Ser Leu Ser Val Ile Asp Gln Asp Gly Asp Val Ile Pro Ala Arg
385                 390                 395                 400

Val Leu Glu Arg Gly Asp Phe Leu Gly Gln Thr Thr Leu Thr Arg Glu
                405                 410                 415

Pro Val Leu Ala Thr Ala His Ala Leu Glu Glu Val Thr Val Leu Glu
            420                 425                 430

Met Ala Arg Asp Glu Ile Glu Arg Leu Val His Arg Lys Pro Ile Leu
            435                 440                 445

Leu His Val Ile Gly Ala Val Ile Ala Asp Arg Arg Ala His Glu Leu
            450                 455                 460

Arg Leu Met Asp Ser Gln Asp
465                 470

<210> SEQ ID NO 173
<211> LENGTH: 2172
<212> TYPE: DNA
<213> ORGANISM: Mycobacterium vaccae

<400> SEQUENCE: 173
tagatgacaa ttctgccctg gaatgcgcga acgtctgaac acccgacgcg aaaaagacgc        60
gggcgctacc acctcctgtc gcggatgagc atccagtcca agttgctgct gatgctgctt       120
ctgaccagca ttctctcggc tgcggtggtc ggtttcatcg gctatcagtc cggacggtcc       180
tcgctgcgcg catcggtgtt cgaccgcctc accgacatcc gcgagtcgca gtcgcgcggg       240
ttggagaatc agttcgcgga cctgaagaac tcgatggtga tttactcgcg cggcagcact       300
gccacggagg cgatcggcgc gttcagcgac ggtttccgtc agctcggcga tgcgacgatc       360
aataccgggc aggcggcgtc attgcgccgt tactacgacc ggacgttcgc caacaccacc       420
ctcgacgaca gcggaaaccg cgtcgacgtc cgcgcgctca tcccgaaatc caacccccag       480
cgctatctgc aggcgctcta tacccgccg tttcagaact gggagaaggc gatcgcgttc       540
gacgacgcgc gcgacggcag cgcctggtcg gccgccaatg ccagattcaa cgagttcttc       600
cgcgagatcg tgcaccgctt caacttcgag gatctgatgc tgctcgacct cgagggcaac       660
gtggtgtact ccgcctacaa ggggccggat ctcgggacaa acatcgtcaa cggcccctat       720
cgcaaccggg aactgtcgga agcctacgag aaggcggtcg cgtcgaactc gatcgactat       780
gtcggtgtca ccgacttcgg gtggtacctg cctgccgagg aaccgaccgc ctggttcctg       840

-continued

```
tccccggtcg ggttgaagga ccgagtcgac ggtgtgatgg cggtccagtt cccgatcgcg      900
cggatcaacg aattgatgac ggcgcgggga cagtggcgtg acaccgggat gggagacacc      960
ggtgagacca tcctggtcgg accggacaat ctgatgcgct cggactcccg gctgttccgc     1020
gagaaccggg agaagttcct ggccgacgtc gtcgagggg gaaccccgcc ggaggtcgcc      1080
gacgaatcgg ttgaccgccg cggcaccacg ctggtgcagc cggtgaccac ccgctccgtc     1140
gaggaggccc aacgcggcaa caccgggacg acgatcgagg acgactatct cggccacgag     1200
gcgttacagg cgtactcacc ggtggacctg ccgggactgc actgggtgat cgtggccaag     1260
atcgacaccg acgaggcgtt cgccccggtg gcgcagttca ccaggaccct ggtgctgtcg     1320
acggtgatca tcatcttcgg cgtgtcgctg gcggccatgc tgctggcgcg gttgttcgtc     1380
cgtccgatcc ggcggttgca ggccggcgcc agcagatca gcggcggtga ctaccgcctc      1440
gctctgccgg tgttgtctcg tgacgaattc ggcgatctga caacagcttt caacgacatg     1500
agtcgcaatc tgtcgatcaa ggacgagctg ctcggcgagg agcgcgccga gaaccaacgg     1560
ctgatgctgt ccctgatgcc cgaaccggtg atgcagcgct acctcgacgg ggaggagacg     1620
atcgcccagg accacaagaa cgtcacggtg atcttcgccg acatgatggg cctcgacgag     1680
ttgtcgcgca tgttgacctc cgaggaactg atggtggtgg tcaacgacct gacccgccag     1740
ttcgacgccg ccgccgagag tctcggggtc gaccacgtgc ggacgctgca cgacgggtac     1800
ctggccagct gcgggttagg cgtgccgcgg ctggacaacg tccggcgcac ggtcaatttc     1860
gcgatcgaaa tggaccgcat catcgaccgg cacgccgccc agtccgggca cgacctgcgg     1920
ctccgcgcgg gcatcgacac cgggtcggcg gccagcgggc tggtggggcg gtccacgttg     1980
gcgtacgaca tgtggggttc ggcggtcgat gtcgctaacc aggtgcagcg cggctccccc     2040
cagcccggca tctacgtcac ctcgcgggtg cacgaggtca tgcaggaaac tctcgacttc     2100
gtcgccgccg gggaggtcgt cggcgagcgc ggcgtcgaga cggtctggcg gttgcagggc     2160
caccggcgat ga                                                         2172
```

<210> SEQ ID NO 174
<211> LENGTH: 722
<212> TYPE: PRT
<213> ORGANISM: Mycobacterium vaccae

<400> SEQUENCE: 174

```
Met Thr Ile Leu Pro Trp Asn Ala Arg Thr Ser Glu His Pro Thr Arg
  1               5                  10                  15

Lys Arg Arg Gly Arg Tyr His Leu Leu Ser Arg Met Ser Ile Gln Ser
             20                  25                  30

Lys Leu Leu Leu Met Leu Leu Leu Thr Ser Ile Leu Ser Ala Ala Val
         35                  40                  45

Val Gly Phe Ile Gly Tyr Gln Ser Gly Arg Ser Leu Arg Ala Ser
     50                  55                  60

Val Phe Asp Arg Leu Thr Asp Ile Arg Glu Ser Gln Ser Arg Gly Leu
 65                  70                  75                  80

Glu Asn Gln Phe Ala Asp Leu Lys Asn Ser Met Val Ile Tyr Ser Arg
                 85                  90                  95

Gly Ser Thr Ala Thr Glu Ala Ile Gly Ala Phe Ser Asp Gly Phe Arg
            100                 105                 110

Gln Leu Gly Asp Ala Thr Ile Asn Thr Gly Gln Ala Ala Ser Leu Arg
        115                 120                 125

Arg Tyr Tyr Asp Arg Thr Phe Ala Asn Thr Thr Leu Asp Asp Ser Gly
```

```
         130                 135                 140
Asn Arg Val Asp Val Arg Ala Leu Ile Pro Lys Ser Asn Pro Gln Arg
145                 150                 155                 160

Tyr Leu Gln Ala Leu Tyr Thr Pro Pro Phe Gln Asn Trp Glu Lys Ala
                165                 170                 175

Ile Ala Phe Asp Asp Ala Arg Asp Gly Ser Ala Trp Ser Ala Ala Asn
                180                 185                 190

Ala Arg Phe Asn Glu Phe Phe Arg Glu Ile Val His Arg Phe Asn Phe
            195                 200                 205

Glu Asp Leu Met Leu Leu Asp Leu Glu Gly Asn Val Val Tyr Ser Ala
            210                 215                 220

Tyr Lys Gly Pro Asp Leu Gly Thr Asn Ile Val Asn Gly Pro Tyr Arg
225                 230                 235                 240

Asn Arg Glu Leu Ser Glu Ala Tyr Glu Lys Ala Val Ala Ser Asn Ser
                245                 250                 255

Ile Asp Tyr Val Gly Val Thr Asp Phe Gly Trp Tyr Leu Pro Ala Glu
                260                 265                 270

Glu Pro Thr Ala Trp Phe Leu Ser Pro Val Gly Leu Lys Asp Arg Val
            275                 280                 285

Asp Gly Val Met Ala Val Gln Phe Pro Ile Ala Arg Ile Asn Glu Leu
            290                 295                 300

Met Thr Ala Arg Gly Gln Trp Arg Asp Thr Gly Met Gly Asp Thr Gly
305                 310                 315                 320

Glu Thr Ile Leu Val Gly Pro Asp Asn Leu Met Arg Ser Asp Ser Arg
                325                 330                 335

Leu Phe Arg Glu Asn Arg Glu Lys Phe Leu Ala Asp Val Val Glu Gly
            340                 345                 350

Gly Thr Pro Pro Glu Val Ala Asp Glu Ser Val Asp Arg Arg Gly Thr
            355                 360                 365

Thr Leu Val Gln Pro Val Thr Thr Arg Ser Val Glu Glu Ala Gln Arg
            370                 375                 380

Gly Asn Thr Gly Thr Thr Ile Glu Asp Asp Tyr Leu Gly His Glu Ala
385                 390                 395                 400

Leu Gln Ala Tyr Ser Pro Val Asp Leu Pro Gly Leu His Trp Val Ile
                405                 410                 415

Val Ala Lys Ile Asp Thr Asp Glu Ala Phe Ala Pro Val Ala Gln Phe
                420                 425                 430

Thr Arg Thr Leu Val Leu Ser Thr Val Ile Ile Phe Gly Val Ser
            435                 440                 445

Leu Ala Ala Met Leu Leu Ala Arg Leu Phe Val Arg Pro Ile Arg Arg
            450                 455                 460

Leu Gln Ala Gly Ala Gln Gln Ile Ser Gly Gly Asp Tyr Arg Leu Ala
465                 470                 475                 480

Leu Pro Val Leu Ser Arg Asp Glu Phe Gly Asp Leu Thr Thr Ala Phe
                485                 490                 495

Asn Asp Met Ser Arg Asn Leu Ser Ile Lys Asp Glu Leu Leu Gly Glu
            500                 505                 510

Glu Arg Ala Glu Asn Gln Arg Leu Met Leu Ser Leu Met Pro Glu Pro
            515                 520                 525

Val Met Gln Arg Tyr Leu Asp Gly Glu Glu Thr Ile Ala Gln Asp His
            530                 535                 540

Lys Asn Val Thr Val Ile Phe Ala Asp Met Met Gly Leu Asp Glu Leu
545                 550                 555                 560
```

```
Ser Arg Met Leu Thr Ser Glu Glu Leu Met Val Val Asn Asp Leu
                565                 570                 575

Thr Arg Gln Phe Asp Ala Ala Ala Glu Ser Leu Gly Val Asp His Val
            580                 585                 590

Arg Thr Leu His Asp Gly Tyr Leu Ala Ser Cys Gly Leu Gly Val Pro
            595                 600                 605

Arg Leu Asp Asn Val Arg Arg Thr Val Asn Phe Ala Ile Glu Met Asp
            610                 615                 620

Arg Ile Ile Asp Arg His Ala Ala Glu Ser Gly His Asp Leu Arg Leu
625                 630                 635                 640

Arg Ala Gly Ile Asp Thr Gly Ser Ala Ala Ser Gly Leu Val Gly Arg
                645                 650                 655

Ser Thr Leu Ala Tyr Asp Met Trp Gly Ser Ala Val Asp Val Ala Asn
                660                 665                 670

Gln Val Gln Arg Gly Ser Pro Gln Pro Gly Ile Tyr Val Thr Ser Arg
                675                 680                 685

Val His Glu Val Met Gln Glu Thr Leu Asp Phe Val Ala Ala Gly Glu
            690                 695                 700

Val Val Gly Glu Arg Gly Val Glu Thr Val Trp Arg Leu Gln Gly His
705                 710                 715                 720

Arg Arg

<210> SEQ ID NO 175
<211> LENGTH: 898
<212> TYPE: DNA
<213> ORGANISM: Mycobacterium vaccae

<400> SEQUENCE: 175
gagcaaccgt tccggctcgg cgactggatc accgtcccca ccgcggcggg ccggccgtcc      60
gcccacggcc gcgtggtgga agtcaactgg cgtgcaacac atatcgacac cggcggcaac     120
ctgctggtaa tgcccaacgc cgaactcgcc ggcgcgtcgt tcaccaatta cagccggccc     180
gtgggagagc accggctgac cgtcgtcacc accttcaacg ccgcggacac ccccgatgat     240
gtctgcgaga tgctgtcgtc ggtcgcggcg tcgctgcccg aactgcgcac cgacggacag     300
atcgccacgc tctatctcgg tgcggccgaa tacgagaagt cgatcccgtt gcacacaccc     360
gcggtggacg actcggtcag gagcacgtac ctgcgatggg tctggtacgc cgcgcgccgg     420
caggaacttc gcctaacggc gtcgccgacg attcgacacg ccggaacgga tcgcctcggc     480
catgcgggct gtggcgtcca cactgcgctt ggcagacgac gaacagcagg agatcgccga     540
cgtggtgcgt ctggtccgtt acggcaacgg ggaacgcctc cagcagccgg gtcaggtacc     600
gaccgggatg aggttcatcg tagacggcag ggtgagtctg tccgtgatcg atcaggacgg     660
cgacgtgatc ccggcgcggg tgctcgagcg tggcgacttc ctgggcaga ccacgctgac     720
gcgggaaccg gtactggcga ccgcgcacgc gctggaggaa gtcaccgtgc tggagatggc     780
ccgtgacgag atcgagcgcc tggtgcaccg aaagccgatc ctgctgcacg tgatcggggc     840
cgtgatcgcc gaccggcgcg cgcacgaact tcggttgatg gcggactcgc aggactga     898

<210> SEQ ID NO 176
<211> LENGTH: 2013
<212> TYPE: DNA
<213> ORGANISM: Mycobacterium vaccae

<400> SEQUENCE: 176
```

```
ggctatcagt ccggacggtc ctcgctgcgc gcatcggtgt tcgaccgcct caccgacatc      60
cgcgagtcgc agtcgcgcgg gttggagaat cagttcgcgg acctgaagaa ctcgatggtg     120
atttactcgc gcggcagcac tgccacgagg gcgatcggcg cgttcagcga cggtttccgt     180
cagctcggcg atgcgacgat caataccggg caggcggcgt cattgcgccg ttactacgac     240
cggacgttcg ccaacaccac cctcgacgac agcggaaacc gcgtcgacgt ccgcgcgctc     300
atcccgaaat ccaaccccca gcgctatctg caggcgctct ataccccgcc gtttcagaac     360
tgggagaagg cgatcgcgtt cgacgacgcg cgcgacggca gcgcctggtc ggccgccaat     420
gccagattca acgagttctt ccgcgagatc gtgcaccgct tcaacttcga ggatctgatg     480
ctgctcgacc tcgagggcaa cgtggtgtac tccgcctaca aggggccgga tctcgggaca     540
aacatcgtca acggcccta tcgcaaccgg gaactgtcgg aagcctacga gaaggcggtc     600
gcgtcgaact cgatcgacta tgtcggtgtc accgacttcg ggtggtacct gcctgccgag     660
gaaccgaccg cctggttcct gtccccggtc gggttgaagg accgagtcga cggtgtgatg     720
gcggtccagt tcccgatcgc gcggatcaac gaattgatga cggcgcgggg acagtggcgt     780
gacaccggga tgggagacac cggtgagacc atcctggtcg gaccggacaa tctgatgcgc     840
tcggactccc ggctgttccg cgagaaccgg gagaagttcc tggccgacgt cgtcgagggg     900
ggaaccccgc cggaggtcgc cgacgaatcg gttgaccgcc gcggcaccac gctggtgcag     960
ccggtgacca cccgctccgt cgaggaggcc aacgcggca acaccgggac gacgatcgag    1020
gacgactatc tcgccacga ggcgttacag gcgtactcac cggtggacct gccgggactg    1080
cactgggtga tcgtgccaa gatcgacacc gacgaggcgt tcgccccggt ggcgcagttc    1140
accaggaccc tggtgctgtc gacggtgatc atcatcttcg gcgtgtcgct ggcggccatg    1200
ctgctggcgc ggttgttcgt ccgtccgatc cggcggttgc aggccggcgc ccagcagatc    1260
agcggcggtg actaccgcct cgctctgccg gtgttgtctc gtgacgaatt cggcgatctg    1320
acaacagctt tcaacgacat gagtcgcaat ctgtcgatca aggacgagct gctcggcgag    1380
gagcgcgccg agaaccaacg gctgatgctg tccctgatgc ccgaaccggt gatgcagcgc    1440
tacctcgacg gggaggagac gatcgcccag gaccacaaga acgtcacggt gatcttcgcc    1500
gacatgatgg gcctcgacga gttgtcgcgc atgttgacct ccgaggaact gatggtggtg    1560
gtcaacgacc tgacccgcca gttcgacgcc gccgccgaga gtctcggggt cgaccacgtg    1620
cggacgctgc acgacgggta cctggccagc tgcgggttag gcgtgccgcg gctggacaac    1680
gtccggcgca cggtcaattt cgcgatcgaa atggaccgca tcatcgaccg gcacgccgcc    1740
gagtccgggc acgacctgcg gctccgcgcg ggcatcgaca ccgggtcggc ggccagcggg    1800
ctggtggggc ggtccacgtt ggcgtacgac atgtggggtt cggcggtcga tgtcgctaac    1860
caggtgcagc gcggctcccc ccagcccggc atctacgtca cctcgcgggt gcacgaggtc    1920
atgcaggaaa ctctcgactt cgtcgccgcc ggggaggtcg tcggcgagcg cggcgtcgag    1980
acggtctggc ggttgcaggg ccaccggcga tga                                2013
```

<210> SEQ ID NO 177
<211> LENGTH: 297
<212> TYPE: PRT
<213> ORGANISM: Mycobacterium vaccae
<220> FEATURE:
<221> NAME/KEY: UNSURE
<222> LOCATION: (145)...(145)
<221> NAME/KEY: UNSURE
<222> LOCATION: (151)...(151)

```
<400> SEQUENCE: 177

Glu Gln Pro Phe Arg Leu Gly Asp Trp Ile Thr Val Pro Thr Ala Ala
 1               5                  10                  15

Gly Arg Pro Ser Ala His Gly Arg Val Val Glu Val Asn Trp Arg Ala
             20                  25                  30

Thr His Ile Asp Thr Gly Gly Asn Leu Leu Val Met Pro Asn Ala Glu
         35                  40                  45

Leu Ala Gly Ala Ser Phe Thr Asn Tyr Ser Arg Pro Val Gly Glu His
     50                  55                  60

Arg Leu Thr Val Val Thr Phe Asn Ala Ala Asp Thr Pro Asp Asp
 65                  70                  75                  80

Val Cys Glu Met Leu Ser Ser Val Ala Ala Ser Leu Pro Glu Leu Arg
                 85                  90                  95

Thr Asp Gly Gln Ile Ala Thr Leu Tyr Leu Gly Ala Ala Glu Tyr Glu
                100                 105                 110

Lys Ser Ile Pro Leu His Thr Pro Ala Val Asp Asp Ser Val Arg Ser
            115                 120                 125

Thr Tyr Leu Arg Trp Val Trp Tyr Ala Ala Arg Gln Glu Leu Arg
        130                 135                 140

Xaa Asn Gly Val Ala Asp Xaa Phe Asp Thr Pro Glu Arg Ile Ala Ser
145                 150                 155                 160

Ala Met Arg Ala Val Ala Ser Thr Leu Arg Leu Ala Asp Asp Glu Gln
                165                 170                 175

Gln Glu Ile Ala Asp Val Val Arg Leu Val Arg Tyr Gly Asn Gly Glu
            180                 185                 190

Arg Leu Gln Gln Pro Gly Gln Val Pro Thr Gly Met Arg Phe Ile Val
        195                 200                 205

Asp Gly Arg Val Ser Leu Ser Val Ile Asp Gln Asp Gly Asp Val Ile
    210                 215                 220

Pro Ala Arg Val Leu Glu Arg Gly Asp Phe Leu Gly Gln Thr Thr Leu
225                 230                 235                 240

Thr Arg Glu Pro Val Leu Ala Thr Ala His Ala Leu Glu Glu Val Thr
                245                 250                 255

Val Leu Glu Met Ala Arg Asp Glu Ile Glu Arg Leu Val His Arg Lys
                260                 265                 270

Pro Ile Leu Leu His Val Ile Gly Ala Val Ala Asp Arg Arg Ala His
            275                 280                 285

Glu Leu Arg Leu Met Asp Ser Gln Asp
        290                 295

<210> SEQ ID NO 178
<211> LENGTH: 670
<212> TYPE: PRT
<213> ORGANISM: Mycobacterium vaccae

<400> SEQUENCE: 178

Gly Tyr Gln Ser Gly Arg Ser Ser Leu Arg Ala Ser Val Phe Asp Arg
 1               5                  10                  15

Leu Thr Asp Ile Arg Glu Ser Gln Ser Arg Gly Leu Glu Asn Gln Phe
             20                  25                  30

Ala Asp Leu Lys Asn Ser Met Val Ile Tyr Ser Arg Gly Ser Thr Ala
         35                  40                  45

Thr Glu Ala Ile Gly Ala Phe Ser Asp Gly Phe Arg Gln Leu Gly Asp
     50                  55                  60
```

-continued

```
Ala Thr Ile Asn Thr Gly Gln Ala Ala Ser Leu Arg Arg Tyr Tyr Asp
 65                  70                  75                  80

Arg Thr Phe Ala Asn Thr Thr Leu Asp Asp Ser Gly Asn Arg Val Asp
                 85                  90                  95

Val Arg Ala Leu Ile Pro Lys Ser Asn Pro Gln Arg Tyr Leu Gln Ala
            100                 105                 110

Leu Tyr Thr Pro Pro Phe Gln Asn Trp Glu Lys Ala Ile Ala Phe Asp
        115                 120                 125

Asp Ala Arg Asp Gly Ser Ala Trp Ser Ala Ala Asn Ala Arg Phe Asn
    130                 135                 140

Glu Phe Phe Arg Glu Ile Val His Arg Phe Asn Phe Glu Asp Leu Met
145                 150                 155                 160

Leu Leu Asp Leu Glu Gly Asn Val Val Tyr Ser Ala Tyr Lys Gly Pro
                165                 170                 175

Asp Leu Gly Thr Asn Ile Val Asn Gly Pro Tyr Arg Asn Arg Glu Leu
            180                 185                 190

Ser Glu Ala Tyr Glu Lys Ala Val Ala Ser Asn Ser Ile Asp Tyr Val
        195                 200                 205

Gly Val Thr Asp Phe Gly Trp Tyr Leu Pro Ala Glu Pro Thr Ala
    210                 215                 220

Trp Phe Leu Ser Pro Val Gly Leu Lys Asp Arg Val Asp Gly Val Met
225                 230                 235                 240

Ala Val Gln Phe Pro Ile Ala Arg Ile Asn Glu Leu Met Thr Ala Arg
                245                 250                 255

Gly Gln Trp Arg Asp Thr Gly Met Gly Asp Thr Gly Glu Thr Ile Leu
            260                 265                 270

Val Gly Pro Asp Asn Leu Met Arg Ser Asp Ser Arg Leu Phe Arg Glu
        275                 280                 285

Asn Arg Glu Lys Phe Leu Ala Asp Val Val Glu Gly Gly Thr Pro Pro
    290                 295                 300

Glu Val Ala Asp Glu Ser Val Asp Arg Arg Gly Thr Thr Leu Val Gln
305                 310                 315                 320

Pro Val Thr Thr Arg Ser Val Glu Glu Ala Gln Arg Gly Asn Thr Gly
                325                 330                 335

Thr Thr Ile Glu Asp Asp Tyr Leu Gly His Glu Ala Leu Gln Ala Tyr
            340                 345                 350

Ser Pro Val Asp Leu Pro Gly Leu His Trp Val Ile Val Ala Lys Ile
        355                 360                 365

Asp Thr Asp Glu Ala Phe Ala Pro Val Ala Gln Phe Thr Arg Thr Leu
    370                 375                 380

Val Leu Ser Thr Val Ile Ile Phe Gly Val Ser Leu Ala Ala Met
385                 390                 395                 400

Leu Leu Ala Arg Leu Phe Val Arg Pro Ile Arg Arg Leu Gln Ala Gly
                405                 410                 415

Ala Gln Gln Ile Ser Gly Gly Asp Tyr Arg Leu Ala Leu Pro Val Leu
            420                 425                 430

Ser Arg Asp Glu Phe Gly Asp Leu Thr Thr Ala Phe Asn Asp Met Ser
        435                 440                 445

Arg Asn Leu Ser Ile Lys Asp Glu Leu Leu Gly Glu Glu Arg Ala Glu
    450                 455                 460

Asn Gln Arg Leu Met Leu Ser Leu Met Pro Glu Pro Val Met Gln Arg
465                 470                 475                 480

Tyr Leu Asp Gly Glu Glu Thr Ile Ala Gln Asp His Lys Asn Val Thr
```

```
                485                 490                 495
Val Ile Phe Ala Asp Met Met Gly Leu Asp Glu Leu Ser Arg Met Leu
                500                 505                 510

Thr Ser Glu Glu Leu Met Val Val Val Asn Asp Leu Thr Arg Gln Phe
            515                 520                 525

Asp Ala Ala Ala Glu Ser Leu Gly Val Asp His Val Arg Thr Leu His
        530                 535                 540

Asp Gly Tyr Leu Ala Ser Cys Gly Leu Gly Val Pro Arg Leu Asp Asn
545                 550                 555                 560

Val Arg Arg Thr Val Asn Phe Ala Ile Glu Met Asp Arg Ile Ile Asp
                565                 570                 575

Arg His Ala Ala Glu Ser Gly His Asp Leu Arg Leu Ala Gly Ile
                580                 585                 590

Asp Thr Gly Ser Ala Ala Ser Gly Leu Val Gly Arg Ser Thr Leu Ala
                595                 600                 605

Tyr Asp Met Trp Gly Ser Ala Val Asp Val Ala Asn Gln Val Gln Arg
            610                 615                 620

Gly Ser Pro Gln Pro Gly Ile Tyr Val Thr Ser Arg Val His Glu Val
625                 630                 635                 640

Met Gln Glu Thr Leu Asp Phe Val Ala Ala Gly Glu Val Val Gly Glu
                645                 650                 655

Arg Gly Val Glu Thr Val Trp Arg Leu Gln Gly His Arg Arg
                660                 665                 670

<210> SEQ ID NO 179
<211> LENGTH: 520
<212> TYPE: DNA
<213> ORGANISM: Mycobacterium vaccae

<400> SEQUENCE: 179
gtgatcgacg aaaccctctt ccatgccgag gagaagatgg agaaggccgt ctcggtggca      60
cccgacgacc tggcgtcgat tcgtaccggc cgcgcgaacc ccggcatgtt caaccggatc     120
aacatcgact actacggcgc ctccaccccg atcacgcagc tgtccagcat caacgtgccc     180
gaggcgcgca tggtggtgat caagccctac gaggcgagcc agctgcgcct catcgaggat     240
gcgatccgca actccgacct cggcgtcaat ccgaccaacg acggcaacat catccgggtg     300
tcgatcccgc agctcaccga ggagcgccgc cgcgacctgg tcaagcaggc caaggccaag     360
ggcgaggacg ccaaggtgtc ggtgcgcaac atccgtcgca cgatatgaa cacctttcgc     420 atcgcaccgg tacggctgcc gacgccaccg ccgtcgtaga agcgacagag gatcgcaggt     480
aacggtattg gccacgcctt ctgtggcggg ccgacaccac                           520

<210> SEQ ID NO 180
<211> LENGTH: 1071
<212> TYPE: DNA
<213> ORGANISM: Mycobacterium vaccae

<400> SEQUENCE: 180
cgtggggaag gattgcactc tatgagcgaa atcgcccgtc cctggcgggt tctggcaggt      60
ggcatcggtg cctgcgccgc gggtatcgcc ggggtgctga gcatcgcggt caccacggcg     120
tcggcccagc cgggcctccc gcagccccg ctgcccgccc tgccacagt gacgcaaacc     180 gtcacggttg cgcccaacgc cgcgccacaa ctcatcccgc gccccggtgt gacgcctgcc     240
accggcggcg ccgccgcggt gccgccgggg gtgagcgccc cggcggtcgc gccggccccc     300
```

-continued

```
gcgctgcccg cccgcccggt gtccacgatc gccccggcca cctcgggcac gctcagcgag    360
ttcttcgccg ccaagggcgt cacgatggag ccgcagtcca gccgcgactt ccgcgccctc    420
aacatcgtgc tgccgaagcc gcggggctgg gagcacatcc cggacccgaa cgtgccggac    480
gcgttcgcgg tgctggccga ccgggtcggc ggcaacggcc tgtactcgtc gaacgcccag    540
gtggtggtct acaaactcgt cggcgagttc gaccccaagg aagcgatcag ccacggcttc    600
gtcgacagcc agaagctgcc ggcgtggcgt tccaccgacg cgtcgctggc cgacttcggc    660
ggaatgccgt cctcgctgat cgagggcacc taccgcgaga acaacatgaa gctgaacacg    720
tcccggcgcc acgtcattgc caccgcgggg cccgaccact acctggtgtc gctgtcggtg    780
accaccagcg tcgaacaggc cgtggccgaa gccgcggagg ccaccgacgc gattgtcaac    840
ggcttcaagg tcagcgttcc gggtccgggt ccggccgcac cgccacctgc acccggtgcc    900
cccggtgtcc cgcccgcccc cggcgccccg gcgctgccgc tggccgtcgc accacccccg    960
gctcccgctg ttcccgccgt ggcgcccgcg ccacagctgc tgggactgca gggatagacg   1020
tcgtcgtccc ccgggcgaag cctggcgccc gggggacgac ggcccctttc t            1071

<210> SEQ ID NO 181
<211> LENGTH: 152
<212> TYPE: PRT
<213> ORGANISM: Mycobacterium vaccae

<400> SEQUENCE: 181

Val Ile Asp Glu Thr Leu Phe His Ala Glu Glu Lys Met Glu Lys Ala
 1               5                  10                  15

Val Ser Val Ala Pro Asp Asp Leu Ala Ser Ile Arg Thr Gly Arg Ala
            20                  25                  30

Asn Pro Gly Met Phe Asn Arg Ile Asn Ile Asp Tyr Tyr Gly Ala Ser
        35                  40                  45

Thr Pro Ile Thr Gln Leu Ser Ser Ile Asn Val Pro Glu Ala Arg Met
    50                  55                  60

Val Val Ile Lys Pro Tyr Glu Ala Ser Gln Leu Arg Leu Ile Glu Asp
65                  70                  75                  80

Ala Ile Arg Asn Ser Asp Leu Gly Val Asn Pro Thr Asn Asp Gly Asn
                85                  90                  95

Ile Ile Arg Val Ser Ile Pro Gln Leu Thr Glu Glu Arg Arg Arg Asp
            100                 105                 110

Leu Val Lys Gln Ala Lys Ala Lys Gly Glu Asp Ala Lys Val Ser Val
        115                 120                 125

Arg Asn Ile Arg Arg Asn Asp Met Asn Thr Phe Arg Ile Ala Pro Val
    130                 135                 140

Arg Leu Pro Thr Pro Pro Pro Ser
145                 150

<210> SEQ ID NO 182
<211> LENGTH: 331
<212> TYPE: PRT
<213> ORGANISM: Mycobacterium vaccae

<400> SEQUENCE: 182

Met Ser Glu Ile Ala Arg Pro Trp Arg Val Leu Ala Gly Gly Ile Gly
 1               5                  10                  15

Ala Cys Ala Ala Gly Ile Ala Gly Val Leu Ser Ile Ala Val Thr Thr
            20                  25                  30

Ala Ser Ala Gln Pro Gly Leu Pro Gln Pro Pro Leu Pro Ala Pro Ala
```

```
                   35                  40                  45
Thr Val Thr Gln Thr Val Thr Val Ala Pro Asn Ala Ala Pro Gln Leu
         50                  55                  60
Ile Pro Arg Pro Gly Val Thr Pro Ala Thr Gly Ala Ala Ala Val
 65                  70                  75                  80
Pro Ala Gly Val Ser Ala Pro Ala Val Ala Pro Ala Pro Ala Leu Pro
                 85                  90                  95
Ala Arg Pro Val Ser Thr Ile Ala Pro Ala Thr Ser Gly Thr Leu Ser
                100                 105                 110
Glu Phe Phe Ala Ala Lys Gly Val Thr Met Glu Pro Gln Ser Ser Arg
            115                 120                 125
Asp Phe Arg Ala Leu Asn Ile Val Leu Pro Lys Pro Arg Gly Trp Glu
    130                 135                 140
His Ile Pro Asp Pro Asn Val Pro Asp Ala Phe Ala Val Leu Ala Asp
145                 150                 155                 160
Arg Val Gly Gly Asn Gly Leu Tyr Ser Ser Asn Ala Gln Val Val Val
                165                 170                 175
Tyr Lys Leu Val Gly Glu Phe Asp Pro Lys Glu Ala Ile Ser His Gly
            180                 185                 190
Phe Val Asp Ser Gln Lys Leu Pro Ala Trp Arg Ser Thr Asp Ala Ser
    195                 200                 205
Leu Ala Asp Phe Gly Gly Met Pro Ser Ser Leu Ile Glu Gly Thr Tyr
210                 215                 220
Arg Glu Asn Asn Met Lys Leu Asn Thr Ser Arg Arg His Val Ile Ala
225                 230                 235                 240
Thr Ala Gly Pro Asp His Tyr Leu Val Ser Leu Ser Val Thr Thr Ser
                245                 250                 255
Val Glu Gln Ala Val Ala Glu Ala Ala Glu Ala Thr Asp Ala Ile Val
            260                 265                 270
Asn Gly Phe Lys Val Ser Val Pro Gly Pro Gly Pro Ala Ala Pro Pro
    275                 280                 285
Pro Ala Pro Gly Ala Pro Gly Val Pro Pro Ala Pro Gly Ala Pro Ala
    290                 295                 300
Leu Pro Leu Ala Val Ala Pro Pro Ala Pro Ala Val Pro Ala Val
305                 310                 315                 320
Ala Pro Ala Pro Gln Leu Leu Gly Leu Gln Gly
                325                 330
```

<210> SEQ ID NO 183
<211> LENGTH: 207
<212> TYPE: DNA
<213> ORGANISM: Mycobacterium vaccae

<400> SEQUENCE: 183
acctacgagt tcgagaacaa ggtcacgggc ggccgcatcc cgcgcgagta catcccgtcg    60
gtggatgccg gcgcgcagga cgccatgcag tacggcgtgc tggccggcta cccgctggtt   120
aacgtcaagc tgacgctgct cgacggtgcc taccacgaag tcgactcgtc ggaaatggca   180
ttcaaggttg ccggctccca ggtcata                                      207

<210> SEQ ID NO 184
<211> LENGTH: 69
<212> TYPE: PRT
<213> ORGANISM: Mycobacterium vaccae

<400> SEQUENCE: 184

```
Thr Tyr Glu Phe Glu Asn Lys Val Thr Gly Gly Arg Ile Pro Arg Glu
 1               5                  10                  15

Tyr Ile Pro Ser Val Asp Ala Gly Ala Gln Asp Ala Met Gln Tyr Gly
                20                  25                  30

Val Leu Ala Gly Tyr Pro Leu Val Asn Val Lys Leu Thr Leu Leu Asp
            35                  40                  45

Gly Ala Tyr His Glu Val Asp Ser Ser Glu Met Ala Phe Lys Val Ala
    50                  55                  60

Gly Ser Gln Val Ile
65
```

<210> SEQ ID NO 185
<211> LENGTH: 898
<212> TYPE: DNA
<213> ORGANISM: Mycobacterium vaccae
<220> FEATURE:
<221> NAME/KEY: unsure
<222> LOCATION: (637)...(637)
<221> NAME/KEY: unsure
<222> LOCATION: (662)...(662)

<400> SEQUENCE: 185

```
cgacctccac ccgggcgtga ggccaaccac taggctggtc accagtagtc gacggcacac     60
ttcaccgaaa aaatgaggac agaggagaca cccgtgacga tccgtgttgg tgtgaacggc    120
ttcggccgta tcgacgcaa cttcttccgc gcgctgacg cgcagaaggc cgaaggcaag     180
aacaaggaca tcgagatcgt cgcggtcaac gacctcaccg acaacgccac gctggcgcac    240
ctgctgaagt tcgactcgat cctgggccgg ctgccctacg acgtgagcct cgaaggcgag    300
gacaccatcg tcgtcggcag caccaagatc aaggcgctcg aggtcaagga aggcccggcg    360
gcgctgccct ggggcgacct gggcgtcgac gtcgtcgtcg agtccaccgg catcttcacc    420
aagcgcgaca aggcccaggg ccacctcgac gcgggcgcca agaaggtcat catctccgcg    480
ccggccaccg atgaggacat caccatcgtg ctcggcgtca cgacgacaa gtacgacggc    540
agccagaaca tcatctccaa cgcgtcgtgc accacgaact gcctcggccc gctggcgaag    600
gtcatcaacg acgagttcgg catcgtcaag ggcctgntga ccaccatcca cgcctacacc    660
cnggtccaga acctgcagga cggcccgcac aaggatctgc gccgggcccg cgccgccgcg    720
ctgaacatcg tgccgacctc caccggtgcc gccaaggcca tcggactggt gctgcccgag    780
ctgaagggca agctcgacgg ctacgcgctg cgggtgccga tccccaccgg ctcggtcacc    840
gacctgaccg ccgagctggg caagtcggcc accgtggacg agatcaacgc cgcgatga     898
```

<210> SEQ ID NO 186
<211> LENGTH: 268
<212> TYPE: PRT
<213> ORGANISM: Mycobacterium vaccae
<220> FEATURE:
<221> NAME/KEY: U

```
                35                  40                  45
His Leu Leu Lys Phe Asp Ser Ile Leu Gly Arg Leu Pro Tyr Asp Val
 50                  55                  60

Ser Leu Glu Gly Glu Asp Thr Ile Val Val Gly Ser Thr Lys Ile Lys
 65                  70                  75                  80

Ala Leu Glu Val Lys Glu Gly Pro Ala Ala Leu Pro Trp Gly Asp Leu
                 85                  90                  95

Gly Val Asp Val Val Val Glu Ser Thr Gly Ile Phe Thr Lys Arg Asp
                100                 105                 110

Lys Ala Gln Gly His Leu Asp Ala Gly Ala Lys Lys Val Ile Ile Ser
                115                 120                 125

Ala Pro Ala Thr Asp Glu Asp Ile Thr Ile Val Leu Gly Val Asn Asp
130                 135                 140

Asp Lys Tyr Asp Gly Ser Gln Asn Ile Ile Ser Asn Ala Ser Cys Thr
145                 150                 155                 160

Thr Asn Cys Leu Gly Pro Leu Ala Lys Val Ile Asn Asp Glu Phe Gly
                165                 170                 175

Ile Val Lys Gly Leu Xaa Thr Thr Ile His Ala Tyr Thr Xaa Val Gln
                180                 185                 190

Asn Leu Gln Asp Gly Pro His Lys Asp Leu Arg Arg Ala Arg Ala Ala
                195                 200                 205

Ala Leu Asn Ile Val Pro Thr Ser Thr Gly Ala Ala Lys Ala Ile Gly
210                 215                 220

Leu Val Leu Pro Glu Leu Lys Gly Lys Leu Asp Gly Tyr Ala Leu Arg
225                 230                 235                 240

Val Pro Ile Pro Thr Gly Ser Val Thr Asp Leu Thr Ala Glu Leu Gly
                245                 250                 255

Lys Ser Ala Thr Val Asp Glu Ile Asn Ala Ala Met
                260                 265

<210> SEQ ID NO 187
<211> LENGTH: 41
<212> TYPE: PRT
<213> ORGANISM: Mycobacterium vaccae
<220> FEATURE:
<221> NAME/KEY: UNSURE
<222> LOCATION: (39)...(39)

<400> SEQUENCE: 187

Met Asn Lys Ala Glu Leu Ile Asp Val Leu Thr Glu Lys Leu Gly Ser
 1               5                  10                  15

Asp Arg Arg Gln Ala Thr Ala Val Glu Asn Val Val Asp Thr Ile
                20                  25                  30

Val Ala Ala Val Pro Lys Xaa Val Val
             35                  40

<210> SEQ ID NO 188
<211> LENGTH: 26
<212> TYPE: DNA
<213> ORGANISM: Artificial Sequence
<220> FEATURE:
<223> OTHER INFORMATION: Made in a lab
<220> FEATURE:
<221> NAME/KEY: unsure
<222> LOCATION: (12)...(12)

<400> SEQUENCE: 188
atgaayaarg cngarctsat ygaygt                                    26
```

-continued

<210> SEQ ID NO 189
<211> LENGTH: 20
<212> TYPE: DNA
<213> ORGANISM: Artificial Sequence
<220> FEATURE:
<223> OTHER INFORMATION: Made in a lab

<400> SEQUENCE: 189
atsgtrtgva cvacgttytc                                                        20

<210> SEQ ID NO 190
<211> LENGTH: 84
<212> TYPE: DNA
<213> ORGANISM: Artificial Sequence
<220> FEATURE:
<223> OTHER INFORMATION: Made in a lab
<220> FEATURE:
<221> NAME/KEY: unsure
<222> LOCATION: (2)...(2)

<400> SEQUENCE: 190
gnactcattg acgtactcac tgagaagctg ggctcggatt gtcggcaagc gactgcggca            60
atggagaacg tggtccacac cata                                                   84

<210> SEQ ID NO 191
<211> LENGTH: 337
<212> TYPE: DNA
<213> ORGANISM: Mycobacterium vaccae
<220> FEATURE:
<221> NAME/KEY: unsure
<222> LOCATION: (2)...(2)

<400> SEQUENCE: 191
gnactcattg acgtactcac tgagaagctg ggctcggatt gtcggcaagc gactgcggcg            60
gtggagaatg ttgtcgacac catcgtgcgc gccgtgcaca agggtgagag cgtcaccatc           120
acgggcttcg gtgttttcga gcagcgtcgt cgcgcagcac gcgtggcacg caatccgcgc           180
accggcgaga ccgtgaaggt caagcccacc tcagtcccgg cattccgtcc cggcgctcag           240
ttcaaggctg ttgtctctgg cgcacagaag cttccggccg agggtccggc ggtcaagcgc           300
ggtgtgaccg cgacgagcac cgcccgcaag gcagcca                                   337

<210> SEQ ID NO 192
<211> LENGTH: 111
<212> TYPE: PRT
<213> ORGANISM: Mycobacterium vaccae
<220> FEATURE:
<221> NAME/KEY: UNSURE
<222> LOCATION: (1)...(1)

<400> SEQUENCE: 192

Xaa Leu Ile Asp Val Leu Thr Glu Lys Leu Gly Ser Asp Arg Gln Ala
 1               5                  10                  15

Thr Ala Ala Val Glu Asn Val Val Asp Thr Ile Val Arg Ala Val His
            20                  25                  30

Lys Gly Glu Ser Val Thr Ile Thr Gly Phe Gly Val Phe Glu Gln Arg
        35                  40                  45

Arg Arg Ala Ala Arg Val Ala Arg Asn Pro Arg Thr Gly Glu Thr Val
    50                  55                  60

Lys Val Lys Pro Thr Ser Val Pro Ala Phe Arg Pro Gly Ala Gln Phe
65                  70                  75                  80

Lys Ala Val Val Ser Gly Ala Gln Lys Leu Pro Ala Glu Gly Pro Ala

```
                85                  90                  95
Val Lys Arg Gly Val Thr Ala Thr Ser Thr Ala Arg Lys Ala Ala
                100                 105                 110

<210> SEQ ID NO 193
<211> LENGTH: 1164
<212> TYPE: DNA
<213> ORGANISM: Mycobacterium vaccae

<400> SEQUENCE: 193
ggtggcgcgc atcgagaagc gcccgccccg gttcacgggc gcctgatcat ggtgcgggcg      60
gcgctgcgct acggcttcgg gacggcctca ctgctggccg gcgggttcgt gctgcgcgcc     120
ctgcagggca cgcctgccgc cctcggcgcg actccgggcg aggtcgcgcc ggtggcgcgc     180
cgctcgccga actaccgcga cggcaagttc gtcaacctgg agccccgtc gggcatcacg      240 atggatcgcg acctgcagcg gatgctgttg cgcgatctgg ccaacgccgc atcccagggc     300
aagccgcccg gaccgatccc gctggccgag ccgccgaagg gggatcccac tcccgcgccg     360
gcggcggcca gctggtacgg ccattccagc gtgctgatcg aggtcgacgg ctaccgcgtg     420
ctggccgacc cggtgtggag caacagatgt tcgccctcac gggcggtcgg accgcagcgc     480
atgcacgacg tcccggtgcc gctggaggcg cttcccgccg tggacgcggt ggtgatcagc     540
cacgaccact acgaccacct cgacatcgac accatcgtcg cgttggcgca cacccagcgg     600
gccccgttcg tggtgccgtt gggcatcggc gcacacctgc gcaagtgggg cgtccccgag     660
gcgcggatcg tcgagttgga ctggcacgaa gcccaccgca tagacgacct gacgctggtc     720
tgcacccccg cccggcactt ctccggacgg ttgttctccc gcgactcgac gctgtgggcg     780
tcgtgggtgg tcaccggctc gtcgcacaag gcgttcttcg gtggcgacac cggatacacg     840
aagagcttcg ccgagatcgg cgacgagtac ggtccgttcg atctgaccct gctgccgatc     900
ggggcctacc atcccgcgtt cgccgacatc acatgaacc ccgaggaggc ggtgcgcgcc      960
catctggacc tgaccgaggt ggacaacagc ctgatggtgc ccatccactg gcgacattc      020 cgcctcgccc gcatccgtg gtccgagccc gccgaacgcc tgctgaccgc tgccgacgcc     080
gagcgggtac gcctgaccgt gccgattccc ggtcagcggg tggacccgga gtcgacgttc     140
gacccgtggt ggcggttctg aacc                                            164

<210> SEQ ID NO 194
<211> LENGTH: 370
<212> TYPE: PRT
<213> ORGANISM: Mycobacterium vaccae

<400> SEQUENCE: 194

Met Val Arg Ala Ala Leu Arg Tyr Gly Phe Gly Thr Ala Ser Leu Leu
1               5                   10                  15

Ala Gly Gly Phe Val Leu Arg Ala Leu Gln Gly Thr Pro Ala Ala Leu
                20                  25                  30

Gly Ala Thr Pro Gly Glu Val Pro Val Ala Arg Arg Ser Pro Asn
                35                  40                  45

Tyr Arg Asp Gly Lys Phe Val Asn Leu Glu Pro Pro Ser Gly Ile Thr
        50                  55                  60

Met Asp Arg Asp Leu Gln Arg Met Leu Leu Arg Asp Leu Ala Asn Ala
65                  70                  75                  80

Ala Ser Gln Gly Lys Pro Pro Gly Pro Ile Pro Leu Ala Glu Pro Pro
                85                  90                  95
```

-continued

```
Lys Gly Asp Pro Thr Pro Ala Pro Ala Ala Ser Trp Tyr Gly His
            100             105             110

Ser Ser Val Leu Ile Glu Val Asp Gly Tyr Arg Val Leu Ala Asp Pro
        115             120             125

Val Trp Ser Asn Arg Cys Ser Pro Ser Arg Ala Val Gly Pro Gln Arg
    130             135             140

Met His Asp Val Pro Val Pro Leu Glu Ala Leu Pro Ala Val Asp Ala
145             150             155             160

Val Val Ile Ser His Asp His Tyr Asp His Leu Asp Ile Asp Thr Ile
            165             170             175

Val Ala Leu Ala His Thr Gln Arg Ala Pro Phe Val Val Pro Leu Gly
            180             185             190

Ile Gly Ala His Leu Arg Lys Trp Gly Val Pro Glu Ala Arg Ile Val
            195             200             205

Glu Leu Asp Trp His Glu Ala His Arg Ile Asp Asp Leu Thr Leu Val
            210             215             220

Cys Thr Pro Ala Arg His Phe Ser Gly Arg Leu Phe Ser Arg Asp Ser
225             230             235             240

Thr Leu Trp Ala Ser Trp Val Val Thr Gly Ser Ser His Lys Ala Phe
            245             250             255

Phe Gly Gly Asp Thr Gly Tyr Thr Lys Ser Phe Ala Glu Ile Gly Asp
            260             265             270

Glu Tyr Gly Pro Phe Asp Leu Thr Leu Leu Pro Ile Gly Ala Tyr His
            275             280             285

Pro Ala Phe Ala Asp Ile His Met Asn Pro Glu Glu Ala Val Arg Ala
            290             295             300

His Leu Asp Leu Thr Glu Val Asp Asn Ser Leu Met Val Pro Ile His
305             310             315             320

Trp Ala Thr Phe Arg Leu Ala Pro His Pro Trp Ser Glu Pro Ala Glu
            325             330             335

Arg Leu Leu Thr Ala Ala Asp Ala Glu Arg Val Arg Leu Thr Val Pro
            340             345             350

Ile Pro Gly Gln Arg Val Asp Pro Glu Ser Thr Phe Asp Pro Trp Trp
            355             360             365

Arg Phe
370
```

METHODS FOR THE TREATMENT OF IMMUNOLOGICALLY-MEDIATED SKIN DISORDERS

REFERENCE TO RELATED APPLICATIONS

This application is a continuation-in-part of U.S. patent application Ser. No. 08/997,080, filed Dec. 23, 1997 now U.S. Pat. No. 5,968,524.

TECHNICAL FIELD

This invention relates generally to the treatment by vaccination or immunotherapy of skin disorders such as psoriasis, atopic dermatitis, allergic contact dermatitis, alopecia areata, and the skin cancers basal cell carcinoma, squamous cell carcinoma and melanoma. In particular, the invention is related to the use of compounds which are present in or have been derived from *Mycobacterium vaccae* (*M. vaccae*) or from the culture filtrate of *M. vaccae*.

BACKGROUND OF THE INVENTION

This invention deals with treatment of disorders of skin which appear to be associated with factors that influence the balance of thymus-derived (T) immune cells known as Th1 and Th2. These T cells are identified by their cytokine secretion phenotype. A common feature of treatment is the use of compounds prepared from *M. vaccae* which have immunomodulating properties that alter the balance of activities of these T cells as well as other immune cells.

Psoriasis is a common, chronic inflammatory skin disease which can be associated with various forms of arthritis in a minority of patients. The defect in psoriasis appears to be overly rapid growth of keratinocytes and shedding of scales from the skin surface. Drug therapy is directed at slowing down this process. The disease may become manifest at any age. Spontaneous remission is relatively rare, and life-long treatment is usually necessary. Psoriasis produces chronic, scaling red patches on the skin surface. Psoriasis is a very visible disease, it frequently affects the face, scalp, trunk and limbs. The disease is emotionally and physically debilitating for the patient, detracting significantly from the quality of life. Between one and three million individuals in the United States have psoriasis with nearly a quarter million new cases occurring each year. Conservative estimates place the costs of psoriasis care in the United States currently at $248 million a year.

There are two major hypotheses concerning the pathogenesis of psoriasis. The first is that genetic factors determine abnormal proliferation of epidermal keratinocytes. The cells no longer respond normally to external stimuli such as those involved in maintaining epidermal homeostasis. Abnormal expression of cell membrane cytokine receptors or abnormal transmembrane signal transduction might underlie cell hyperproliferation. Inflammation associated with psoriasis is secondary to the release of pro-inflammatory molecules from hyperproliferative keratinocytes.

A second hypothesis is that T cells interacting with antigen-presenting cells in skin release pro-inflammatory and keratinocyte-stimulating cytokines (Hancock, G. E. et al., *J. Exp. Med.* 168:1395–1402, 1988). Only T cells of genetically predetermined individuals possess the capacity to be activated under such circumstances. The keratinocytes themselves may be the antigen-presenting cell. The cellular infiltrate in psoriatic lesions show an influx of CD4+ T cells and, more prominently, CD8+ T cells (Bos, J. D. et al., *Arch. Dermatol. Res.* 281:23–3, 1989; Baker, B. S., *Br. J. Dermatol.* 110:555–564, 1984).

As the majority (90%) of psoriasis patients have limited forms of the disease, topical treatments which include dithranol, tar preparations, corticosteroids and the recently introduced vitamin D3 analogues (calcipotriol, calcitriol) can be used. A minority (10%) of psoriasis patients have a more serious condition, for which a number of systemic therapeutic modalities are available. Specific systemic therapies include UVB, PUVA, methotrexate, vitamin A derivatives (acitretin) and immuno-suppressants such as Cyclosporin A. The effectiveness of Cyclosporin and FK-506 for treating psoriasis provides support for the T cell hypothesis as the prime cause of the disease (Bos, J. D. et al., *Lancet II*:1500–1502, 1989; Ackerman, C. et al., *J. Invest. Dermatol.* 96:536 [abstract], 1991).

Atopic dermatitis is a chronic pruritic inflammatory skin disease which usually occurs in families with an hereditary predisposition for various allergic disorders such as allergic rhinitis and asthma. Atopic dermatitis occurs in approximately 10% of the general population. The main symptoms are dry skin, dermatitis (eczema) localised mainly in the face, neck and on the flexor sides and folds of the extremities accompanied by severe itching. It typically starts within the first two years of life. In about 90% of the patients this skin disease disappears during childhood but the symptoms can continue into adult life. It is one of the commonest forms of dermatitis world-wide. It is generally accepted that in atopy and in atopic dermatitis, a T cell abnormality is primary and that the dysfunction of T cells which normally regulate the production of IgE is responsible for the excessive production of this immunoglobulin.

Allergic contact dermatitis is a common non-infectious inflammatory disorder of the skin. In contact dermatitis, immunological reactions cannot develop until the body has become sensitised to a particular antigen. Subsequent exposure of the skin to the antigen and the recognition of these antigens by T cells result in the release of various cytokines, proliferation and recruitment of T cells and finally in dermatitis (eczema).

Only a small proportion of the T cells in a lesion of allergic contact dermatitis are specific for the relevant antigen. Activated T cells probably migrate to the sites of inflammation regardless of antigen-specificity. Delayed-type hypersensitivity can only be transferred by T cells ($CD4^+$ cells) sharing the MHC class II antigens. The 'response' to contact allergens can be transferred by T cells sharing either MHC class I ($CD8^+$ cells) or class II ($CD4^+$ cells) molecules (Sunday, M. E. et al., *J. Immunol.* 125:1601–1605, 1980). Keratinocytes can produce interleukin-1 which can facilitate the antigen presentation to T cells. The expression of the surface antigen intercellular adhesion molecule-1 (ICAM-1) is induced both on keratinocytes and endothelium by the cytokines tumor necrosis factor (TNF) and interferon-gamma (IFN-$\gamma$).

If the causes can be identified, removal alone will cure allergic contact dermatitis. During active inflammation, topical corticosteroids are useful. An inhibitory effect of cyclosporin has been observed in delayed-type hypersensitivity on the pro-inflammatory function(s) of primed T cells in vitro (Shidani, B. et al., *Eur. J. Immunol.* 14:314–318, 1984). The inhibitory effect of cyclosporin on the early phase of T cell activation in mice has also been reported (Milon, G. et al., *Ann. Immunol.* (*Inst. Pasteur*) 135d:237–245, 1984).

Alopecia areata is a common hair disease, which accounts for about 2% of the consultations at dermatological outpatient clinics in the United States. The hallmark of this disease is the formation of well-circumscribed round or oval patches of nonscarring alopecia which may be located in any hairy area of the body. The disease may develop at any age. The onset is usually sudden and the clinical course is varied.

At present, it is not possible to attribute all or indeed any case of alopecia areata to a single cause (Rook, A. and Dawber, R, *Diseases of the Hair and Scalp*, Blackwell Scientific Publications 1982: 272–30). There are many factors that appear to be involved. These include genetic factors, atopy, association with disorders of supposed autoimmune etiology, Down's syndrome and emotional stress. The prevalence of atopy in patients with alopecia areata is increased. There is evidence that alopecia areata is an autoimmune disease. This evidence is based on consistent histopathological findings of a lymphocytic T cell infiltrate in and around the hair follicles with increased numbers of Langerhans cells, the observation that alopecia areata will respond to treatment with immunomodulating agents, and that there is a statistically significant association between alopecia areata and a wide variety of autoimmune diseases (Mitchell, A. J. et al., *J. Am. Acad. Dermatol.* 11:763–775, 1984). Alopecia areata is associated with abnormal antibody production, which is believed to be associated with a Th2 immune response.

Immunophenotyping studies on scalp biopsy specimens shows expression of HLA-DR on epithelial cells in the presumptive cortex and hair follicles of active lesions of alopecia areata, as well as a T cell infiltration with a high proportion of helper/inducer T cells in and around the hair follicles, increased numbers of Langerhans cells and the expression of ICAM-1 (Messenger, A. G. et al., *J. Invest. Dermatol.* 85:569–576, 1985; Gupta, A. K. et al., *J. Am. Acad. Dermatol.* 22:242–250, 1990).

The large variety of therapeutic modalities in alopecia areata can be divided into four categories: (i) non-specific topical irritants; (ii) 'immune modulators' such as systemic corticosteroids and PUVA; (iii) 'immune enhancers' such as contact dermatitis inducers, cyclosporin and inosiplex; and (iv) drugs of unknown action such as minoxidil (Dawber, R. P. R. et al., Textbook of Dermatology, Blackwell Scientific Publications, $5^{th}$ Ed, 1982:2533–2638). Non-specific topical irritants such as dithranol may work through as yet unidentified mechanisms rather than local irritation in eliciting regrowth of hair. Topical corticosteroids may be effective but prolonged therapy is often necessary. Intralesional steroids have proved to be more effective but their use is limited to circumscribed patches of less active disease or to maintain regrowth of the eyebrows in alopecia totalis. Photochemotherapy has proved to be effective, possibly by changing functional subpopulations of T cells. Topical immunotherapy by means of induction and maintenance of allergic contact dermatitis on the scalp may result in hair regrowth in as many as 70% of the patients with alopecia areata. Diphencyprone is a potent sensitiser free from mutagenic activity. Oral cyclosporin can be effective in the short term (Gupta, A. K. et al., *J. Am. Acad. Dermatol.* 22:242–250, 1990). Inosiplex, an immunostimulant, has been used with apparent effectiveness in an open trial. Topical 5% minoxidil solution has been reported to be able to induce some hair growth in patients with alopecia areata. The mechanism of action is unclear.

Carcinomas of the skin are a major public health problem because of their frequency and the disability and disfigurement that they cause. Carcinoma of the skin is principally seen in individuals in their prime of life, especially in fair skinned individuals exposed to large amounts of sunlight. The annual cost of treatment and time loss from work exceeds $250 million dollars a year in the United States alone. The three major types—basal cell cancer, squamous cell cancer, and melanoma—are clearly related to sunlight exposure.

Basal cell carcinomas are epithelial tumours of the skin. They appear predominantly on exposed areas of the skin. In a recent Australian study, the incidence of basal cell carcinomas was 652 new cases per year per 100,000 of the population. This compares with 160 cases of squamous cell carcinoma or 19 of malignant melanoma (Giles, G. et al., *Br. Med. J.* 296:13–17, 1988). Basal cell carcinomas are the most common of all cancers. Lesions are usually surgically excised. Alternate treatments include retinoids, 5-fluorouracil, cryotherapy and radiotherapy. Alpha or gamma interferon have also been shown to be effective in the treatment of basal cell carcinomas, providing a valuable alternative to patients unsuitable for surgery or seeking to avoid surgical scars (Cornell et al., *J. Am. Acad. Dermatol.* 23:694–700, 1990; Edwards, L. et al., *J. Am. Acad. Dermatol.* 22:496–500, 1990).

Squamous cell carcinoma (SCC) is the second most common cutaneous malignancy, and its frequency is increasing. There are an increasing number of advanced and metastatic cases related to a number of underlying factors. Currently, metastatic SCC contributes to over 2000 deaths per year in the United States; the 5 year survival rate is 35%, with 90% of the metastases occurring by 3 years. Metastasis almost always occurs at the first lymphatic drainage station. The need for medical therapy for advanced cases is clear. A successful medical therapy for primary SCC of the skin would obviate the need for surgical excision with its potential for scarring and other side effects. This development may be especially desirable for facial lesions.

Because of their antiproliferative and immunomodulating effects in vitro, interferons (IFNs) have also been used in the treatment of melanoma (Kirkwood, J. M. et al., *J. Invest. Dermatol.* 95:180S–4S, 1990). Response rates achieved with systemic IFN-α, in either high or low dose, in metastatic melanoma were in the range 5–30%. Recently, encouraging results (30% response) were obtained with a combination of IFN-α and DTIC. Preliminary observations indicate a beneficial effect of IFN-α in an adjuvant setting in patients with high risk melanoma. Despite the low efficacy of IFN monotherapy in metastatic disease, several randomised prospective studies are now being performed with IFNs as an adjuvant or in combination with chemotherapy (McLeod, G. R. et al., *J. Invest. Dermatol.* 95:185S–7S, 1990; Ho, V. C. et al., *J. Invest. Dermatol.* 22:159–76, 1990).

Of all the available therapies for treating cutaneous viral lesions, only interferon possesses a specific antiviral mode of action, by reproducing the body's immune response to infection. Interferon treatment cannot eradicate the viruses however, although it may help with some manifestations of the infection. Interferon treatment is also associated with systemic adverse effects, requires multiple injections into each single wart and has a significant economic cost (Kraus, S. J. et al., *Review of Infectious Diseases* 2(6):S620–S632, 1990; Frazer, I. H., *Current Opinion in Immunology* 8(4):484–491, 1996).

Many compositions have been developed for topical application to treat skin disorders. Such topical treatments generally have limited beneficial effects. International Patent Publication WO 91/02542 discloses treatment of chronic inflammatory disorders in which a patient demonstrates an abnormally high release of IL-6 and/or TNF or in which the patient's IgG shows an abnormally high proportion of agalactosyl IgG. Among the disorders mentioned in this publication are psoriasis, rheumatoid arthritis, mycobacterial disease, Crohn's disease, primary biliary cirrhosis, sarcoidosis, ulcerative colitis, systemic lupus erythematosus, multiple sclerosis, Guillain-Barre syndrome, primary diabetes mellitus, and some aspects of graft rejection. The therapeutic agent preferably comprises autoclaved *M. vaccae* administered by injection in a single dose. This publication does not disclose any clinical results.

Several other patents and publications disclose treatment of various conditions by administering mycobacteria, including *M. vaccae*, or certain mycobacterial fractions. U.S. Pat. No. 4,716,038 discloses diagnosis of, vaccination against and treatment of autoimmune diseases of various types, including arthritic diseases, by administering mycobacteria, including *M. vaccae*. U.S. Pat. No. 4,724,144 discloses an immunotherapeutic agent comprising antigenic material derived from *M. vaccae* for treatment of mycobacterial diseases, especially tuberculosis and leprosy, and as an adjuvant to chemotherapy. International Patent Publication WO 91/01751 discloses the use of antigenic and/or immunoregulatory material from *M. vaccae* as an immunoprophylactic to delay and/or prevent the onset of AIDS. International Patent Publication WO 94/06466 discloses the use of antigenic and/or immunoregulatory material derived from *M. vaccae* for therapy of HIV infection, with or without AIDS and with or without associated tuberculosis.

U.S. Pat. No. 5,599,545 discloses the use of mycobacteria, especially whole, inactivated *M. vaccae*, as an adjuvant for administration with antigens which are not endogenous to *M. vaccae*. This publication theorises that the beneficial effect as an adjuvant may be due to heat shock protein 65 (hsp 65). International Patent Publication WO 92/08484 discloses the use of antigenic and/or immunoregulatory material derived from *M. vaccae* for the treatment of uveitis. International Patent Publication WO 93/16727 discloses the use of antigenic and/or immunoregulatory material derived from *M. vaccae* for the treatment of mental diseases associated with an autoimmune reaction initiated by an infection. International Patent Publication WO 95/26742 discloses the use of antigenic and/or immunoregulatory material derived from *M. vaccae* for delaying or preventing the growth or spread of tumors.

*M. vaccae* is apparently unique among known mycobacterial species in that heat-killed preparations retain vaccine and immunotherapeutic properties. For example, *M. bovis*-BCG vaccines, used for vaccination against tuberculosis, employ live strains. Heat-killed *M. bovis* BCG and *M. tuberculosis* have no protective properties when employed in vaccines. A number of compounds have been isolated from a range of mycobacterial species which have adjuvant properties. The effect of such adjuvants is essentially to stimulate a particular immune response mechanism against an antigen from another species.

There are two general classes of compounds which have been isolated from mycobacterial species that exhibit adjuvant properties. The first are water soluble wax D fractions (R. G. White, I. Bernstock, R. G. S. Johns and E. Lederer, *Immunology*, 1:54, 1958; U.S. Pat. No. 4,036,953). The second are muramyl dipeptide-based substances (N-acetyl glucosamine and N-glycolymuramic acid in approximately equimolar amounts) as described in U.S. Pat. Nos. 3,956,481 and 4,036,953. These compounds differ from the delipidated and deglycolipidated *M. vaccae* (DD-*M. vaccae*) of the present invention in the following aspects of their composition:

1. They are water-soluble agents, whereas DD-*M. vacccae* is insoluble in aqueous solutions.
2. They consist of a range of small oligomers of the mycobacterial cell wall unit, either extracted from bacteria by various solvents, or digested from the cell wall by an enzyme. In contrast, DD-*M. vaccae* contains highly polymerised cell wall.
3. All protein has been removed from their preparations by digestion with proteolytic enzymes. The only constituents of their preparations are the components of the cell wall peptidoglycan structure, namely alanine, glutamic acid, diaminopimelic acid, N-acetyl glucosamine, and N-glycolylmuramic acid. In contrast, DD-*M. vaccae* contains 50% w/w protein, comprising a number of distinct protein species.

There thus remains a need in the art for effective compositions and methods for the treatment of skin disorders that are inexpensive and cause few undesirable side effects.

SUMMARY OF INVENTION

Briefly stated, the present invention provides methods for the treatment of the skin disorders, including psoriasis, atopic dermatitis, allergic contact dermatitis, alopecia areata, scleroderma and skin cancers, such methods comprising administering an immunotherapeutic composition which is believed to have antigenic and/or adjuvant properties. The immunotherapeutic compositions are preferably administered by intradermal injection.

In a first aspect, the inventive methods comprise administering one or more doses of a composition including a component selected from the group consisting of inactivated *M. vaccae* cells, delipidated and deglycolipidated *M. vaccae* cells, and components that are present in or derived from either *M. vaccae* cells or *M. vaccae* culture filtrate. Specific examples of components present in or derived from either *M. vaccae* cells or *M. vaccae* culture filtrate include polypeptides that comprise an immunogenic portion of an antigen, or a variant thereof, wherein the antigen includes a sequence selected from the group consisting of SEQ ID NOS: 1–4, 9–16, 18–21, 23, 25, 26, 28, 29, 44, 45, 47, 52–55, 63, 64, 70, 75, 89, 94, 98, 100–105, 109, 110, 112, 121, 124, 125, 134, 135, 140, 141, 143, 145, 147, 152, 154, 156, 158, 160, 165, 166, 170, 172, 174, 177, 178, 181, 182, 184, 186, 187, 192 and 194.

In a second aspect, the inventive methods comprise administering a first dose of an immunotherapeutic composition at a first point in time and administering a second dose of the composition at a second, subsequent, point in time. Preferably, the multiple doses are administered at intervals of about 2–4 weeks. In one embodiment, compositions which may be usefully employed in such methods comprise a component selected from the group consisting of inactivated *M. vaccae* cells, *M. vaccae* culture filtrate, delipidated and deglycolipidated *M. vaccae* cells, and constituents and combinations thereof. In a second embodiment, compositions for use in such methods comprise at least one compound which is present in or derived from either *M. vaccae* cells or *M. vaccae* culture filtrate. Examples of such compounds include polypeptides comprising an immunogenic portion of an antigen, or a variant thereof, wherein the antigen includes a sequence selected from the group consisting of SEQ ID NOS: 1–4, 9–16, 18–21, 23, 25, 26, 28, 29, 44, 45, 47, 52–55, 63, 64, 70, 75, 89, 94, 98, 100–105, 109, 110, 112, 121, 124, 125, 134, 135, 140, 141, 143, 145, 147, 152, 154, 156, 158, 160, 165, 166, 170, 172, 174, 177, 178, 181, 182, 184, 186, 187, 192 and 194.

Additional compositions which may be usefully employed in the inventive methods comprise a DNA molecule encoding one or more of the above polypeptides. Compositions comprising a fusion protein, wherein the fusion protein includes at least one of the above polypeptides, together with DNA molecules encoding such fusion proteins, may also be usefully employed in the methods of the present invention.

The compositions employed in the present invention may additionally include a non-specific immune response enhancer, or adjuvant. Such adjuvants may include *M. vaccae* culture filtrate, delipidated and deglycolipidated *M. vaccae* cells, or a polypeptide comprising an immunogenic portion of an antigen, or a variant thereof, wherein said antigen includes a sequence provided in SEQ ID NOS: 114, 117 or 118.

The present invention further provides a method for treating psoriasis in a patient comprising administering a composition including a component selected from the group consisting of: inactivated *M. vaccae* cells; and delipidated and deglycolipidated *M. vaccae* cells, wherein the patient has a PASI score of less than about 10 following treatment.

In yet further aspects, methods are provided for inhibiting a Th2 immune response, and for treating skin disorders that are caused, at least in part, by a Th2 immune response (for example, atopic dermatitis, allergic contact dermatitis, alopecia areata, skin disorders associated with systemic lupus erythematosus, and other antibody-mediated skin diseases) such methods comprising administering a composition comprising inactivated *M. vaccae* cells, or delipidated and deglycolipidated *M. vaccae* cells. Methods are also provided for stimulating the production of IL-10 and thereby inhibiting skin inflammation, such methods comprising administering a composition comprising a component selected from the group consisting of: inactivated *M. vaccae* cells, and delipidated and deglycolipidated *M. vaccae* cells (DD-*M. vaccae* cells).

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIGS. 3A(i)–(iv) illustrate the non-specific immune amplifying effects of 10 µg, 100 µg and 1 mg autoclaved *M. vaccae* and 75 µg unfractionated culture filtrates of *M. vaccae*, respectively.

FIGS. 3B(i) and (ii) illustrate the non-specific immune amplifying effects of autoclaved *M. vaccae*, and delipidated and deglycolipidated *M. vaccae*, respectively.

FIG. 3C(i) illustrates the non-specific immune amplifying effects of whole autoclaved *M. vaccae*.

FIG. 3C(ii) illustrates the non-specific immune amplifying effects of soluble *M. vaccae* protein extracted with SDS from delipidated and deglycolipidated *M. vaccae*.

FIG. 3C(iii) illustrates that the non-specific immune amplifying effects of the preparation of FIG. 3C(ii) are destroyed by treatment with the proteolytic enzyme Pronase.

FIG. 3D illustrates the non-specific immune amplifying effects of heat-killed *M. vaccae* (FIG. 3D(i)), whereas a non-specific immune amplifying effect was not seen with heat-killed preparations of *M. tuberculosis* (FIG. 3D(ii)), *M. bovis* BCG (FIG. 3D(iii)), *M. phlei* (FIG. 3D(iv)) or *M. smegmatis* (FIG. 3D(v)).

FIGS. 4A and B show the effect of administering either 10 or 1000 µg of heat-killed *M. vaccae* (FIG. 4A), or 10, 100 or 200 µg of DD-*M. vaccae* (FIG. 4B) intranasally 4 weeks before intranasal challenge with ovalbumin on eosinophil numbers in BAL cells.

FIGS. 4C and D show the effect of administering to mice either 1000 µg of heat-killed *M. vaccae* (FIG. 4C) or 200 µg of DD-*M. vaccae* (FIG. 4D) intranasally one week before ovalbumin challenge. In FIG. 4E, immunisation was with either 1 mg of heat-killed *M. vaccae* or 200 µg of DD-*M. vaccae*, given either intranasally (i.n.) or subcutaneously (s.c.). In the same experiment, the effect of immunization with *M. bovis* BCG of the Pasteur (BCG-P) and Connought (BCG-C) strains prior to challenge was determined.

DETAILED DESCRIPTION OF THE INVENTION

Figure 1:
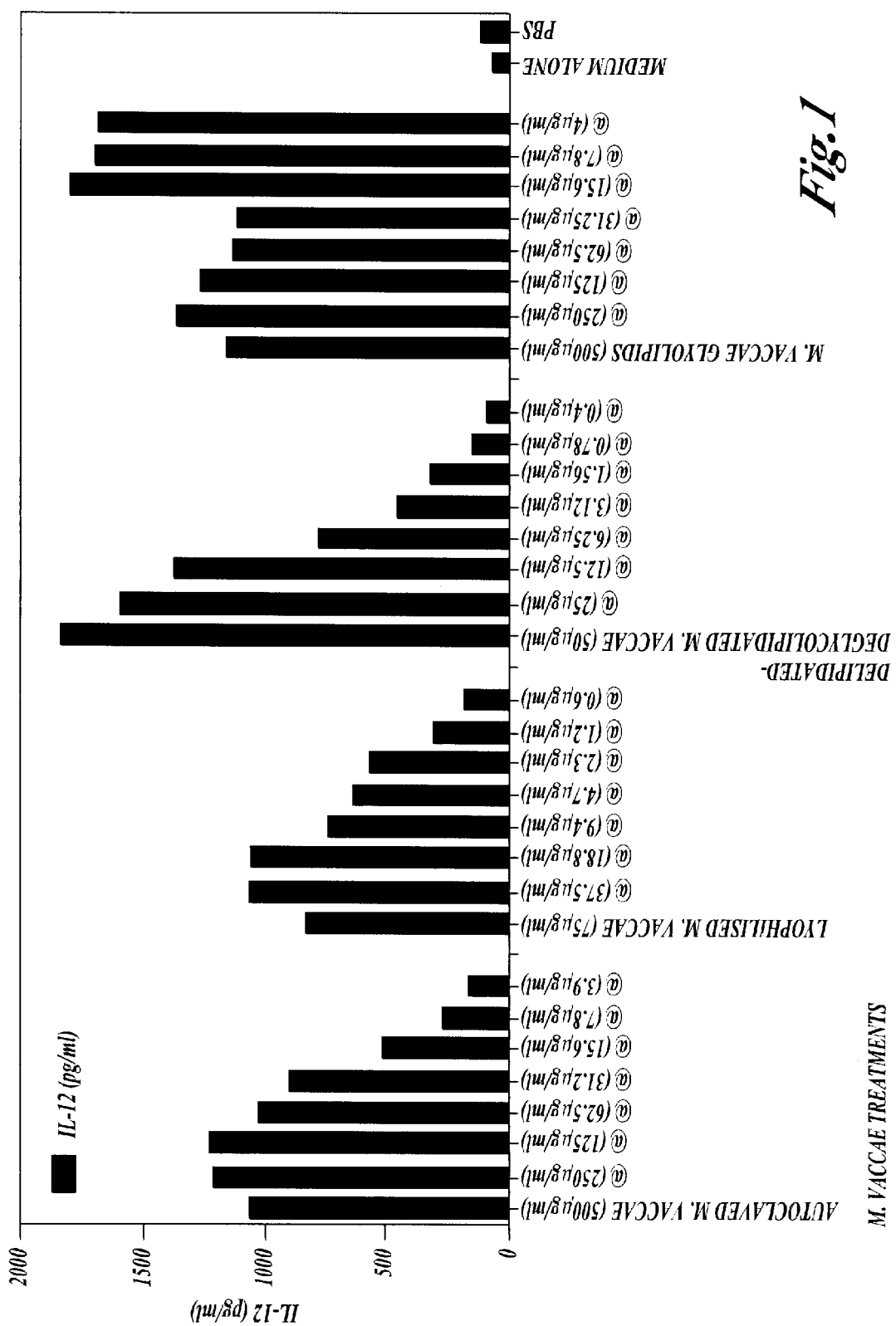
FIG. 1 compares the stimulation of Interleukin 12 (IL-12) production in macrophages by different concentrations of heat-killed (autoclaved) *M. vaccae*, lyophilised *M. vaccae*, delipidated and deglycolipidated *M. vaccae*, and *M. vaccae* glycolipids.

Effective vaccines that provide protection against infectious microorganisms contain at least two functionally different components. The first is an antigen, which may be polypeptide or carbohydrate in nature, and which is processed by macrophages and other antigen-presenting cells and displayed for CD4$^+$ T cells or for CD8$^+$ T cells. This antigen forms the "specific" target of an immune response. The second component of a vaccine is a non-specific immune response amplifier, termed an adjuvant, with which the antigen is mixed or is incorporated into. An adjuvant amplifies either cell-mediated or antibody immune responses to a structurally unrelated compound or polypeptide. Several known adjuvants are prepared from microbes such as *Bordetella pertussis*, *M. tuberculosis* and *M. bovis* BCG. Adjuvants may also contain components designed to protect polypeptide antigens from degradation, such as aluminum hydroxide or mineral oil. While the antigenic component of a vaccine contains polypeptides that direct the immune attack against a specific pathogen, such as *M. tuberculosis*, the adjuvant is often capable of broad use in many different vaccine formulations. Certain known proteins, such as bacterial enterotoxins, can function both as an antigen to elicit a specific immune response and as an adjuvant to enhance immune responses to unrelated proteins.

Certain pathogens, such as *M. tuberculosis*, as well as certain cancers, are effectively contained by an immune attack directed by CD4$^+$ and CD8$^+$ T cells, known as cell-mediated immunity. Other pathogens, such as poliovirus, also require antibodies, produced by B cells, for containment. These different classes of immune attack (T cell or B cell) are controlled by different subpopulations of CD4$^+$ T cells, commonly referred to as Th1 and Th2 cells.

A desirable property of an adjuvant is the ability to selectively amplify the function of either Th1 or Th2 populations of CD4+ T cells. Many skin disorders, including psoriasis, atopic dermatitis, alopecia, and skin cancers appear to be influenced by differences in the activity of these Th cell subsets.

Two types of Th cell subsets have been described in a murine model and are defined by the cytokines they release upon activation. The Th1 subset secretes IL-2, INF-γ and tumor necrosis factor, and mediates macrophage activation and delayed-type hypersensitivity response. The Th2 subset releases IL-4, IL-5, IL-6 and IL-10, and stimulate B cell activation. The Th1 and Th2 subsets are mutually inhibiting, so that IL-4 inhibits Th1-type responses, and INF-γ inhibits Th2-type responses. Similar Th1 and Th2 subsets have been found in humans, with release of the identical cytokines observed in the murine model. In particular, the majority of T-cell clones from atopic human lymphocytes resemble the murine Th2 cell that produces IL-4, whereas very few clones produce IFN-γ. Therefore, the selective expression of the Th2 subset with subsequent production of IL-4 and decreased levels of IFN-γ-producing cells could lead to preferential enhancement of IgE production.

Inactivated *M. vaccae* and compounds derived from *M. vaccae* have both antigen and adjuvant properties which function to ehance Th1-type immune responses. The methods of the present invention employ one or more of these antigen and adjuvant compounds from *M. vaccae* and/or its culture filtrates to redirect immune activities of T cells in patients. Mixtures of such compounds are particularly effective in the methods disclosed herein. While it is well known that all mycobacteria contain many cross-reacting antigens, it is not known whether they contain adjuvant compounds in common. As shown below, inactivated *M. vaccae* and a modified (delipidated and deglycolipidated) from of inactivated *M. vaccae* have been found to have adjuvant properties of the Th1-type which are not shared by a number of other mycobacterial species. In addition, it has been found that inactivated *M. vaccae* and delipidated and deglycolipidated *M. vaccae* (DD-*M. vaccae*) inhibit Th2 immune responses. DD-*M. vaccae* has also been shown to stimulate the production of IL-10 and may therefore be effectively employed to inhibit skin inflammation. Furthermore, it has been found that *M. vaccae* produces compounds in its own culture filtrate which amplify the immune response to *M. vaccae* antigens also found in culture filtrate, as well as to antigens from other sources.

The present invention provides methods for the immunotherapy of skin disorders, including psoriasis, atopic dermatitis, alopecia, and skin cancers in patients, in which immunotherapeutic agents are employed to alter or redirect an existing state of immune activity by altering the function of T cells to a Th1-type of immune response, or to suppress a Th2 immune response. As used herein, a "patient" refers to any warm-blooded animal, preferably a human. Compositions which may be usefully employed in the inventive methods comprise at least one of the following components: inactivated *M. vaccae* cells; *M. vaccae* culture filtrate; modified *M. vaccae* cells; and constituents and compounds present in or derived from *M. vaccae* and/or its culture filtrate. As detailed below, multiple administrations of such compositions, preferably by intradermal injection, have been shown to be highly effective in the treatment of psoriasis.

As used herein the term "inactivated *M. vaccae*" refers to *M. vaccae* that have either been killed by means of heat, as detailed below in Examples 1 and 2, or subjected to radiation, such as $^{60}$Cobalt at a dose of 2.5 megarads. As used herein, the term "modified *M. vaccae*" includes delipidated *M. vaccae* cells, deglycolipidated *M. vaccae* cells and *M. vaccae* cells that have been both delipidated and deglycolipidated.

The preparation of delipidated and deglycolipidated-*M. vaccae* (DD-*M. vaccae*) and its chemical composition are described below in Example 1. As detailed below, the inventors have shown that removal of the glycolipid constituents from *M. vaccae* results in the removal of molecular components that stimulate interferon-gamma production in natural killer (NK) cells, thereby significantly reducing the non-specific production of a cytokine that has numerous harmful side-effects.

Compounds present in or derived from *M. vaccae* and/or from *M. vaccae* culture filtrate that may be usefully employed in the inventive methods include polypeptides that comprise at least one immunogenic portion of an *M. vaccae* antigen, or a variant thereof, or at least one adjuvant portion of an *M. vaccae* protein. In specific embodiments, such polypeptides comprise an immunogenic portion of an antigen, or a variant thereof, wherein the antigen includes a sequence selected from the group consisting of SEQ ID NOS: 1–4, 9–16, 18–21, 23, 25, 26, 28, 29, 44, 45, 47, 52–55, 63, 64, 70, 75, 89, 94, 98, 100–105, 109, 110, 112, 121, 124, 125, 134, 135, 140, 141, 143, 145, 147, 152, 154, 156, 158, 160, 165, 166, 170, 172, 174, 177, 178, 181, 182, 184, 186, 187, 192 and 194.

As used herein, the term "polypeptide" encompasses amino acid chains of any length, including full length proteins (i.e. antigens), wherein the amino acid residues are linked by covalent peptide bonds. Thus, a polypeptide comprising an immunogenic portion of an antigen may consist entirely of the immunogenic portion, or may contain additional sequences. The additional sequences may be derived from the native *M. vaccae* antigen or may be heterologous, and such sequences may (but need not) be immunogenic. As detailed below, polypeptides of the present invention may be isolated from *M. vaccae* cells or culture filtrate, or may be prepared by synthetic or recombinant means.

"Immunogenic", as used herein, refers to the ability of a polypeptide to elicit an immune response in a patient, such as a human, or in a biological sample. In particular, immunogenic antigens are capable of stimulating cell proliferation, interleukin-12 production or interferon-γ production in biological samples comprising one or more cells selected from the group of T cells, NK cells, B cells and macrophages, where the cells are derived from an individual previously exposed to tuberculosis. Exposure to an immunogenic antigen usually results in the generation of immune memory such that upon re-exposure to that antigen, an enhanced and more rapid response occurs.

Immunogenic portions of the antigens described herein may be prepared and identified using well known techniques, such as those summarised in Paul, *Fundamental Immunology*, 3d ed., Raven Press, 1993, pp. 243–247. Such techniques include screening polypeptide portions of the native antigen for immunogenic properties. The representative proliferation and cytokine production assays described herein may be employed in these screens. An immunogenic portion of a polypeptide is a portion that, within such representative assays, generates an immune response (e.g., cell proliferation, interferon-γ production or interleukin-12 production) that is substantially similar to that generated by the full-length antigen. In other words, an immunogenic portion of an antigen may generate at least about 20%, preferably about 65%, and most preferably about 100% of the proliferation induced by the full-length antigen in the model proliferation assay described herein. An immunogenic portion may also, or alternatively, stimulate the production of at least about 20%, preferably about 65% and most preferably about 100%, of the interferon-γ and/or interleukin-12 induced by the full length antigen in the model assay described herein.

A *M. vaccae* adjuvant is a compound found in or derived from *M. vaccae* cells or *M. vaccae* culture filtrates which non-specifically stimulates immune responses. Adjuvants enhance the immune response to immunogenic antigens and the process of memory formation. In the case of *M. vaccae* antigens, these memory responses favor Th1-type immunity. Adjuvants are also capable of stimulating interleukin-12 production or interferon-γ production in biological samples comprising one or more cells selected from the group of T cells, NK cells, B cells and macrophages, where the cells are derived from healthy individuals. Adjuvants may or may not stimulate cell proliferation. Such *M. vaccae* adjuvants include, for example, the antigens of SEQ ID NOS: 114, 117, 118.

The compositions which may be employed in the inventive methods also encompass variants of the described polypeptides. As used herein, the term "variant" covers any sequence which has at least about 40%, more preferably at least about 60%, more preferably yet at least about 75% and most preferably at least about 90% identical residues (either nucleotides or amino acids) to a sequence of the present invention. The percentage of identical residues is determined by aligning the two sequences to be compared, determining the number of identical residues in the aligned portion, dividing that number by the total length of the inventive, or queried, sequence and multiplying the result by 100.

Polynucleotide or polypeptide sequences may be aligned, and percentage of identical nucleotides in a specified region may be determined against another polynucleotide, using computer algorithms that are publicly available. Two exemplary algorithms for aligning and identifying the similarity of polynucleotide sequences are the BLASTN and FASTA algorithms. The similarity of polypeptide sequences may be examined using the BLASTP or FASTX algorithms. Both the BLASTN and BLASTP software are available on the NCBI anonymous FTP server. The BLASTN algorithm version 2.0.4 [Feb-24-1998], set to the default parameters described in the documentation and distributed with the algorithm, is preferred for use in the determination of variants according to the present invention. The use of the BLAST family of algorithms, including BLASTN and BLASTP, is described at NCBI's website and in the publication of Altschul, Stephen F., et al. (1997), "Gapped BLAST and PSI-BLAST: a new generation of protein database search programs", *Nucleic Acids Res.* 25:3389–3402. The computer algorithm FASTA is available on the Internet. Version 2.0u4, February 1996, set to the default parameters described in the documentation and distributed with the algorithm, is preferred for use in the determination of variants according to the present invention. The use of the FASTA algorithm is described in W. R. Pearson and D. J. Lipman, "Improved Tools for Biological Sequence Analysis," *Proc. Natl. Acad. Sci. USA* 85:2444–2448 (1988) and W. R. Pearson, "Rapid and Sensitive Sequence Comparison with FASTP and FASTA," *Methods in Enzymology* 183:63–98 (1990). The use of the FASTX algorithm is described in Pearson, W. R., Wood, T., Zhang, Z. and Miller, W., "Comparison of DNA sequences with protein sequences," *Genomics* 46(1):24–36 (1997).

The following running parameters are preferred for determination of alignments and similarities using BLASTN that contribute to the E values and percentage identity: Unix running command: blastall -p blastn -d embldb -e 10 -G 1 -E 1 -r 2 -v 50 -b 50 -i queryseq -o results; and parameter default values:
—p Program Name [String]
—d Database [String]
—e Expectation value (E) [Real]
—G Cost to open a gap (zero invokes default behavior) [Integer]
—E Cost to extend a gap (zero invokes default behavior) [Integer]
—r Reward for a nucleotide match (blastn only) [Integer]
—v Number of one-line descriptions (V) [Integer]
—b Number of alignments to show (B) [Integer]
—i Query File [File In]
—o BLAST report Output File [File Out] Optional
For BLASTP the following running parameters are preferred: blastall -p blastp -d swissprotdb -e 10 -G 1 -E 1 -v 50 -b 50 -i queiyseq -o results
—p Program Name [String]
—d Database [String]
—e Expectation value (E) [Real]
—G Cost to open a gap (zero invokes default behavior) [Integer]
—E Cost to extend a gap (zero invokes default behavior) [Integer]
—v Number of one-line descriptions (v) [Integer]
—b Number of alignments to show (b) [Integer]
—I Query File [File In]
—o BLAST report Output File [File Out] Optional The "hits" to one or more database sequences by a queried sequence produced by BLASTN, BLASTP, FASTA, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN and FASTA algorithms also produce "Expect" values for alignments. The Expect value (E) indicates the number of hits one can "expect" to see over a certain number of contiguous sequences by chance when searching a database of a certain size. The Expect value is used as a significance threshold for determining whether the hit to a database, such as the preferred EMBL database, indicates true similarity. For example, an E value of 0.1 assigned to a hit is interpreted as meaning that in a database of the size of the EMBL database, one might expect to see 0.1 matches over the aligned portion of the sequence with a similar score simply by chance. By this criterion, the aligned and matched portions of the sequences then have a probability of 90% of being the same. For sequences having an E value of 0.01 or less over aligned and matched portions, the probability of finding a match by chance in the EMBL database is 1% or less using the BLASTN or FASTA algorithm.

According to one embodiment, "variant" polynucleotides, with reference to each of the polynucleotides of the present invention, preferably comprise sequences having the same number or fewer nucleic acids than each of the polynucleotides of the present invention and producing an E value of 0.01 or less when compared to the polynucleotide of the present invention. That is, a variant polynucleotide is any sequence that has at least a 99% probability of being the same as the polynucleotide of the present invention, measured as having an E value of 0.01 or less using the BLASTN or FASTA algorithms set at the default parameters. According to a preferred embodiment, a variant polynucleotide is a sequence having the same number or fewer nucleic acids than a polynucleotide of the present invention that has at least a 99% probability of being the same as the polynucleotide of the present invention, measured as having an E value of 0.01 or less using the BLASTN or FASTA algorithms set at the default parameters.

Variant polynucleotide sequences will generally hybridize to the recited polynucleotide sequence under stringent conditions. As used herein, "stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

Polypeptide constituents and variants of the antigens and adjuvants present in or derived from M. vaccae or M. vaccae culture filtrate may be isolated from M. vaccae or culture filtrate, or may be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems, Inc. (Foster City, Calif.), and may be operated according to the manufacturer's instructions. Variants of a native antigen or adjuvant may be prepared using standard mutagenesis techniques, such as oligonucleotide-directed site specific mutagenesis. Sections of the DNA sequence may also be removed using standard techniques to permit preparation of truncated polypeptides, polypeptide fragments, and the like.

The polypeptides of the present invention may be altered or modified, as is well known in the art, to confer desirable properties. A polypeptide of the present invention may, for example, be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region. Other modifications may similarly be made without changing the activity of the polypeptide with respect to treatment of immunologically-mediated skin disorders. All such modified polypeptides are within the scope of the present invention.

In general, M. vaccae antigens and adjuvants, and DNA sequences encoding such antigens and adjuvants, may be prepared using any of a variety of procedures. For example, soluble antigens and adjuvants may be isolated from M. vaccae culture filtrate as described below. Antigens or adjuvants may also be produced recombinantly by inserting a DNA sequence that encodes the antigen or adjuvant into an expression vector and expressing the antigen or adjuvant in an appropriate host. Any of a variety of expression vectors known to those of ordinary skill in the art may be employed. Expression may be achieved in any appropriate host cell that has been transformed or transfected with an expression vector containing a DNA molecule that encodes recombinant polypeptide. Suitable host cells include prokaryotes, yeast and higher eukaryotic cells. Preferably, the host cells employed are *E. coli*, yeast or a mammalian cell line such as COS or CHO. The DNA sequences expressed in this manner may encode naturally occurring antigens, portions of naturally occurring antigens or adjuvants, or other variants thereof.

DNA sequences encoding M. vaccae antigens or adjuvants may be obtained by screening an appropriate M. vaccae cDNA or genomic DNA library for DNA sequences that hybridize to degenerate oligonucleotides derived from partial amino acid sequences of isolated soluble antigens or adjuvants. Suitable degenerate oligonucleotides may be designed and synthesized, and the screen may be performed as described, for example, in Sambrook J, Fritsch EF and Maniatis T, eds., *Molecular Cloning: A Laboratory Manual*, 2nd ed., Cold Spring Harbor Laboratory Press, Cold Spring Harbor: N.Y., 1989. As described below, polymerase chain reaction (PCR) may be employed to isolate a nucleic acid probe from genomic DNA, or a cDNA or genomic DNA library. The library screen may then be performed using the isolated probe.

DNA molecules encoding M. vaccae antigens may also be isolated by screening an appropriate M. vaccae cDNA or genomic DNA expression library with anti-sera (e.g., rabbit or monkey) raised specifically against M. vaccae antigens, as detailed below.

Regardless of the method of preparation, the antigens described herein have the ability to induce an immunogenic response. More specifically, the antigens have the ability to induce cell proliferation and/or cytokine production (for example, interferon-γ and/or interleukin-12 production) in T cells, NK cells, B cells or macrophages derived from an M. tuberculosis-immune individual. A M. tubercuilosis-immune individual is one who is considered to be resistant to the development of tuberculosis by virtue of having mounted an effective T cell response to M. tuberculosis. Such individuals may be identified based on a strongly positive (i.e., greater than about 10 mm diameter induration) intradermal skin test response to tuberculosis proteins (PPD), and an absence of any symptoms of tuberculosis infection. Among these immunogenic antigens, polypeptides having superior therapeutic properties may be distinguished based on the magnitude of the responses in the assays described below.

Assays for cell proliferation or cytokine production in T cells, NK cells, B cell macrophages may be performed, for example, using the procedures described below. The selection of cell type for use in evaluating an immune response to an antigen will depend on the desired response. For example, interleukin-12 or interferon-γ production is most readily evaluated using preparations containing T cells, NK cells, B cells and macrophages derived from individuals using methods well known in the art. For example, a preparation of peripheral blood mononuclear cells (PBMCs) may be employed without further separation of component cells. PBMCs may be prepared, for example, using density centrifugation through FiColl™ (Winthrop Laboratories, NY). T cells for use in the assays described herein may be purified directly from PBMCs.

In general, regardless of the method of preparation, the polypeptides employed in the inventive methods are prepared in substantially pure form. Preferably, the polypeptides are at least about 80% pure, more preferably at least about 90% pure and most preferably at least about 99% pure. In certain preferred embodiments, described in detail below, the substantially pure polypeptides are incorporated into pharmaceutical compositions or vaccines for use in one or more of the methods disclosed herein.

Fusion proteins comprising a first and a second inventive polypeptide disclosed herein or, alternatively, a polypeptide disclosed herein and a known *M. tuberculosis* antigen, such as the 38 kDa antigen described in Andersen and Hansen, *Infect. Immun.* 57:2481–2488, 1989, together with variants of such fusion proteins, may also be employed in the inventive methods. Such fusion proteins may include a linker peptide between the first and second polypeptides. A DNA sequence encoding such a fusion protein is constructed using known recombinant DNA techniques to assemble separate DNA sequences encoding the first and second polypeptides into an appropriate expression vector. The end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. No. 4,935,233) and U.S. Pat. No. 4,751,180. The linker sequence may be from 1 to about 50 amino acids in length. Peptide linker sequences are not required when the first and second polypeptides have non-essential N-terminal amino acid regions that can be used to separate the functional domains and prevent steric interference. The ligated DNA sequences encoding the fusion proteins are cloned into suitable expression systems using techniques known to those of ordinary skill in the art.

For use in the inventive methods, the inactivated *M. vaccae* cells; *M. vaccae* culture filtrate; modified *M. vaccae* cells; or compounds present in or derived from *M. vaccae* and/or its culture filtrate are generally present within a pharmaceutical composition or a vaccine, with the pharmaceutical composition or vaccine being in a form suitable for delivery via intradermal injection. Pharmaceutical compositions may comprise one or more components selected from the group consisting of inactivated *M. vaccae* cells, *M. vaccae* culture filtrate, modified *M. vaccae* cells, and compounds present in or derived from *M. vaccae* and/or its culture filtrate, together with a physiologically acceptable carrier. Vaccines may comprise one or more components selected from the group consisting of inactivated *M. vaccae* cells, *M. vaccae* culture filtrate, modified *M. vaccae* cells, and compounds present in or derived from *M. vaccae* and/or its culture filtrate, together with a non-specific immune response amplifier. Such pharmaceutical compositions and vaccines may also contain other mycobacterial antigens, either, as discussed above, incorporated into a fusion protein or present within a separate polypeptide.

Alternatively, a vaccine or pharmaceutical composition for use in the methods of the present invention may contain DNA encoding one or more polypeptides as described above, such that the polypeptide is generated in situ. In such vaccines, the DNA may be present within any of a variety of delivery systems known to those of ordinary skill in the art, including nucleic acid expression systems, bacterial and viral expression systems. Appropriate nucleic acid expression systems contain the necessary DNA sequences for expression in the patient (such as a suitable promoter and terminator signal). Bacterial delivery systems involve the administration of a bacterium (such as Bacillus Calmette-Guerin) that expresses an immunogenic portion of the polypeptide on its cell surface. In a preferred embodiment, the DNA may be introduced using a viral expression system (e.g., vaccinia or other poxvirus, retrovirus, or adenovirus), which may involve the use of a non-pathogenic, or defective, replication competent virus. Techniques for incorporating DNA into such expression systems are well known in the art. The DNA may also be "naked," as described, for example, in Ulmer et al., *Science* 259:1745–1749, 1993 and reviewed by Cohen, *Science* 259:1691–1692. 1993. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. For intradermal injection, the carrier preferably comprises water, saline, alcohol, a fat, a lipid or a buffer. Biodegradable microspheres (e.g., polylactic galactide) may also be employed as carriers for the pharmaceutical compositions and/or vaccines of this invention. Suitable biodegradable microspheres are disclosed, for example, in U.S. Pat. Nos. 4,897,268 and 5,075,109. Any of a variety of adjuvants may be employed in the vaccines of this invention to non-specifically enhance the immune response.

While the frequency of administration, as well as dosage, will vary from individual to individual, multiple doses are preferably administered at intervals of about 2–4 weeks, more preferably at intervals of about 3 weeks and preferably by means of intradermal injection. Alternate protocols may be appropriate for individual patients. In some patients a booster dose may be administered on an annual basis.

The following examples are offered by way of illustration and are not limiting.

EXAMPLE 1

PREPARATION AND IMMUNE MODULATING PROPERTIES OF DELIPIDATED AND DEGLYCOLIPIDATED (DD-) *M. VACCAE*

This example illustrates the processing of different constituents of *M. vaccae* and their immune modulating properties.

Heat-killed *M. vaccae* and *M. vaccae* Culture Filtrate

*M. vaccae* (ATCC Number 15483) was cultured in sterile Medium 90 (yeast extract, 2.5 g/l; tryptone, 5 g/l; glucose 1 g/l) at 37° C. The cells were harvested by centrifugation, and transferred into sterile Middlebrook 7H9 medium (Difco Laboratories, Detroit, Mich., USA) with glucose at 37° C. for one day. The medium was then centrifuged to pellet the bacteria, and the culture filtrate removed. The bacterial pellet was resuspended in phosphate buffered saline at a concentration of 10 mg/ml, equivalent to $10^{10}$ M. vaccae organisms per ml. The cell suspension was then autoclaved for 15 min at 120° C. The culture filtrate was passaged through a 0.45 μM filter into sterile bottles.

Preparation of Delipidated and Deglycolipidated (DD-) M. vaccae and Compositional Analysis To prepare delipidated M. vaccae, the autoclaved M. vaccae was pelleted by centrifugation, the pellet washed with water, collected again by centrifugation and then freeze-dried. Freeze-dried M. vaccae was treated with chloroform/methanol (2:1) for 60 mins at room temperature to extract lipids, and the extraction was repeated once. The delipidated residue from chloroform/methanol extraction was further treated with 50% ethanol to remove glycolipids by refluxing for two hours. The 50% ethanol extraction was repeated two times. The pooled 50% ethanol extracts were used as a source of M. vaccae glycolipids (see below). The residue from the 50% ethanol extraction was freeze-dried and weighed. The amount of delipidated and deglycolipidated M. vaccae prepared was equivalent to 11.1% of the starting wet weight of M. vaccae used. For bioassay, the delipidated and deglycolipidated M. vaccae, referred to as DD-M. vaccae, was resuspended in phosphate-buffered saline by sonication, and sterilized by autoclaving.

The compositional analyses of heat-killed M. vaccae and DD-M. vaccae are presented in Table 1. Major changes are seen in the fatty acid composition and amino acid composition of DD-M. vaccae as compared to the insoluble fraction of heat-killed M. vaccae. The data presented in Table 1 show that the insoluble fraction of heat-killed M. vaccae contains 10% w/w of lipid, and the total amino acid content is 2750 nmoles/mg, or approximately 33% w/w. DD-M. vaccae contains 1.3% w/w of lipid and 4250 nmoles/mg amino acids, which is approximately 51% w/w.

TABLE 1

Compositional analyses of heat-killed M. vaccae and DD-M. vaccae

| sugar alditol | M. vaccae | DD-M. vaccae |
|---|---|---|
| MONOSACCHARIDE COMPOSITION | | |
| Inositol | 3.2% | 1.7% |
| Ribitol* | 1.7% | 0.4% |
| Arabinitol | 22.7% | 27.0% |
| Mannitol | 8.3% | 3.3% |
| Galactitol | 11.5% | 12.6% |
| Glucitol | 52.7% | 55.2% |
| Fatty acid | M. vaccae | DD-M. vaccae |
| FATTY ACID COMPOSITION | | |
| C14:0 | 3.9% | 10.0% |
| C16:0 | 21.1% | 7.3% |
| C16:1 | 14.0% | 3.3% |
| C18:0 | 4.0% | 1.5% |
| C18:1* | 1.2% | 2.7% |
| C18:1w9 | 20.6% | 3.1% |
| C18:1w7 | 12.5% | 5.9% |
| C22:0 | 12.1% | 43.0% |
| C24:1* | 6.5% | 22.9% |
| nmoles/mg | M. vaccae | DD-M. vaccae |
| AMINO ACID COMPOSITION | | |
| ASP | 231 | 361 |
| THR | 170 | 266 |
| SER | 131 | 199 |
| GLU | 319 | 505 |

TABLE 1-continued

Compositional analyses of heat-killed M. vaccae and DD-M. vaccae

| PRO | 216 | 262 |
|---|---|---|
| GLY | 263 | 404 |
| ALA | 416 | 621 |
| CYS* | 24 | 26 |
| VAL | 172 | 272 |
| MET* | 72 | 94 |
| ILE | 104 | 171 |
| LEU | 209 | 340 |
| TYR | 39 | 75 |
| PHE | 76 | 132 |
| GlcNH2 | 5 | 6 |
| HIS | 44 | 77 |
| LYS | 108 | 167 |
| ARG | 147 | 272 |

The total amino acid content of the insoluble fraction of heat-killed M. vaccae is 2750 nmoles/mg, or approximately 33% w/w. The total amino acid content of DD-M. vaccae is 4250 nmoles/mg, or approximately 51% w/w.

M. vaccae Glycolipids

The pooled 50% ethanol extracts described above were dried by rotary evaporation, redissolved in water and freeze-dried. The amount of glycolipid recovered was 1.2% of the starting wet weight of M. vaccae used. For bioassay, the glycolipids were dissolved in phosphate-buffered saline.

Stimulation of Cytokine Synthesis

Whole heat-killed M. vaccae and DD-M. vaccae were shown to have different cytokine stimulation properties. The stimulation of a Th1 immune response is enhanced by the production of interleukin-12 (IL-12) from macrophages. The ability of different M. vaccae preparations to stimulate IL-12 production was demonstrated as follows.

A group of C57BL/6J mice were injected intraperitoneally with DIFCO thioglycolate and, after three days, peritoneal macrophages were collected and placed in cell culture with interferon-gamma for three hours. The culture medium was replaced and various concentrations of whole heat-killed M. vaccae, heat-killed M. vaccae which was lyophilised and reconstituted for use in phosphate-buffered saline, DD-M. vaccae, or M. vaccae glycolipids were added. After three days at 37° C., the culture supernatants were assayed for the presence of IL-12 produced by macrophages. As shown in FIG. 1, all the M. vaccae preparations stimulated the production of IL-12 from macrophages.

Figure 2:
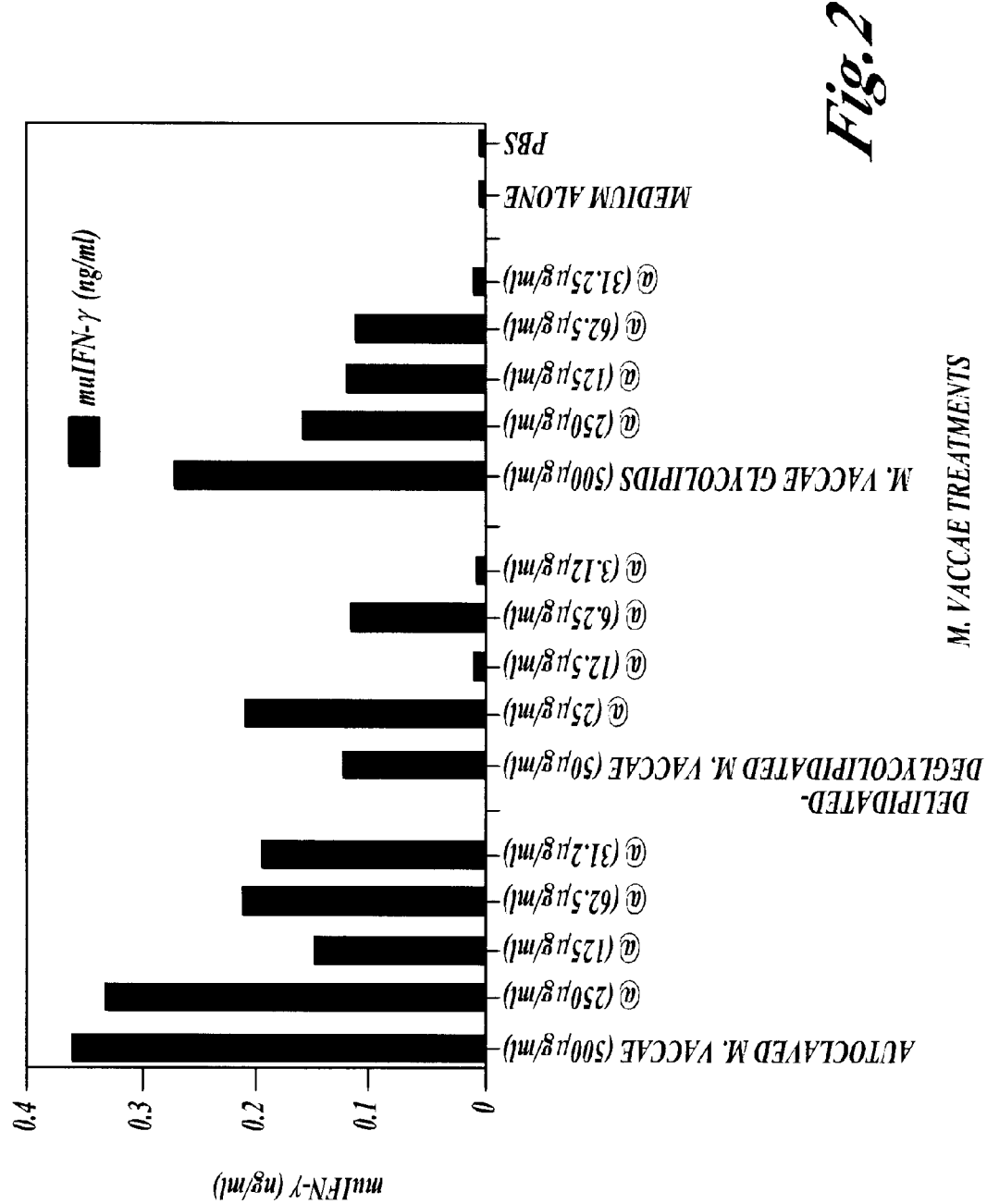
FIG. 2 compares the in vitro stimulation of interferon-gamma production in spleen cells from Severe Combined ImmunoDeficient (SCID) mice by different concentrations of heat-killed (autoclaved) *M. vaccae*, delipidated and deglycolipidated *M. vaccae*, and *M. vaccae* glycolipids.

By contrast, these same M. vaccae preparations were examined for the ability to stimulate interferon-gamma production from Natural Killer (NK) cells. Spleen cells were prepared from Severe Combined Immunodeficient (SCID) mice. These populations contain 75–80% NK cells. The spleen cells were incubated at 37° C. in culture with different concentrations of heat-killed M. vaccae, DD-M. vaccae, or M. vaccae glycolipids. The data shown in FIG. 2 demonstrates that, while heat-killed M. vaccae and M. vaccae glycolipids stimulate production of interferon-gamma, DD-M. vaccae stimulated relatively less interferon-gamma. The combined data from FIGS. 1 and 2 indicate that, compared with whole heat-killed M. vaccae, DD-M. vaccae is a better stimulator of IL-12 than interferon gamma.

These findings demonstrate that removal of the lipid glycolipid constituents from M. vaccae results in the removal of molecular components that stimulate interferon-gamma from NK cells, thereby effectively eliminating an important cell source of a cytokine that has numerous harmful side-effects. DD-M. vaccae thus retains Th1 immune enhancing capacity by stimulating IL-12 production, but has lost the non-specific effects that may come through the stimulation of interferon-gamma production from NK cells.

The adjuvant effect of DD-*M. vaccae* and a number of *M. vaccae* recombinant antigens of the present invention was determined by measuring stimulation of IL-12 secretion from murine peritoneal macrophages. The cloning and purification of the recombinant proteins are described in Examples 4 to 10. Recombinant proteins that exhibited adjuvant properties are listed in Table 2.

TABLE 2

Recombinant *M. vaccae* proteins that exhibit adjuvant properties

| Antigen | Mouse strain | |
|---|---|---|
|  | C57BL/6J | BALB/cByJ |
| GVs-3 | + | + |
| GVc-4P | + | + |
| GV-5 | + | + |
| GV-5P | + | + |
| GVc-7 | + | + |
| GV-22B | + | ND |
| GV-27 | + | + |
| GV-27A | + | + |
| GV-27B | + | + |
| GV-42 | + | ND |
| DD-*M. vaccae* | + | + |

ND = not done

EXAMPLE 2

EFFECT OF INTRADERMAL INJECTION OF HEAT-KILLED *MYCOBACTERIUM VACCAE* ON PSORIASIS IN HUMAN PATIENTS

This example illustrates the effect of two intradermal injections of heat-killed *Mycobacterium vaccae* on psoriasis.

*M. vaccae* (ATCC Number 15483) was cultured in sterile Medium 90 (yeast extract, 2.5 g/l; tryptone, 5 g/l; glucose, 1 g/l) at 37° C. The cells were harvested by centrifugation, and transferred into sterile Middlebrook 7H9 medium (Difco Laboratories, Detroit, Mich., USA) with glucose at 37° C. for one day. The medium was then centrifuged to pellet the bacteria, and the culture filtrate removed. The bacterial pellet was resuspended in phosphate buffered saline at a concentration of 10 mg/ml, equivalent to $10^{10}$ *M. vaccae* organisms per ml. The cell suspension was then autoclaved for 15 min at 120° C. and stored frozen at −20° C. Prior to use the *M. vaccae* suspension was thawed, diluted to a concentration of 5 mg/ml in phosphate buffered saline, autoclaved for 15 min at 120° C. and 0.2 ml aliquoted under sterile conditions into vials for use in patients.

Twenty four volunteer psoriatic patients, male and female, 15–61 years old with no other systemic diseases were admitted to treatment. Pregnant patients were not included. The patients had PASI scores of 12–35. The PASI score is a measure of the location, size and degree of skin scaling in psoriatic lesions on the body. A PASI score of above 12 reflects widespread disease lesions on the body. The study commenced with a washout period of four weeks where the patients did not have systemic anti-psoriasis treatment or effective topical therapy.

The 24 patients were then injected intradermally with 0.1 ml *M. vaccae* (equivalent to 500 μg). This was followed three weeks later with a second intradermal injection with the same dose of M vaccae (500 μg).

Psoriasis was evaluated from four weeks before the first injection of heat-killed *M. vaccae* to twelve weeks after the first injection as follows:

A. The PASI scores were determined at −4, 0, 3, 6 and 12 weeks;

B. Patient questionnaires were completed at 0, 3, 6 and 12 weeks; and

C. Psoriatic lesions: each patient was photographed at 0, 3, 6, 9 and 12 weeks.

The data shown in Table 3 describe the age, sex and clinical background of each patient.

TABLE 3

Patient Data in the Study of the Effect of *M. vaccae* in Psoriasis

| Code No. | Patient | Age/sex | Duration of Disorder | Admission PASI Score |
|---|---|---|---|---|
| PS-001 | D.C. | 49/F | 30 years | 28.8 |
| PS-002 | E.S. | 41/F | 4 months | 19.2 |
| PS-003 | M.G. | 24/F | 8 months | 18.5 |
| PS-004 | D.B. | 54/M | 2 years | 12.2 |
| PS-005 | C.E. | 58/F | 3 months | 30.5 |
| PS-006 | M.G. | 18/F | 3 years | 15.0 |
| PS-007 | L.M. | 27/M | 3 years | 19.0 |
| PS-008 | C.C | 21/F | 1 month | 12.2 |
| PS-009 | E.G | 42/F | 5 months | 12.6 |
| PS-010 | J.G | 28/M | 7 years | 19.4 |
| PS-011 | J.U | 39/M | 1 year | 15.5 |
| PS-012 | C.S | 47/M | 3 years | 30.9 |
| PS-013 | H.B | 44/M | 10 years | 30.4 |
| PS-014 | N.J | 41/M | 17 years | 26.7 |
| PS-015 | J.T | 61/F | 15 years | 19.5 |
| PS-016 | L.P | 44/M | 5 years | 30.2 |
| PS-017 | E.N | 45/M | 5 years | 19.5 |
| PS-018 | E.L | 28/F | 19 years | 16.0 |
| PS-019 | B.A | 38/M | 17 years | 12.3 |
| PS-020 | P.P | 58/F | 1 year | 13.6 |
| PS-021 | L.I | 27/F | 8 months | 22.0 |
| PS-022 | A.C | 20/F | 7 months | 26.5 |
| PS-023 | C.A | 61/F | 10 years | 12.6 |
| PS-024 | F.T | 39/M | 15 years | 29.5 |

All patients demonstrated a non-ulcerated, localised erythematous soft indurated reaction at the injection site. No side effects were noted, or complained of by the patients. The data shown in Table 4, below, are the measured skin reactions at the injection site, 48 hours, 72 hours and 7 days after the first and second injections of heat-killed *M. vaccae*. The data shown in Table 5, below, are the PASI scores of the patients at the time of the first injection of *M. vaccae* (Day 0) and 3, 6, 9, 12 and 24 weeks later.

It can clearly be seen that, by week 9 after the first injection of *M. vaccae*, 16 of 24 patients showed a significant improvement in PASI scores. Seven of fourteen patients who have completed 24 weeks of follow-up remained stable with no clinical sign of redevelopment of severe disease. These results demonstrate the effectiveness of multiple intradermal injections of inactivated *M. vaccae* in the treatment of psoriasis. PASI scores below 10 reflect widespread healing of lesions. Histopathology of skin biopsies indicated that normal skin structure is being restored. Only one of the first seven patients who have completed 28 weeks follow-up has had a relapse.

TABLE 4

Skin Reaction Measurements in Millimeter

| | Time of Measurement | | | | | |
|---|---|---|---|---|---|---|
| | First Injection | | | Second Injection | | |
| Code No. | 48 hours | 72 hours | 7 days | 48 hours | 72 hours | 7 days |
| PS-001 | 12 × 10 | 12 × 10 | 10 × 8 | 15 × 14 | 15 × 14 | 10 × 10 |
| PS-002 | 18 × 14 | 20 × 18 | 18 × 14 | 16 × 12 | 18 × 12 | 15 × 10 |
| PS-003 | 10 × 10 | 14 × 10 | 10 × 8 | 15 × 12 | 15 × 10 | 10 × 10 |
| PS-004 | 14 × 12 | 22 × 18 | 20 × 15 | 20 × 20 | 20 × 18 | 14 × 10 |
| PS-005 | 10 × 10 | 13 × 10 | DNR | DNR | DNR | DNR |
| PS-006 | 10 × 8 | 10 × 10 | 6 × 4 | 12 × 10 | 15 × 15 | 10 × 6 |
| PS-007 | 15 × 15 | 18 × 16 | 12 × 10 | 15 × 13 | 15 × 12 | 12 × 10 |
| PS-008 | 18 × 18 | 13 × 12 | 12 × 10 | 18 × 17 | 15 × 10 | 15 × 10 |
| PS-009 | 13 × 13 | 18 × 15 | 12 × 8 | 15 × 13 | 12 × 12 | 12 × 7 |
| PS-010 | 13 × 11 | 15 × 15 | 8 × 8 | 12 × 12 | 12 × 12 | 5 × 5 |
| PS-011 | 17 × 13 | 14 × 12 | 12 × 11 | 12 × 10 | 12 × 10 | 12 × 10 |
| PS-012 | 17 × 12 | 15 × 12 | 9 × 9 | 10 × 10 | 10 × 6 | 8 × 6 |
| PS-013 | 18 × 11 | 15 × 11 | 15 × 10 | 15 × 10 | 15 × 13 | 14 × 6 |
| PS-014 | 15 × 12 | 15 × 11 | 15 × 10 | 13 × 12 | 14 × 10 | 8 × 5 |
| PS-015 | 15 × 12 | 16 × 12 | 15 × 10 | 7 × 6 | 14 × 12 | 6 × 4 |
| PS-016 | 6 × 5 | 6 × 6 | 6 × 5 | 8 × 8 | 9 × 8 | 9 × 6 |
| PS-017 | 20 × 15 | 15 × 14 | 14 × 10 | 15 × 15 | 17 × 16 | DNR |
| PS-018 | 14 × 10 | 10 × 8 | 10 × 8 | 12 × 12 | 10 × 10 | 10 × 10 |
| PS-019 | 10 × 10 | 14 × 12 | 10 × 8 | DNR | 15 × 14 | 15 × 14 |
| PS-020 | 15 × 12 | 15 × 15 | 12 × 15 | 15 × 15 | 14 × 12 | 13 × 12 |
| PS-021 | 15 × 12 | 15 × 12 | 7 × 4 | 11 × 10 | 11 × 10 | 11 × 8 |
| PS-022 | 12 × 10 | 10 × 8 | 10 × 8 | 15 × 12 | 13 × 10 | 10 × 8 |
| PS-023 | 13 × 12 | 14 × 12 | 10 × 10 | 17 × 17 | 15 × 15 | DNR |
| PS-024 | 10 × 10 | 10 × 10 | 10 × 8 | 10 × 8 | 8 × 7 | 8 × 7 |

DNR = Did not report.

TABLE 5

Clinical Status of Patients after Injection of M. vaccae (PASI Scores)

| Code No. | Day 0 | Week 3 | Week 6 | Week 9 | Week 12 | Week 24 |
|---|---|---|---|---|---|---|
| PS-001 | 28.8 | 14.5 | 10.7 | 2.2 | 0.7 | 0 |
| PS-002 | 19.2 | 14.6 | 13.6 | 10.9 | 6.2 | 0.6 |
| PS-003 | 18.5 | 17.2 | 10.5 | 2.7 | 1.6 | 0 |
| PS-004 | 12.2 | 13.4 | 12.7 | 7.0 | 1.8 | 0.2 |
| PS-005* | 30.5 | DNR | 18.7 | DNR | DNR | 0 |
| PS-006 | 15.0 | 16.8 | 16.4 | 2.7 | 2.1 | 3.0 |
| PS-007 | 19.0 | 15.7 | 11.6 | 5.6 | 2.2 | 0 |
| PS-008 | 12.2 | 11.6 | 11.2 | 11.2 | 5.6 | 0 |
| PS-009 | 12.6 | 13.4 | 13.9 | 14.4 | 15.3 | 13.0 |
| PS-010 | 18.2 | 16.0 | 19.4 | 17.2 | 16.9 | 19.3 |
| PS-011 | 17.2 | 16.9 | 16.7 | 16.5 | 16.5 | 15.5 |
| PS-012 | 30.9 | 36.4 | 29.7 | 39.8** | | |
| PS-013 | 19.5 | 19.2 | 18.9 | 17.8 | 14.7 | 17.8 |
| PS-014 | 26.7 | 14.7 | 7.4 | 5.8 | 9.9 | 24.4*** |
| PS-015 | 30.4 | 29.5 | 28.6 | 28.5 | 28.2 | 24.3 |
| PS-016 | 30.2 | 16.8 | 5.7 | 3.2 | 0.8 | |
| PS-017 | 12.3 | 12.6 | 12.6 | 12.6 | 8.2 | |
| PS-018 | 16.0 | 13.6 | 13.4 | 13.4 | 13.2 | |
| PS-019 | 19.5 | 11.6 | 7.0 | DNR | DNR | |
| PS-020 | 13.6 | 13.5 | 12.4 | 12.7 | 12.4 | |
| PS-021 | 22.0 | 20.2 | 11.8 | 11.4 | 15.5 | |
| PS-022 | 26.5 | 25.8 | 20.7 | 11.1 | 8.3 | |
| PS-023 | 12.6 | 9.2 | 6.6 | 5.0 | 4.8 | |
| PS-024 | 29.5 | 27.5 | 20.9 | 19.0 | 29.8 | |

*Patient PS-005 received only one dose of autoclaved M vaccae.
**Patient PS-012 removed from trial, drug (penicillin) induced dermatitis
***Patient PS-014 was revaccinated
DNR = Did not report
Blank cells indicate pending follow-up

EXAMPLE 3

EFFECT OF INTRADERMAL INJECTION OF DELIPIDATED, DEGLYCOLIPIDATED MYCOBACTERIUM VACCAE (DD-M. VACCAE) ON PSORIASIS IN HUMAN PATIENTS

This example illustrates the effect of two intradermal injections of DD-M. vaccae on psoriasis.

Seventeen volunteer psoriatic patients, male and female, 18–48 years old with no other systemic diseases were admitted to treatment. Pregnant patients were not included. The patients had PASI scores of 12–30. As discussed above, the PASI score is a measure of the location, size and degree of skin scaling in psoriatic lesions on the body. A PASI score of above 12 reflects widespread disease lesions on the body. The study commenced with a washout period of four weeks where the patients did not have systemic anti-psoriasis treatment or effective topical therapy. The 17 patients were then injected intradermally with 0.1 ml DD-M. vaccae (equivalent to 100 µg). This was followed three weeks later with a second intradermal injection with the same dose of DD-M. vaccae (100 µg).

Psoriasis was evaluated from four weeks before the first injection of M. vaccae to 48 weeks after the first injection as follows:

A. the PASI scores were determined at −4, 0, 3, 6, 12, 24, 36 and 48 weeks;

B. patient questionnaires were completed at 0, 3, 6, 9 and 12 weeks and thereafter every 4 weeks; and C. psoriatic lesions: each patient was photographed at 0, 3 weeks and thereafter at various intervals.

The data shown in Table 6 describe the age, sex and clinical background of each patient.

TABLE 6

Patient Data in the Study of the Effect of DD-M. vaccae in Psoriasis

| Code No. | Patient | Age/Sex | Duration of Disorder | Admission PASI Score |
|---|---|---|---|---|
| PS-025 | A.S | 25/F | 2 years | 12.2 |
| PS-026 | M.B | 45/F | 3 months | 14.4 |
| PS-027 | A.G | 34/M | 14 years | 24.8 |
| PS-028 | E.M | 31/M | 4 years | 18.2 |
| PS-029 | A.L | 44/M | 5 months | 18.6 |
| PS-030 | V.B | 42/M | 5 years | 21.3 |
| PS-031 | R.A | 18/M | 3 months | 13.0 |
| PS-032 | | 42/M | 23 years | 30.0 |
| PS-033 | | 37/F | 27 years | 15.0 |
| PS-034 | | 42/M | 15 years | 30.4 |
| PS-035 | | 35/M | 6 years | 13.2 |
| PS-036 | | 43/M | 6 years | 19.5 |
| PS-037 | | 35/F | 4 years | 12.8 |
| PS-038 | | 44/F | 7 months | 12.6 |
| PS-039 | | 20/F | 1 year | 16.1 |
| PS-040 | | 28/F | 8 months | 25.2 |
| PS-041 | | 48/F | 10 years | 20.0 |

All patients demonstrated a non-ulcerated, localised erythematous soft indurated reaction at the injection site. No side effects were noted, or complained of by the patients. The data shown in Table 7 are the measured skin reactions at the injection site, 48 hours, 72 hours and 7 days after the first injection of DD-M. vaccea, and 48 hours and 72 hours after the second injection.

TABLE 7

Skin Reaction Measurements in Millimeters

| | Time of Measurement | | | | |
|---|---|---|---|---|---|
| | First Injection | | | Second Injection | |
| Code No. | 48 hours | 72 hours | 7 days | 48 hours | 72 hours |
| PS-025 | 8 × 8 | 8 × 8 | 3 × 2 | 10 × 10 | 10 × 10 |
| PS-026 | 12 × 12 | 12 × 12 | 8 × 8 | DNR | 14 × 14 |
| PS-027 | 9 × 8 | 10 × 10 | 10 × 8 | 9 × 5 | 9 × 8 |
| PS-028 | 10 × 10 | 10 × 10 | 10 × 8 | 10 × 10 | 10 × 10 |
| PS-029 | 8 × 6 | 8 × 6 | 5 × 5 | 8 × 8 | 8 × 8 |
| PS-030 | 14 × 12 | 14 × 14 | 10 × 10 | 12 × 10 | 12 × 10 |
| PS-031 | 10 × 10 | 12 × 12 | 10 × 6 | 14 × 12 | 12 × 10 |

DNR = Did not report

The data shown in Table 8 are the PASI scores of the 17 patients at the time of the first injection of DD-*M. vaccae* (Day 0), then 3, 6, 12, 24, 36 and 48 weeks later, when available.

TABLE 8

Clinical Status of Patients after Injection of DD-*M. vaccae* (PASI Scores)

| Code No. | Day 0 | Week 3 | Week 6 | Week 12 | Week 24 | Week 36 | Week 48 | Repeat treatment |
|---|---|---|---|---|---|---|---|---|
| PS-025 | 12.2 | 4.1 | 1.8 | 1.4 | 1.7 | 0.2 | 15.8 | Wk 48 |
| PS-026 | 14.4 | 11.8 | 6.0 | 6.9 | 1.4 | 0.4 | | |
| PS-027 | 24.8 | 23.3 | 18.3 | 9.1 | 10.6 | 7.5 | 1.9 | |
| PS-028 | 18.2 | 24.1 | 28.6* | | | | | |
| PS-029 | 18.6 | 9.9 | 7.4 | 3.6 | 0.8 | 0 | 0 | |
| PS-030 | 21.3 | 15.7 | 13.9 | 16.5 | 18.6 | 5.8 | 1.7 | |
| PS-031 | 13.0 | 5.1 | 2.1 | 1.6 | 0.3 | 0 | 0 | |
| PS-032 | 30.0 | 28.0 | 20 | 12.4 | 20.4 | 19.0 | 21.5 | Wk 44 |
| PS-033 | 19.0 | 12.6 | 5.9 | 4.0 | 12.6 | 21.1 (wk 40) | 7.1 (wk 52) | Wk 20 |
| PS-034 | 30.4 | 31.2 | 31.6 | 32.4 | 25.5 | 33.0 | | Wk 20 |
| PS-035 | 13.2 | 11.6 | 10.6 | 1.6 | 1.4 (wk 20) | 1.0 | | |
| PS-036 | 19.5 | 18.0 | 18.0 | 16.8 | 18.0 | 10.2 | | Wk 20, 32 |
| PS-037 | 12.8 | 13.1 | 1.2 | 0 | 0 | 0 | | |
| PS-038 | 12.6 | 12.6 | 12.7 | 10.0 | | | | Wk 12 |
| PS-039 | 16.1 | 17.9 | 18.3 | 17.0 | | | | Wk 12 |
| PS-040 | 25.2 | 3.9 | 0.5 | | | | | |
| PS-041 | 20.0 | 12.7 | 0.8 | | | | | |

*Patent PS-28 removed from trial, exfoliative dermatitis/psoriasis
Blank cells indicate pending follow-up
Wk—weeks after first injection These results show the significant improvement in PASI scores in 16 patients after injection with DD-*M. vaccea*. One patient dropped out of the study at 12 weeks with the diagnosis of exfoliative dermatitis/psoriasis. Patients that relapsed received a second or third injection of DD-*M. vaccae* at the time indicated in Table 8.

At 6 weeks follow-up (n=17), the PASI score improved by >50% in 9 of 17 (53%) patients. At 12 weeks follow up (n=14), the PASI score improved by >50% in 9 of 14 (64.3%) patients. Seven of these patients showed significant clinical improvement with reduction in PASI score to less than 8. At 24 weeks follow tip (n=12), the PASI score improved by >50% in 7 of 12 (58%) patients and at 48 weeks follow up (n=7), the PASI score improved by >50% in 5 of 7 (71%) patients. Again, four of these patients showed significant clinical improvement with reduction in PASI score to less than 2.

EXAMPLE 4

THE NON-SPECIFIC IMMUNE AMPLIFYING PROPERTIES OF HEAT-KILLED *M. VACCAE*, *M. VACCAE* CULTURE FILTRATE AND DD-*M. VACCAE*

This example illustrates the non-specific immune amplifying or 'adjuvant' properties of whole heat-killed *M. vaccae*, DD-*M. vaccae* and *M. vaccae* culture filtrate.

*M. vaccae* bacteria was cultured, pelleted and autoclaved as described in Example 1. Culture filtrates of live *M. vaccae* refer to the supernatant from 24 h cultures of *M. vaccae* in 7H9 medium with glucose. DD-*M. vaccae* was prepared as described in Example 2.

Killed *M. vaccae*, DD-*M. vaccae* and *M. vaccae* culture filtrate were tested for adjuvant activity in the generation of cytotoxic T cell immune response to ovalbumin, a structurally unrelated protein, in the mouse. This anti-ovalbumin-specific cytotoxic response was detected as follows. Groups of C57BL/6J mice were immunised by the intraperitoneal injection of 100 μg of ovalbumin with the following test adjuvants: heat-killed *M. vaccae*; DD-*M. vaccae*; DD-*M. vaccae* with proteins extracted with SDS; the SDS protein extract treated with Pronase (an enzyme which degrades protein); and either heat-killed *M. vaccae*, heat-killed *M. bovis* BCG, *M. phlei*, *M. smeginatis* or *M. vaccae* culture filtrate. After 10 days, spleen cells were stimulated in vitro for a further 6 days with E.G7 cells which are EL4 cells (a C57BL/6J-derived T cell lymphoma) transfected with the ovalbumin gene and thus express ovalbumin. The spleen cells were then assayed for their ability to kill non-specifically EL4 target cells or to kill specifically the E.G7 ovalbumin expressing cells. Killing activity was detected by the release of Chromium with which the EL4 and E.G7 cells have been labelled (100 mCi per $2 \times 10^6$), prior to the killing assay. Killing or cytolytic activity is expressed as % specific lysis using the formula:

$$\frac{\text{cpm in test cultures} - \text{cpm in control cultures}}{\text{total cpm} - \text{cpm in control cultures}} \times 100\%$$

It is generally known that ovalbumin-specific cytotoxic cells are generated only in mice immunised with ovalbumin with an adjuvant but not in mice immunised with ovalbumin alone.

The diagrams that make up FIG. 3 show the effect of various *M. vaccae* derived adjuvant preparations on the generation of cytotoxic T cells to ovalbumin in C57BL/6J mice. As shown in FIG. 3A, cytotoxic cells were generated in mice immunised with (i) 10 μg, (ii) 100 μg or (iii) 1 mg of autoclaved *M. vaccae* or (iv) 75 μg of *M. vaccae* culture filtrate. FIG. 3B shows that cytotoxic cells were generated in mice immunised with (i) 1 mg whole autoclaved *M. vaccae* or (ii) 100 μg DD-*M. vaccae*. As shown in FIG. 3C(i), cytotoxic cells were generated in mice immunised with 1 mg heat-killed *M. vaccae*; FIG. 3C(ii) shows the active material in *M. vaccae* soluble proteins extracted with SDS from DD-*M. vaccae*. FIG. 3C(iii) shows that active material in the adjuvant preparation of FIG. 3C(ii) was destroyed by treatment with the proteolytic enzyme Pronase. By way of comparison, 100 μg of the SDS-extracted proteins had significantly stronger immune-enhancing ability (FIG. 3C(ii)) than did 1 mg heat-killed *M. vaccae* (FIG. 3C(i)).

Mice immunised with 1 mg heat-killed *M. vaccae* (FIG. 3D(i)) generated cytotoxic cells to ovalbumin, but mice immunised separately with 1 mg heat-killed *M. tuberculosis* (FIG. 3D(ii)), 1 mg *M. bovis* BCG (FIG. 3D(iii)), 1 mg *M. phlei* (FIG. 3D(iv)), or 1 mg *M. smegmatis* (FIG. 3D(v)) failed to generate cytotoxic cells.

The significance of these findings is that heat-killed *M. vaccae* and DD-*M. vaccae* have adjuvant properties not seen in other mycobacteria. Further, delipidation and deglycolipidation of *M. vaccae* removes an NK cell-stimulating activity but does not result in a loss of T cell-stimulating activity.

In subsequent studies, more of the SDS-extracted proteins described above were prepared by preparative SDS-PAGE on a BioRad Prep Cell (Hercules, Calif.). Fractions corresponding to molecular weight ranges were precipitated by trichloroacetic acid to remove SDS before assaying for adjuvant activity in the anti-ovalbumin-specific cytotoxic response assay in C57BL/6J mice as described above. The adjuvant activity was highest in the 60–70 kDa fraction. The most abundant protein in this size range was purified by SDS-PAGE blotted on to a polyvinylidene difluoride (PVDF) membrane and then sequenced. The sequence of the first ten amino acid residues is provided in SFQ ID NO:76. Comparison of this sequence with those in the gene bank as described above, revealed homology to the heat shock protein 65 (GroEL) gene from *M. tuberculosis*, indicating that this protein is an *M. vaccae* member of the GroEL family.

An expression library of M. vaccaegenomic DNA in BamH1-lambda ZAP-Express (Stratagene) was screened using sera from cynomolgous monkeys immunised with *M. tuberculosis* secreted proteins prepared as described above. Positive plaques were identified using a colorimetric system. These plaques were re-screened until plaques were pure following standard procedures. pBK-CMV phagemid 2-1 containing an insert was excised from the lambda ZAP-Express (Stratagene) vector in the presence of ExAssist helper phage following the manufacturer's protocol. The base sequence of the 5' end of the insert of this clone, hereinafter referred to as GV-27, was determined using Sanger sequencing with fluorescent primers on Perkin Elmer/Applied Biosystems Division automatic sequencer. The determined nucleotide sequence of the partial *M. vaccae* GroEL-homologue clone GV-27 is provided in SEQ ID NO:77 and the predicted amino acid sequence in SEQ ID NO:78. This clone was found to have homology to *M. tuberculosis* GroEL.

A partial sequence of the 65 kDa heat shock protein of *M. vaccae* has been published by Kapur et al. (*Arch. Pathol. Lab. Med.* 119:131–138, 1995). However, this sequence did not overlap with the GV-27 sequence provided herein. The nucleotide sequence of the Kapur et al. fragment is shown in SEQ ID NO:79 and the predicted amino acid sequence in SEQ ID NO:80.

In subsequent studies, an extended DNA sequence (full-length except for the predicted 51 terminal residues) for GV-27 was obtained (SEQ ID NO: 113). The corresponding predicted amino acid sequence is provided in SEQ ID NO: 114. Further studies led to the isolation of the full-length DNA sequence for GV-27 (SEQ ID NO: 159). The corresponding predicted amino acid sequence is provided in SEQ ID NO: 160. This sequence shows 93.7% identity to the *M. tuberculosis* GroEL sequence. Two peptide fragments, comprising the N-terminal sequence (hereinafter referred to as GV-27A) and the carboxy terminal sequence of GV-27 (hereinafter referred to as GV-27B) were prepared using techniques well known in the art. The nucleotide sequences for GV-27A and GV-27B are provided in SEQ ID NOS: 115 and 116, respectively, with the corresponding amino acid sequences being provided in SEQ ID NOS: 117 and 118. Subsequent studies led to the isolation of an extended DNA sequence for GV-27B. This sequence is provided in SEQ ID NO: 161, with the corresponding amino acid sequence being provided in SEQ ID NO: 162. The sequence of GV-27A shows 95.8% identity to the published *M. tuberculosis* GroEL sequence and contains the *M. vaccae* sequence of Kapur et al. discussed above. The sequence of GV-27B is about 92.2% identical to the published *M. tuberculosis* sequence.

Following the same protocol as for the isolation of GV-27, pBK-CMV phagemid 3-1 was isolated. The antigen encoded by this DNA was named GV-29. The determined nucleotide sequences of the 5' and 3' ends of the gene are provided in SEQ ID NOS: 163 and 164, respectively, with the predicted corresponding amino acid sequences being provided in SEQ ID NOS: 165 and 166 respectively. GV-29 showed homology to yeast urea amidolyase. The DNA encoding GV-29 was sub-cloned into the vector pET16 (Novagen, Madison, Wis.) for expression and purification according to standard protocols.

EXAMPLE 5

PURIFICATION AND CHARACTERIZATION OF POLYPEPTIDES FROM M. VACCAECULTURE FILTRATE

This example illustrates the preparation of *M. vaccae* soluble proteins from culture filtrate. Unless otherwise noted, all percentages in the following example are weight per volume.

*M. vaccae* (ATCC Number 15483) was cultured in sterile Medium 90 at 37° C. The cells were harvested by centrifugation, and transferred into sterile Middlebrook 7H9 medium with glucose at 37° C. for one day. The medium was then centrifuged (leaving the bulk of the cells) and filtered through a 0.45 μl filter into sterile bottles.

The culture filtrate was concentrated by lyophilization, and redissolved in MilliQ water. A small amount of insoluble material was removed by filtration through a 0.45 m membrane. The culture Filtrate was desalted by membrane filtration in a 400 ml Amicon stirred cell which contained a 3,000 Da molecular weight cut-off (MWCO) membrane. The pressure was maintained at 50 psi using nitrogen gas. The culture filtrate was repeatedly concentrated by membrane filtration and diluted with water until the conductivity of the sample was less than 1.0 mS. This procedure reduced the 20 l volume to approximately 50 ml. Protein concentrations were determined by the Bradford protein assay (Bio-Rad, Hercules, Calif., USA).

The desalted culture filtrate was fractionated by ion exchange chromatography on a column of Q-Sepharose™ (Pharmacia Biotech, Uppsala, Sweden) (16×100 mm) equilibrated with 10 mM Tris HCl buffer pH 8.0. Polypeptides were eluted with a linear gradient of NaCl from 0 to 1.0 M in the above buffer system. The column eluent was monitored at a wavelength of 280 nm.

The pool of polypeptides eluting from the ion exchange column was concentrated in a 400 ml Amicon stirred cell which contained a 3,000 Da MWCO membrane. The pressure was maintained at 50 psi using nitrogen gas. The polypeptides were repeatedly concentrated by membrane filtration and diluted with 1% glycine until the conductivity of the sample was less than 0.1 mS.

The purified polypeplitides were then fractionated by preparative isoelectric focusing in a Rotofor device (Bio-Rad, Hercules, Calif., USA). The pH gradient was established with a mixture of Ampholytes (Pharmacia Biotech) comprising 1.6% pH 3.5–5.0 Ampholytes and 0.4% pH 5.0–7.0 Ampholytes. Acetic acid (0.5 M) was used as the anolyte, and 0.5 M ethanolamine as the catholyte. Isoelectric focusing, was carried out at 12 W constant power for 6 hours, following the manufacturer's instructions. Twenty fractions were obtained.

Fractions from isoelectric focusing were combined, and the polypeptides were purified on a VYDAC C4 column (Separations Group, Hesperia, Calif., USA) 300 Angstrom pore size, 5 micron particle size (10×250 mm). The polypeptides were eluted from the column with a linear gradient of acetonitrile (0–80% v/v) in 0.05% (v/v) trifluoroacetic acid (TFA). The flow-rate was 2.0 ml/min and the HPLC eluent was monitored at 220 nm. Fractions containing polypeptides were collected to maximize the purity of the individual samples.

Relatively abundant polypeptide fi-actions were rechromatographed on a VYDAC C4 column (Separations Group) 300 Angstrom pore size, 5 micron particle size (4.6×250 mm). The polypeptides were eluted from the column with a linear gradient from 20–60% (v/v) of acetonitrile in 0.05% (v/v) TFA at a flow-rate of 1.0 ml/min. The column eluent was monitored at 220 nm. Fractions containing the eluted polypeptides were collected to maximise the purity of the individual samples. Approximately 20 polypeptide samples were obtained and they were analysed for purity on a polyacrylamide gel according to the procedure of Laemmli (Laemmli, U. K., Nature 277:680–685, 1970).

The polypeptide fractions wich were shown to contain significant contamination were further purified using a MONO Q column (Pharmacia Biotech) 10 micron particle size (5×50 mm) or a VYDAC Dipheniyl column (Separations Group) 300 Angstrom pore size, 5 micron particle size (4.6×250 mm). From a MONO Q column, polypeptides were eluted with a linear gradient from 0–0.5 M NaCl in 10 mM Tris.HCl pH 8.0. From a VYDAC Diphenyl column, polypeptides were eluted with a linear gradient of acetonitrile (20–60% v/v) in 0.1% TFA. The flow-rate was 1.0 ml/min and the column eluent was monitored at 220 nm for both columns. The polypeptide peak fi-actions were collected and analysed for purity on a 15% polyacrylamide gel as described above.

For sequencing, the polypeptides were individually dried onto Biobrene™ (Perkin Elmer/Applied BioSystems Division, Foster City, Calif.)-treated glass fiber filters. The filters with polypeptide were loaded onto a Perkin Elmer/Applied BioSystems Procise 492 protein sequencer and the polypcptides were sequenced from the amino terminal end using traditional Edman chemistry. The amino acid sequence was determined for each polypeptide by comparing the retention time of the PTH amino acid derivative to the appropriate PTH derivative standards.

Internal sequences were also determined on some antigens by digesting the antigen with the endoprotcase Lys-C, or by chemically cleaving the antigen with cyanogen bromide. Peptides resulting from either of these procedures were separated by reversed-phase HPLC on a VYDAC C18 column using a mobile phase of 0.05% (v/v) trifluoroacetic acid (TFA) with a gradient of acetonitrile containing 0.05% (v/v) TFA (1%/min). The eluent was monitored at 214 nm. Major internal peptides were identified by their UV absorbance, and their N-terminal sequences were determined as described above.

Using the procedures described above, six soluble M. vaccae antigens, designated GVc-1, GVc-2, GVc-7, GVc-13, GVc-20 and GVc-22, were isolated. Determined N-terminal and internal sequences for GVc-1 are shown in SEQ ID NOS: 1, 2 and 3, respectively; the N-terminal sequence for GVc-2 is shown in SEQ ID NO: 4; internal sequences for GVc-7 are shown in SEQ ID NOS: 5–8; internal sequences for GVc-13 are shown in SEQ ID NOS: 9–11; internal sequence for GVc-20 is shown in SEQ ID NO: 12; and N-terminal and internal sequences for GVc-22 are shown in SEQ ID NO:56–59, respectively. Each of the internal peptide sequences provided herein begins with an amino acid residue which is assumed to exist in this position in the polypeptide, based on the known cleavage specificity of cyanogen bromide (Met) or Lys-C (Lys).

Three additional polypeptides, designated GVc-16, GVc-18 and GVc-21, were isolated employing a preparative sodium dodecyl sulfate-polyacrylamide gel electrophoresis (SDS-PAGE) purification step in addition to the preparative isoelectric focusing procedure described above. Specifically, fractions comprising mixtures of polypeptides from the preparative isoelectric focusing purification step previously described, were purified by preparative SDS-PAGE on a 15% polyacrylamide gel. The samples were dissolved in reducing sample buffer and applied to the gel. The separated proteins were transferred to a polyvinylidene difluoride (PVDF) membrane by electroblotting in 10 mM 3-(cyclolexylamino)-1-propanesulfonic acid (CAPS) buffer pH 11 containing 10% (v/v) methanol. The transferred protein bands were identified by staining the PVDF membrane with Coomassie blue. Regions of the PVDF membrane containing the most abundant polypeptide species were cut out and directly introduced into the sample cartridge of the Perkin Elmer/Applied BioSystems Procise 492 protein sequencer. Protein sequences were determined as described above. The N-terminal sequences for GVc-16, GVc-18 and GVc-21 are provided in SEQ ID NOS: 13, 14 and 15, respectively.

Additional antigenis, designated GVc-12, GVc-14, GVc-15, GVc-17 and GVc-19, were isolated employing a preparative SDS-PAGE purification step in addition to the chromatographic procedures described above. Specifically, fractions comprising a mixture of antigens from the VYDAC C4 HPLC purification step previously described were fractionated by preparative SDS-PAGE on a polyacrylamlide gel. She samples were dissolved in non-reducing sample buffer and applied to the gel. The separated proteins were transferred to a PVDF membrane by electroblotting, in 10 mM CAPS buffer, pH 11 containing 10% (v/v) methanol. The transferred protein bands were identified by staining the PVDF membrane with Coomassie blue. Regions of the PVDF membrane containinig the most abundant polypeptide species were cut out and directly introduced into the sample cartridge of the Perkin Elmer/Applied BioSystems Procise 492 protein sequencer. Protein sequences were determined as described above. The determined N-terminal Sequences for GVc-12, GVc-14, GVc-15, GVc-17 and GVc-19 are provided in SEQ ID NOS: 16–90, respectively.

All of the above amino acid sequences were compared to known amino acid sequences in the SwissProt data base (version R32) using the GeneAssist system. No significant homologies to the amino acid sequences GVc-2 to GVc-22 were obtained. The amino acid sequence for GVc-1 was found to bear some similarity to sequences previously identified from M. bovis and M. tuberculosis. In particular, GVc-1 was found to have some homology with M. tuberculosis MPT83, a cell surface protein, as well as MPT70. These proteins form part of a protein family (Harboe et al., Scand. J. Immunol. 42:46–51, 1995).

Subsequent studies led to the isolation of DNA sequences for GVc-13, GVc-14 and GVc-22 (SEQ ID NO: 142, 107 and 108 respectively). The corresponding predicted amino acid sequences for GVc-13, GVc-14 and GVc-22 are provided in SEQ ID NO: 143, 109 and 110, respectively. Further studies with GVc-22 suggested that only a part of the gene encoding GVc-22 was cloned. When sub-cloned into the expression vector pET16, no protein expression was obtained. Subsequent screening of the M. vaccae BamHI genomic DNA library with the incomplete gene fragment led to the isolation of the complete gene encoding GVc-22. To distinguish between the full-length clone and the partial GVc-22, the antigen expressed by the full-length gene was called GV-22B. The determined nucleotide sequence of the gene encoding GV-22B and the predicted amino acid sequence are provided in SEQ ID NOS: 144 and 145 respectively.

Amplifications primers AD86 find AD112 (SEQ ID NOS: 60 and 61, respectively) were designed from the amino acid sequence of GVc-1 (SEQ ID NO: 1) and the M. tuberculosis MPT70 gene sequence. Using these primers, a 310 bp fragment was amplified from M. vaccae genomic DNA and cloned into EcoRV-digested vector pBluescript II SK+ (Stratagene). The sequence of the cloned insert is provided in SEQ ID NO: 62. The insert of this clone was used to screen a M. vaccae genomic DNA library constructed in lambda ZAP-Express (Stratgene, La Jolla, Calif.). The clone isolated contained an open reading frame with homology to the M. tuberculosis antigen MPT83 and was re-named GV-1/83. This gene also had homology to the M. bovis antigen MPB83. The determined nucleotide sequence and predicted amino acid sequences are provided in SEQ ID NOS: 146 and 147 respectively.

From the amino acid sequences provided in SEQ ID NOS: 1 and 2, degenerate oligonucleotides EV59 and EV61 (SEQ ID NOS: 148 and 149 respectively) were designed. Using PCR, a 100 bp fragment was amplified, cloned into plasmid pbluescript II SK+ and sequenced (SEQ ID NO: 150) following standard procedures (Sambrook et al., Ibid) The cloned insert was used to screen a M. vaccae genomic DNA library constructed in lambda ZAP-Express. The clone isolated had homology to M. tuberculosis antigen MPT70 and M. bovis antigen MPB70, and was named GV-1/70. The determined nuclcotide sequence and predicted amino acid sequence for GV-1/70 are provided in SEQ ID NOS: 151 and 152, respectively.

For expression and purification, the genes encoding GV1/83, GV1/70, GVc-13, GVc-14 and GV-22B were sub-cloned into the expression vector pET16 (Novagen, Madison, Wis.). Expression and purification were carried out according to the manufacturer's protocol.

The purified polypeptides were screened for the ability to induce T-cell proliferation and IFN-γ in peripheral blood cells from immune human donors. These donors were known to be PPD (purified protein derivative from M. tuberculosis) skin test positive and their T cells were shown to proliferate in response to PPD. Donor PBMCs and crude soluble proteins from M. vaccae culture filtrate were cultured in medium comprising RPMI 1640 supplemented with 10% (v/v) autologous serum, penicillin (60 mg/ml), streptomycin (100 mg/ml), and glutamine (2 mM).

After 3 days, 50 µl of medium was removed from each well for the determination of IFN-γ levels, as described below. The plates were cultured for a further 4 days and then pulsed with 1 mCi/well of tritiated thymidine for a further 18 hours, harvested and tritium uptake determined using a scintillation counter. Fractions that stimulated proliferation in both replicates two-fold greater than the proliferation observed in cells cultured in medium alone were considered positive.

INF-γ was measured usinig an enzyme-linked immunosorbent assay (ELISA). ELISA plates were coated with a mouse nonoclonal antibody directed to human IFN-g (Endogen, Wobural, Mass.) 1 mg/min phosphate-buffered saline (PBS) for 4 hours at 4° C. Wells were blocked with PBS containing 0.2% Tween 20™ for 1 hour at room temperature. The plates were then washed four times in PBS/0.2% Tween 20™, and samples diluted 1:2 in culture medium in the ELISA plates were incubated overnight at room temperature. The plates were again washed, and a biotinylated polyclonal rabbit anti-human IFN-γ serum (Endogen), diluted to 1 mg/ml in PBS, was added to each well. The plates were then incubated for 1 hour at room temperature, washed, and horseradish peroxidase-coupled avidin A (Vector Laboratories, Burlingame, Calif.) was added at a 1:4,000 dilution in PBS. After a further 1 hour incubation at room temperature, the plates were washed and orthophenylenediaminie (OPD) substrate added. The reaction was stopped after 10 min with 10% (v/v) HCl. The optical density (OD) was determined at 490 nm. Fractions that resulted in both replicates giving an OD two-fold greater than the mean OD from cells cultured in medium alone were considered positive.

Examples of polypeptides containing sequences that stimulate peripheral blood mononuclear cells (PBMC) T cells to proliferate and produce IFN-γ are shown in Table 9, wherein (−) indicates a lack of activity. (+/−) indicates polypcptides having a result less than twice higher than background activity of control media, (+) indicates polypeptides having activity two to four times above background, and (++) indicates polypeptides having activity greater than four times above background.

TABLE 9

Examples of Polypeptides Stimulating Human
Peripheral Blood Mononuclear Cells

| Antigen | Proliferation | IFN-γ |
|---------|---------------|-------|
| GVc-1   | ++            | +/−   |
| GVc-2   | +             | ++    |
| GVc-7   | +/−           | −     |
| GVc-13  | +             | ++    |
| GVc-14  | ++            | +     |
| GVc-15  | +             | +     |
| GVc-20  | +             | +     |

EXAMPLE 6

PURIFICATION AND CHARACTERISATION OF POLYPEPTIDES FROM M. VACCAE CULTURE FILTRATE BY 2-DIMENSIONAL POLYACRYLAMIDE GEL ELECTROPHORESIS

M. vaccae soluble proteins were isolated from culture filtrate using 2-dimensional polyacrylamide gel electrophoresis as described below. Unless otherwise noted, all percentages in the following example are weight per volume.

M. vaccae (ATCC Number 15483) was cultured in sterile Medium 90 at 37° C. M. tuberculosis strain H37Rv (ATCC by number 27294) was cultured in sterile Middlebrook 7H9 medium with Tween 80™ and oleic acid/albumin/dextrose/catalase additive (Difco Laboratories, Detroit, Mich.). The cells were hartvested by centrifugation, and transferred into sterile Middlebrook 7H9 medium with glucose at 37° C. for one day. The medium was then centrifuged (leaving the bulk of the cells) and filtered through a 0.45 μm filter into sterile bottles. The culture filtrate was concentrated by lyophililsation, and re-dissolved in MILLIQ water. A small amount of insoluble material was removed by filtration through a 0.45 μm membrane filter.

The culture filtrate was desalted by membrane filtration in a 400 ml Amicon stirred cell which contained a 3,000 Da MWCO membrane. The pressure was maintained at 60 psi using nitrogen gas. The culture filtrate was repeatedly concentrated by membrane filtration and diluted with water until the conductivity of the sample was less than 1.0 mS. This procedure reduced the 20 l volume to approximately 50 ml. Protein concentrations were determined by the Bradford protein assay (Bio-Rad, Hercules, Calif., USA).

The desalted culture filtrate was fractionated by ion exchange chromatography on a column of Q-Sepharose™ (Pharmacia Biotech) (16×100 mm) equilibrated with 10 mM TrisHCl buffer pH 8.0. Polypcptides were eluted with a linear gradient of NaCl from 0 to 1.0 M in the above buffer system. The column eluent was monitored at a wavelength of 280 nm.

Figure 4A:
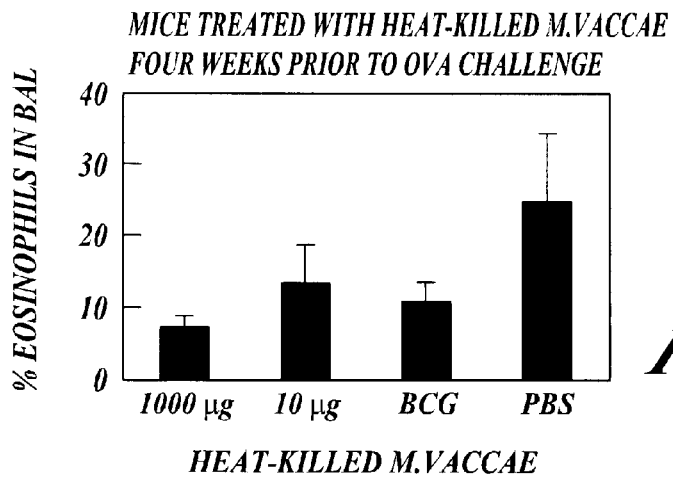
FIGS. 4A–E illustrate the effect of intranasal administration of heat-killed *M. vaccae*, DD-*M. vaccae* or *M. bovis* BCG on the number of eosinophils in BAL cells of mice sensitised and challenged with ovalbumin. Control mice received PBS.
Figure 4B:
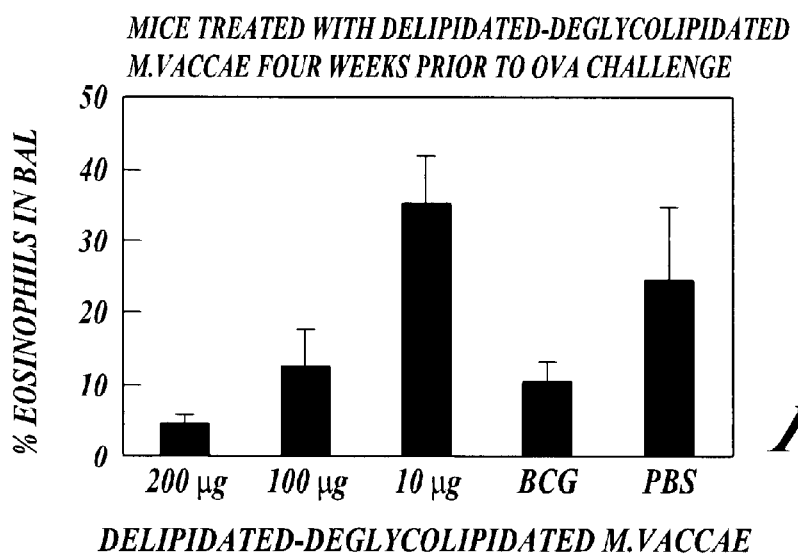

The pool of polypeptides eluting from the ion exchange column were fractionated by preparative 2-D gel electrophoresis. Samples containing 200–500 μg of polypeptide were made 8M in urea and applied to polyacrylamide isoelectric focusing rod gels (diameter 2 mm, length 150 mm, pH 5–7). After the isoelectric focusing step, the first dimension gels were equilibrated with reducing buffer and applied to second dimension gels (16% polyacrylamide). FIGS. 4A and 4B are the 2-D gel patterns observed with M. vaccae culture filtrate and M. tuberculosis H37Rv culture filtrate, respectively. Polypeptides from the second dimension separation were transferred to PVDF membranes by electroblotting in 10 mM CAPS buffer pH 11 containing 10% (v/v) methanol. The PVIDF membranes were stained for protein with Coomassie blue. Regions of PVDF containing polypeptides of interest were cut out and directly introduced into the sample cartridge of the Perkin Elmer/Applied BioSystems Procise 492 protein sequencer. The polypeptides were sequenced from the amino terminal end using traditional Edman chemistry. The amino acid sequence was determined for each polypeptide by comparing the retention time of the PTH amino acid derivative to the appropriate PTH derivative standards. Using these procedures, eleven polypeptides, designated GVs-1, GVs-3, GVs-4, GVs-5, GVs-6, GVs-8, GVs-9, GVs-10, GVs-11, GV-34 and GV-35 were isolated. The determined N-terminal sequences for these polypeptides are shown in SEQ ID NOS: 21–29, 63 and 64, respectively. Using the purification procedure described above, more protein was purified to extend the amino acid sequence previously obtained for GVs-9. The extended amino acid sequence for GVs-9 is provided in SEQ ID NO:65. Further studies resulted in the isolation of the DNA sequences for GVs-9 (SEQ ID NO: 111) and GV-35 (SEQ ID NO: 155). The corresponding predicted amino acid sequences are provided in SEQ ID NOS: 112 and 156, respectively. An extended DNA sequence for GVs-9 is provided in SEQ ID NO: 153, with the corresponding predicted amino acid sequence being provided in SEQ ID NO: 154.

All of these amino acid sequences were compared to known amino acid sequences in the SwissProt data base (version R32) using the GeneAssist system. No significant homologies were obtained, with the exceptions of GVs-3, GVs-4, GVs-5 and GVs-9. GVs-9 was found to bear some homology to two previously identified M. tuberculosis proteins, namely M. tuberculosis cutinase precurso and a M. tuberculosis hypothetical 22.6 kDa protein. GVs-3, GVs-4 and GVs-5 were found to bear some similarity to the antigen 85A and 85B proteins from M. leprae (SEQ ID NOS: 30 and 31, respectively), M. tuberculosis (SEQ ID NOS: 32 and 33, respectively) and M. bovis (SEQ ID NOS: 34 and 35, respectively), and the antigen 85C proteins from M. leprae (SEQ ID NO: 36) and M. tuberculosis (SEQ ID NO: 37).

EXAMPLE 7

DNA CLONING STRATEGY FOR THE M. VACCAE ANTIGEN 85 SERIES

Probes for antigens 85A, 85B, and 85C were prepared by the polymerase chain reaction (PCR) using degenerate oligonucleotides (SEQ ID NOS: 38 and 39) designed to regions of antigen 85 genomic sequence that are conserved between family members in a given mycobacterial species, and between mycobacterial species. These oligonucleotides were used under reduced stringency conditions to amplify target sequences from M. vaccae genomic DNA. An appropriately-sized 485 bp band was identified, purified, and cloned pBluescript II SK+ (Stratagene, La Jolla, Calif.). Twenty-four individual clones were screened at random for the presence of the antigen 85 PCR product, then sequenced using the Perkin Elmre/Applied Biosystems Model 377 automated sequencer and the M13-based primers, T3 and T7. Homology searches of the GenBank™ databases showed that twenty-three clones contained insert with significant homology to published antigen 85 genes from M. tuberculosis and M. bovis. Approximately half were most homologous to antigen 85C gene sequences, with the remainder being more similar to antigen 85B sequences. In addition, these two putative *M. vaccae* antigen 85 genomic sequences were 80% homologous to one another. Because of this high similarity, the antigen 85C PCR fragment was chosen to screen *M. vaccae* genomic libraries at low stringency for all three antigen 85 genes.

An *M. vaccae* genomic library was created in lambda Zap-Express (Stratagene, La Jolla, Calif.) by cloning BamHI partially-digested *M. vaccae* genomic DNA into similarly-digested vector, with $3.4 \times 10^5$ independent plaque-forming units resulting. For screening purposes, twenty-seven thousand plaques from this non-amplified library were plated at low density onto eight 100 $cm^2$ plates. For each plate, duplicate plaque lifts were taken onto Hybond-N$^+$ nylon membrane (Amersham International, United Kingdom), and hybridised under reduced-stringency conditions (55° C.) to the radiolabelled antigen 85C PCR product. Autoradiography demonstrated that seventy-nine plaques consistently hybridised to the antigen 85C probe under these conditions. Thirteen positively-hybridising plaques were selected at random for further analysis and removed from the library plates, with each positive clone being, used to generate secondary screening plates containing about two hundred plaques. Duplicate lifts of each plate were taken using Hybond-N$^+$ nylon membrane, and liybridised unlider the conditions used in primary screening. Multiple positively-hybridising plaques were identified on each of the thirteen plates screened. Two well-isolated positive phage from each secondary plate were picked for further analysis. Using in vitro excision, twenty-six plaques were converted into phagemid, and restriction-mapped. It was possible to group clones into four classes on the basis of this mapping. Sequence data from the 5' and 3' ends of inserts from several representatives of each group was obtained using the Perkin Elmer/Applied Biosystems Division Model 377 automated sequencer and the T3 and T7 primers. Sequence homologies were determined using FASTA analysis of the GenBank databases with the GeneAssist software package. Two of these sets of clones were found to be homologous to *M. bovis* and *M. tuberculosis* antige 85A genes, each containing either the 5' or 3' ends of the *M. vaccae* one (this gene was cleaved during library construction as it contains an internal BamHI site). The remaining clones were found to contain sequences homologous to antigens 85B and 85C from a number of mycobacterial species. To determine the remaining nucleotide sequence for each gene, appropriate subclones were constructed and sequenced. Overlaping, sequences were aligned using the DNA Strider software. The determined DNA sequences for *M. vaccae* antigenis 85A, 85B and 85C are shown in SEQ ID NOS: 40–42, respectively, with the predicted amino acid sequences being shown in SEQ ID NOS: 43–45, respectively.

The *M. vaccae* antigenis GVs-3 and GVs-5 were expressed and purified as follows. Amplification primers were designed from the insert sequences of GVs-3 and GVs-5 (SEQ ID NO: 40 and 42, respectively) using, sequence data downstream from the putative leader sequence and the 3' end of the clone. The sequences of the primers for GVs-3 are provided in SEQ ID NOS: 66 and 67, and the sequences of the primers for GVs-5 are provided in SEQ ID NOS: 68 and 69). A XhoI restriction site was added to the primers for GVs-3, and EcoRI and BamHI restriction sites were added to the primers for GVs-5 for cloning convenience. Following amplification from genomic *M. vaccae* DNA, fragments were cloned into the appropriate site of pProEX HT prokaryotic expression vector (Gibco BRL, Life Technologies, Gaithersburg, Md.) and submitted for sequencing to confirm the correct reading frame and orientation. Expression and purification of the recombinant protein was performed according to the manufacturer's protocol.

Expression of a fragment of the *M. vaccae* antigen GVs-4 (antigen 85B homolog) was performed as follows. The primers AD58 and AD59, described above, were used to amplify a 485 bp fragment from *M. vaccae* genomic DNA. This fragment was gel-purified using standard techniques and clones into EcoRV-digested pBluescript. The base sequences of inserts from five clones were determined and found to be identical to each other. These inserts had lighest homologly to Ag85B from *M. tuberculosis*. The insert from one of the clones was subcloned into the EcoRI/XhoI sites of pProEX HT prokaryotic expression vector (Gibco BRL), expressed and purified according to the manufacturer's protocol. This clone was renamed GV-4P because only a part of the gene was expressed. The amino acid and DNA sequences for the partial clone GV-4P are provided in SEQ ID NOS: 70 and 106, respectively.

Similar to the cloninig of GV-4P, the amplification primers AD58 and AD59 were used to amplify a 485 bp fragment from a clone containinig VGs-5 (SEQ ID NO:42). This fragment was cloned into the expression vector pET16 and was called GV-5P. The determined nulcleotide sequence and predicted amino acid sequence of GV-5P are provided in SEQ ID NOS: 157 and 158, respectively.

The ability of purified recombinant GVs-3, GV-4P and GVs-5 to stimulate proliferation of T cells and interferon-γ production in human PBL was assayed as deseribed above in Example 4. The results of this assay are show in Table 10, wherein (−) indicates a lack of activity, (+/−) indicates polypeptides having a result less than twice higher than background activity of control media, (+) indicates polypeptides having activity two to four times above background, (++) indicates polypeptides having activity greater than four times above background, and ND indicates not determined.

TABLE 10

| | Donor G97005 | | Donor G97006 | | Donor G97007 | | Donor G97008 | | Donor G97009 | | Donor G97010 | |
|---|---|---|---|---|---|---|---|---|---|---|---|---|
| | Prolif | IFN-γ | Prolif | INF-γ | Prolif | IFN-γ | Prolif | IFN-γ | Prolif | IFN-γ | Prolif | IFN-γ |
| GVs-3 | ++ | + | ND | ND | ++ | ++ | ++ | ++ | ++ | +/− | + | ++ |
| GV-4P | + | +/− | ND | ND | + | ++ | ++ | ++ | +/− | +/− | +/− | ++ |
| GVs-5 | ++ | ++ | ++ | ++ | ++ | ++ | + | ++ | ++ | + | + | ++ |

EXAMPLE 8

DNA CLONING STRATEGY FOR *M. VACCAE* ANTIGENS

An 84 bp probe for the *M. vaccae* antigen GVc-7 was amplified using degenerate oligonucleotides designed to the determined amino acid sequence of GVc-7 (SEQ ID NOS: 5–8). This probe was used to screen a *M. vaccae* genomic DNA library as described in Example 4. The determined necleotide sequence for GVc-7 is shown in SEQ ID NO: 46 and predicted amino acid sequence in SEQ ID NO: 47. Comparison of these sequences with those in the databank revealed homology to a hypothetical 15.8 kDa membrane protein of *M. tuberculosis*.

The sequnce of SEQ ID NO: 46 was used to design amplification primers (provided in SEQ ID NOS: 71 and 72) for expression cloninig of the GVc-7 gene using sequence data downstream from the putative leader sequence. A XhoI restriction site was added to the primers for cloning convenience. Following amplification from genomic *M. vaccae* DNA, fragments were cloned into the XhoI-site of pProEX HT prokaryotic expression vector (Gibco BRL) and submitted for sequencing to confirm the correct reading frame and orientation. Expression and purification of the fusion protein was perfomed according to the manufacturer's protocol.

The ability of purified recombinant GVc-7 to stimulate proliferation of T-cells and stimulation of interferon-γ production in human PBL was assayed as described previously in Example 4. The results are shown in Table 11, wherein (−) indicates a lack of activity, (+/−) indicates polypeptidees having a result less than twice higher than background activity of control media, (+) indicates polypeptides having activity two to four times above background, and (++) indicates polypcptides having activity greater than four times above background.

TABLE 11

| Donor | Proliferation | Interferon-γ |
|---|---|---|
| G97005 | ++ | +/− |
| G97008 | ++ | + |
| G97009 | + | +/− |
| G97010 | +/− | ++ |

A redundant oligonucleotide probe SEQ ID NO: 73, referred to as MPG15) was designed to the GVs-8 peptide sequence shown in SEQ ID NO: 26 and used to screen a *M. vaccae* genomic DNA library using standard protocols.

A genomic clone containing genes encoding four different antigens was isolated. The determined DNA sequences for GVs-8A (re-named GV-30), GVs-8B (re-named GV-31), GVs-8C (re-named GV-32) and CVs-8D (re-named GV-33) are shown in SEQ ID NOS: 48–51, respectively, with the corresponding amino acid sequences being shown in SEQ ID NOS: 52–55, respectively. GV-30 contains regions showing some similarity to known prokaryotic valyl-tRNA synthetases; GV-31 shows some similarity to *M. smegmatis* aspartate semialdehyde dehydrogenase; and GV-32 shows some similarity to the *H. influenza* folylpolyglutamate synthase gene. GV-33 contains an open reading frame which shows some similarity to sequences previously identified in *M. tuberculosis* and *M. leprae*, but whose function has not been identified.

The determined partial DNA sequence for GV-33 is provided in SEQ ID NO:74 with the corresponding predicted amino acid sequence being provided in SEQ ID NO:75. Sequence data from the 3' end of the clone showed homology to a previously identified 40.6 kDa outer membrane protein of *M. tuberculosis*. Subsequent studies led to the isolation of the full-length DNA sequence for GV-33 (SEQ ID NO: 193). The corresponding predicted amino acid sequence is provided in SEQ ID NO: 194.

The gene encoding, GV-33 was amplified from *M. vaccae* genomic DNA with primers based on the determined nucleotide sequence. This DNA fragment was cloned into EcoRv-digested pBluescript II SK+ (Stratagene), and then transferred to pET16 expression vector. Recombinant protein was purified following the manufacturer's protocol.

The ability of purified recombinant GV-33 to stimulate proliferation of T-cells and stimulation of interferon-γ production in human PBL was assayed as described previously in Example 5. The results are shown in Table 12, wherein (−) indicates a lack of activity, (+/−) indicates polypeptides having a result less than twice higher than background activity of control media, (+) indicates polypetides having activity two to four times above background, and (++) indicates polypeptides having activity greater than four times above background.

TABLE 12

Stimulatory Activity of Polypeptides

| Donor | Proliferation | Interferon-γ |
|---|---|---|
| G97005 | ++ | + |
| G97006 | ++ | ++ |
| G97007 | − | +/− |
| G97008 | +/− | − |
| G97009 | +/− | − |
| G97010 | +/− | ++ |

EXAMPLE 9

DNA CLONING STRATEGY FOR THE *M. VACCAE* ANTIGENES GV-23, GV-24, GV-25, GV-26, GV-38A and GV-38B

*M. vaccae* (ATCC Number 15483) was grown in sterile Medium 90 at 37° C. for 4 days and harvested by centrifugation. Cells were resuspended in 1 ml TRIzol (Gibco BRL, Life Technologies, Gaithersburg, Md.) and RNA extracted according to the standard manufacturer's protocol. *M. tuberculosis* strain H37Rv (ATCC Number 27294) was grown in sterile Middlebrooke 7119 medium with Tween 80™ and oleic acid/albumin/dextrose/catalase additive (Difco Laboratories, Detroit, Mich.) at 37° C. and harvested under appropriate laboratory safety conditions. Cells were resuspended in 1 ml TRIzol (Gibco BRL) and RNA extracted according, to the manufacturer's standard protocol.

Total *M. tuberculosis* and *M. vaccae* RNA was depleted of 16S and 23S ribosomal RNA (rRNA) by hybridisation of the total RNA fraction to oligonuelcotides AD10 and AD11 (SEQ ID NOS: 81 and 82) complementary to *M. tuberculosis* rRNA. These oligonucleotides were designed from mycobacterial 16S rRNA sequences published by Bottger (*FEMS Microbiol. Lett.* 65:171–176, 1989) and from sequences deposited in the databanks. Depletion was done by hybridisation of total RNA to oligonucleotides AD10 and AD11 immobilised on nylon membranes (Hybond N, Amersham International, United Kingdom). Hybridisation was repeated until rRNA bands were not visible on etihdium bromide-stained agarose gels. An oligonucleotide, AD12 (SEQ ID NO: 83), consisting of 20 dATP-residues, was ligated to the 3' ends of the enriched mRNA fraction using RNA ligase. First strand cDNA synthesis was performed following standard protocols, using oligonucleotide AD7 (SEQ ID NO:84) containing a poly(dT) sequence.

The *M. tuberculosis* and *M. vaccae* cDNA was used as template for single-sided-specific PCR (3S-PCR). For this protocol, a degenerated oligonucleotide AD1 (SEQ ID NO:85) was designed based on conserved leader sequences and membrane protein sequences. After 30 cycles of amplification using primer AD1 as 5'-primer and AD7 as 3'-primer, products were separated on a urea/polyacrylamide gel. DNA bands unique to M. vaccae were excised and re-amplified using primers AD1 and AD7. After gel purification, bands were cloned into pGEM-T (Promega) and the base sequence determined.

Searches with the determined nucleotide and predicted amino acid sequences of band 12B21 (SEQ ID NOS: 86 and 87, respectively) showed homology to the pota gene of Escherichia coli encoding the ATP-binding protein of the spermidine/putrescine ABC transporter complex published by Furuchi et al. (J. Biol. Chem. 266:20928–20933, 1991). The spermidine/putrescine transporter complex of E. coli consists of four gene and is a member of the ABC transporter family. The ABC (ATP-binding Cassette) transporters typically consist of four genes: an ATP-binding gene, a periplasmic, or substrate binding, gene and two transmembrane genes. The transmembrane genes encode proteins each characteristically having six membrane-spanning regions. homolognes (by similarity) of this ABC transporter have been identified in the genomes of Haemophilus influeza (Fleischmann et al. Science 269:496–512, 1995) and Mycoplasma genitalium (Fraser, et al. Science, 270:397–403, 1995).

A M. vaccae genomic DNA library constructed in BamH1-digested lambda ZAP Express (Stratagene) was probed with the radiolabelled 238 bp band 12B21 following standard protocols. A plaque was purified to purity by repetitive screening and a phagemid containing a 4.5 kb insert was identified by Southern blotting, and hybridisation. The nucleotide sequence of the full-length M. vaccae homologue of pota (ATP-binding protein) was identified by sub-cloning of the 4.5 kb fragment and base sequencing). The gene consisted of 1449 bp including an untranslated 5' region of 320 bp containing putative −10 and −35 promoter elements. The nucleotide and predicted amino acid sequences of the M. vaccae pota (homologue are provided in SEQ ID NOS: 88 and 89, respectively.

The nucleotide sequence of the M. vaccae pota gene was used to design primers EV24 and EV25 (SEQ ID NO: 90 and 91) for expression cloning,. The amplified DNA fragment was cloned into pProEX HT prokaryotic expression system (Gibeo BRL) and expression in an appropriate E. coli host was induced by addition of 0.6 mM isopropylthio-β-galactoside (IPTG). The recombinant protein was named GV-23 and purified from inclusion bodies according to the manufacturer's protocol.

A 322 bp Sal1-BamH1 subclone at the 3'-end of the 4.5 kb insert described above showed homology to the potd gene, (periplasmic protein), of the spermidine/putrescine ABC transporter complex of E. coli. The nueleotidie sequence of this subclone is shown in SEQ ID NO:92. To identify the gene, the radiolabelled insert of this subclone was used to probe an M. vaccae genomic DNA library constructede in the Sal1-site of lambda Zap-Express (Stratagene) following standard protocols. A clone was identified of which 1342 bp showed homology with the potd gene of E. coli. The potd homologue of M. vaccae was identified by sub-cloning and base sequencing. The determined inucleotide and predicted amino acid sequences are shown in SEQ ID NOS: 93 and 94.

For expression cloning, primers IV26 and EV27 (SEQ ID NOS:95–96) were designed from the determined M. vaccae potd homologue. The amplified fragment was cloned into pProEX HT Prokaryotic expression system (Gibco BRL). Expression in an appropriate E. coli host was induced by addition of 0.6 mM IPTG and the recombinant protein named GV-24. The recombinant antigen was purified from inclusion bodies according to the protocol of the supplier.

To improve the solubility of the purified recombinant antigen, the gene encoding GV-24, but excluding the signal peptide, was re-cloned into the expression vector, employing. amplification primers EV101 and EV102 (SEQ ID NOS: 167 and 168). The construct was designated GV-24B. The nucleotide sequence of GV-24B is provided in SEQ ID NO: 169 and the predicted amino acid sequence in SFQ ID NO: 170. This fragment was cloned into pET16 for expression and purification of GV-24B according to the manufacturer's protocols.

The ability of purified recombinant protein (CV-23 and GV-24 to stimulate proliferation of T cells and interferon-production in human PBL was determined as described in Example 4. The results of these assays are provide in Table 13, wherein (−) indicates a lack of activity, (+/−) indicates polypeptidees having a result less than twice higher than background activity of control media, (+) indicates polypeptides having, activity two to four times above background, (++) indicates polypepticles having, activity greater than four times above background, and (ND) indicates not determined.

TABLE 13

| | Donor G97005 | | Donor G97006 | | Donor G97007 | | Donor G97008 | | Donor G97009 | | Donor G97010 | |
|---|---|---|---|---|---|---|---|---|---|---|---|---|
| | Prolif | IFN-γ | Prolif | INF-γ | Prolif | IFN-γ | Prolif | IFN-γ | Prolif | IFN-γ | Prolif | IFN-γ |
| GV-23 | ++ | ++ | ++ | ++ | + | + | ++ | ++ | + | − | + | ++ |
| GV-24 | ++ | + | ++ | + | ND | ND | + | +/− | + | +/− | +/− | ++ |

Base sequence adjacent to the M. vaccae potd gene-homologue was found to show homology to the potb gene of the speremidine/putrescine ABC transporter complex of E. coli, which is one of two transmembrane proteins in the ABC transporter complex. The M. vaccae potb homiologue (referred to as GV-25) was identified through, further sub-cloning and base sequencing. The determined nuclcotide and predicted amino acid sequences for GV-25 are shown in SEQ ID NOS: 97 and 98, respectively.

Futher subcloning, and base sequence analysis of the adjacent 509 bp failed to reveal significant homology to PotC, the second transmembrane protein of E. coli, and suggests that a second transmembrane protein is absent in the, M. vaccae homologue of the ABC transporter. An open reading frame with homology to M. tuberculosis acetyl-CoA acetyl transferase, however, was identified starting, 530 bp downstream of the transmembrane protein and the translated protein was named GV-26. The determined partial nucleotide sequence and predicted amino acid sequence for GV-26 are showing SEQ ID NOS:99 and 100.

Using a protocol similar to that described above for the isolation of GV-23, the 3S-PCR band 12B28 (SEQ ID NO: 119) was used to screen the *M. vaccae* genomic library constructed in the BamHI-site of lambda ZAP-Express (Stratagene). The clone isolated from the library contained a novel open reading, frame and the antigen encoded by this gene was named GV-38A. The determined nucleotide sequence and predicted amino acid sequence of GV-38A are shown in SEQ ID NOS: 120 and 121, respectively. Subsequent studies led to the isolation of an extended DNA sequence for GV-38A, provided in SEQ ID NOS: 171. The corresponding amino acid sequence is provided in SEQ ID NO: 172. Comparison of these sequences with those in the database revealed only a limited amount of homology to an unknown *M. tuberculosis* protein previously identified in cosmid MTCY428.12.

Upstream of the GV-35A gene, a second novel open reading frame was identified and the antigen encoded by this gene was named GV-31S3. The determined 5' and 3' nucleotide sequences for GV-38B are provide in SEQ ID NOS: 122 and 123, respectively, with the corresponding predicted amino acid sequences being, provided in SEQ ID NOS: 124 and 125, respectively. Further studies led to the isolation of the full-length DNA sequence for GV-38B, provided in SEQ ID NO: 173. The corresponding amino acid sequence is provided in SEQ ID NO: 174. This protein was found to show only a limited amount of homology to an unknown *M. tuberculosis* protein identified as a putative open reading frame in cosmid MTCY428.11 (SPTREMBL: P71914).

Both the GV-38A and GV-38B antigens were amplified for expression cloning into pET16 (Novagen). GV-38A was amplified with primers KR11 and KR12 (SEQ ID NOS: 126 and 127) and GV-38B with primers KZ13 and KR14 (SEQ ID NOS: 128 and 129). Protein expression in the host cells BL21(DE3) was induced with 1 mM IPTG, however no protein expression was obtained from these constructs. Hydrophobic regions were identified in the N-termini of antigens GV-38A and GV-38B which may inhibit expression of these constructs. The hydrophobic region present in GV-38A was identified as a possible transmembrane motif with six membrane spanning regions. To express the antigens without the hydrophobic regions, primers KR20 for GV-38A, (SEQ ID NO: 130) and KR21 for GV-38B (SEQ ID NO: 131) were designed. The truncated GV-38A gene was amplified with primers KR20 and KR12, and t he truncated GV-38B gene with KR21 and KR14. The determined nulcleotide sequences of truncated GV-38A and GV-38B are shown in SEQ ID NOS: 132 and 133 respectively, with the corresponding predicted amino acid sequences being showing in SEQ ID NOS: 134 and 135, respectively. Extended DNA sequence for truncated GV-38A and GV-38B are provided in SEQ ID NOS: 175 and 176, respectively, with the corresponding, amino acid sequences being provided in SEQ ID NOS: 177 and 178. respectively.

EXAMPLE 10

PURIFICATION AND CHARACTERISATION OF POLYPEPTIDES FROM *M. VACCAE* CULTURE FILTRATED BY PREPARATIVE ISOELECTRIC FOCUSING AND PREPARATIVE POLYACRYLAMIDE GEL ELECTROPHORESIS

*M. vaccae* soluble proteins were isolated from culture filtrate using preparative isoelectric focusing and preparative polyacrylamide gel electrophoresis as described below. Unless otherwise noted, all percentages in the Following example are weight per volume.

*M. vaccae* (ATCC Number 15483) was cultured in 250 l sterile Medium 90 which had been factionated by ultrafiltration to remove all proteins of greater than 10 kDa molecular weight. The medium was centrifuged to remove, the bacteria, and sterilised by filtration through a 0.45μ filter. The sterile filtrate was concentrated by ultrafiltration over a 10 kDa molecular weight cut-off membrane.

Proteins were isolated from the concentrated culture filtrate by precipitation with 10% trichloroacetic acid. The precipitaited proteins were re-dissolved in 100 mM Tris.HCl pH 8.0 and re-precipitated by the addition of an equal volume of acetone. The acetone precipitate was dissolved in water, and proteins were re-precipitated by the addition of an equal volume of chloroform:methanol 2:1 (v/v). The chloroform:methanol precipitate was dissolved in water, The freeze-dried protein was dissolved in iso-electric focusing, buffer, containing 8 M deionised urea, 2% Triton X100™, 10 mM dithiothreitol and 2% ampholytes (pH 2.5–5.0). The sample was fractionated by preparative iso-electric focusing a horizontal bed of ULTRODEX gel at 8 watts constant power for 16 hours. Proteins were eluted from the gel bed fractions with water and concentrated by precipitation with 10% trichloroacetic acid.

Pools of fractions containig proteins of interest were identified by analytical polyacrylamide gel electrotphoresis and fractionated by preparative polyacrylamide gel electrophoresis. Samples were fractioned on 12.5% SDS-PAGE gels, and electroblotted onto nitrocellulose membranes. Proteins were located on the membranes by staining with Ponceau Red, destained with water and eluted from the membranes with 40% acetonitrile/0.1M ammonium bicarbonate pH 8.9 and then concentrated by lyoplilisation.

Eluted proteins were assayed for their ability to induce proliferation and interferon-γ secretion from the peripheral blood lymphocytes of immune donors as detailed in Example 4. Proteins inducing a strong response in these assays were selected for further study.

Selected proteins were further purified reversed-phase chromatography on a Vydac Protein C4 column, using a trifloroacetic acid-acetonitrile system. Purified proteins were prepared for protein sequence determination by SDS-polyacrylamide gel electrophoresis, and electroblotted onto PVDF membranes. Protein sequences were determined as in Example 5. The proteins were named GV-40, GV-41, GV-42, GV-43 and GV-44. The determined N-terminal sequence for these polypeptides are shown in SEQ ID NOS:101–105, respectively. Subsequent studies led to the isolation of a 5', middle fragment and 3' DNA sequence for GV-42 (SEQ ID NOS: 136, 137 and 138, respectively). The corresponding predicted amino acid sequences are provided in SEQ ID NOS: 139, 140 and 141, respectively.

Following, standard DNA amplification and cloning procedures as described in Example 7, the genes encoding, GV-41 and GV-42 were cloned. The determined nucleotide sequences are provided in SEQ ID NOS: 179 and 180, respectively, and the predicted amino acid sequences in SEQ ID NOS: 181 and 182. CV-41 had homology to the ribosome recycling factor of *M. tuberculosis* and *M. leprae*, and GV-42 had homology to a *M. avium* fibronectin attachment protein FAP-A. Within the full-length sequence of GV-42, the amino acid sequence determined for GV-43 (SEQ ID NO:104) was identified, indicating that the amino acid sequences for GV-42 and GV-43 were obtained form the same protein.

Murine polyclonal antisera were prepared against GV-40 and GV-44 following standard procedures. These antisera were used to screen a M. vaccae genomic DNA library consisting of randomly sheared DNA fragments. Clones encoding GV-40 and GV-44 were identified and sequenced. The determined nucleotide sequence of the partial gene encoding GV-40 is provided in SEQ ID NO: 183 and the predicted amino acid sequence in SEQ ID NO: 184. The nucleotide sequence of the gene encoding GV-44 is provided in SEQ ID NO: 185, and the predicted amino acid sequence in SEQ ID NO: 186. Homology of GV-40 to M. leprae Elongation factor G was found. GV-44 had homology to M. leprae glyceraldehyde-3-phosphate dehydrogenase.

EXAMPLE 11

DNA CLONING STRATEGY FOR THE DD-M. VACCAE ANTIGEN GV-45

Proteins were extracted from DD-M. vaccae (500 mg; prepared as described in Example 1) by suspension in 10 ml 2% SDS/PBS and heating, to 50° C. for 2 h. The insoluble residue was removed by centrifuation, and proteins precipitated from the supernatant by adding an equal volume of acetone and incubating at −20° C. for 1 hr. The precipitated proteins were collected by centrifugation, dissolved in reducing sample buffer, and fractionated by preparative SDS-polyacrylamide gel electrophoresis. The separated proteins were electroblotted onto PVDF membrane in 10 mM CAPS/0.01% SDS pH 11.0, and N-terminal sequences were determined in a gas-phase sequenator.

The amino acid sequence obtained from these experiments was designated GV-45. The determined N-terminal sequence for GV-45 is provided in SEQ ID NO: 187.

From the amino acid sequence of GV-45, degenerate oligonucleotides KR32 and KR33 (SEQ ID NOS: 188 and 189, respectively) were designed. A 100 bp fragment was amplified, cloned into plasmid pBluescript II SK⁺ (Stratagene, La Jolla, Calif.) and sequenced (SEQ ID NO:190) following standard procedures (Sambrook et al., Ibid). The cloned insert was used to screen a M. vaccae genomic DNA showed constructed in the BamHI-site of lambda ZAP-Express (Stratagene). The isolated clone showed homology to a 35 kDa M. tuberculosis and a 22 kDa M. leprae protein containing bacterial histone-like motifs at the N-terminus and a unique C-terminus consisting of a five amino acid basic repeat. The determined nuclcotide sequence for GV-45 is provided in SEQ ID NO: 191, with the corresponding predicted amino acid sequence being provided in SEQ ID NO: 192.

EXAMPLE 12

EFFECT OF IMMUNIZATION WITH M. VACCAE ON IMMUNE SYSTEM DISORDERS IN MICE

This example illustrates that both heat-killed M. vaccae and DD-M. vaccae, when administered to mice via the intranasal route, are able to inhibit the development of an allergic immune response in the lungs and to suppress Th2 immune responses. Such responses are believed to play a role in skin disorders such as atopic dermatitis and allergic contact dermatitis. The ability of heat-killed M. vaccae and DD-M. vaccae to inhibit the development of allergic immune responses was demonstrated in a mouse model of the asthma-like allergen specific lung disease. The severity of this allergic disease is reflected in the large numbers of eosinophils that accumulate in the lungs.

C57BL/6J mice were 2 µg ovalbumin in 100 µl alum (Aluminium hydroxide) adjuvant by the intraperitoneal rout at time 0 and 14 days, and subsequently given 100 µg ovalbumin in 50 µl phosphate buffer saline (PBS) by the intranasal route on day 28. The mice accumulated eosinophils in their lungs as detected by washing the airways of the anaesthetised mice with saline, collecting the washings (broncheolar lavage or BAL), and counting the numbers of eosinophils.

As shown in FIGS. 4A and B, groups of seven mice administered either 10 or 1000 µg of heat-killed M. vaccae (FIG. 4A), or 100 or 200 µg of DD-M. vaccae (FIG. 4B) intranasally 4 weeks before intranasal challenge with ovalbumin, had reduced percentages of eosinophils in the BAL cells collected 5 days after challenge with ovalbumin compared to control mice. Control mice were given intranasal PBS. Live M. bovis BCG at a dose of 2×10⁵ colony forming units also reduced lung eosinophils. The data in FIGS. 4A and B show the mean and SEM per group of mice.

Figure 4C:
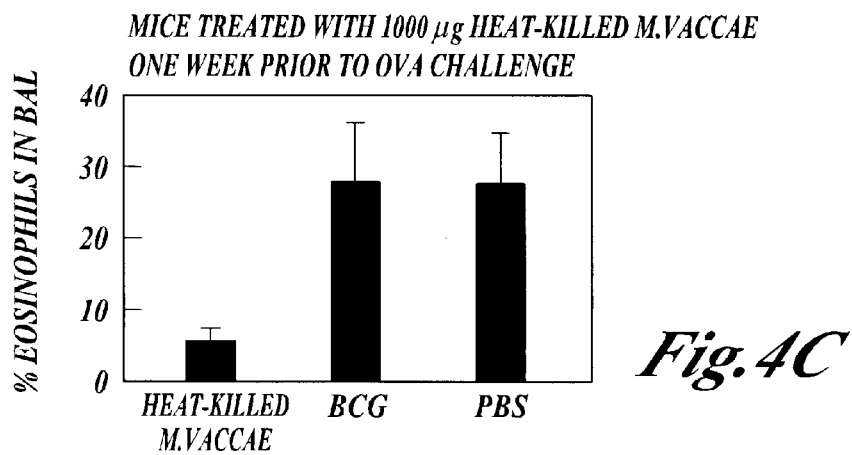
Figure 4D:
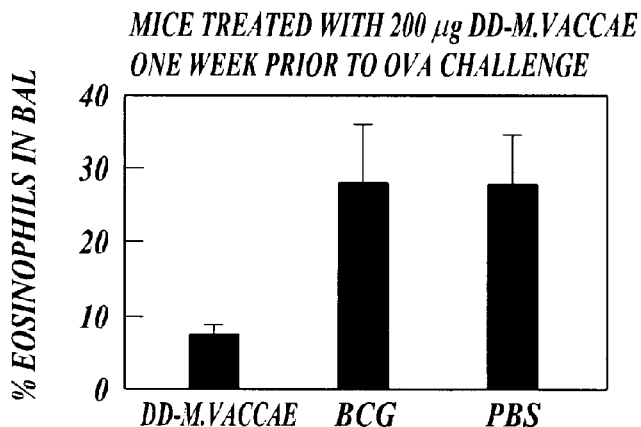

FIGS. 4C and D show that mice given either 1000 µg of heat-killed M. vaccae (FIG. 4C) or 200 µg of DD-M. vaccae (FIG. 4D) intranasally as late as one week before challenge with ovalbumin had reduced percentage of eosinophils compared to control mice. In contrast, treatment with live BCG one week before challenge with ovalbumin did not inhibit the development of lung eosinophils when compared with control mice.

Figure 4E:
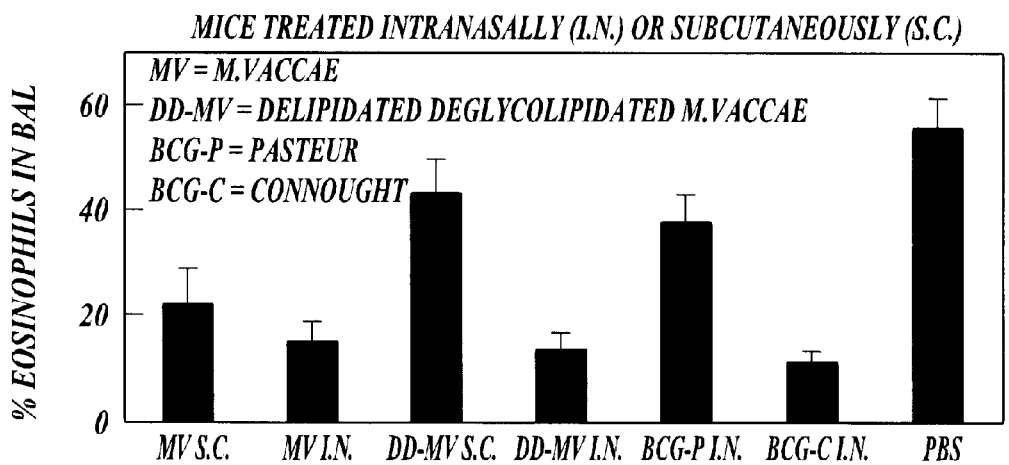

As shown in FIG. 4E, immunization with either 1 mg of heat-killed M. vaccae or 200 µg of DD-M. vaccae given either intranasally (i.n.) or subcutaneously (s.c.), reduced lung eosinoplilia following, challenge with ovalbumin when compared to control animals given PBS. In the same experiment, immunization with BCG of the Pasteur (BCG-P) and Connought (BCG-C) strains prior to challenge with ovalbumin also reduced the percentage of eosinophils in the BAL of mice.

Eosinophils are blood cells that are prominent in the airways in allergic asthma. The secreted products of eosinoplils contribute to the swelling and inflammation of the mucosal linings of the airways in allergic asthma. The data shown in FIGS. 4A–E indicate that treatment with heat-killed M. vaccae or DD-M. vaccae reduces the accumulation of lung eosinophils, and may be useful in reducing inflammation associated with eosinophils in the airways, nasal mucosal and upper respiratory tract. Administration of heat-killed M. vaccae or DD-M. vaccae may therefor reduce the severity of asthma and other diseases that involve similar immune abnormalities, such as allergic rhinitis and certain allergic skin disorders.

In addition, serum samples were collected from mice in the experiment described in FIG. 4E and the level of antibodies to ovalbumin was measured by standard enzyme-linked immunoassay (EIA). As showing in Table 14 below, sera from mice infected with BCG had higher levels of ovalbumin specific IgG1 than sera from PBS controls. In contrast, mice immunized with M. vaccae or DD-M. vaccae had similar or lower levels of ovalbumin-specific IgG1. As IgG1 antibodies are characteristic of a Th2 immune response, these results are consistent with the suppressive effects of heat-killed M. vaccae and DD-M. vaccae on the asthma-inducing Th2 immune responses, and indicate that heat-killed M. vaccae and DD-M. vaccae may be usefully to suppress Th2 immune responses in skin disorders such as atopic dermatitis, allergic contact dermatitis and alopecia areata.

TABLE 14

LOW ANTIGEN-SPECIFIC IgG1 SERUM LEVELS
IN MICE IMMUNIZED WITH HEAT-KILLED M. VACCAE OR
DD-M. VACCAE

| Treatment Group | Serum IgG1 | |
|---|---|---|
| | Mean | SEM |
| M. vaccae i.n. | 185.00 | 8.3 |
| M. vaccae s.c. | 113.64 | 8.0 |
| DD-M. vaccae i.n. | 96.00 | 8.1 |
| DD-M. vaccae s.c. | 110.00 | 4.1 |
| BCG, Pasteur | 337.00 | 27.2 |
| BCG, Connaught | 248.00 | 46.1 |
| PBS | 177.14 | 11.4 |

Note: Ovalbumin-specific IgG1 was detected using anti-mouse IgG1 (Serotec). Group means are expressed as the reciprocal of the EU50 end point etitre.

EXAMPLE 14

EFFECT OF DD-M. VACCAE ON IL-10 PRODUCTION IN THP-1 CELLS

Psoriasis is characterised by pronounced T cell infiltrate that is thought to be central in driving ongoing skin inflammation. Various studies have shown that these cells produce a wide variety of cytokines, such as interlink-2 (IL-2), IFNγ and TNFα, which are known to be produced by Th1 cells. IL-10 inhibitis the cytokine production of Th1 cells and plays a key role in the suppression of experimetally-induced inflammatory response in skin (Berg et al., *J. Exp. Med.*, 82:99–108, 1995). Recently, IL-10 has been used successfully in two clinical trials to treat psoriatic patients (Reich et al., *J. Invest. Dermatol.*, 11:1235–1236, 1998 and Asadullah et al., *J. Clin. Invest.*, 101:783–794, 1998). It is therefore possible that DD-M. vaccae inhibits skin inflammation in psoriasis patients by stilmulating production of IL-10. To test this hypothesis, the levels of IL-10 produced by a human monocytic cell line (THP-1) cultured in the presence of DD-M. vaccae were assessed.

Figure 5:
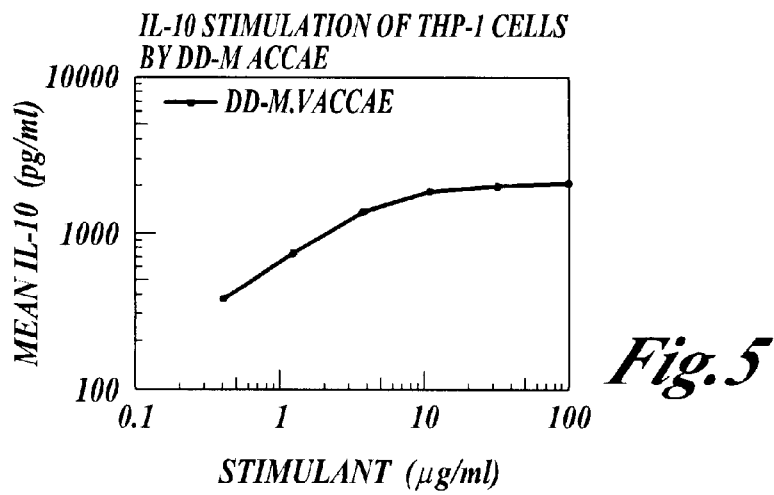
FIG. 5 shows the stimulation of IL-10 production in THP-1 cells by DD-*M. vaccae*.

THP-1 cells (ATCC (Marossas, Va.), TIB-202) were cultured in RPMI medium (Gibco BRL Life Technologies) supplemented with 0.5 mg/l streptomycin, 500 U/l penicillin, 2 mg/l L-glutamine, $5 \times 10^{-5}$ M β-mercaptoethanol and 5% fetal bovine serum (FBS). One day prior to the assay, the cells were subcultured in fresh media at $5 \times 10^5$ cells/ml. Cells were incubated at 37° C. in humidified air containing 5% $CO_2$ for 24 hours and then aspirated and washed by centrifugation with 50 ml of media. The cells were re-suspended in 5 ml of media and the cell concentration and viability determined by staining, with Trypan blue (Sigma, St Louis Mo.) and analysis under a haemocytometer. DD-M. vaccae (prepared as described above) in 50 μl PBS and control stimulants were added in triplicate to wells of a 96 well plate containing 100 μl of medium and appropriate dilutions were prepared. Lipopolysaccharide (LPS) (300 μg/ml; Sigma) and PBS were used as controls. To each well, 100 μl of cells were added at a concentration of $2 \times 10^6$ cell/ml and the plates incubated at 37° C. in humidified air containing 5% $CO_2$ for 24hours. The level of IL-10 in each well was determined using the Human IL-10 ELISA reagents (PharMigen, San Diego Calif.) according to the manufacturer's protocol. As shown in FIG. 5, LD-M. vaccae was found to stimulate significant levels of IL-10 production, suggesting that this may be the mechanism for the therapeutic action of DD-M. vaccae in psoriasis. The PBS control did not stimulate THP-1 cells to produce IL-10.

Although the present invention has been described in some detail by way of illustration and example for purposes of clarity of understanding, changes and modifications can be carried out without departing from the scope of the invention which is intended to be limited only by the scope of the claims.

We claim:

1. A method for inhibiting skin inflammation associated with a skin disorder selected from the group consisting of psoriasis atopic dermatitis; and allergic contact dermatitis, the method comprising administering a composition comprising delipidated and deglycolipidated *Mycobacterium vaccae* cells.

2. A method for inhibiting skin inflammation associated with a skin disorder selected from the group consisting of: psoriasis; atopic dermatitis; and allergic contact dermatitis, the method comprising administering a composition comprising *Mycobacterium vaccae* culture filtrate.

3. The method of claim 1, wherein the composition is administered by means of intradermal injection.

4. The method of claim 1, wherein the composition additionally comprises an adjuvant.

5. The method of claim 4, wherein the adjuvant comprises an isolated polypeptide, the polypeptide comprising an immunogenic portion of an antigen, wherein the antigen includes an amino acid sequence selected from the group consisting of SEQ ID NOS: 114, 117 and 118.

6. The method of claim 1, wherein the delipidated and deglycolipidated, *M. vaccae* cells comprise less than 10% by weight of lipids.

7. The method of claim 1, wherein the delipidated and deglycolipidated *M. vaccae* cells comprise more than 33% by weight of amino acids.

8. The method of claim 2, wherein the composition is administered by means of intradermal injection.

9. The method of claim 2, wherein the composition additionally comprises an adjuvant.

* * * * *